US011703800B2

United States Patent
Marshel et al.

(10) Patent No.: US 11,703,800 B2
(45) Date of Patent: Jul. 18, 2023

(54) METHODS FOR TEMPORAL AND SPATIAL MULTIPLEXING OF SPATIAL LIGHT MODULATORS AND SYSTEMS FOR SAME

(71) Applicant: The Board of Trustees of the Leland Stanford Junior University, Stanford, CA (US)

(72) Inventors: James Marshel, Stanford, CA (US); Karl A. Deisseroth, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 241 days.

(21) Appl. No.: 16/957,926

(22) PCT Filed: Mar. 21, 2019

(86) PCT No.: PCT/US2019/023403
§ 371 (c)(1),
(2) Date: Jun. 25, 2020

(87) PCT Pub. No.: WO2019/183376
PCT Pub. Date: Sep. 26, 2019

(65) Prior Publication Data
US 2021/0063964 A1 Mar. 4, 2021

Related U.S. Application Data

(60) Provisional application No. 62/792,752, filed on Jan. 15, 2019, provisional application No. 62/646,244, filed on Mar. 21, 2018.

(51) Int. Cl.
*G03H 1/22* (2006.01)
*A61N 5/06* (2006.01)
(Continued)

(52) U.S. Cl.
CPC ......... *G03H 1/2294* (2013.01); *A61N 5/0622* (2013.01); *G03H 1/0005* (2013.01);
(Continued)

(58) Field of Classification Search
CPC .............. G03H 1/2294; G03H 1/0005; G03H 1/2286; G03H 2001/2655; A61N 5/0622;
(Continued)

(56) References Cited

U.S. PATENT DOCUMENTS 6,662,039 B2    12/2003   Yuste et al.
6,823,286 B2    11/2004   Yuste et al.
(Continued)

FOREIGN PATENT DOCUMENTS

AU    2014206165    8/2014
AU    2016206262    8/2016
(Continued)

OTHER PUBLICATIONS

Baker et al. (2008) "Genetically encoded fluorescent sensors of membrane potential" Brain Cell Bioi., 36: 53-67.
(Continued)

*Primary Examiner* — Jade R Chwasz
(74) *Attorney, Agent, or Firm* — Edward J. Baba; Bozicevic, Field & Francis LLP

(57) ABSTRACT

Methods for selectively stimulating a plurality of light-responsive neurons in a sample are provided. Methods according to certain embodiments include irradiating a sample comprising a plurality of light-responsive neurons with a plurality of holographic images that are each configured to stimulate one or more light-responsive neurons in the sample, wherein the holographic images are created by light projection system that includes a plurality of light sources; a plurality of optical adjustment components; a plurality of spatial light modulators; a controller; a processor; and a
(Continued)

computer-readable medium comprising instructions that, when executed by the processor, cause the controller to operate the light sources, optical adjustment components and spatial light modulators to generate and display a plurality of holographic images; direct each of the holographic images to a projection location; and project the holographic images onto the sample at a rate greater than 1 kHz. Light projection systems for irradiating a sample having light-responsive neurons with holographic images are also described.

30 Claims, 115 Drawing Sheets

(51) Int. Cl.
G03H 1/00 (2006.01)
A61N 5/073 (2006.01)
(52) U.S. Cl.
CPC ............... *G03H 1/2286* (2013.01); *A61N 2005/0659* (2013.01); *A61N 2005/0662* (2013.01); *A61N 2005/073* (2013.01)
(58) Field of Classification Search
CPC .... A61N 2005/0659; A61N 2005/0662; A61N 2005/073
USPC .......................................................... 359/9
See application file for complete search history.

(56) References Cited

U.S. PATENT DOCUMENTS

| | | | |
|---|---|---|---|
| 8,063,216 B2 | 11/2011 | Etchenique et al. | |
| 8,178,496 B2 | 5/2012 | Trauner | |
| 8,475,506 B1 | 7/2013 | Bendett et al. | |
| 8,562,658 B2 | 10/2013 | Shoham et al. | |
| 8,629,256 B2 | 1/2014 | Lee et al. | |
| 9,744,236 B2 | 8/2017 | Yuste et al. | |
| 10,228,554 B2 | 3/2019 | Waller et al. | |
| 10,474,035 B2 | 11/2019 | Tang et al. | |
| 10,520,712 B2 | 12/2019 | Yuste et al. | |
| 2002/0123947 A1 | 9/2002 | Yuste et al. | |
| 2003/0009103 A1 | 1/2003 | Yuste et al. | |
| 2004/0015310 A1 | 1/2004 | Yuste et al. | |
| 2008/0176940 A1 | 7/2008 | Etchenique et al. | |
| 2011/0085173 A1 | 4/2011 | Waller et al. | |
| 2011/0233046 A1 | 9/2011 | Nikolenko et al. | |
| 2012/0220922 A1 | 8/2012 | Yuste et al. | |
| 2013/0224756 A1 | 8/2013 | Cohen et al. | |
| 2014/0268263 A1 | 9/2014 | Redford | |
| 2015/0323787 A1 | 11/2015 | Yuste et al. | |
| 2016/0176907 A1 | 6/2016 | Etchenique et al. | |
| 2017/0003491 A1 | 1/2017 | Waller et al. | |
| 2017/0146788 A1 | 5/2017 | Waller et al. | |
| 2018/0048811 A1 | 2/2018 | Waller et al. | |
| 2018/0177401 A1* | 6/2018 | Yang | G01N 21/6458 |
| 2019/0107655 A1 | 4/2019 | Waller et al. | |
| 2019/0227490 A1 | 7/2019 | Waller et al. | |
| 2021/0080709 A1* | 3/2021 | Ronzitti | G03F 7/70 |

FOREIGN PATENT DOCUMENTS

| | | |
|---|---|---|
| CA | 2979592 | 9/2016 |
| EP | 2847632 | 3/2015 |
| EP | 2910992 | 8/2015 |
| EP | 3096171 | 11/2016 |
| ES | 1033926 U | 11/2016 |
| JP | 2016-041746 | 3/2016 |
| JP | 2017-207767 | 11/2017 |
| WO | 2011/023593 | 3/2011 |
| WO | 2018/185323 | 10/2018 |

OTHER PUBLICATIONS

Berndt and Deisseroth (2015) "Expanding the optogenetics toolkit: A naturally occurring channel for inhibitory optogenetics is discovered" Science, 349(6248): 590-591.

Berndt et al. (2014) "Structure-Guided Transformation of Channelrhodopsin into a Light-Activated Chloride Channel" Science, 344(6182): 420-424.

Fan et al. (1999) "Video-Rate Scanning Two-Photon Excitation Fluorescence Microscopy and Ratio Imaging with Cameleons" Biophysical Journal, 76(5): 2412-2420.

Guru et al. (2015) "Making Sense of Optogenetics" Inti. J. Neuropsychopharmacol., 1-8.

Hochbaum et al. (2014) "All-optical electrophysiology in mammalian neurons using engineered microbial rhodopsins" Nat Methods, 11(8): 825-833.

Mehta et al. (2011) "Reporting from the Field: Genetically Encoded Fluorescent Reporters Uncover Signaling Dynamics in Living Biological Systems" Annu Rev Biochem., 80: 375-401.

Mutoh et al. (2011) "Optogenetic monitoring of membrane potentials" Exp Physiol., 96: 13-18.

Noguchi et al. (2011) "In vivo two-photon uncaging of glutamate revealing the structure-function relationships of dendritic spines in the neocortex of adult mice" J Physiol., 589: 2447-2457.

Packer et al. (2012) "Two-photon optogenetics of dendritic spines and neural circuits" Nature Methods, 9: 1202-1205.

Prakash et al. (2012) "Two-photon optogenetic toolbox for fast inhibition, excitation and bistable modulation" Nature Methods, 9(12): 1171-1179.

Reutsky-Gefen et al. (2013) "Holographic optogenetic stimulation of patterned neuronal activity for vision restoration" Nature Communications, 4: 1509.

\* cited by examiner

E

Single SLM

Hologram 1  Hologram 2

▨ Intensity Measurement

MultiSLM
Temporal Multiplex

SLM1  SLM2

Hologram 1  Hologram 2

▨ Intensity Measurement $$P_{MultiSLM} = \frac{P_{SLM} + d}{N_{SLMs}}$$

B 0.71mm

Depth
Δz = 60μ

F

AAV8-CaMKIIa-GCaMP6m-p2a-ChRmine-TS-Kv2.1-HA

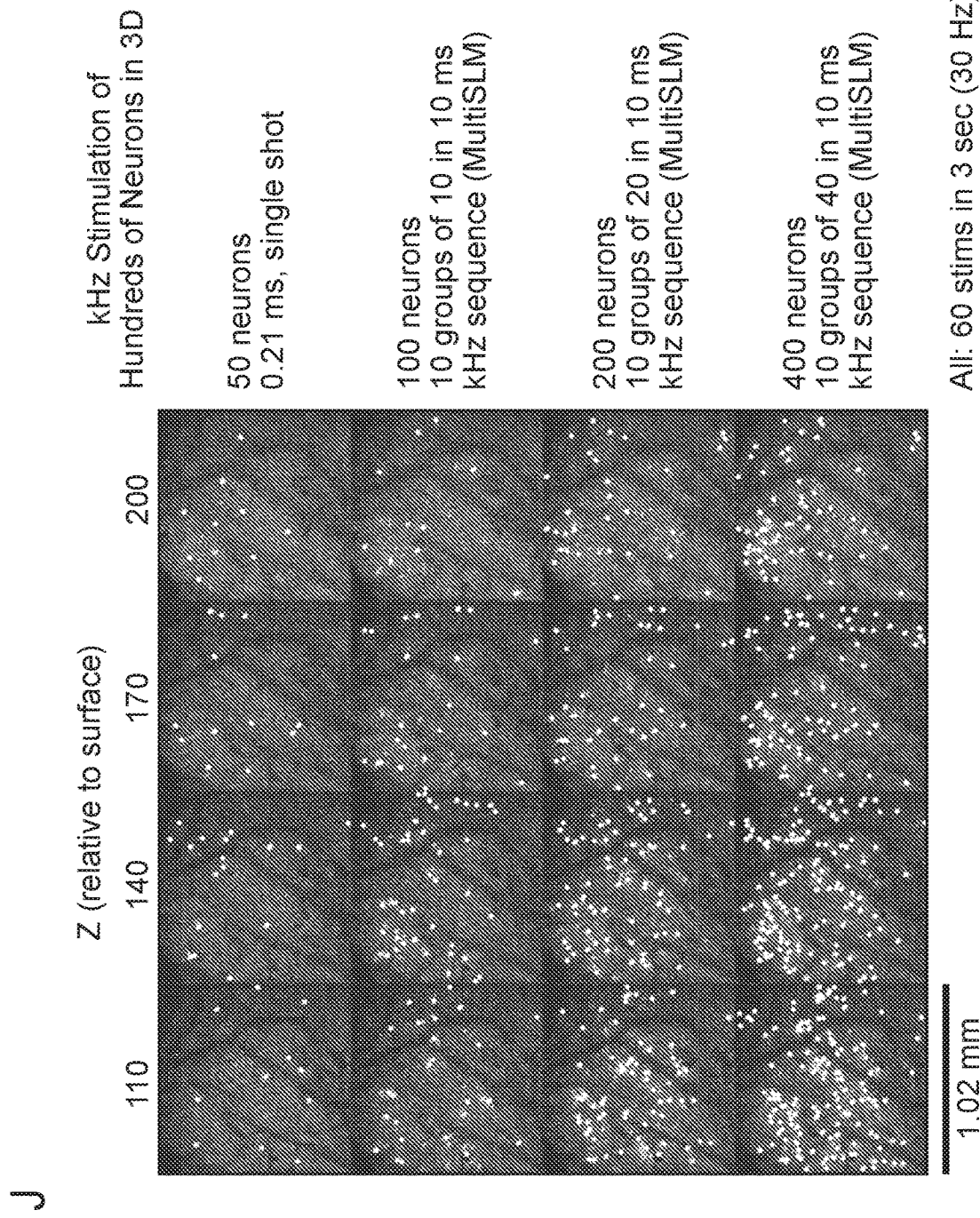

AAV8-CaMKIIa-GCaMP6m-p2a-ChRmine-TS-Kv2.1-HA

B

A

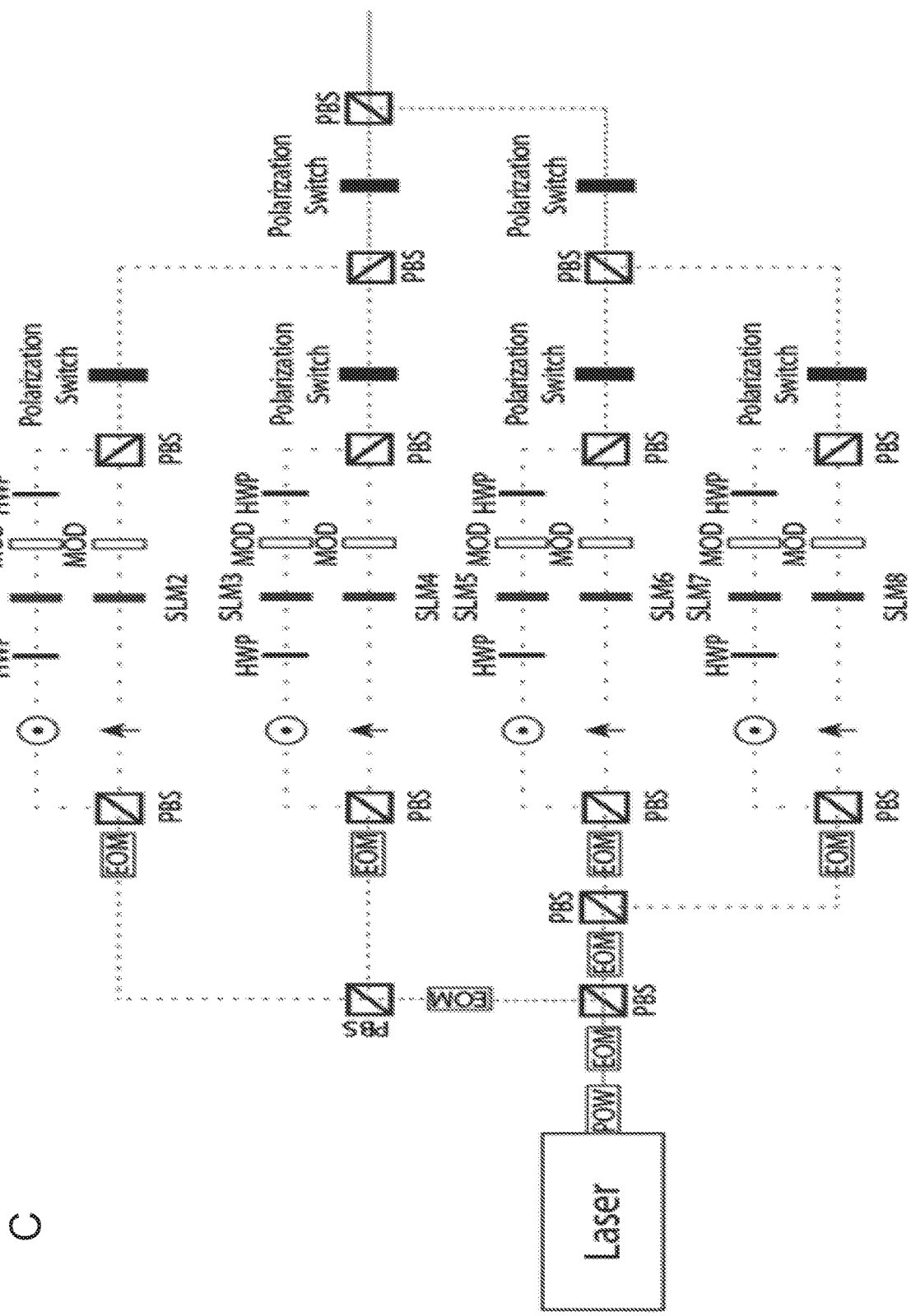
FIG. 8 (Cont.) C

A

Multiplexed FOV

B

Single SLM

C

Tiling 4xSLM into independent quadrants

B

C

K

L

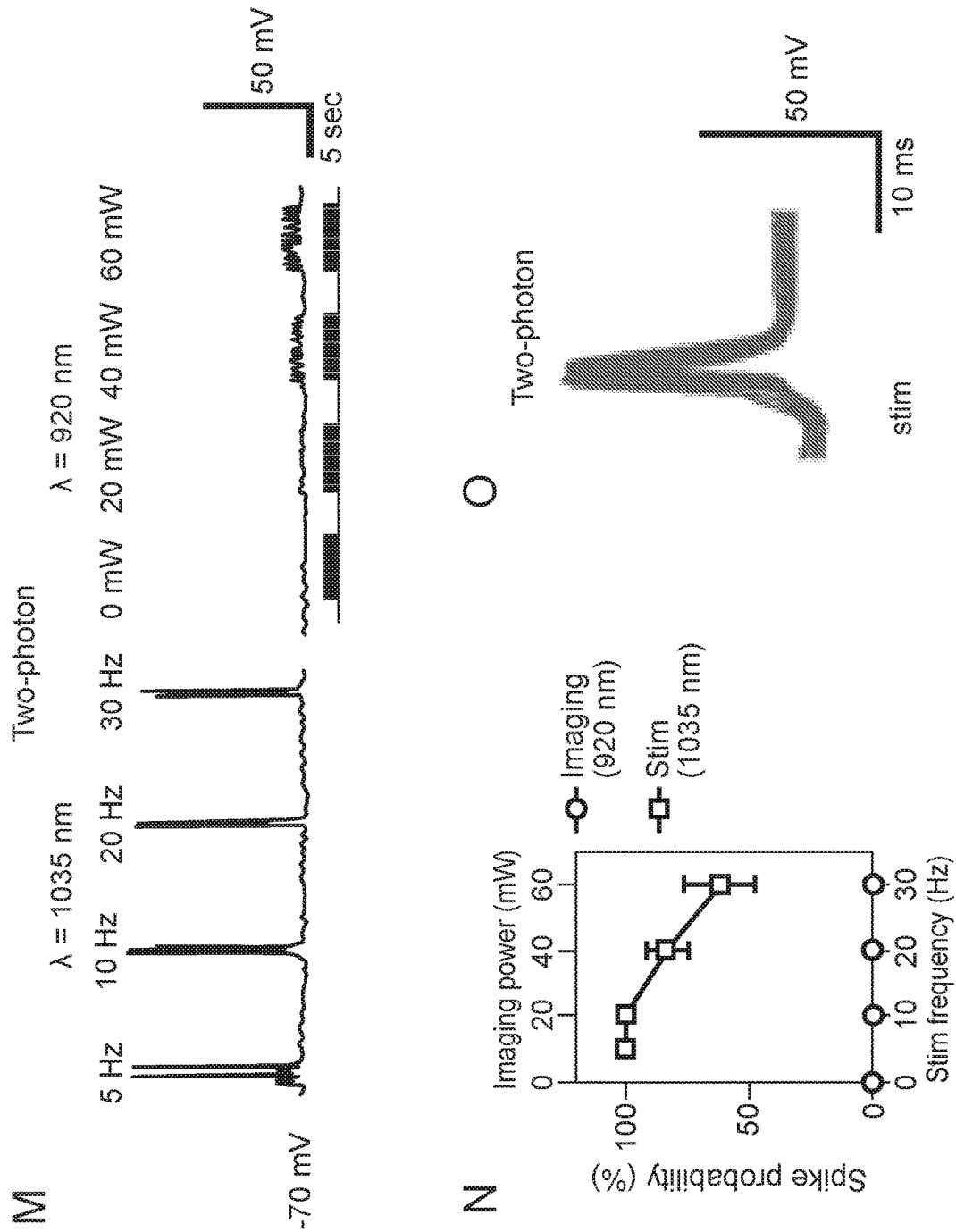

```
                1                                        10                   20
                |                                         |                    |
ChRmine         ...........................................APGTDQ.MFYVGTMDGWLDTK
GtACR1          MSSIT......................................CDPAIYGE.WSRENQFC.VEKS.LITL..
GtACR2          MAS........................................QVVYGE..WASTHTEC.YNMS.RIDS..
CrChR1          MSRRPWLLALALAWALAAGSAGASTGSDATVPVATQDGPD...VEHRAHERML..FQTSY..TLENNG..
CrChR2          MD.........................................YGGALSAVGRE..LLFVT..NPVVVN..
VChR1           MD.........................................YPVARS........LIVRY..PTDLGN..
Chrimson        MAELISSATRSLFAAGGINPWPNPYHHEDMGCGGMTPGECFSTEWWCDPS.YG...ISDAGYG..YCEVEATGGYLVV.
```

TM1

```
                                    30                    40                    50                    60                    70
                                     |                     |                     |                     |                     |
ChRmine         LNS.........................VAIGAHWSCFIVLTTTPLLGVESWTSRGPSKRTSFYAGQEEQNLALHVNE
GtACR1          ...........................DGIKYVQLVMAVSACQVF.YLPTTEM
GtACR2          ...........................TEVSLLQLVWAVSGCTIL.YLPPVES
CrChR1          .SVICIPPNGQEFCLAWLKSNGTNAEKLAANILQWITTALSALCLMFYGYQTWKSTC.GWEEI.YVCATEM
CrChR2          .GSVLVPED.QCYCAGWIESRGTNGAQTASNVLQWLAAGFSILLMFYAYQTWKSTC.GWEEI.YVCATEM
VChR1           .GTVCMP.RGQCYCEGWLRSRGTSIEKTIAITLQWVFALSVACLGWVAYQAWRATC.GWEEV.YVATEM
Chrimson        .KQAWLHSRGTPGEKIGAQVCQWIALTTFVGFSANKATC.GWEEV.YVCCVEV
```

FIG. 16 (Cont.)

```
              TM7
         ∞∞∞∞∞∞∞∞∞∞∞∞∞∞∞∞∞∞∞∞
                           230         240         250         260         270         280
∞∞∞∞∞∞          |           |           |           |           |           |           |
ChRmine    LFPLVWAICPRGFGWIDDNWEVAHCVCDIVAKSCYGTALARFRKTVDEFRL·········· ········LEQL······
GtACR1     AYPILWSFSSTGACIMSENTSSVLYLLIGDALCKNTYGILWATTW··············· ········NMP·······
GtACR2     MFPIVNLISPTGCVIHENVSAILYLLIAG·LCKTNTGVILWSTAW·····GLINGKWDRDYVKGRN···VDGTLMP······
CrChR1     MFPLFLLGPEGFGHINQFNSAAKAILDIASKANAWSMMGHFLRVKIHEHILLIHGDI·GVLEGKWDPACLPGQEKPEADDPGL·
CrChR2     MFPILFILGPEGFGVLSVGSTVGHTIIDLIS·TIIDLMSKNCWGLLIGHYLRVLIHEHILIIHGDI·RKKQEVN···VAGQEMEVEIM·
VChR1      MFPVLFLLGTEGFGHISPYGSAIGHSILDLIAKNMWGVLGNYLRVKIHEHILIHGDI·RKKTKLN···IGTEHEVETL·
Chrimson   SYPILWAVGPEGLKKLSPYANSIGHSICDIIAKEFWTFLAHHLRIKIHEHILIHGDI·RKTTKME···HAGQEMEVETL······
                                                                        ·GGERVEVEEF
```

```
             290         300
              |           |
ChRmine    GHDEDEFQKL·····ELDMRLSSNGERLRRLS·····················
GtACR1     ·EYE···QDLEKGNTERYEDARAGET···························
GtACR2     ·NHE···KNAPPNDEVNIRMEGR······························
CrChR1     VHEEDDETQKVPTAKYANRDSE·······························
CrChR2     VEDEAEAGAV···········································
VChR1      VAEEDDTVKQSTAKYASRDSEITMRNRMREKGLEVR·················
Chrimson   VEEDEDEDTV···········································
```

B

E

H

1 - Time-delay from image start (τ)
2 - SLM1 artifact band
3 - SLM2 artifact band C
20 Trial averaged w/ dithered optogenetic stim.

D
20 Trial averaged w/ omission of per-trial artifact

E

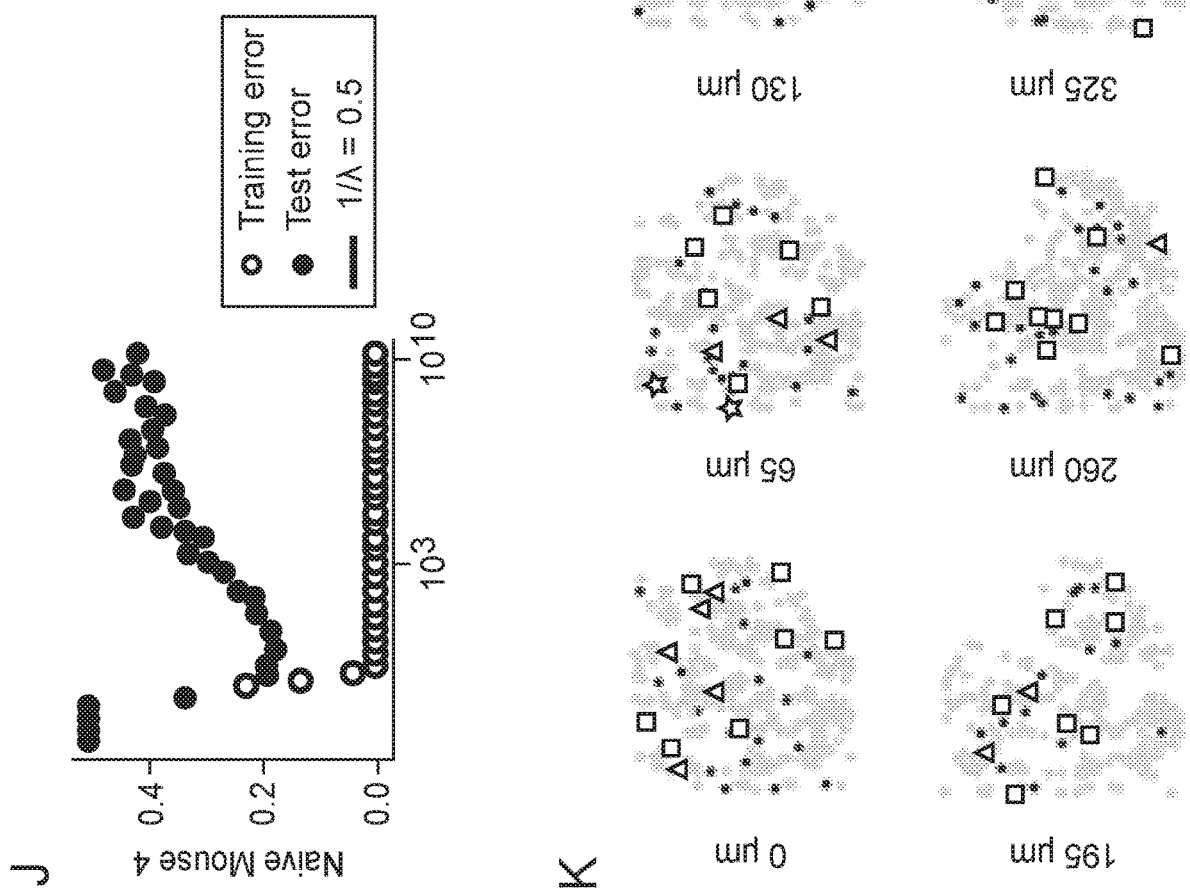

METHODS FOR TEMPORAL AND SPATIAL MULTIPLEXING OF SPATIAL LIGHT MODULATORS AND SYSTEMS FOR SAME

CROSS-REFERENCE TO RELATED APPLICATIONS

This application claims priority to U.S. Provisional Application No. 62/646,244 filed Feb. 21, 2018 and to U.S. Provisional Application No. 62/792,752 filed Jan. 15, 2019, which are both herein incorporated by reference in their entirety.

INTRODUCTION

Brain activity involves concerted activity patterns between thousands of neurons across circuit layers and brain areas. At a fundamental level, these activity patterns are made up of individual, millisecond-duration action potentials in single neurons. This spiking activity combines across ensembles of neurons in time to drive downstream activity patterns in postsynaptic neurons and ensembles. At a population level, activity typically appears sparse in space and time, but may be governed by circuitry binding specific ensembles together to propagate, modulate and compute specific information and integration time constants that determine if and how two or more inputs to a neuron will be added to elicit an action potential in that neuron. To study the causal role of specific activity patterns on circuit dynamics and behavior, suitable systems capable of eliciting and emulating patterns of natural neural activity for a targeted volume, while recording activity from the population in awake behaving animals are of interest. Optogenetic methods of manipulating the activity of excitable cells, such as neurons, by altering the membrane potential of excitable cells expressing light-activated proteins that depolarize or hyperpolarize cells in response to light are of interest.

SUMMARY

Provided herein is a method for selectively stimulating a plurality of light-responsive neurons in a sample. Methods according to embodiments include irradiating a sample comprising a plurality of light-responsive neurons with a plurality of holographic images that are each configured to stimulate one or more light-responsive neurons in the sample, wherein the holographic images are created by light projection system that includes: a plurality of light sources; a plurality of optical adjustment components; a plurality of spatial light modulators; a controller; a processor; and a computer-readable medium comprising instructions that, when executed by the processor, cause the controller to: operate the light sources, optical adjustment components and spatial light modulators to generate and display a plurality of holographic images; direct each of the holographic images to a projection location; and project the holographic images onto the sample at a rate greater than 1 kHz.

In some embodiments, the light source is a fixed wavelength light source. Each light source independently has a wavelength of from 200 nm to 1800 nm, such as from 400 nm to 1600 nm, such as from 600 nm to 1400 nm, such as from 1000 nm to 1200 nm (e.g., 1035 nm, 1060 nm, 1080 nm). In some embodiments, the fixed wavelength light source has a wavelength that ranges from 200 nm to 800 nm, for example 480 nm, 532 nm or 800 nm. In other embodiments, the fixed wavelength light source has a wavelength that ranges from 800 nm to 1200 nm, for example 1035 nm, 1060 nm or 1080 nm. In yet other embodiments, the fixed wavelength light source has a wavelength that ranges from 1200 nm to 1800 nm, for example 1700 nm. In embodiments, methods may include projecting a plurality of holographic images onto a sample with a light projection system having 2 or more light sources, such as from 4 to 8 light sources. In some embodiments, the plurality of light sources includes one or more lasers. In certain instances, each of the plurality of light sources is a laser. The lasers may be pulsed lasers. For example, one or more of the light sources may be a pulsed laser having a pulse width of from 100 µs to 1000 µs, such as from 250 µs to 500 µs, for instance 375 µs. In some embodiments, one or more lasers are ultra-short pulsed lasers, such as lasers which have femtosecond pulses ranging from 25 fs to 500 fs, such as from 50 fs to 450 fs, such as from 75 fs to 400 fs and including from 100 fs to 250 fs. The frequency of laser pulse may vary for each laser, ranging from 0.01 MHz to 100 MHz, such as from 0.05 MHz to 95 MHz, such as from 0.1 MHz to 90 MHz, such as from 0.25 MHz to 80 MHz, such as from 0.5 MHz to 75 MHz and including from 1 MHz to 50 MHz. In embodiments, methods include reducing or altogether eliminating interference resulting from overlap of laser pulses. In some embodiments, each laser in the light projection system is configured to pulse out of phase with each other. In some instances, the lasers are synchronized. In these instances, methods may also include configuring the lasers to include temporal delay between pulses from each laser, such as a delay of 5 µs or more, such as 25 µs or more.

Light projection systems according to methods of the present disclosure include a plurality of optical adjustment components. In some embodiments, light projection systems include a plurality of optical adjustment components for adjusting one or more parameters of the light from the plurality of light sources before propagating the light through the spatial light modulation components. In some instances, systems include a beam splitter, such as a beam splitter which splits the beam of each of the plurality of light sources (e.g., lasers). In some embodiments, systems include a beam polarizer configured to rotate the polarization of light from the laser. In certain embodiments, light projection systems include a polarizing beam splitter. Optical adjustment components for projecting a holographic image on the sample may also include a light modulation component. In some instances, the light modulation component is an electro-optic light modulator, such as a Pockels cell. In other instances, the light modulation component is an acousto-optic modulator.

Light projection systems also include a plurality of spatial light modulators for generating a plurality of holographic images for projecting onto the sample. For example, systems may include 2 to 24 spatial light modulators, such as 4 to 16 spatial light modulators, for instance 8 spatial light modulators. The spatial light modulators may be configured to project any sized shape such as a spot, a polygon, an assymetric shape or a desired image, such as a hologram of a neuron (e.g., cell body and/or with neural process such as dendrites/spines/axons). The spatial light modulators of interest may have a refresh rate that varies, such as 50 Hz or more, such as 150 Hz or more, such as 200 Hz or more and including 300 Hz or more, for example a refresh rate of about 333 Hz or about 500 Hz.

In some embodiments, light projection systems of interest include one or more optical adjustment components for combining the beams of light from the spatial light modulators, such as beam splitters, beam combiners, polarizers, dichroics, lenses and mirrors. In some embodiments, the light projection system further includes a galvanometer mirror for moving or scanning the projected holographic image from the spatial light modulators. In certain embodiments, the holographic images from the spatial light modulators are propagated to a resonant scanner two photon microscope.

In embodiments, the subject light projection system is configured to project the holographic image onto the sample for an excitation duration of 10 μs or more, such as from 10 μs to 10000 μs. In certain embodiments, methods include projecting the holographic image onto the sample for an excitation duration of about 210 μs, 375 μs or about 600 μs. In some instances, the plurality of holographic images are sequentially projected onto the sample. In these instances, the transition time between each projected holographic image is 3 ms or less, such as 2 ms or less, such as 1 ms or less, such as 0.5 ms or less and including 0.1 ms or less.

Methods according to embodiments provided herein include irradiating a sample having a plurality of light-responsive neurons. The sample may include one or more functionally-defined collections of a plurality of neurons. The neurons may have a neural activity-dependent fluorescent moiety. In some instances, the neural activity-dependent fluorescent moiety is a light-activated polypeptide. The light-activated polypeptide may be a depolarizing or hyperpolarizing light-activated polypeptide. The light-activated polypeptide may be an ion channel or an ion pump. In certain embodiments, the light-activated polypeptide is selected from the group consisting of ChR2, iC1C2, C1C2, GtACR2, NpHR, eNpHR3.0, C1V1, VChR1, VChR2, SwiChR, Arch, ArchT, KR2, ReaChR, ChiEF, Chronos, ChRGR, CsChrimson, bReaCh-ES, and variants thereof. In certain embodiments, the neural activity-dependent fluorescent moiety includes a genetically-encoded indicator dye. Methods according to certain embodiments, include irradiating an in vivo tissue, such as an in vivo tissue in a freely moving animal.

Also provided is a light projection system for practicing the subject methods, where the system includes a plurality of light sources; a plurality of optical adjustment components; a plurality of spatial light modulators; a controller; a processor; and a computer-readable medium comprising instructions that, when executed by the processor, cause the controller to: operate the light sources, optical adjustment components and spatial light modulators to generate and display a plurality of holographic images; direct each of the holographic images to a projection location; and project the holographic images onto the sample at a rate greater than 1 kHz. In embodiments, the light source may be an light emitting diode (LED) or a laser. Detectors of the subject systems suitable for practicing methods described herein may include a charge-coupled device (CCD), a complementary metal oxide semiconductor (CMOS) device, a photomultiplier tube (PMT) or a combination thereof.

DESCRIPTION OF THE FIGURES

The invention may be best understood from the following detailed description when read in conjunction with the accompanying drawings. Included in the drawings are the following figures:

FIGS. 2A, 2B: MacroSLM, a high resolution, high-speed spatial light modulator (SLM) optimized for addressing large populations of neurons in vivo. FIG. 2C: Multiple spatially overlapping photostimulation paths modulated by 2 MacroSLMs are added to a resonant scanner multi-photon microscope. Inset in upper right shows a 3D printed 2×MultiSLM module, including orthogonal beam paths for illuminating each SLM using a custom prism, shortening path length, as well as polarization-based beam combination with a PBS (PC=Pockels cell, BE=beam expander, HWP=half wave plate, RL=custom relay lens, BB=zero order beam block, RGS=resonant galvanometer system, PGS=photostimulation galvanometer system, SL=scan lens, TL=tube lens, FLTR_EM=emission filter, PMT=photomultiplier tube, piezo=piezoelectric motor, OBJ=objective). FIG. 2D Theoretical modeling of implementation high-resolution MacroSLM combined with custom optical stimulation path to increase addressable area by at least 12×/26× relative to typical all-optical 512×512 SLM implementation, depending on the objective used (spatial modes #1 and 2, respectively, compared to prior 200×200 um FOV) while maintaining the necessary excitation numerical aperture for cellular stimulation. FIG. 2E: The rate at which an SLM photostimulation system can address new ensembles of neurons depends on the sum of rise time, r, (or fall, f, generally faster than r) of hologram generation by the liquid crystal display and the duration of excitation once the hologram has formed (d), in addition to any inherent jitter in latency (L) from a trigger. The present design minimizes all of these parameters of the SLM system, and combines multiple SLMs to increase the overall ensemble refresh rate. For example, interleaving two SLMs in time halves the period of a single SLM system. For kilohertz ensemble stimulation rate implementation, the period of each ensemble stimulation, $P_{MultiSLM}$, is 1 ms, where the hologram generation period for a single SLM, $P_{SLM}$, is 1.79 ms, the duration of stimulation, d, is 0.21 ms, and the number of SLMs in the MultiSLM system, $N_{SLMs}$, is 2. FIG. 2F: Volumetric imaging is acquired by piezo-induced motion of the microscope objective, serially sampling the volume in time. Independently in space and time, three-dimensional photostimulation patterns simultaneously excite dozens of neurons expressing red-shifted ChRmine opsin (<1 ms stimulation of all cells) within the total acquisition volume, independent of the piezo position (the piezo motion is anticipated and compensated by the SLM hologram software).

FIG. 3A: In contrast to previously published 10-20 ms photo-stimulation durations, here unique ensembles of dozens of neurons can be optically stimulated within 0.21 ms at up to 1 kHz temporal resolution to more closely mimic natural activity timescales. FIG. 3B: Kilohertz ensemble sequences written into a volume of layer 2/3 neurons with MultiSLM, while reading out activity with sequential, piezo volumetric scanning. FIGS. 3C, 3D: The increased temporal resolution allows targeting a greater number of cells on timescales relevant to rate coding by rapidly stimulating subgroups of neurons (6 groups of 25 simultaneously stimulated neurons, with each group stimulated 1 ms apart; each subgroup stimulated at 30 Hz overall for 3 seconds), with all cells stimulated within 5.2 ms. FIG. 3E: Temporal precision is further improved by time-lagged, burst-mode photostimulation (BM), where, after the completion of the first group, the second group/ensemble of cells is stimulated with a variable time lag down to nearly instantaneous succession (e.g., both subgroups stimulated in <0.5 ms). FIGS. 3F: 3G: Multiplexed, high speed photostimulation of hundreds of neurons while reading out from hundreds of neurons in a 1 mm2 field of view with sequences at 500 Hz. GCaMP6m and ChRmine are both encoded in a single viral construct, and target opsin expression to the cell body using the Kv2.1 motif. 12 groups of up to 25 neurons each were rapidly stimulated all within 24 ms (0.6 ms simultaneous stimulation of each subgroup, separated in time by 2 ms; each neuron subgroup stimulated at 29 Hz for 3 seconds). FIG. 3H: Pair-wise distance measurements between all pairs of stimulated neurons (within the larger stimulated ensembles) demonstrate photostimulation is successful for almost every pair of neurons separated by distances up to 1.3 mm. FIGS. 3I and 3J: 3-D depiction of photostimulation of neurons implementing 1 kHz stimulation over 1 mm$^2$ field of view. FIG. 3I depicts baseline where red dots indicate locations of stimulation. FIG. 3J depicts white flashes in locations where activity of the neurons in response to stimulation is detected. The first row depicts stimulation of 50 neurons with a 0.21 ms single shot; the second row depicts stimulation of 100 neurons (10 groups of 10 neurons in a 10 ms kHz sequence); the third row depicts stimulation of 200 neurons (10 groups of 20 neurons in a 10 ms kHz sequence) and the fourth row depicts stimulation of 400 neurons (10 groups of 40 neurons in a 10 ms kHz sequence).

FIG. 4A: Virally-induced reporter/affector expression is uniform across the field-of-view and across LII/III and LV in V1. Notably, expression by this vector largely excludes cell body expression in LIV, however, dendrites and axons of neurons labeled elsewhere course through LIV; we used this as an opportunity to test the resolution of the excitation system, and to provide the basis for a control for an experiment to explore inter-laminar circuit recruitment between LII/III and LV. FIG. 4B: Neurons across layers LII/III to LV are simultaneously photostimulated with a 600 μs write-in spatial pattern of the desired targets at 30 Hz, while activity is measured across layers. FIGS. 4C, 4D: Imaging the full volume while stimulating either LII/III or LV reveals high success rate of stimulation, as confirmed by robust, time-locked GCaMP6m responses (top panels), and causes follow-on activity patterns in the held out layer beyond any activity observed in the LIV and no stim controls. FIG. 4E: The activity of these cell populations can be categorized using tSNE, further visualizing the similarity of the controls. Each point represents activity on a single trial, and color coding for randomly interleaved stimulation conditions are assigned after the tSNE analysis is completed. FIG. 4F: The transverse excitation resolution of the photostimulation is confirmed to match that of a typical cell width.

FIG. 6A: A 90° optical path for illuminating and reflecting off an SLM is achieved with a 50/50 beamsplitter. While this arrangement is convenient, results in 0° angle of incidence (AOI) on the SLM face (optimal) and allows the next optical element to be placed very close to the SLM, it results in only ≤25% of the original optical power at the output of the beamsplitter, and backreflections are a concern (25% of the light will propagate backwards along the illumination path). FIG. 6B: A SLM illumination strategy that conserves optical power using a shallow (typically ~10° AOI), nonzero AOI on the SLM to illuminate it as close to 0° AOI as possible while also allowing room for optical elements in the path. In holographic systems, the first optical element after the SLM is typically the first lens in a 4f relay. Given the beam width (expanded to fill the SLM), the distance from the SLM face to the first optical element is generally several hundred centimeters. FIG. 6C: Refracting prism-based illumination strategy employed here to greatly reduce the footprint needed to illuminate the SLM, as well as permitting an optical element to be placed in the path very close to the SLM face. The angle of incidence was 13° on the SLM (the SLM is tilted to achieve effectively a 90° turn of the optical path). This arrangement reduced the diameter of first lens in the 4f system sufficient to capture all diffracted rays from the SLM, as well as important for placing phase modulating elements as close to the SLM plane (fourier plane in the microscope). This design achieves effectively a 90° optical path configuration similar to (FIG. 6A), while maintaining all optical power.

FIG. 7A: A single 2× MultiSLM module. Two SLMs are illuminated with independent beams. Refractive prisms (FIG. 6C) create essentially 90° optical path layout for illuminating the SLM. Polarization is $P_{pol}$ is used to illuminate each SLM, so a half waveplate (HWP) is used to rotate the polarization of one beam after the SLM so that both beams can be combined with a polarization beamsplitter (PBS). FIG. 7B: The MultiSLM module is integrated with another custom 3D printed breadboard which holds the 4f lens relay system and folds the beam path using folding mirrors, reducing the overall footprint and more readily integrating with a multiphoton microscope, which contains a galvanometer system for photostimulation. FIG. 7C: 4×MultiSLM system. Similar to (FIG. 7A) but adds prisms to each of 4 SLM paths to add constant tilt the beam. These tilting prisms are removable via quick-release magnetic mounts. Each 2×MultiSLM module is illuminated with a different laser wavelength (1060 nm or 1080 nm), and both modules (and thus all 4 SLM paths) are combined onto a single beam path with a dichroic. FIG. 7D: Conceptually the same as FIG. 7B, but demonstrating configuration for combining 4 SLMs into the microscope.

FIG. 8A: Modular design for multiplexing two SLMs. This design was used to enable temporal multiplexing of two SLMs in time to achieve better than kilohertz hologram refresh rate. In this implementation, the laser contains an acousto-optic modulator (AOM) to rapidly modulate power (200 kHz). The electro-optic modulator (EOM; Pockels cell) rapidly switches polarization (200 kHz, between S polarization, Spol, and P polarization, Ppol). A polarization beamsplitter (PBS) determines the subsequent optical path based on polarization of the beam, and therefore either SLM1 or SLM2, for hologram generation. Half waveplates (HWP) rotate polarization before and after SLM1 to optimize illumination of the SLM (Ppol is optimal for MacroSLM; alternatively, the SLM could be rotated 90° to achieve the same effect). A polarization beamsplitter (PBS) combines both SLM-modulated paths together onto a single beam path. In this configuration, only one SLM path is illuminated at any time. FIG. 8B: Multiplexing four SLMs using polarization, similar to FIG. 8A, and wavelength. Power is modulated on each independent SLM path (POW; either a Pockels cell with PBS, or AOM in our setup). A prism after each SLM is used to add constant tilt to the beam, effectively increasing the maximum deflection angle of the modulated path. Adding this tilt at 90° rotations for each SLM path allow each quadrant of a larger FOV to be addressed. A PBS combines both polarizations of each single wavelength, and a dichroic mirror combines both wavelengths. All four SLM paths can be illuminated and combined fully simultaneously. In our setup, both lasers lines are synchronized to one another (and we have two 40 W laser amplifiers available at each wavelength, fully synchronized, such that all four SLMs can receive a full 40 W beam), and given inherently different path lengths for each SLM modulated beam, the combined beams from all beams do not interfere with one another given their low duty cycle on the femtosecond scale. Orthogonal polarizations should also effectively eliminate any interference, and wavelength differences should also significantly reduce possible interference. Removing the prism from the beam paths (using a magnetic mount in our setup) re-centers each SLM on the same FOV, allowing full 4× multiplex of the same addressable volume in time. FIG. 8C: Multiplexing strategy using polarization switching to combine many SLM-modulated beams onto a single path. Similar to FIG. 8A, an EOM and PBS select different beam paths. This same strategy continues to split the beam onto different, orthogonal paths, for a total of 8 paths shown (more paths are possible with additional beam splitting and combining using polarization switching). Following each SLM, optional modulators (e.g., prism as in FIG. 8B to tile a larger FOV, a lens to defocus each SLM path to "tile" the axial dimension, or more generally, a static or dynamic phasemask (i.e., SLM) to apply any modulation), allow tiling of a larger volume. Polarization switches, operate in sync with corresponding EOMs to recombine the split beams onto a single path. In this configuration, two SLM paths of orthogonal polarizations can be illuminated and combined simultaneously, otherwise, all paths are interleaved in time following precise timing and synchronization of polarization control in the setup. Power is shown to be modulated at the laser source (POW) for fully temporally multiplexed implementation. Power can be modulated on each independent SLM beam path for simultaneous illumination applications. The dwell time for hologram illumination (determined in our experiments by the duration of the spiral activation stimulus) determines half the number of SLMs that can be combined in time such that stimulation occurs at 100% duty cycle, and all optical paths are used and required. While large aperture polarization switches can be modulated fast (kilohertz scale), they may also limit the total number of beam paths that can be interleaved in time. Should a large number of SLM-modulated paths be desired, an additional telescoping relay shrinking the beam to accommodate small aperture, fast (hundreds of kHz) polarization switches could be used.

FIG. 9A: 4 SLMs (512×512 resolution, see Methods) each address a quadrant of the overall imaged FOV. In this case, using a 25×1.05NA objective, we imaged and addressed a 450 μm FOV at high efficiency. Tilting prisms in the optical path, near each SLM face add a constant 1° tilt to each beam. Each tilting prism is rotated 90° for each SLM such that 4 SLMs tile the full, square FOV, with each addressing a different quadrant. This configuration substantially improves two photon efficiency of diffracted spots across the field of view. FIG. 9B: single SLM efficiency; FIG. 9C: 4× MultiSLM efficiency, scale bars 50 μm). Values for two photon efficiency (contours) take into account diffraction efficiency (at 0.5NA, theoretical) and the quadratic dependence of the two photon effect. With larger angle tilting prisms, this configuration could theoretically achieve 4× the addressable field of view of a single SLM. FIG. 9D: A random subset of 50 neurons expressing C1V1T/T and GCaMP6m are targeted for stimulation in a 450×450×100 μm volume of layer 2/3 cortical cells (green, targeted cell showing statistically significant GCaMP response, $p<0.001$, blue, targeted cell not showing a response, white, other cells). FIG. 9E: The majority of targeted cells show a robust, statistically significant response. Successful targets are found throughout the volume, regardless of position.

FIG. 10A: Schematics of multi-step opsin-like genome mining. In silico screening was performed on data from the Marine Microbial Eukaryote Transcriptome Sequencing Project. Subsequent phylogenetic analysis was performed to search for functionally novel opsin genes. To discover ChRs with predicted high cation conductance following the validated pore surface electrostatic model, we focused on sequences with more negatively charged amino acids in transmembrane domains 1-3 and 7 along with the requisite lysine in TM7 as shown (red), defining putative ion-conducting pathways. Then, candidate opsin genes were transfected into primary cultured hippocampal neurons for in vitro electrophysiology, for testing both light sensitivity (1 s light at 390 nm, 485 nm, 513 nm, 585 nm and 650 nm; 0.7 mW/mm$^2$) and reversal potential (photocurrents measured with holding membrane potentials steps from −70 mV, every 10 mV stepwise to +60 mV). FIG. 10B: Circular phylogenetic tree of multiple type-I opsin genes including ChRmine (left, arrow) and rectangular phylogenetic tree categorizing the opsins into different subfamilies (scale bar: fractional change in amino acid sequence. Phylogenetically ChRmine is situated uniquely, distinct from canonical cation-conducting ChRs, and closer to ion pumps and anion channels. FIG. 10C: Left—representative voltage-clamp traces of red-shifted ChRs in cultured neurons responding to 1 s orange light (585 nm, 0.7 mW/mm$^2$) or red light (650 nm, 0.7 mW/mm$^2$). Right: action spectra in cultured neurons using peak currents after 1 s stim (0.7 mW/mm$^2$) (mean±s.e.m. n=5-7 cells. $p<0.01$, *$p<0.001$, one-way ANOVA with Tukey correction). FIG. 10D: ChR I-V curves, −70 mV to +60 mV, in HEK cells. n=5-7 cells. FIG. 10E: Probability of evoking spikes for different light pulse widths delivered at 5 Hz for 2 s and 0.7 mW/mm$^2$. (mean±s.e.m. n=5-7 cells. **$p<0.0001$, one-way ANOVA, Tukey correction). FIG. 10F: Probability of evoking spikes at different intensities light at 5 Hz for 2 s, pulse width 5 ms (mean±s.e.m. n=5-7 cells. $p<0.01$, *$p<0.001$, one-way ANOVA, Tukey correction). FIG. 10G: Top: current-clamp traces; ChRmine reliably induced spikes with orange light (585 nm, 5 ms pulse width, 5 Hz pulses at 100 μW/mm$^2$) but less so with blue light (470 nm, 5 ms pulse width, 5 Hz pulses at 100 μW/mm$^2$). Bottom: summary of ChRmine spike fidelity in response to orange or blue light (mean±s.e.m. n=5 cells) FIG. 10H: Representative Ca$^{2+}$ imaging traces: 585-nm stimulation in cells expressing GCaMP6m and: ChRmine (left), CsChrimson (middle), or bReaChES (right) at pH$_{ext}$ 7.4. Responses to light pulses (orange) at indicated power and duration shown with blue intensity scale. Data collection across opsins was randomized and counterbalanced to minimize cross-group differences in expression. FIG. 10I: Trial-averaged Ca$^{2+}$ peak-amplitude response to ChRmine (red), CsChrimson (orange) or bReaChES (green) stimulation with pulses of 2, 5, 25, 100, 400, or 800 ms (585 nm light as in FIG. 10H. FIG. 10J: Trial-averaged kinetics of ChRmine (red), CsChrimson (orange) and bReaChES (green). Data in FIG. 10I and FIG. 10J are mean±s.e.m., n=5-7 cells, p<0.01, ***p<0.001; one-way ANOVA, Tukey correction). FIG. 10K: Two-photon power spectrum of ChRmine across 7 different powers at λ=1035 nm (0, 5, 10, 15, 20, 25, 30 mW). FIG. 10L: Two-photon wavelength action spectrum of ChRmine: 6 different wavelengths, taken from voltage clamp recordings in neurons at holding voltage of −70 mV (n=6 cells, 20 mW, 12 rotations per spiral, 25 um diameter spirals, 4 ms duration, 80 MHz laser repetition rate; same setup as FIG. 10K. FIG. 10M: Spike fidelity across stimulation frequencies (left) alongside voltage clamp traces during different imaging exposure (right) (λ=920 nm, 2.8 Hz frame-rate). Note reliable 2P spiking fidelity at 5-30 Hz (left). With imaging power up to 60 mW, depolarization was minimal (right; <10 mV). FIG. 10N: Summary of experiments in FIG. 10M (mean±s.e.m., n=6 for stimulation experiment and n=5 for imaging experiment). No spiking was observed under any imaging condition, whereas reliable (>60%) spiking fidelity was observed at stimulation frequencies up to 20-30 Hz. FIG. 10O: Low jitter in 2P-elicited spikes: overlaid traces, 10 consecutive ChRmine spikes in train, aligned to 2P pulse timing (1035 nm, 20 mW, 12 rotations, 4 ms exposure).

FIG. 11A: Hardware schematic detailing multi-photon 3D imaging and optogenetic stimulation light paths utilizing a pair of custom, large field-of-view spatial light modulators (MacroSLMs), an optogenetic galvanometer set for spiral scanning, and a piezo-coupled microscope objective for 3D image scanning. Custom SLM dimensions (inset). FIG. 11B: Typical viral expression of GCaMP6m and ChRmine from the bicistronic virus at two magnifications (green: anti-GFP; magenta: anti-HA, as HA is conjugated to ChRmine-TS-Kv2.1). ChRmine was found to be co-expressed with GCaMP6m in all cell bodies counted (n=610/610 soma across nine 40 μm V1 sections from n=3 mice; ChRmine expression was restricted to the membrane and GCaMP6m was cytosolic, as expected). Dense somatic expression is observed in layers 2/3 and 5, with minimal expression in layers 4 or 6. Unlike GCaMP6m, ChRmine is absent in axons in the white matter (w.m.) and markedly reduced in dendrites extending through layer 1, likely due to trafficking properties of the Kv2.1 soma-targeting motif. FIG. 11C: Simultaneous imaging and photoexcitation across a 1 mm$^2$ field-of-view, showing that successful optogenetic excitation does not depend on neuronal position (90 stimulations at 29 Hz, 20-30 mW per target, aggregation of 160 total targets across 6 groups of neurons, 10 MHz laser repetition rate, λ=1035 nm, spiral diameter=10 μm, 5 spiral revolutions). FIG. 11D: Photostimulation shown of 2 representative cells (identified as C1 and C2), separated by 1.164 mm. FIG. 11E: Temporal interleaving paradigm of the MultiSLM increases the temporal resolution at which N cell ensembles (denoted e$_N$) can be addressed (1 kHz address rate shown here at N=6). FIG. 11F: Six nonoverlapping ensembles of ~27 neurons each were optogenetically excited every 1 ms, in a 1 kHz sequence (in total, 124/160 cells were successfully targeted at this speed in 5.2 ms, p<0.025 positive modulation versus baseline and post-stimulation epochs). Each of the six ensembles showed similar neuron-activation success rates, simultaneously exciting up to 23 neurons per 210 μs exposure. FIG. 11G: Targeting precision is demonstrated; a single neuron (target iv) can be optogenetically driven in isolation (middle column), within a region of nearby, known-responsive cells as targeted on other trials (right column); drawn ROI outlines are slightly enlarged relative to analysis to prevent obscuring cell morphology in the visualization. FIG. 11H: 3D imaging with simultaneous optogenetic control across cortical layers; drawn ROI labels are enlarged for visualization. FIG. 11I: Simultaneous excitation of 27/30 total targets located across cortical layers 2/3 and 5 in V1 (90 exposures at 30 Hz, 10-20 mW per target, 30 total targets, single 0.63 ms exposure using a 15 μm diameter spiral with 8 revolutions, 10 MHz laser repetition rate). FIG. 11F and FIG. 11I are on common z-score scale.

FIG. 12A: Schematic of experimental arrangement. FIG. 12B: Top, illustration of different experimental conditions. On a given trial, naïve mice were presented with one of two orthogonal visual stimuli at a specified contrast (contrasts were 2%, 12%, 25% and 50%, as for trained cohorts in FIGS. 13A-13N. Bottom, mean, normalized Ca$^{2+}$ responses (GCaMP6m) for highly selective neurons (OSI>0.5) to 50% contrast; gray boxes indicate stimulus). FIG. 12C: These tuned/selective ensembles were found intermingled across L2/3 and L5 (green, 0° cells, red, 90° cells). Two separate random ensembles were selected, matching the number of neurons in the tuned ensembles (magenta, ensemble designated as "0°", cyan, ensemble designated as "90°"). FIG. 12D: Following the visual tuning characterization experiment in FIG. 12B, conditions were added to the protocol to include selective or random ensemble optogenetic stimulation without a visual stimulus present (0% contrast). Ensemble stimulation trials were randomly interleaved alongside visual stimulus trials without optogenetic stimulation (visualizations not to scale). FIG. 12E: Mean normalized Ca$^{2+}$ responses for all neurons within each selective or random ensemble during optogenetic stimulation trials (red or gray horizontal bars indicates stimulation time). FIG. 12F: Locations of tuned neurons stimulated and recruited for one experimental session overlaid on average images from each imaging plane through the volume (negative image; black dots, directly-stimulated ensembles; green, secondarily recruited iso-tuned neurons; magenta, secondarily recruited orthogonally-tuned neurons; scale bars are 100 μm; see FIG. 25A for co-activity quantification, co-active neurons are found by two-tailed Wilcoxon signed-rank tests, p<0.05, sample window vs. baseline, Materials and Methods). FIG. 12G: Schematic illustrating classifier and neural trajectory analysis. Classifiers and principal components (for neural trajectory visualization) were trained on fluorescence data taken from neurons that were never optogenetically stimulated. FIG. 12H: Neural trajectories were computed individually for each experimental condition on each experimental day using Principal Components Analysis (PCA). Light blue trajectories show target conditions, light red trajectories show distractor conditions, black dots show trial start, and red and blue dots denote the 1$^{st}$ frame following visual or optogenetic stimulus onset. FIG. 12I: Top row: Mean 0° and 90° visual or optogenetic stimulation fluorescence responses (and their difference) in held out, unstimulated neurons, for one mouse. Mean time series traces taken from all neurons with large classifier weights: (abs (weight)>99$^{th}$ percentile). FIG. 12J: Top row: Mean fluorescence response of all neurons included in the classifier analysis during 0° (positive lines) and 90° (negative lines) conditions multiplied by their classifier weights. Error bars, standard errors across neurons. Bottom row: weighted mean fluorescence responses shown for four mice. The activity from each mouse was normalized to its peak visual response to the 0° stimulus (this amplitude is indicated by the Y-axis scale bar). X-axis scale bar represents five volumes of activity (1.82 seconds). Vertical bars represent timepoints used for training the classifier. FIG. 12K: Percent correct prediction performance of logistic classifiers trained on held-out neuronal responses indicated in panel FIG. 12G during visual stimulation (corresponding to the "sample window" time period in FIGS. 13A-13N). Probabilities were computed using a Wilcoxon signed-rank test to determine if a condition type is decoded with higher efficacy than the one to its right in the plot. p<0.01, **p<0.0001.

FIG. 13A: Mouse behavioral arena under the MultiSLM for simultaneous imaging and ensemble optogenetics. FIG. 13B: Mice learn to discriminate orthogonal drifting gratings (Targets/Go: Vertical bars, Distractors/No Go: Horizontal bars) of varying contrast (trial timings shown; Materials and Methods). FIG. 13C: Visual discrimination performance of representative mouse (statistical significance is seen with ≥12% contrast, p<0.05 Fisher's exact test, Target vs. Distractor conditions for each session). FIG. 13D: Upon stable performance, GCaMP6m signals in visual cortex are imaged across cortical layers with the MultiSLM during task performance. Neurons (n=40.7±8.7 [mean±SD], across n=5 mice) with reliable and selective responses to one 50% contrast orientation (OSI>0.5; Materials and Methods) are used to constitute Target and Distractor Ensembles for all subsequent ensemble optogenetic experiments. Mice perform a variant of the visual discrimination task in which, on randomly interleaved trials, selective tuned (green, Target (0°), or red, Distractor (90°), dots in schematic) or random ensembles (magenta, Target ("0°"), or cyan, Distractor ("90°"), dots in schematic) are stimulated with or without corresponding visual stimuli. Reward and punishment contingencies are similarly applied for visual and/or optogenetic conditions. FIG. 13E: Top: normalized mean visual responses (50% contrast) for Target (0°) and Distractor (90°) selective ensembles. Bottom: ensemble optogenetic stimulation responses of the same populations of tuned and of n-matched random ensembles. FIG. 13F: The lowest-contrast stimulus is alternated from 0% contrast (no visual stimulus) to 2%, 3%, 4%, and 5% (typically in that order, with one low contrast tested in each behavioral session; 12%, 25% and 50% contrast trials are randomly interleaved). Discrimination behavior is significantly enhanced during tuned ensemble stimulation (p<0.05, two-way ANOVA, main effect of stimulation type, n=4 mice; tuned optogenetic ensemble=red, visual stimulus only=black, and random optogenetic ensemble=blue; logit function fits: 50% correct was subtracted from all mean values, values were divided by maximum performance ($P_{max}$), and values<0 were set to 0 for each fit; fits were re-scaled for plotting by multiplying each fit by ($P_{max}$−0.5) and adding 50%). A 5th mouse demonstrated significant discrimination on the first presentation of tuned ensemble stimulation in the absence of visual stimulation and thus immediately advanced to subsequent experiments. FIG. 13G: Following these contrast-ramp experiments, mice demonstrated consistently high behavioral discrimination performance without a visual stimulus in response to stimulation of the tuned ensemble that had been paired with visual stimulus during training (left: p<0.01, n=5, paired t-test before vs. after ramp, 0% contrast), but the response to stimulation of the random ensemble that had been similarly paired with visual stimulus during training was variable and not significant across animals (right: p=0.097). Paired lines in FIGS. 13G-13I and dots in FIGS. 13J-13N are color-coded to reflect mouse identity, as indicated by legend. FIG. 13H: Left, performance was high for tuned ensemble stimulation, compared with the condition of no visual or optogenetic stimulus present (p<0.01, n=5 paired t-test vs. no visual/optogenetic stimulation, two tailed). Intriguingly, a subset of mice appeared to improve performance with random ensemble stimulation vs. no stimulation (middle; overall p=0.07, n=5 paired t-test, two tailed), but mice performed better with tuned ensemble stimulation than random ensemble stimulation (right; p<0.05, paired t-test, two tailed; data points replotted across the three panels). FIG. 13I: Mice immediately discriminated entirely new tuned ensembles that had never been stimulated during training (Δz=30 μm shift to identify a new set of neurons within the same visual field) with high performance compared to no stimulation trials (left, p<0.05, two-tailed paired t-test, n=3) or compared to n-matched random ensembles (right, p<0.01, two-tailed paired t-test, n=3 mice), but mice showed no difference in performance for random ensemble stimulation vs. no stimulation (middle, p>0.1, two-tailed paired t-test, n=3; data points replotted across the three panels as in (H)). FIG. 13J Modest preferential recruitment of iso-tuned neurons versus orthogonally-tuned neurons during tuned ensemble stimulation (without a visual stimulus), before the visual-stimulus contrast ramp experiments. These mice were trained on the visual-only task (p<0.05 iso vs. orthogonally tuned, $\chi^2$ two tailed test, n=6 sessions in 5 mice; co-active neurons are found by two-tailed Wilcoxon signed-rank tests, sample window vs. baseline, p<0.05, Materials and Methods). FIG. 13K: This effect is absent for stimulation of random ensembles initially (p>0.1, $\chi^2$ two tailed test, n=6 sessions in 5 mice). FIG. 13L: Selective recruitment of iso-tuned neurons with tuned ensemble stimulation after contrast ramp pairing (p<0.0001, iso- vs orthogonally-tuned, $\chi^2$ two tailed test, n=15 sessions in 5 mice). FIG. 13M: After the contrast ramp visual-stimulus and random-ensemble pairing, selective recruitment of iso-tuned neurons emerges for random ensemble stimulation (p<0.0001, $\chi^2$ two tailed test, n=13 sessions in 5 mice; same sessions as used for tuned ensemble stimulation in FIG. 13N—with the effect most apparent in mice that learned to discriminate the two ensembles as shown in (FIG. 13H, middle), (color coding for mouse identity preserved across all panels). FIG. 13N: Tuned ensemble stimulation remains more potent than random ensemble stimulation at recruiting iso-tuned cells even after the contrast ramp pairing experiments (p<0.0001, $\chi^2$ two tailed test). The enhanced recruitment of iso-tuned populations after contrast ramp experiment for both tuned and random ensemble stimulation (p<0.0001, $\chi^2$ two tailed test) was consistent with observed improvements on task performance (FIG. 13G). Data were pooled across sessions and mice for each bar in the bar graphs of (FIGS. 13J-13N), and reported with Pearson's $\chi^2$ square test results; pooled data across sessions for each mouse are shown as colored dots (see Materials and Methods for stratified Cochran-Mantel-Haenszel (CMH) tests controlling for mouse identity). *p<0.05, p<0.01, **p<0.0001, †p<0.1, error bars mean+/−s.e.m. throughout figure.

FIG. 14A: All mice maintained high performance discrimination for tuned-ensemble stimulation over several weeks (behavioral session data from each mouse are shown as colored lines signifying mouse identity as in legend). Later sessions include fewer mice. FIG. 14B: Ensemble optogenetic stimulation discrimination performance (right) was indistinguishable from visual discrimination performance (12% visual contrast behavior shown, left, p>0.1 paired t-test, two tailed, n=112 sessions across 5 mice; error bars are standard deviation of the mean). FIG. 14C: Locations of tuned neurons stimulated and recruited for one experimental session overlaid on average images from each imaging plane through the volume (negative image; black dots, directly-stimulated ensembles; green, secondarily recruited iso-tuned neurons; magenta, secondarily recruited orthogonally-tuned neurons; scale bars are 100 µm). FIG. 14D: Non-stimulated iso-tuned neurons are preferentially recruited by ensemble stimulation in the absence of visual stimuli, compared to orthogonally-tuned neurons (p<0.0001, $\chi^2$ two tailed test; co-active neurons are found by two-tailed Wilcoxon signed-rank tests, sample window vs. baseline, p<0.01, Materials and Methods). Data are pooled across sessions and mice for bars and reported Pearson's $\chi^2$ test results (n=58 sessions in 5 mice). Pooled data across sessions for each mouse are shown as colored dots (see legend for mouse identity; same legend corresponds to rest of figure, and FIG. 13; see Materials and Methods for CMH tests controlling for mouse identity). FIG. 14E: Data from all experimental conditions of full ensemble stimulation in the absence of visual stimuli (n=232 data points from 58 sessions in 5 mice). As the number of neurons increases, more iso-tuned neurons are recruited (red, mean+/−s.e.m., Spearman's ρ=0.34, p<0.001, n=116). This effect reverses for recruited orthogonally-tuned neurons (blue, mean+/−s.e.m., Spearman's ρ=−0.24, p<0.01, n=116), with statistically-significant different correlation for recruited iso-tuned than recruited orthogonally-tuned neurons (p<0.0001, Fisher z transformation). FIG. 14F: Neural trajectories were computed individually for each experimental condition on each experimental day using PCA. Only fluorescence time points before reward onset were used. Light blue trajectories show target conditions, light red trajectories show distractor conditions, black dots show trial start, and red and blue dots denote the $1^{st}$ frame following visual or optogenetic stimulus onset. Dark blue or red trajectories denote conditions wherein the mouse performed at <50%, indicating erroneous licking behavior on average. FIG. 14G: Top row: Mean fluorescence time series for all neurons (in representative Mouse 4) with large classifier weights (abs(weight)>$95^{th}$ percentile) shown during target trials. Second row, distractor trials. Third row: first row (target trials)—second row (distractor trials). Bottom row: target—distractor fluorescence responses shown for 1 additional mouse. FIG. 14H: Top row: Mean fluorescence response of all neurons included in classifier analysis during target (positive lines) and distractor (negative lines) conditions multiplied by their classifier weights. Error bars: standard errors across all neurons. Bottom row: weighted mean fluorescence responses for five mice. Activity from each mouse was normalized to its peak visual response to the target stimulus (amplitude is indicated by the Y-axis scale bar). X-axis scale represents five volumes of activity (1.82 seconds). Vertical bars: timepoints for training the classifier. FIG. 14I: Behavioral performance vs. performance of logistic classifiers trained on unstimulated neuronal responses during visual stimuli. Points show different conditions from individual mice. Error bars: s.e.m. across sessions.

FIG. 15A: Recruitment probability for nontargeted cells with different tuning across layers, during stimulation of tuned ensembles in layer 2/3. Non-targeted iso-tuned neurons were preferentially recruited within layer 2/3 and layer 5 compared with ortho-tuned neurons (p<0.0001, $\chi^2$ two tailed test; co-active neurons are found by two-tailed Wilcoxon signed-rank tests, sample window vs. baseline, p<0.01, Materials and Methods; p<0.01, *p<0.001, ****p<0.0001 throughout the figure), and the proportion of recruited neurons was higher overall within layer 2/3 than within layer 5 during layer 2/3 stimulation across all experiments (p<0.0001, $\chi^2$ two tailed test). FIG. 15B: The proportion of recruited iso-tuned neurons in each layer increased with high correlation within both layer 2/3 and layer 5 (Spearman's ρ=0.46, p<0.001 for layer 2/3, Spearman's ρ=0.51, p<0.0001 for layer 5; n=46 experiments in 5 mice, p>0.1, Fisher z transformation comparing p values; fit with logit function that assumes the fraction of recruited neurons will saturate to 1). FIG. 15C same as in FIG. 15A but tuned ensembles in layer 5 instead of 2/3 were stimulated. Non-targeted iso-tuned neurons were preferentially recruited in layer 5 relative to ortho-tuned layer 5 neurons (p<0.0001, $\chi^2$ two tailed test), and relative to iso-tuned layer 2/3 neurons (p<0.0001, $\chi^2$ two tailed test), but selective recruitment of iso-tuned neurons was not observed to layer 2/3 (p>0.1, $\chi^2$ two tailed test). For FIG. 15A and FIG. 15C, data were pooled across sessions and mice for each colored bar and reported with Pearson's $\chi^2$ square test results; pooled data across sessions for each mouse are shown as colored dots (see legend, per FIGS. 4H, 5D; Materials and Methods: stratified CMH tests controlling for mouse identity). FIG. 15D As the number of neurons stimulated in the tuned layer 5 ensemble increased, a greater fraction of iso-tuned layer 5 (Spearman's ρ=0.62, p<0.01) neurons were recruited. However, this correlation was not statistically significant for recruited layer 2/3 neurons (Spearman's ρ=0.19, p=0.38 versus no correlation), and the correlation was stronger for layer 5 vs the weak layer 2/3 trend (p<0.05, Fisher z transformation, n=24 experiments in 4 mice). FIGS. 15E, 15G depicts logistic psychometric functions fit to predictions derived from logistic classifiers trained on either neural data FIG. 15E or behavioral data FIG. 15G. Psychometric curve fits were generated against data pooled across 5 mice (see FIG. 28 for individual mouse data). Each curve relates the average performance of mice in response to stimulation of specific numbers of identified neurons from tuned ensembles. Individual points represent averages across the one or more sessions wherein a particular experimental condition was run (error bars show s.e.m.). Fits were generated independently for experiments where only neurons within layer 2/3 (purple) or layer 5 (green) were stimulated. FIGS. 15F, 15H depicts data from FIG. 15E and FIG. 15G is re-plotted for only the ensemble sizes where comparable numbers of neurons were stimulated. Individual points correspond to experimental conditions taken from single days and single mice; mean±s.e.m. shown for each ensemble size bin (bin size across mice is 4 neurons). This subset of data was used to compute a two-way ANOVA to compare the effect of ensemble laminar position on classifier performance (FIG. 15F) or animal behavior (FIG. 15H). In each case, equivalent numbers of layer 5 neurons were more successful at driving performance (p<0.01 for classifier data, p=0.023 for behavioral data, main effect of layer; Target and Distractor ensembles differ in size by at most 1 neuron (FIG. 15E-15H)). FIG. 15I: In a model network of 1000 excitatory neurons and 1000 inhibitory neurons (Materials and Methods) stimulating a small number of excitatory neurons can lead to reliable ignition events, wherein the percent of the total excitatory neuron population that is secondarily recruited during stimulation exceeds 20% of the total population. Error bars reflect standard error in the estimate for the probability of ignition over 440 stimulation trials neurons (Materials and Methods). FIG. 15J: Example traces showing ignition events wherein stimulation of only 30 neurons triggers transient activation of a substantial fraction of the entire excitatory population, while also maintaining low background probability of spontaneous ignition given certain properties of the network neurons (Materials and Methods). FIG. 15K: Qualitatively, the excitatory subnetwork with low levels of constant inhibition behaves as a bistable system with two stable states corresponding to low and high fractions $f_e$ of active excitatory neurons (blue dots) separated by an unstable state of intermediate activation (red cross); these three fixed points correspond to $$\frac{df_e}{dt} = 0$$

Figure 15:
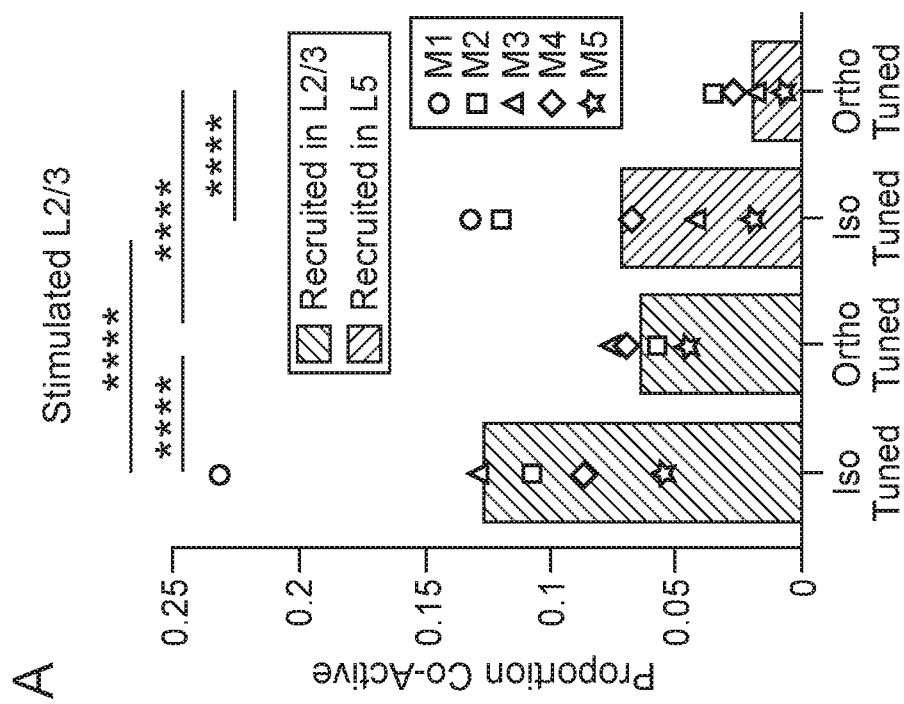
FIG. 15, A-K depicts circuit architecture underlying layer-specific perceptual thresholds.
Figure 15:
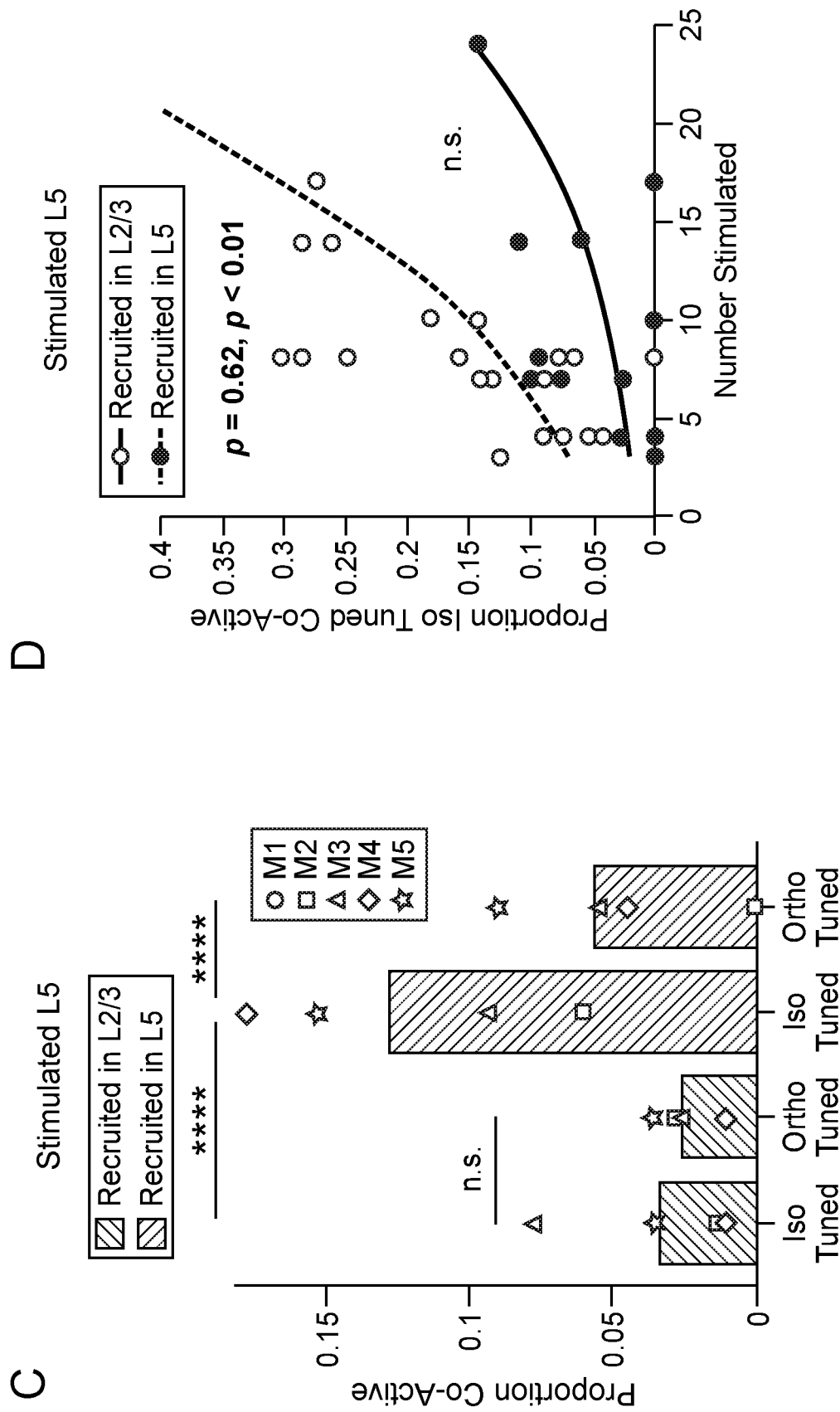
Figure 15:
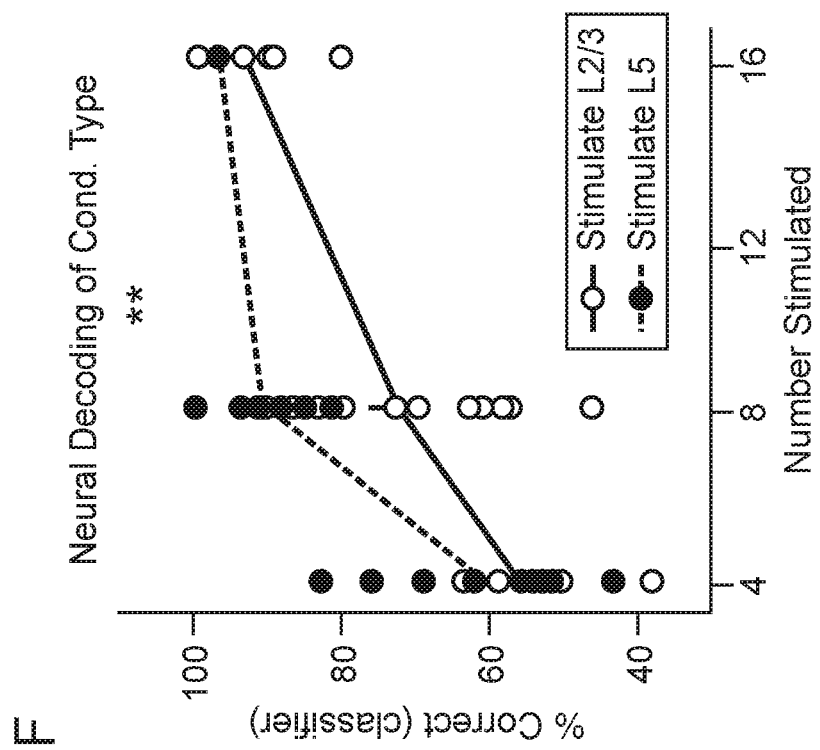
Figure 15:
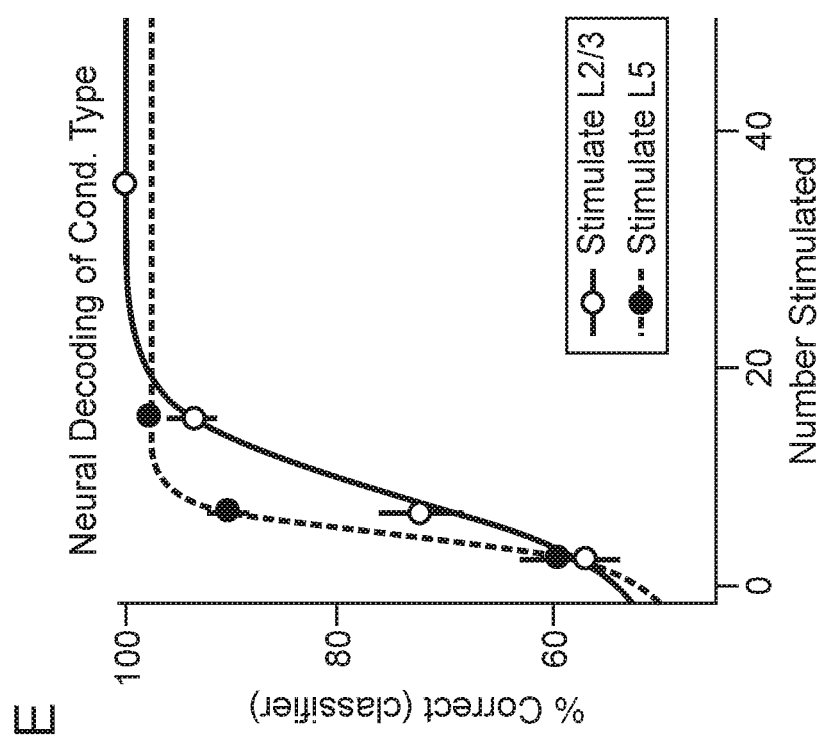
Figure 15:
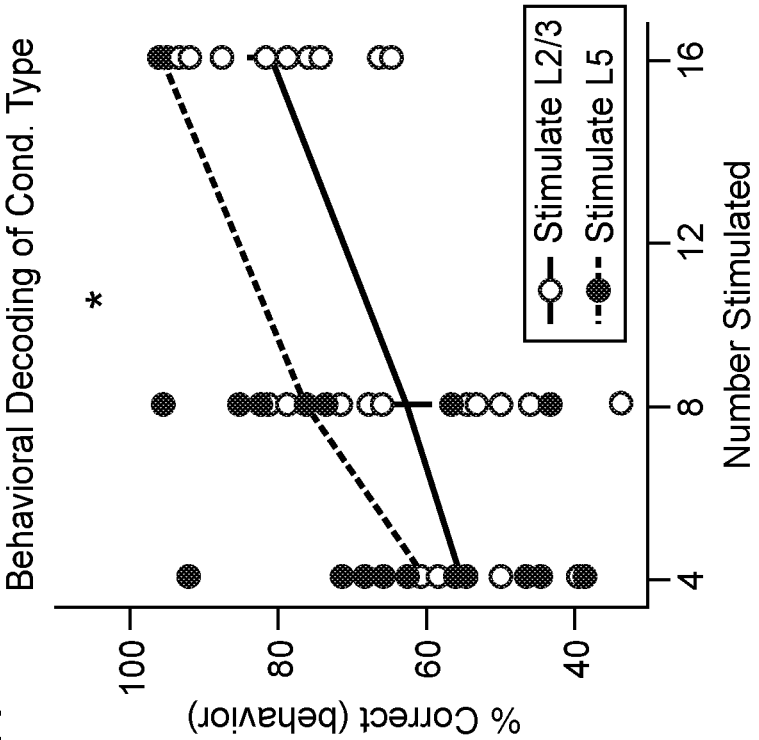
Figure 15:
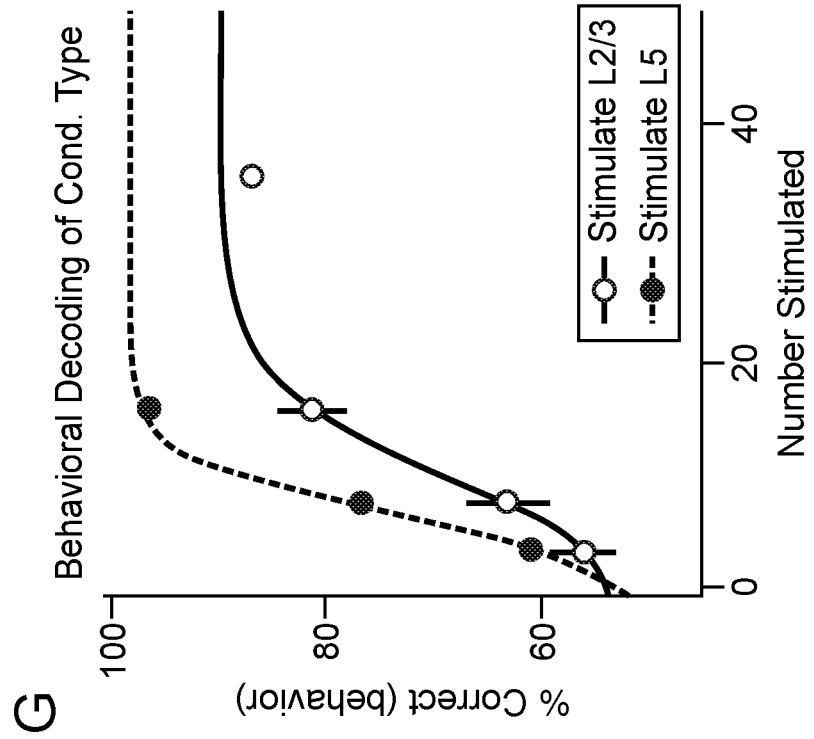
Figure 15:
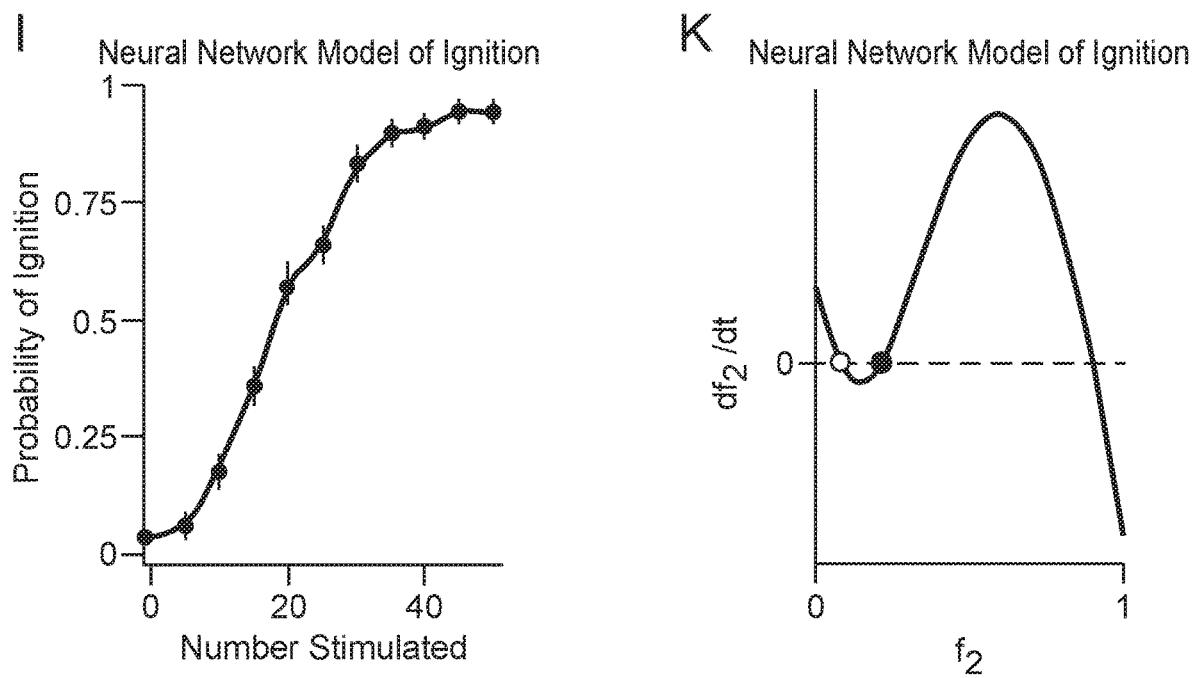
Figure 15:
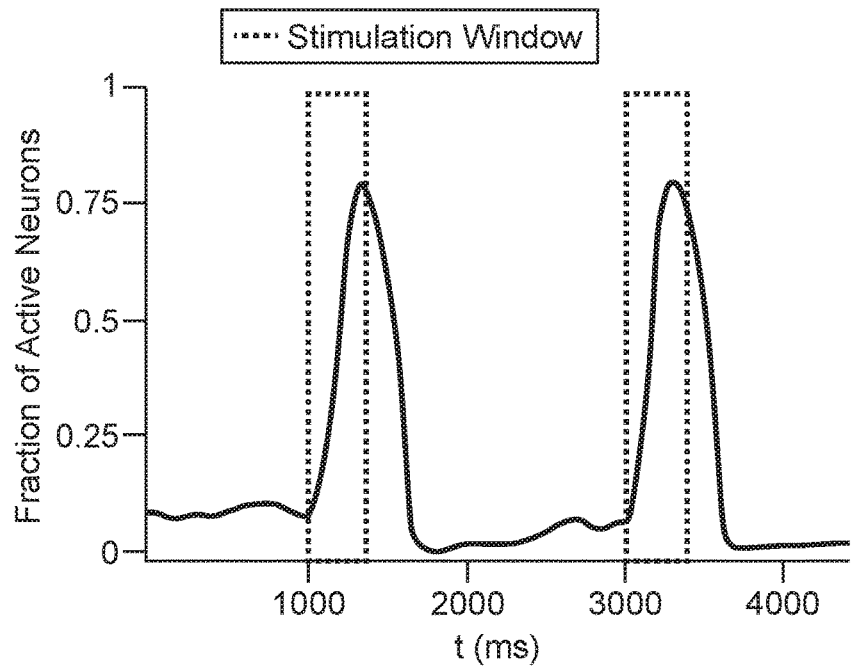

The network is poised near the boundary of instability in that the low stable spontaneous state is close to the unstable state, allowing the activation of a small number of neurons to push the network past the unstable state to trigger ignition to the high activity state. Slower rising inhibition (not shown) then brings the excitatory network back down, as in FIG. 15J.

Figure 16:
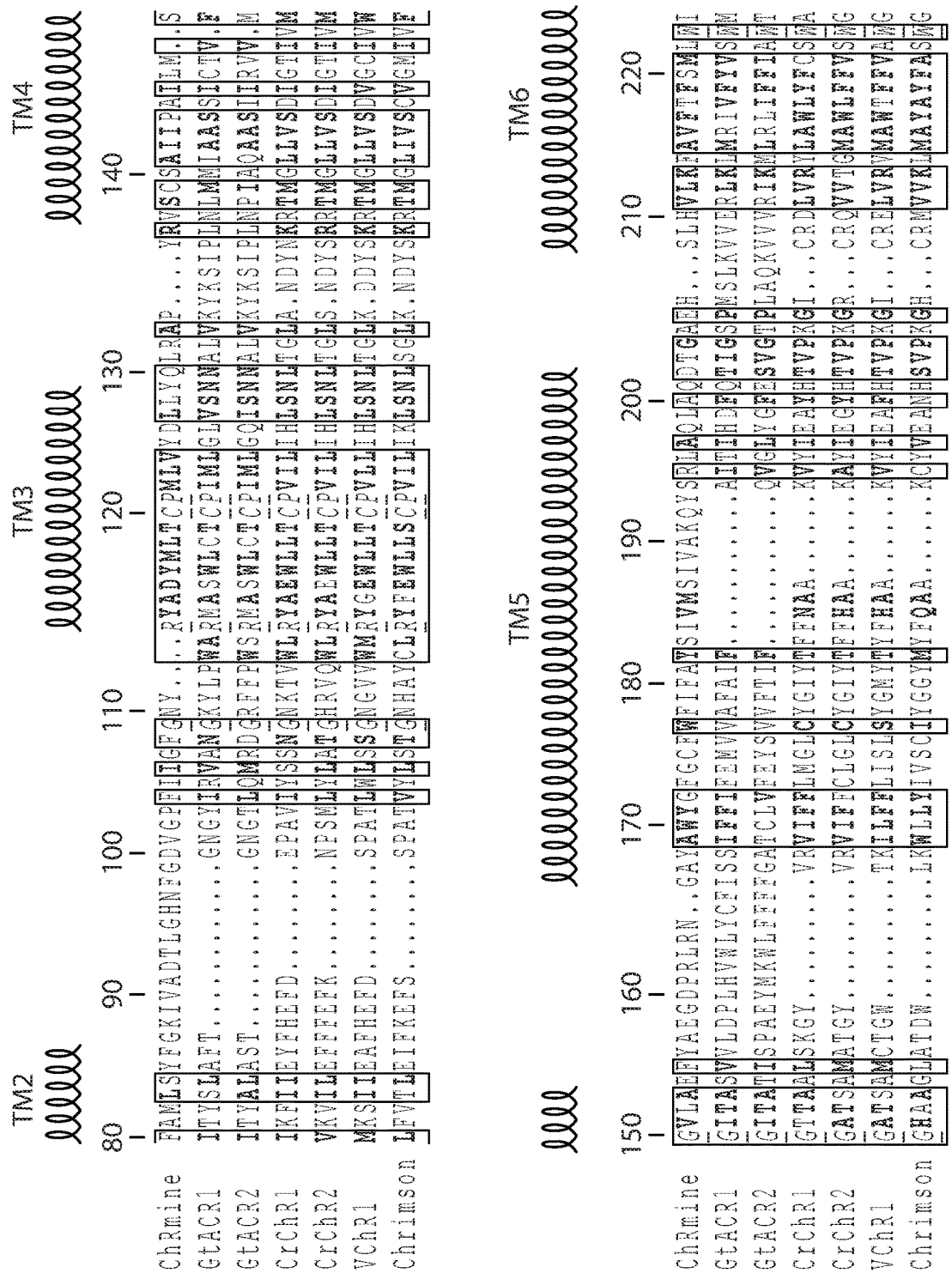

FIG. 16 depicts structure-based sequence alignment of natural channelrhodopsin genes. The sequences are ChRmine (GenBank ID: TBD), GtACR1 (GenBank ID: AKN63094.1), GtACR2 (AKN63095.1), CrChR1 (GenBank ID: 15811379), CrChR2 (GenBank ID: 158280944), VChR1 (UniProtKB ID: B4Y103), and Chrimson (Genbank ID: AHH02126.1). The sequence alignment was created using PROMALS3D and ESPript3, followed by manual re-alignment of TM1s, which were apparently misaligned. Predicted transmembrane domains are shown as coils. Structurally important residues are highlighted with red boxes and white font color, with other residues showing high sequence homology highlighted with blue boxes and red font color.

Figure 10:
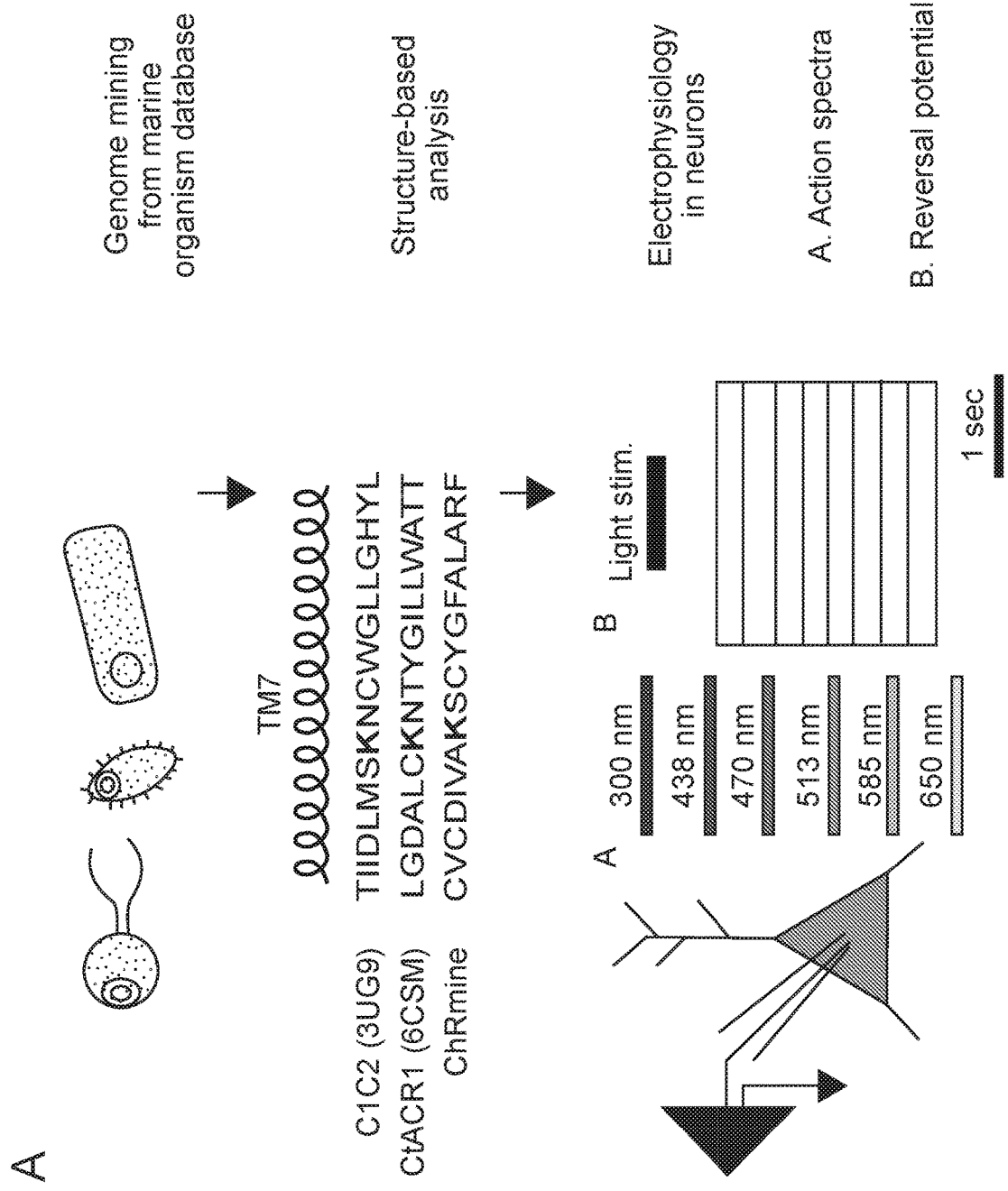
FIG. 10, A-O depict ChRmine: a novel class of opsin, suitable for high fidelity read-write experiments, derived from a marine environment.
Figure 10:
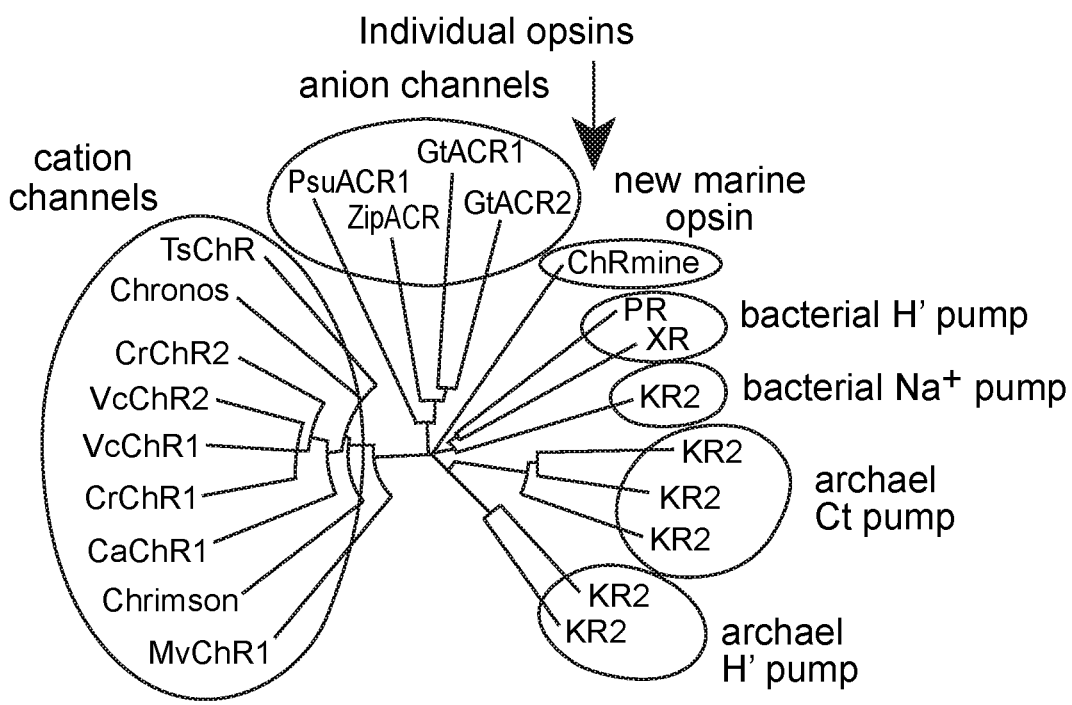
Figure 10:
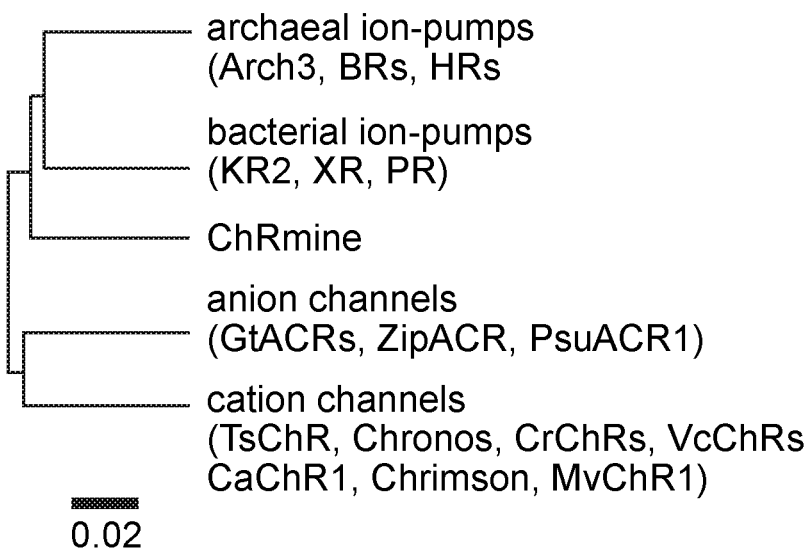
Figure 10:
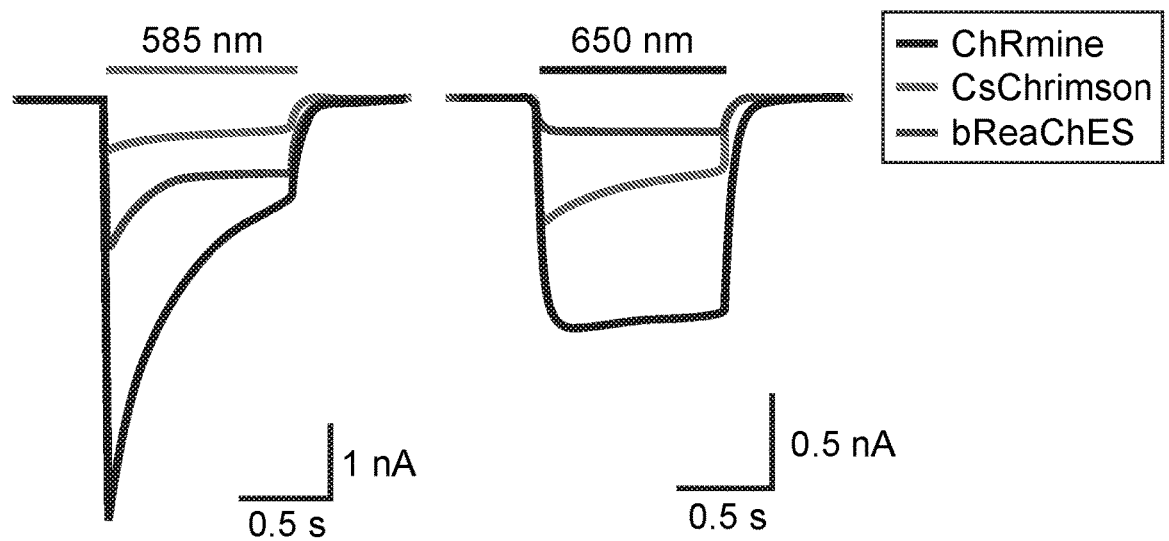
Figure 10:
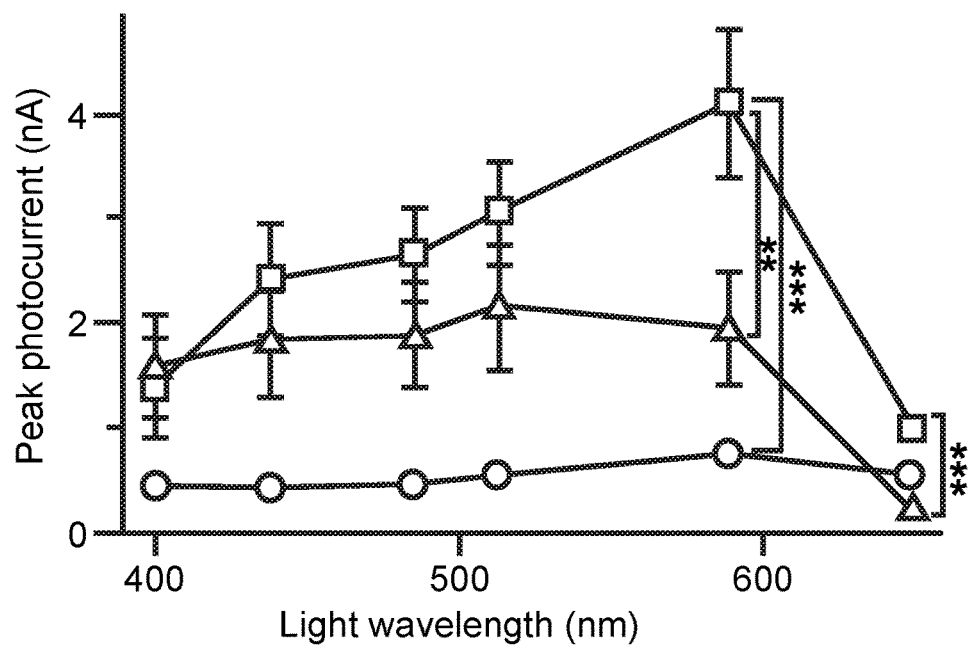
Figure 10:
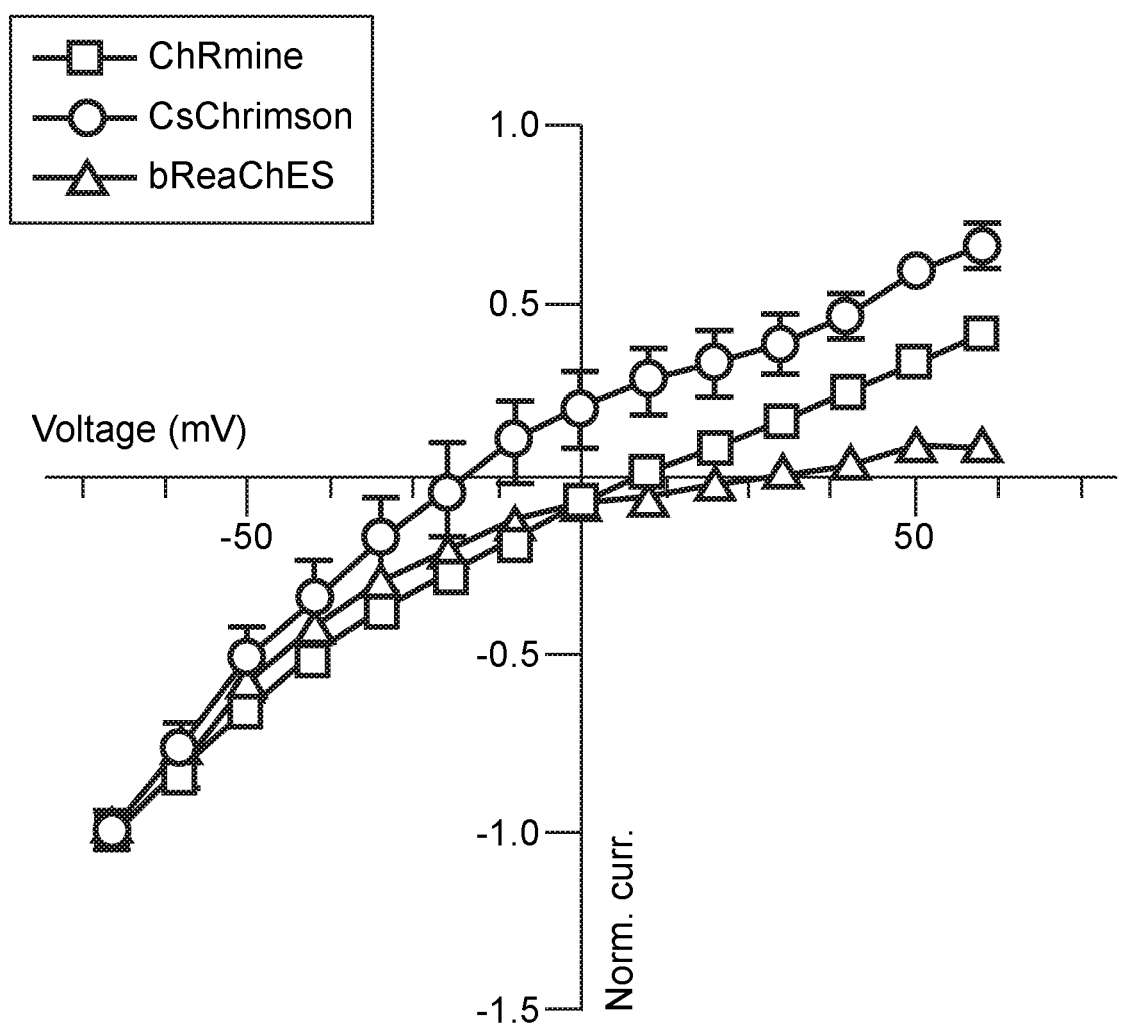
Figure 10:
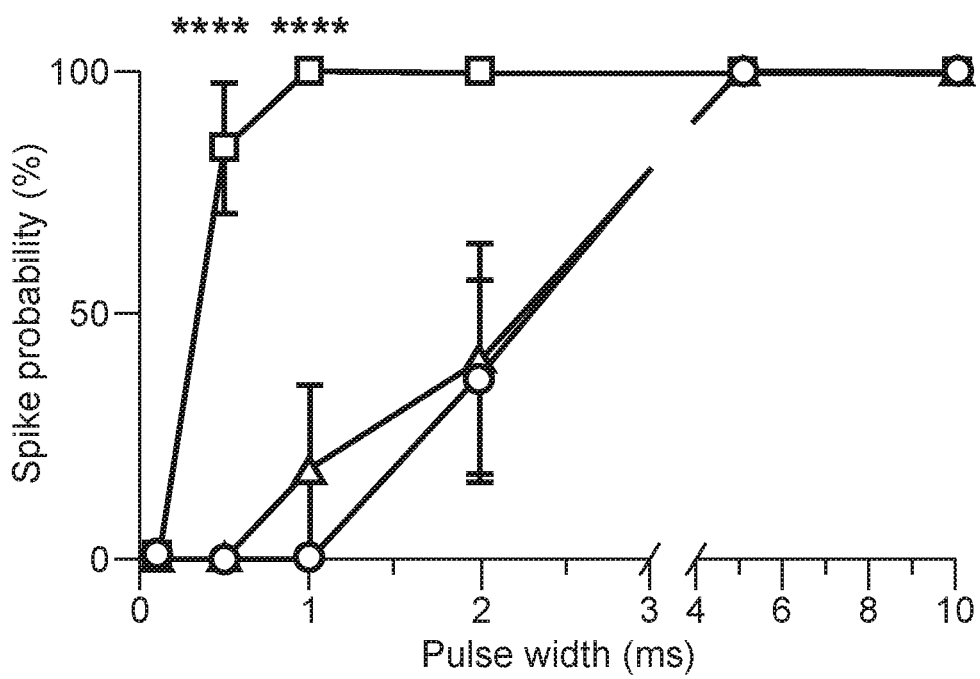
Figure 10:
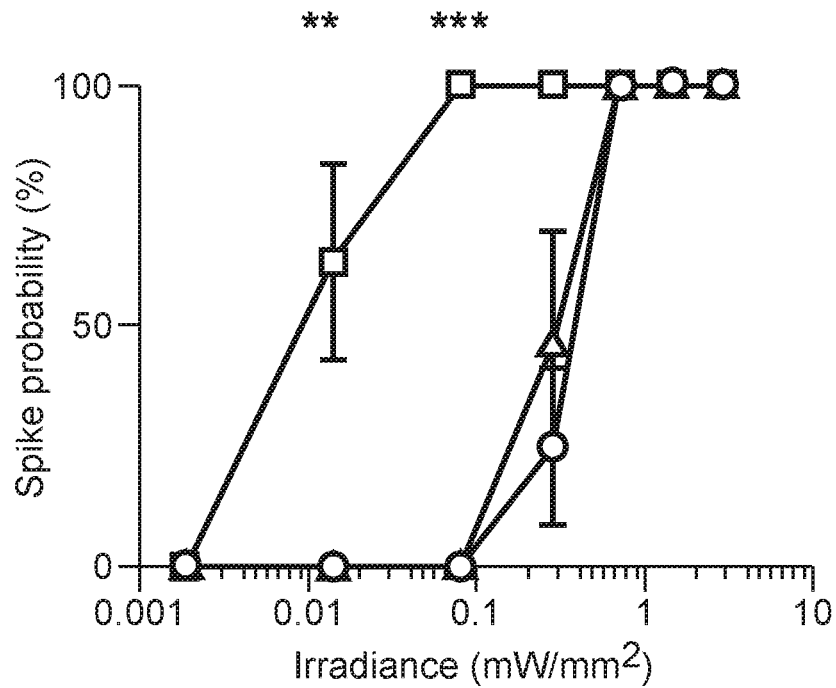
Figure 10:
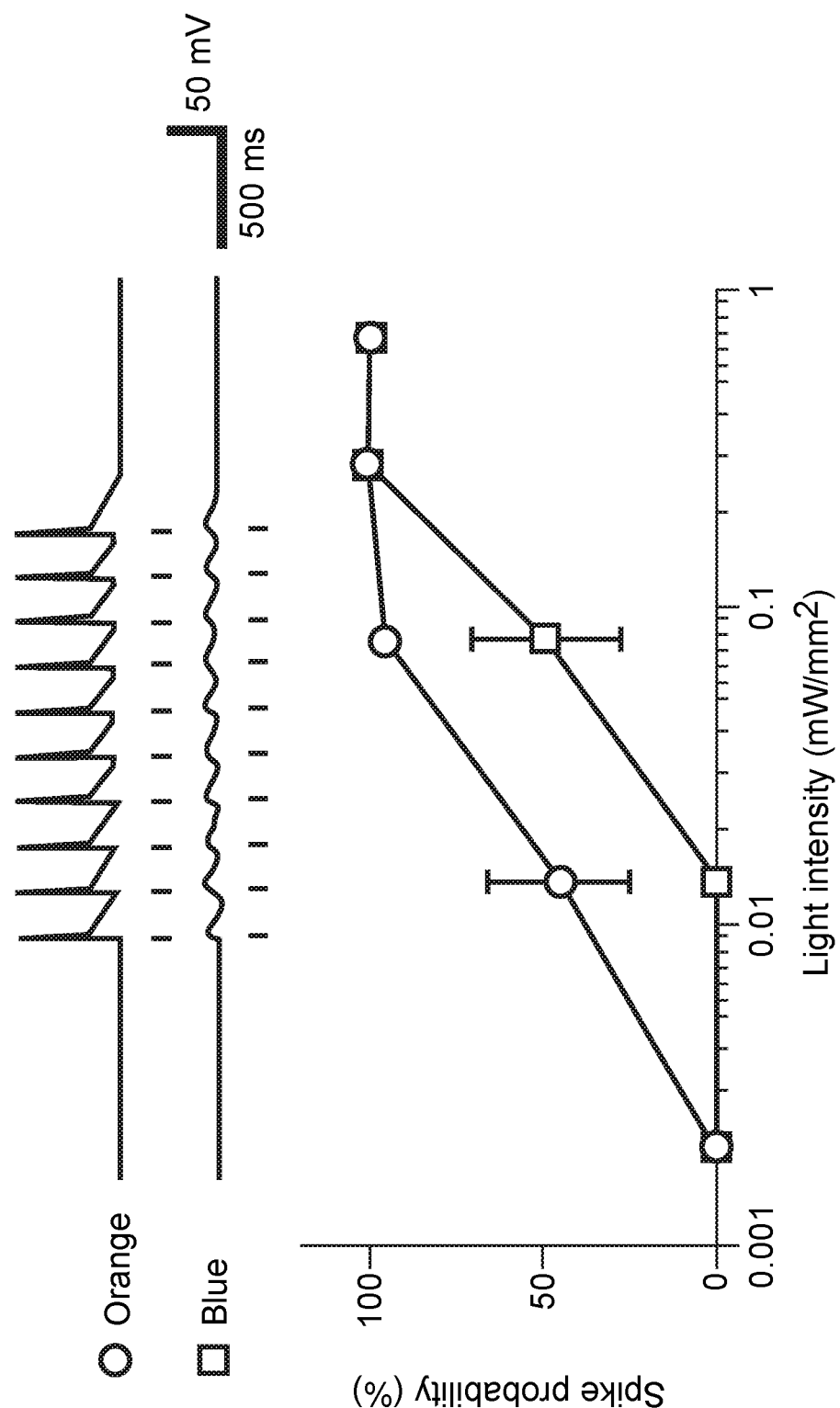
Figure 10:
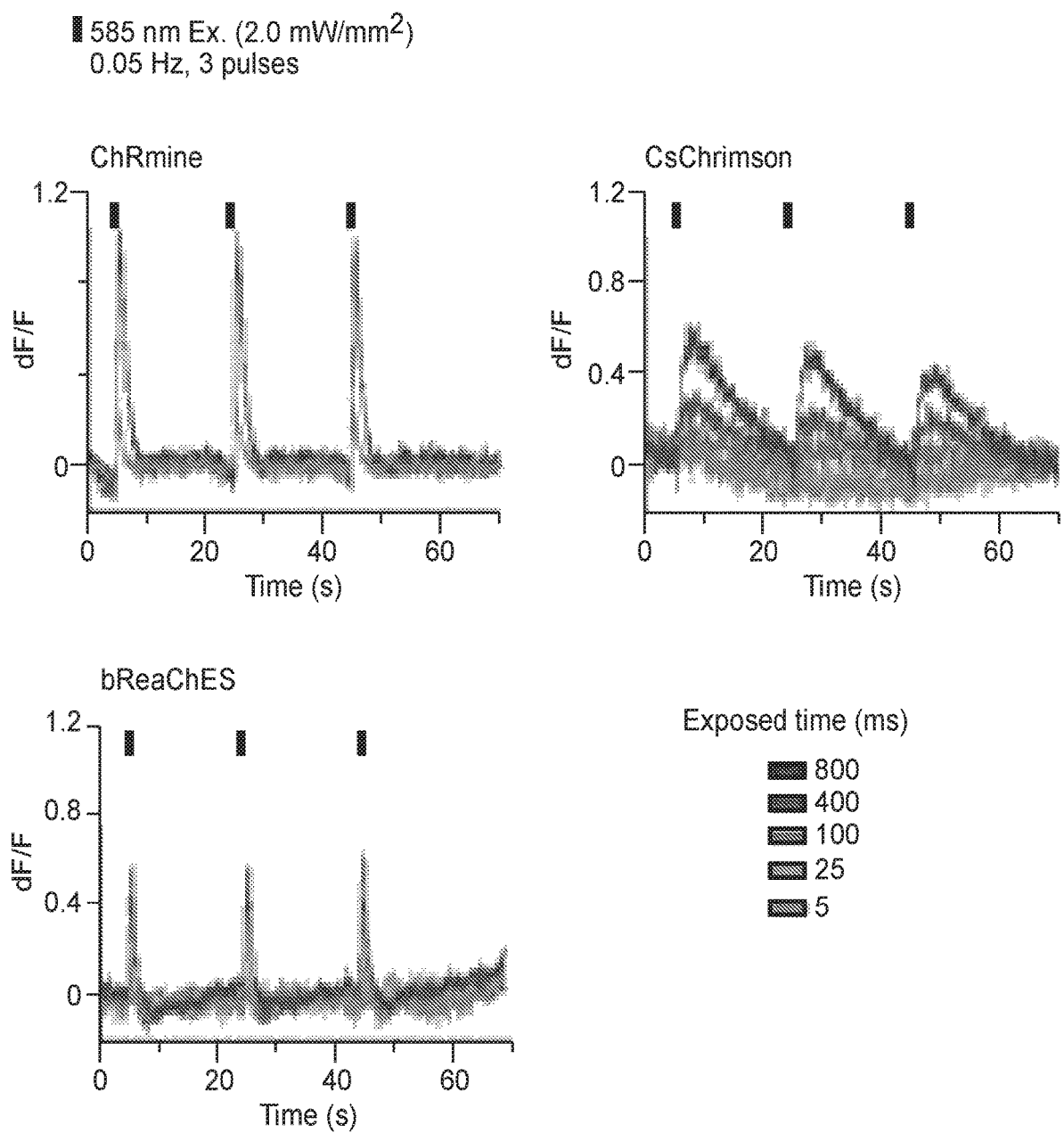
Figure 10:
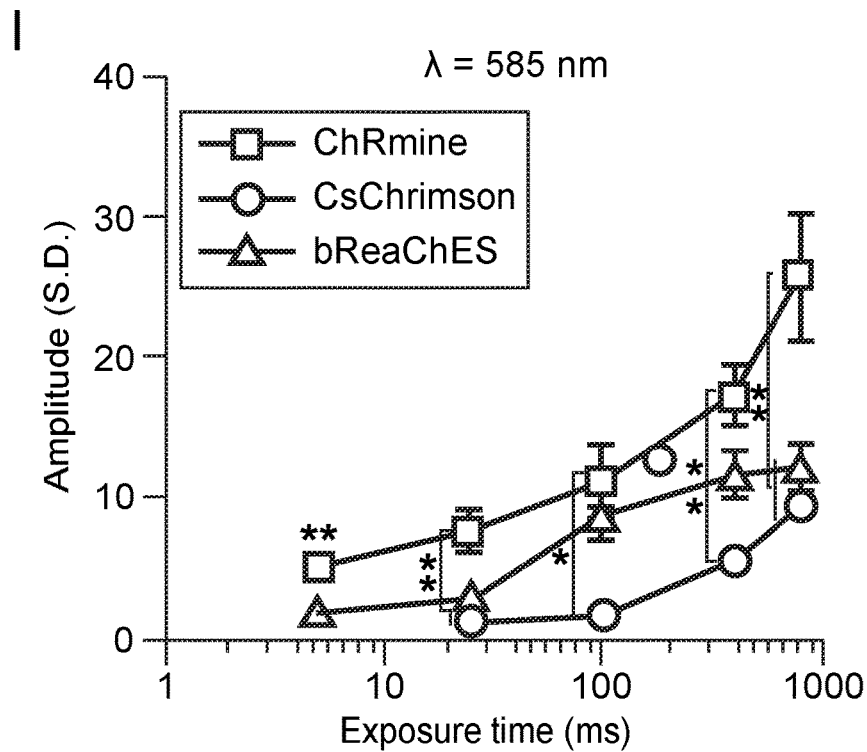
Figure 10:
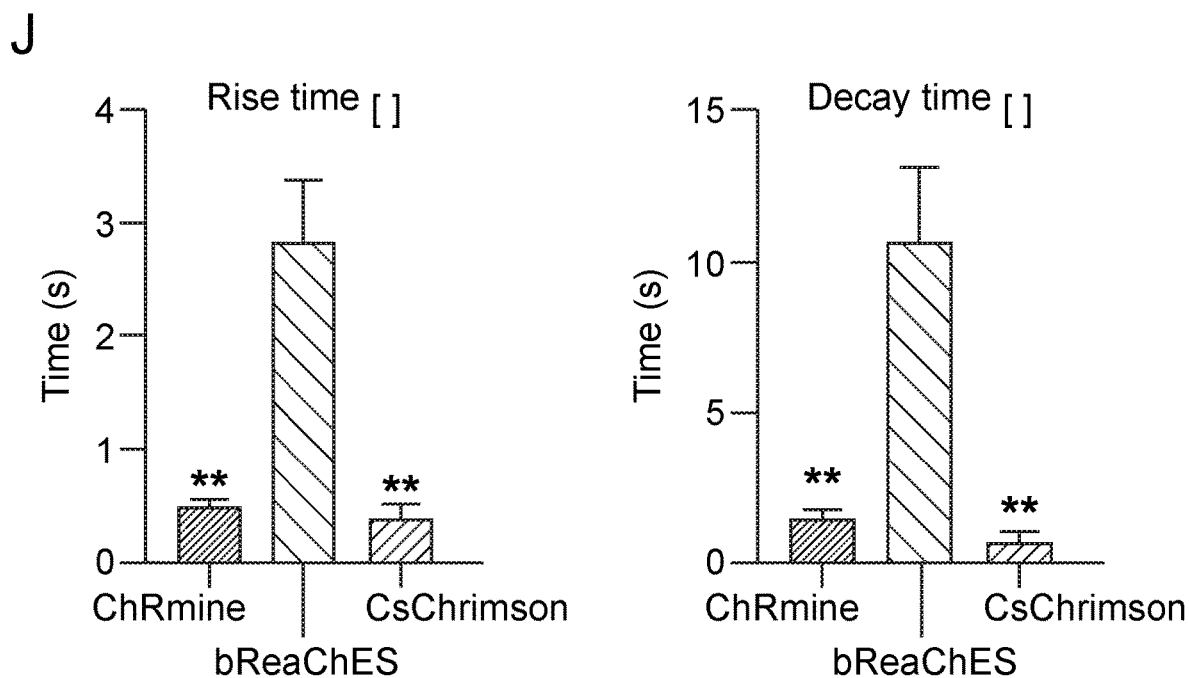
Figure 10:
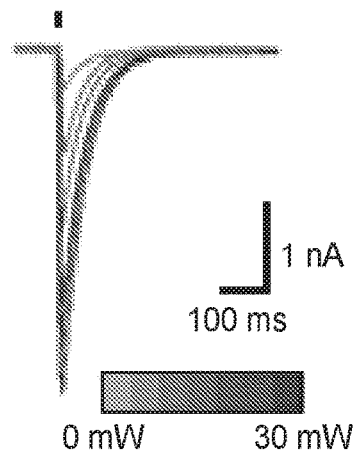
Figure 10:
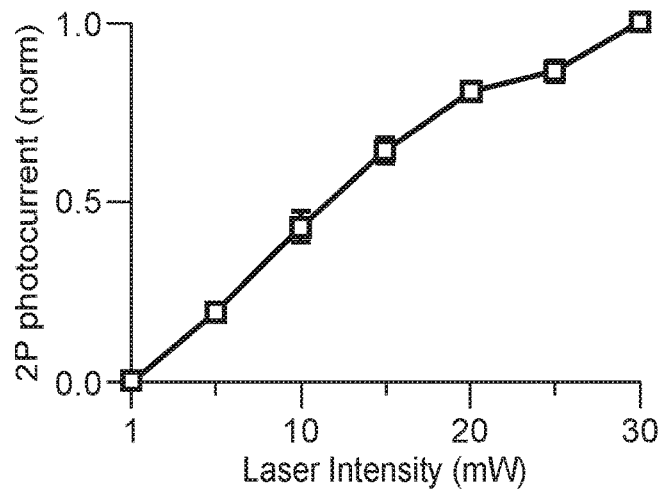
Figure 10:
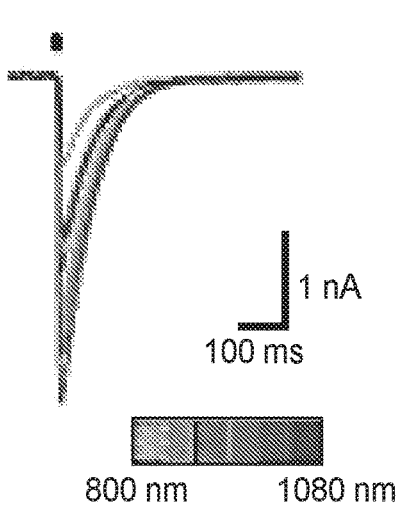
Figure 10:
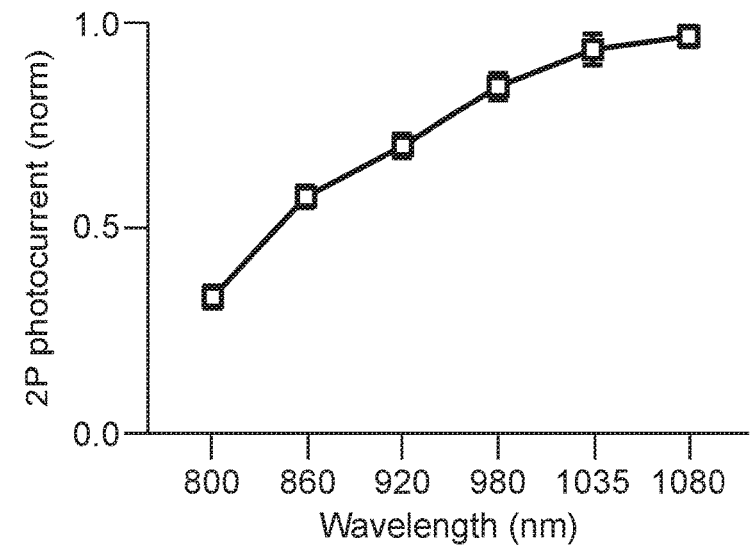
Figure 17:
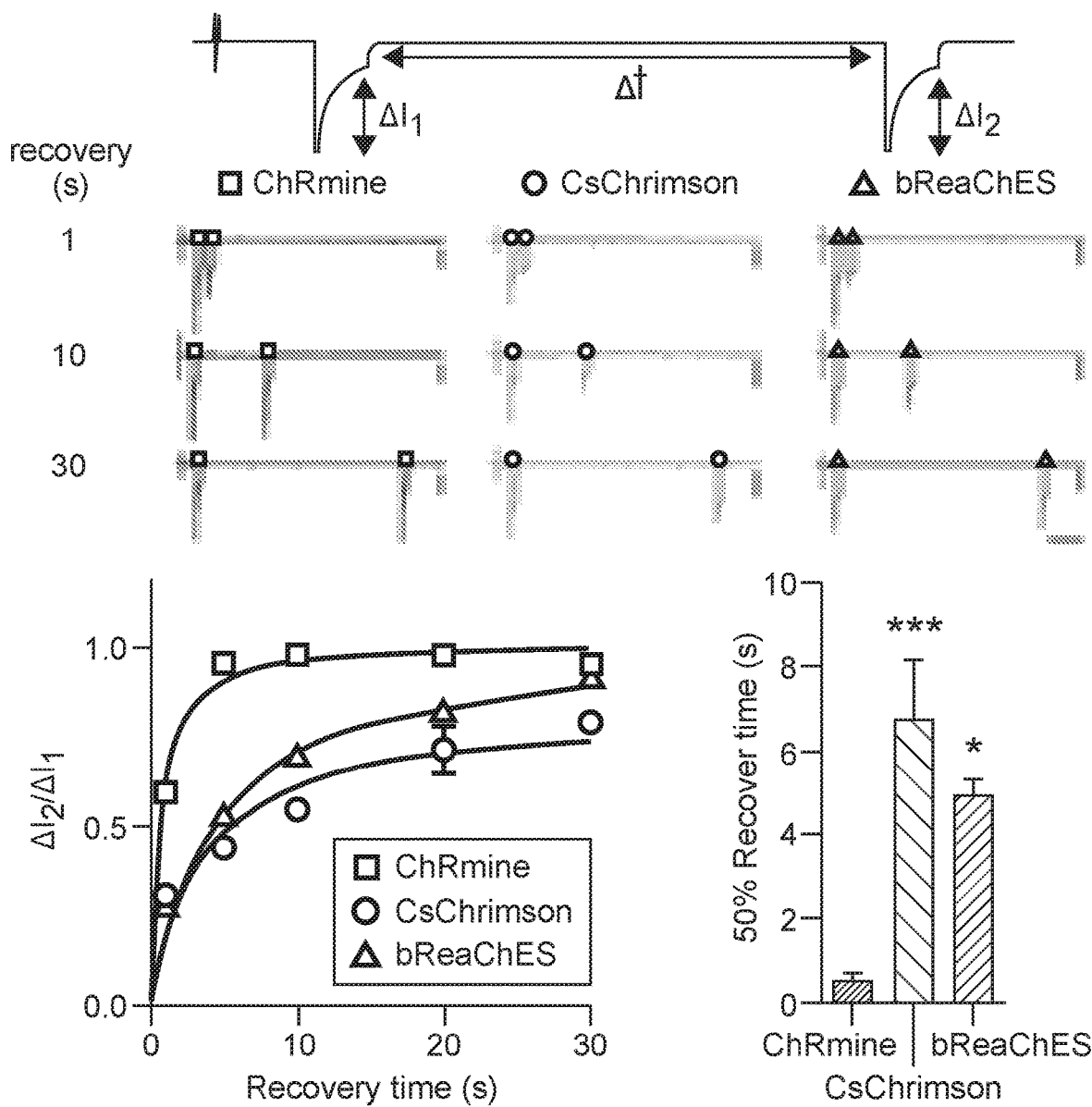
Figure 17:
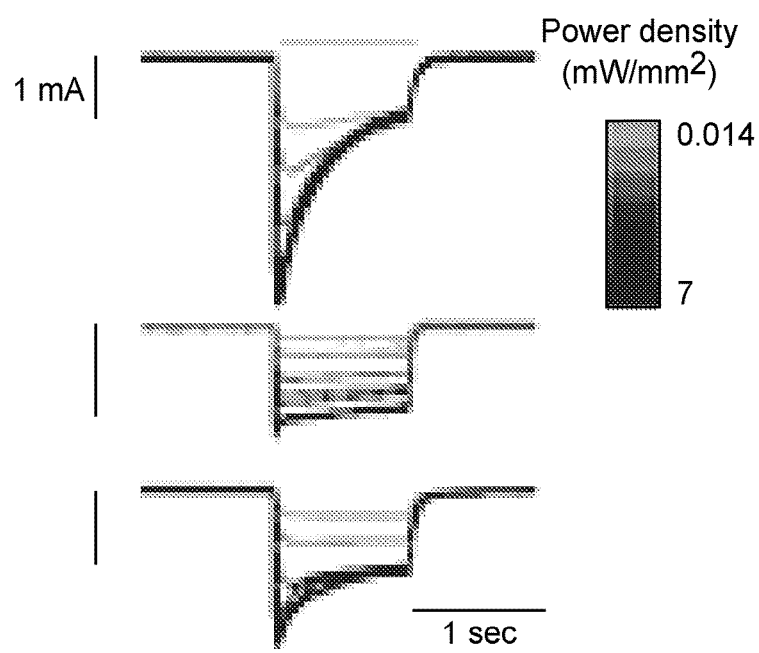
Figure 17:
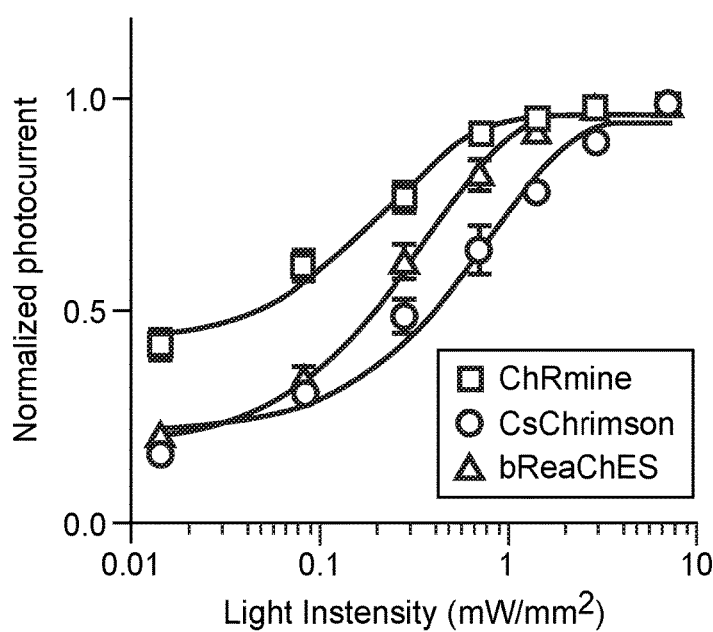
Figure 17:
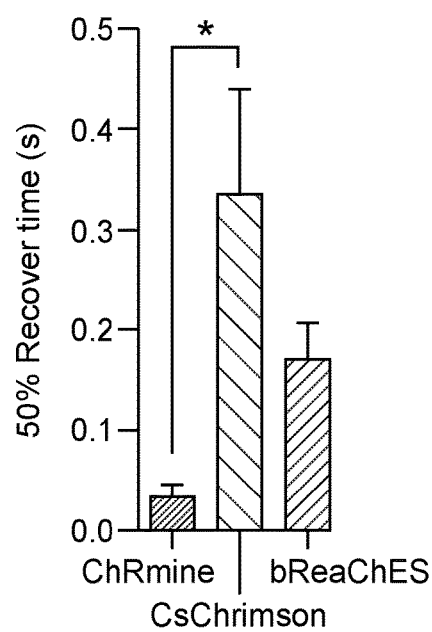
Figure 17:
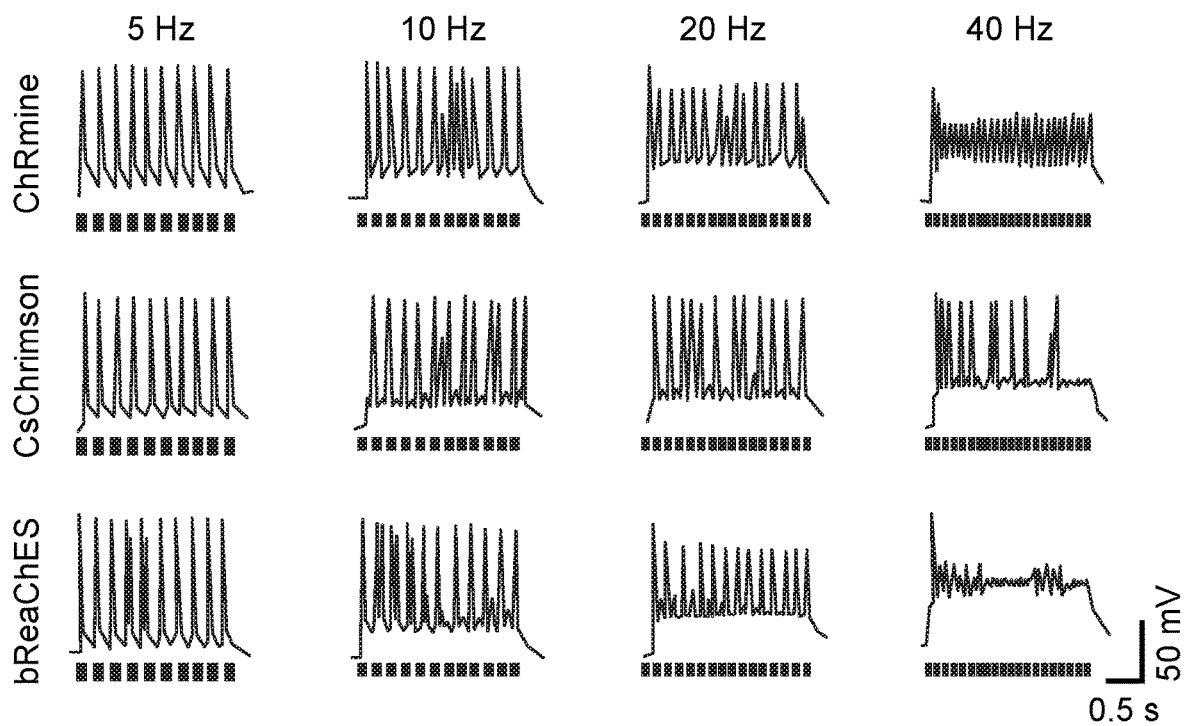
Figure 17:
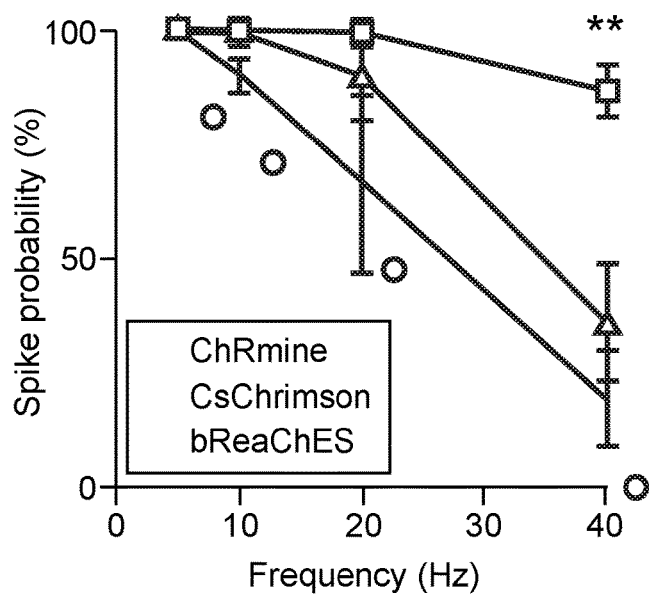
Figure 17:
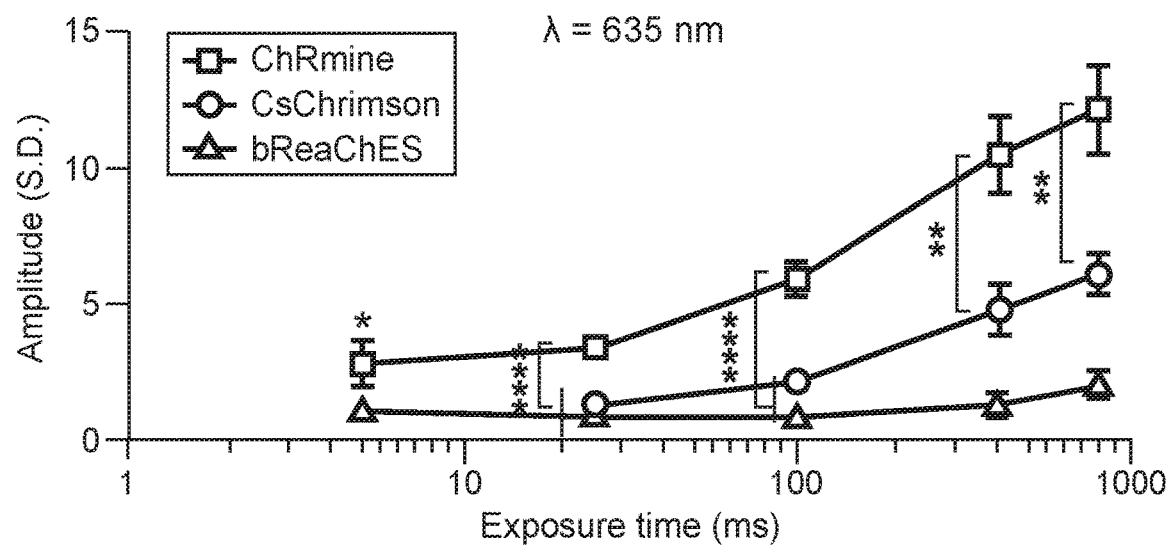
Figure 17:
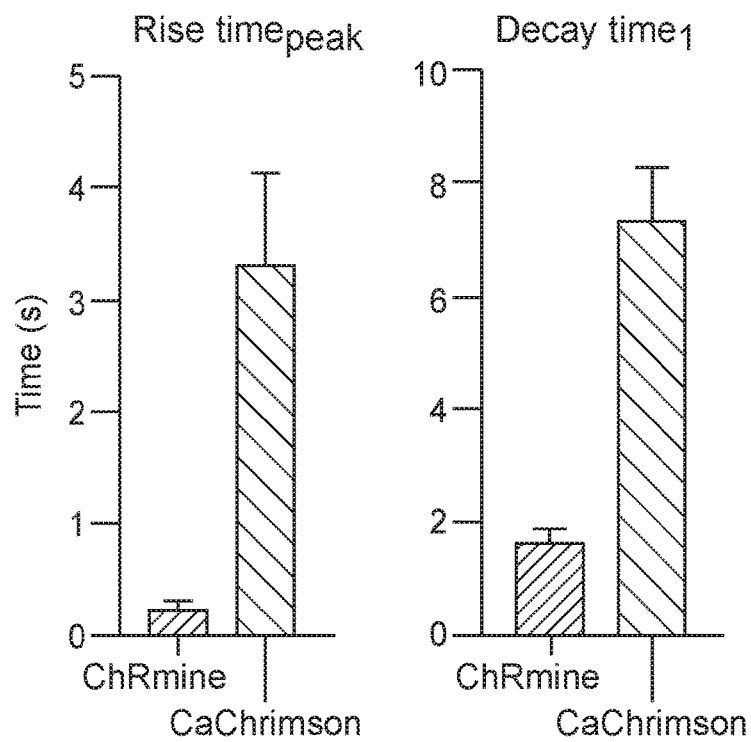
Figure 17:
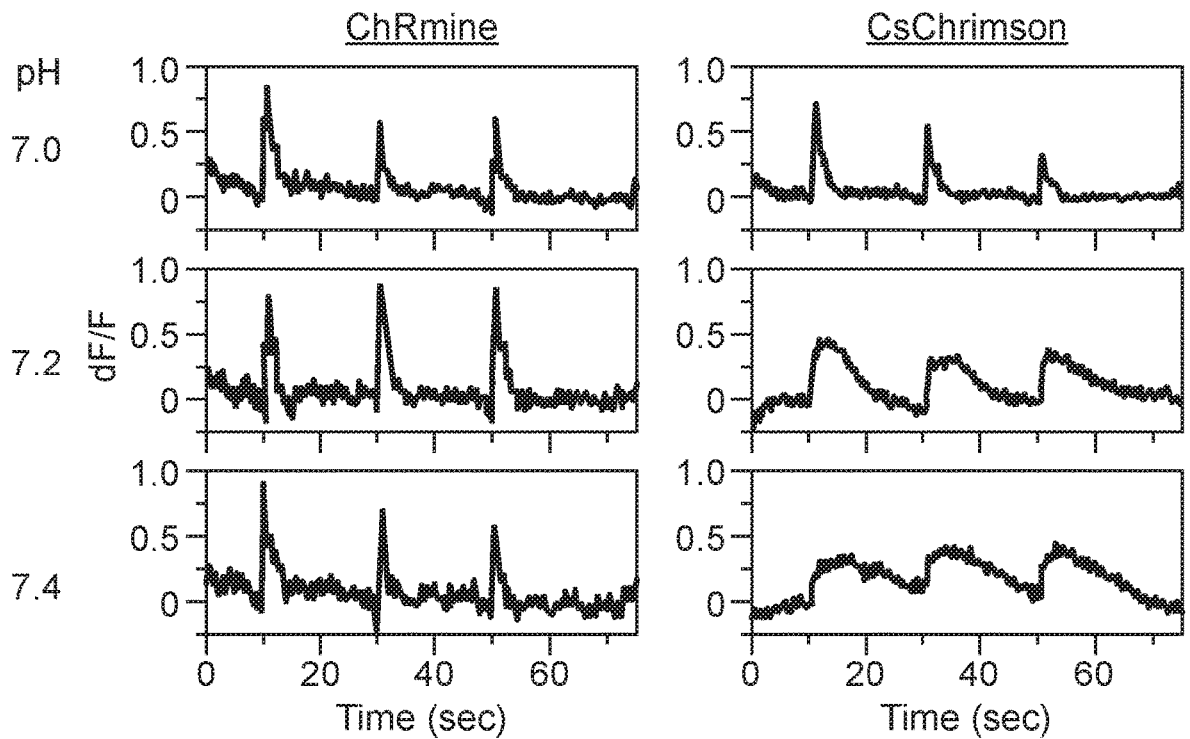
Figure 17:
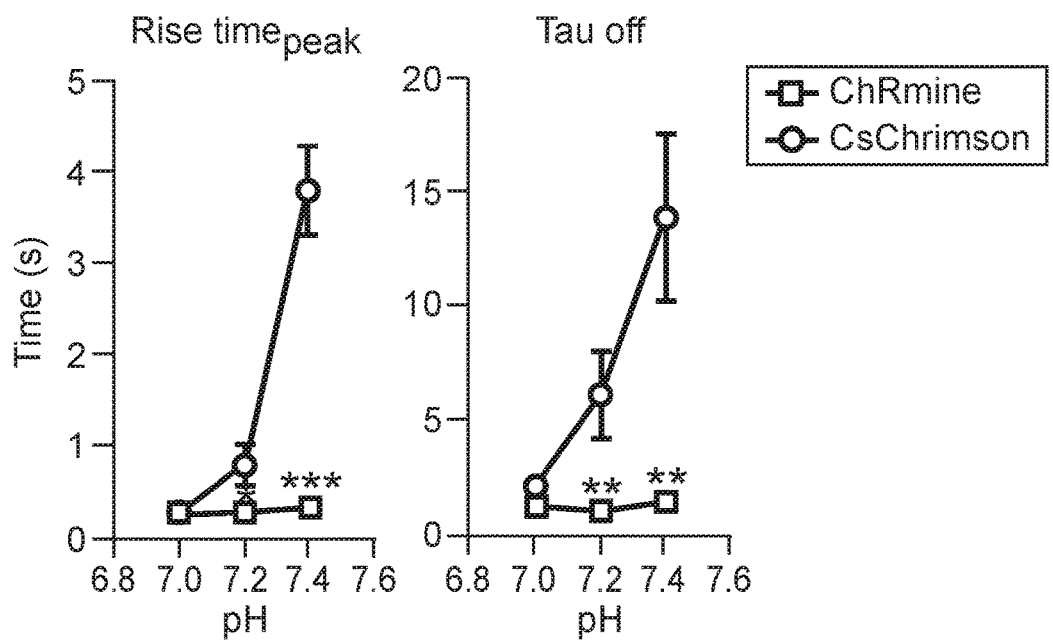
Figure 17:
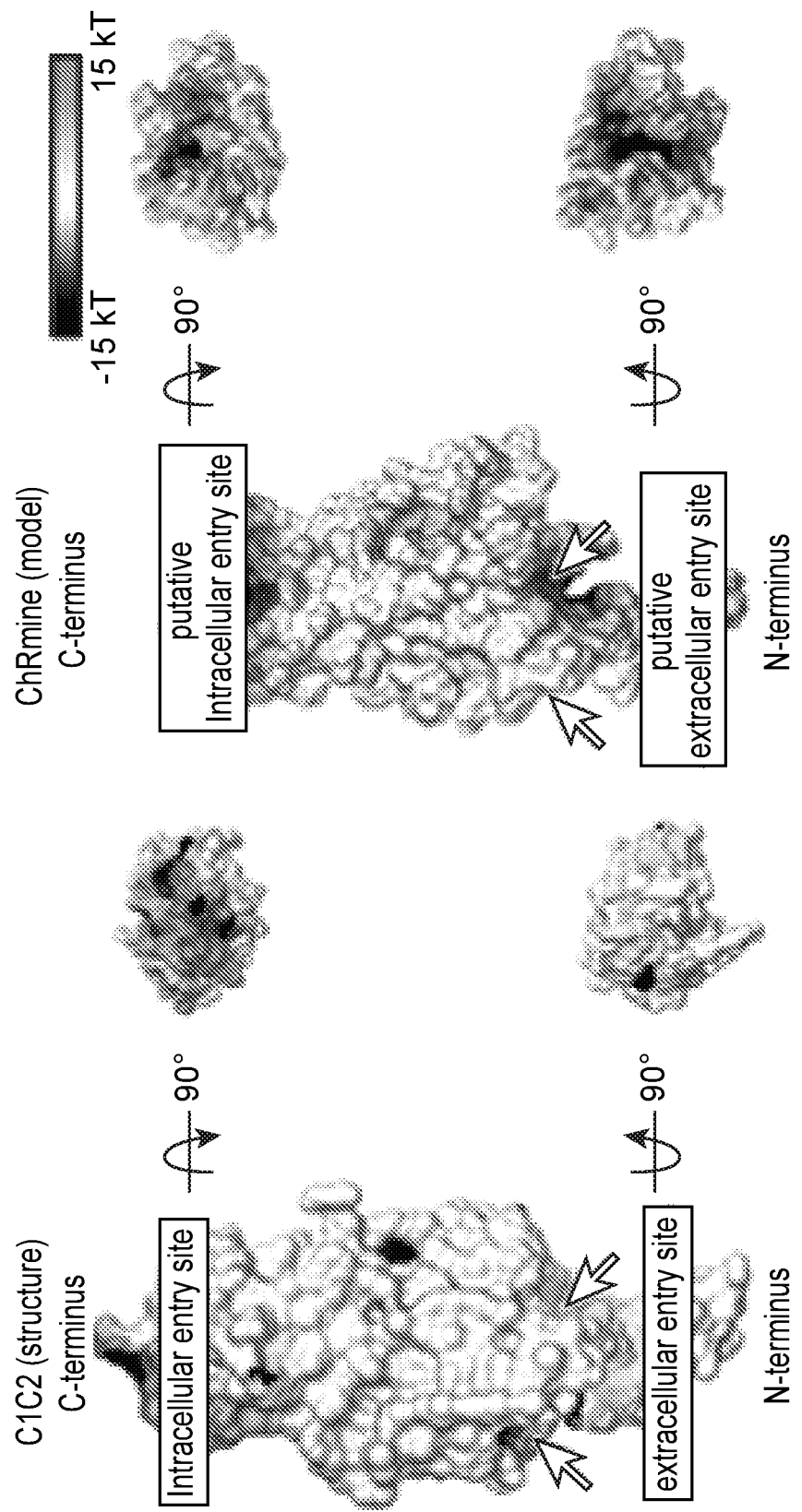

FIG. 17, A-F depicts electrophysiological and structural characterization of ChRmine. FIG. 17A: Top—example traces showing channelrhodopsin recovery from desensitization after 1 s, 10 s and 30 s dark recovery times. Peak photocurrent magnitudes before ($\Delta I_1$, $I_{peak1} - I_{stationary1}$) and after ($\Delta I_2$, $I_{peak2} - I_{stationary2}$) the recovery time interval ($\Delta t$), and 1 second of light illumination periods (585 nm, 0.7 mW/mm$^2$, orange lines) are shown in the scheme. Bottom—time-dependent recovery plotted against the recovery time interval (left). Note that 50% recovery time constant of ChRmine was significantly faster than that of CsChrimson or bReaChES. (right). (means±s.e.m. n=5-6 cells. *p<0.05, ***p<0.001 in one-way ANOVA with Dunnett's test). Vertical scale bars=1 nA current amplitude, horizontal scale bar=1 second. FIG. 17B: Top—examples traces showing channelrhodopsin photocurrents across different light intensities. Photocurrents were measured with 585 nm, 1 sec light stimulation at power densities of (in mW/mm$^2$) 0.014, 0.08, 0.28, 0.7, 1.4, 2.8 and 7. Bottom—normalized photocurrents plotted against the light intensities (left). Note that Effective Power Density for 50% maximal photocurrent (EPD50) for ChRmine is significantly lower than that of CsChrimson (means±s.e.m. n=5-6 cells. *p<0.05 in one-way ANOVA with Dunnett's test). FIG. 17C: Red-shifted channelrhodopsin spike fidelity. All spiking protocols used a train for 2 seconds and 0.7 mW/mm$^2$ light power was used for illumination. For light width, 1 ms for ChRmine and 5 ms for bReaChES and CsChrimson were used, as determined from the light sensitivity measurement from FIG. 10. (means±s.e.m. n=5-7 cells, p<0.01 in one-way ANOVA with Tukey's test). FIG. 17D: Left—Trial-averaged Ca$^{2+}$ response peak amplitude to ChRmine (red), CsChrimson (orange) and bReaChES (green) after pulses of 2, 5, 25, 100, 400, or 800 ms in response to 635 nm light. Right—Summary of rise and decay kinetics of Ca$^{2+}$ transients in response to 635 nm, 800 ms light pulses. bReaChES data not plotted in kinetics since the amplitude is too small for precise analysis (mean±s.e.m, n=5-7 cells, p<0.01, ***p<0.001; one-way ANOVA with Tukey correction). FIG. 17E: Left-representative Ca$^{2+}$ imaging traces response to indicated pH$_{ext}$ (7.0, 7.2, 7.4) at 585 nm light pulse, under the same experimental setup as indicated in (H). Right—trial-averaged Ca$^{2+}$ response kinetics to ChRmine (red) and CsChrimson (orange) at indicated pHs (mean±s.e.m of n=5-7 cells. *p<0.05, p<0.01, *p<0.001 in two-tailed t-test). FIG. 17F: Surface electrostatic potentials of the crystal structure of C1C2 (left) and homology model of ChRmine (right), built using RosettaCM (125), with C1C2 structure as a template. The surface is colored on the basis of electrostatic potential contoured from −15 kT (red) to +15 kT (blue). White denotes 0 kT. Surface potential was calculated using PDB2PQR for both GtACR1 and C1C2 models. Note that homology model-based comparison indicates more electronegative surface potential of ChRmine than that of C1C2.

Figure 18:
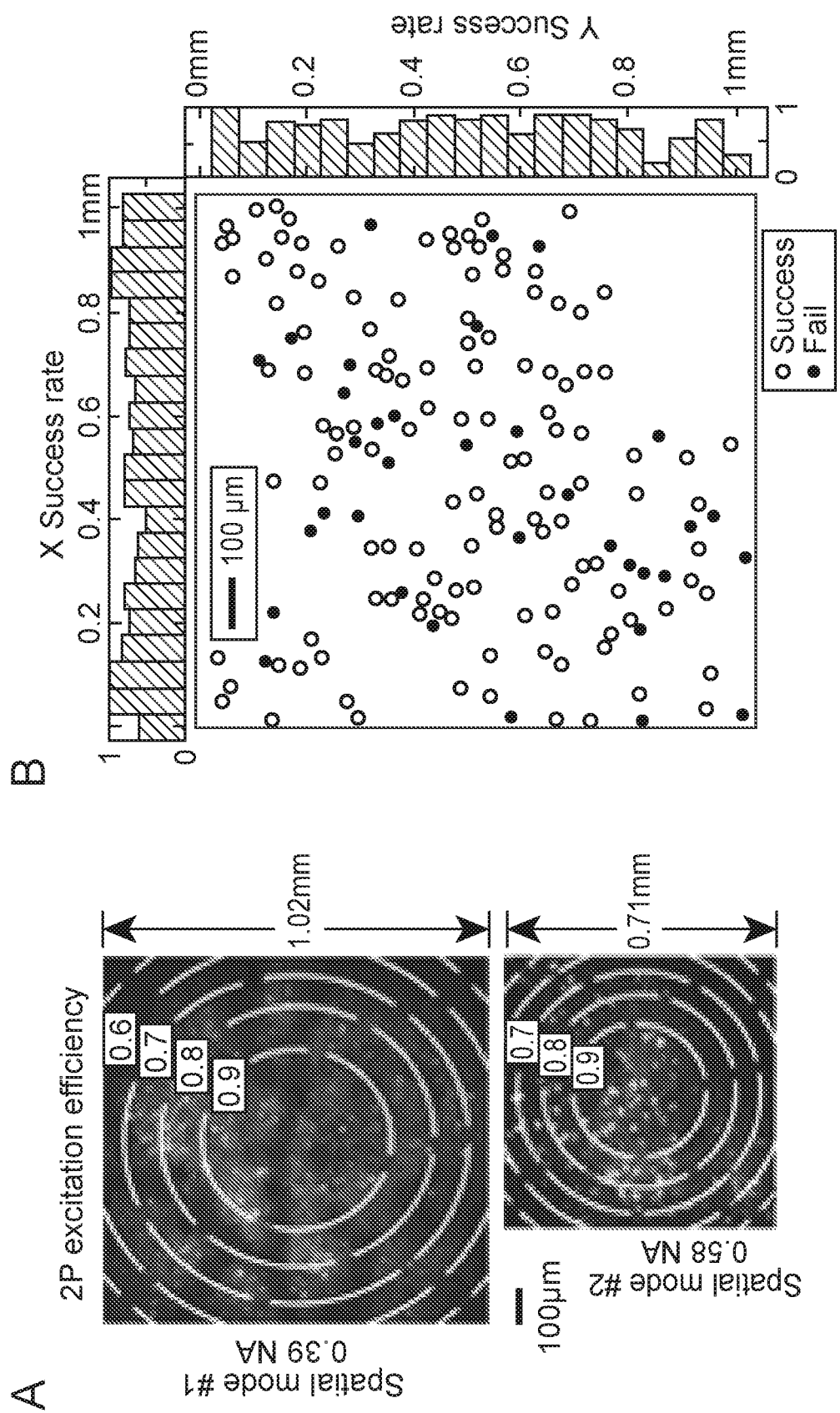
Figure 18:
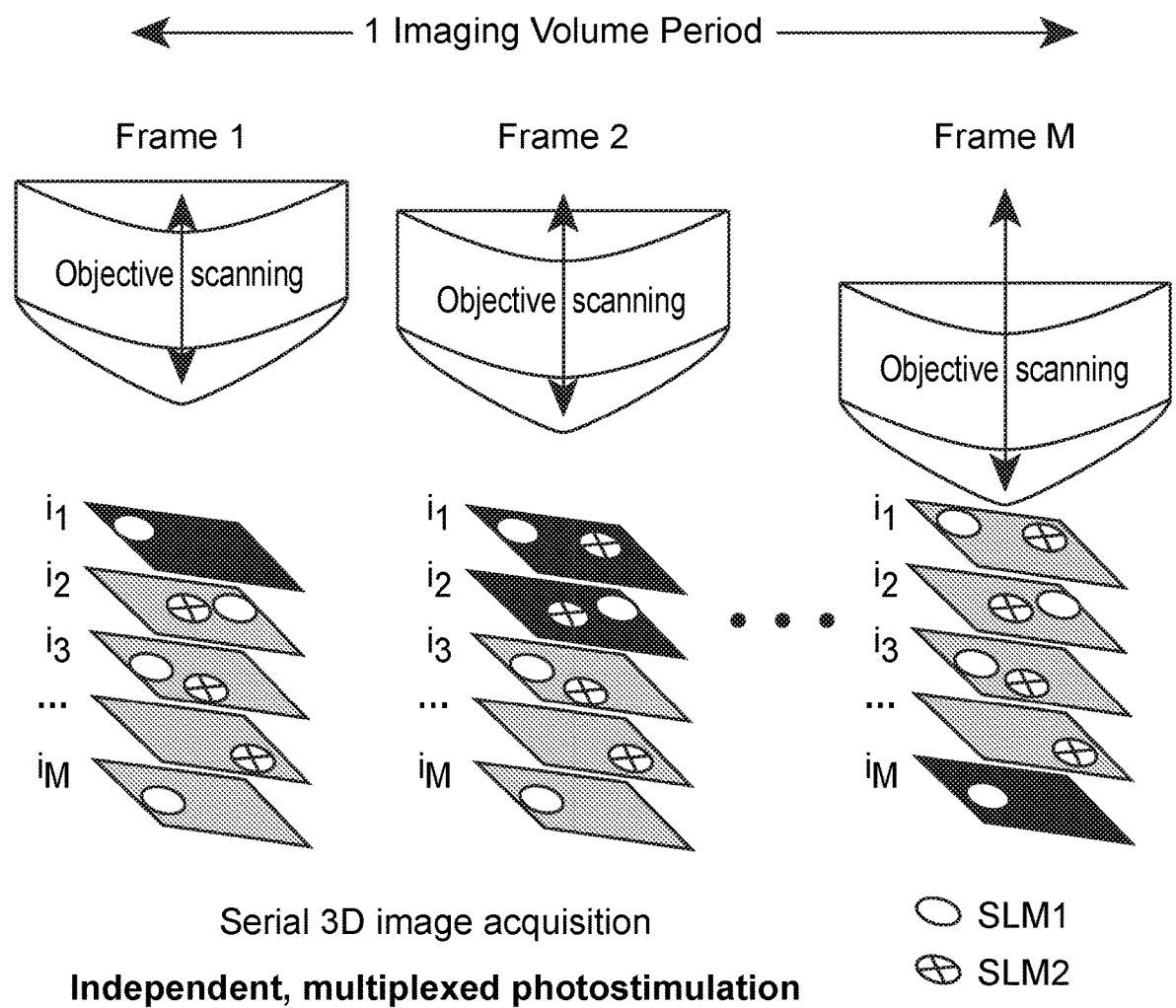
Figure 18:
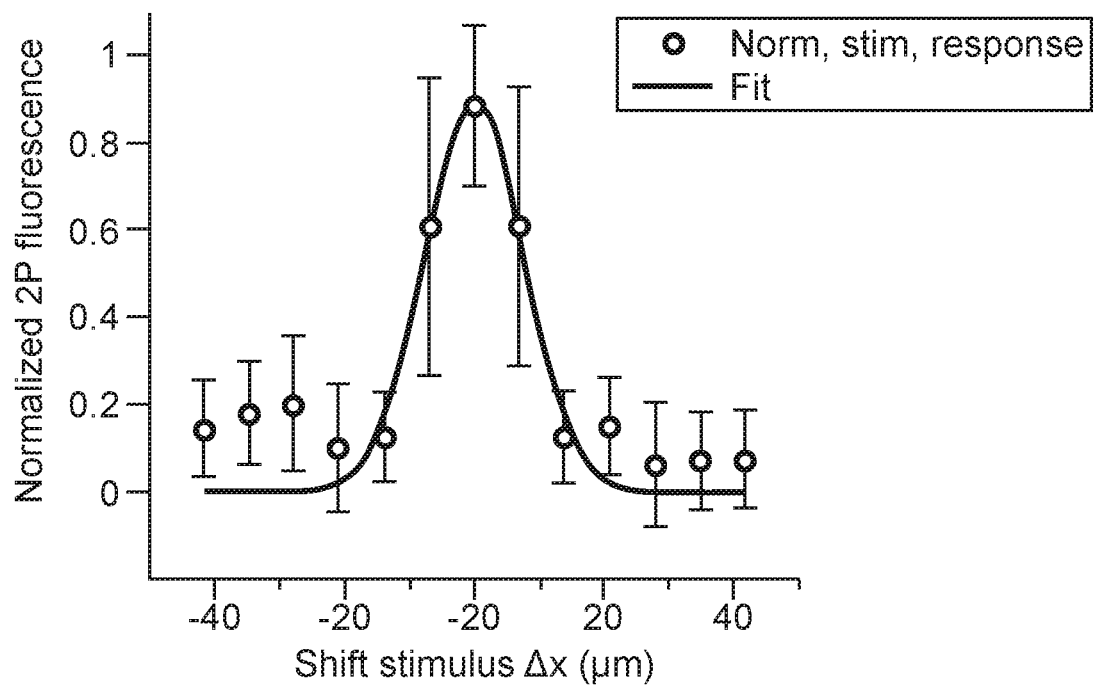
Figure 18:
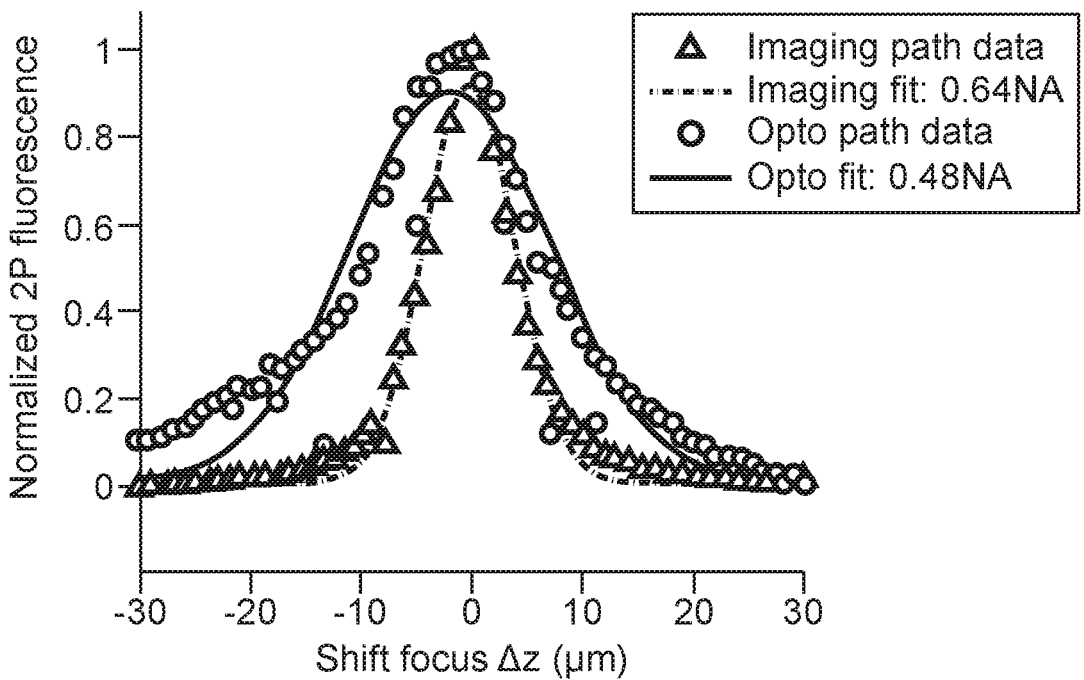
Figure 18:
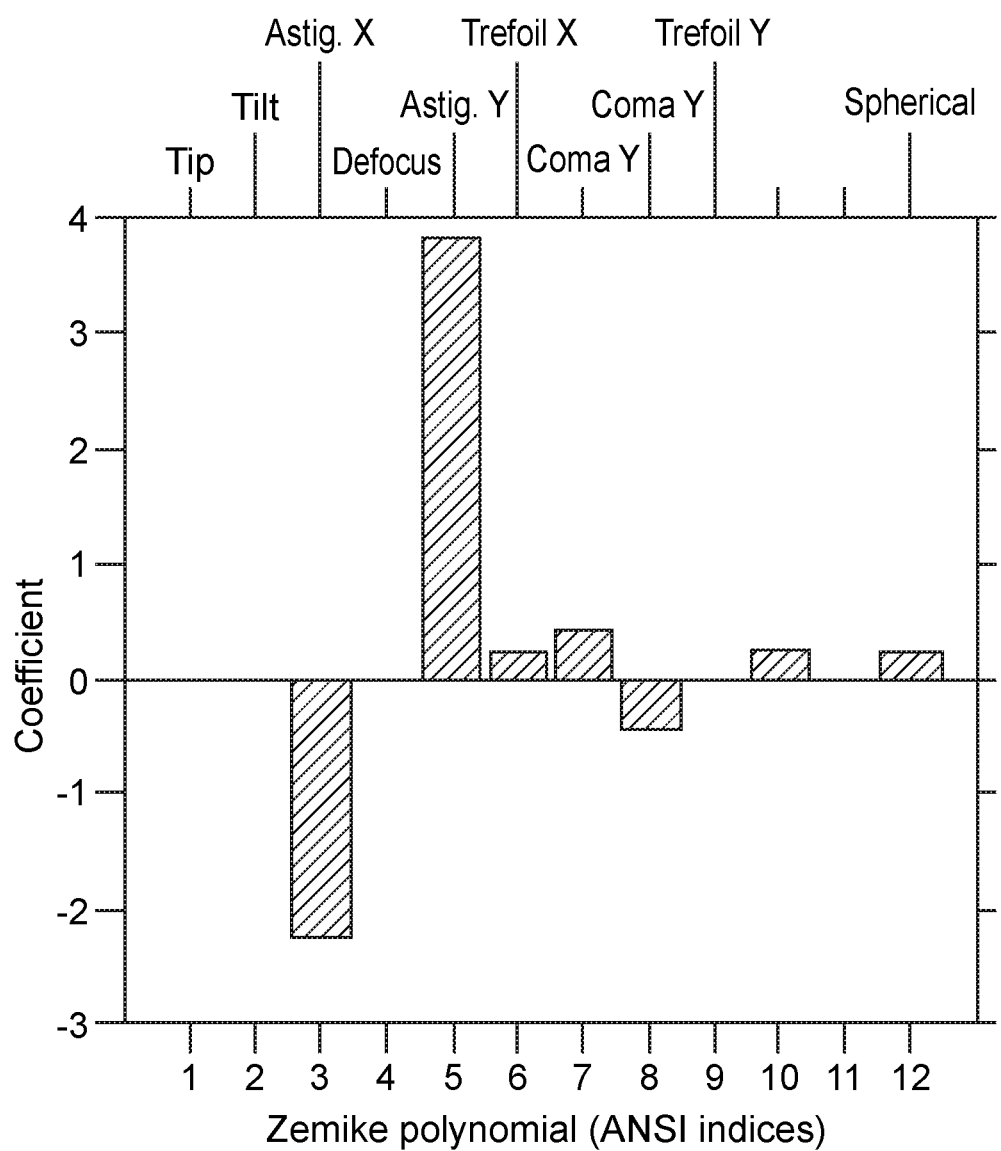
Figure 18:
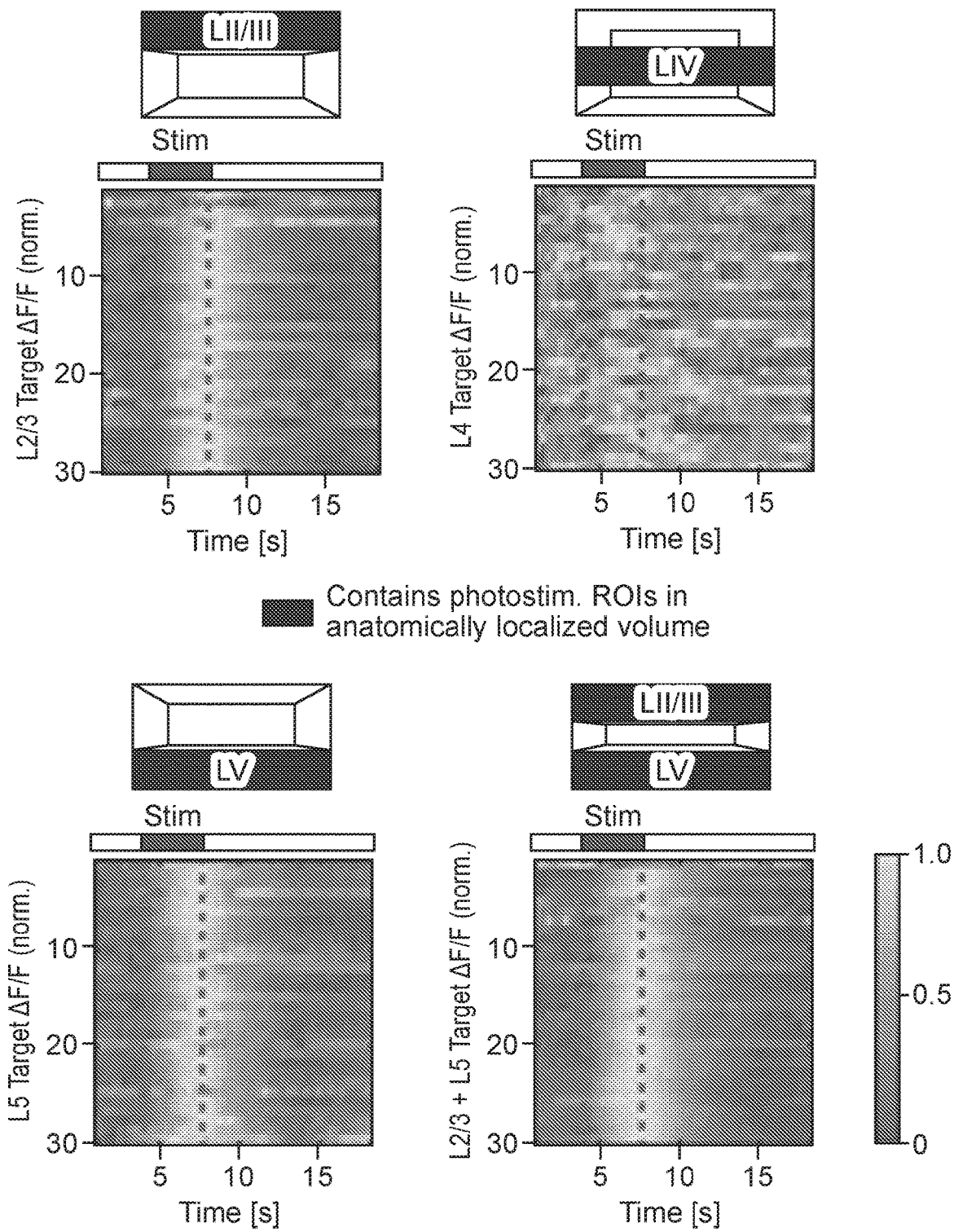
Figure 18:
Figure 18:
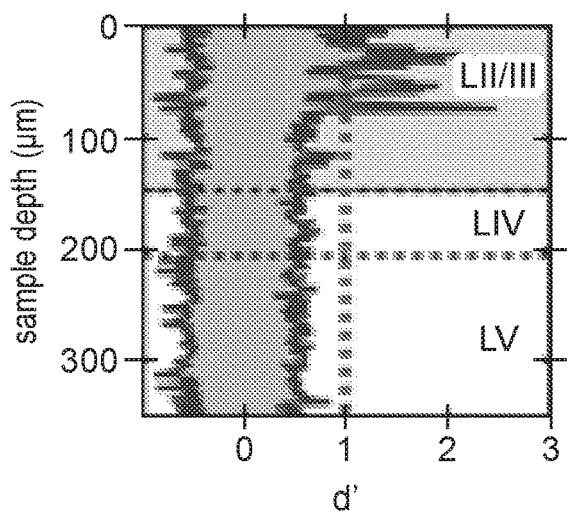
Figure 18:
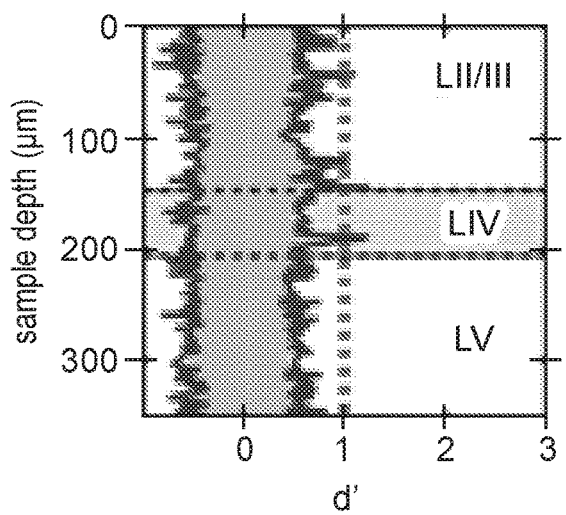
Figure 18:
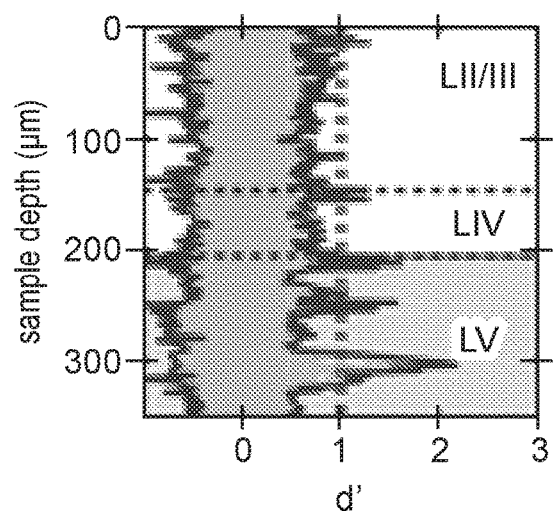
Figure 18:
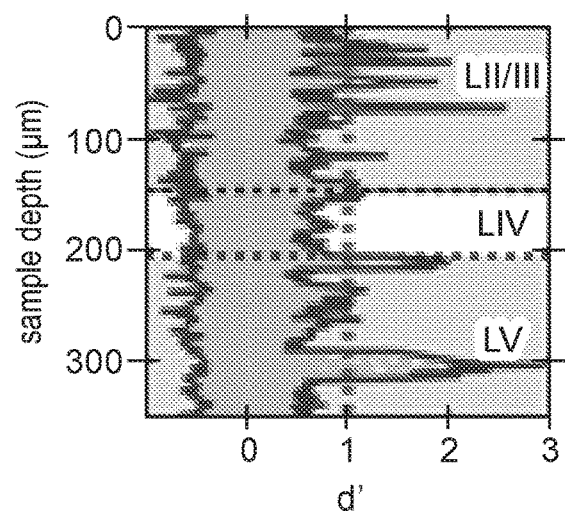

FIG. 18, A-H depicts theoretical and empirical properties of the microscope. FIG. 18A: Theoretical multiphoton excitation efficiency curves for two alternative microscope objectives. The Olympus 10×/0.6NA multiphoton objective affords a large transverse field-of-view (1.02×1.02 mm) at a lower excitation NA (0.39) (top) while the Nikon 16×/0.8NA multiphoton objective compromises on the transverse field size (0.71×0.71 mm) in order to realize a more precise axial point spread function (PSF) (NA=0.56) (bottom). White contour lines document the graded multi-photon excitation efficiency as a function of field position. FIG. 18B: 160 target cells are identified as successful optogenetic stimulations (green) or unsuccessful (red) and used to map the success rate across the imaging field of view. Marginal projections of the spatially binned ratio of successful stimulation targets to the total number of targets are used to estimate the targeting efficiency across the field of view. FIG. 18C: 3D imaging with optogenetic photoexcitation is realized by use of a piezo-coupled microscope objective for imaging while the SLM volumetrically addresses cells for optogenetic stimulation simultaneously across the entire volume. During each frame acquisition (frames 1 to N), all SLMs are able to volumetrically address the sample across N axial image planes ($i_1$ to $i_N$). Because of the piezo movement, the constellation of optogenetic targets will be axially offset during each frame acquisition, requiring a compensating quadratic phase offset to the SLM phase masks for each axial position. FIG. 18D: The physiological response, as characterized by the percentage change in GCaMP fluorescence, when using a 15 µm diameter spiral for optogenetic photostimulation (9-spirals, 0.63 ms duration, as used in behavior experiments; n=10 neurons in vivo, mean response across 5 trials per stimulation location—the spiral was intentionally shifted from center of each cell by the defined lateral offset—randomized and interleaved, normalized to maximum for each cell, fit with a single gaussian function, error bars are s.e.m.). FIG. 18E: Empirical, axial optical PSF measurements of both the optical imaging beam (FWHM=9.6 μm, NAest=0.64) and an optogenetic stimulation beam (FWHM=21.4 μm, NAest=0.48) using the Nikon 16×/0.8 NA microscope objective in the MultiSLM microscope. Data collected by translating a ~3 μm thick fluorescent slide through a focused beam. Best-fit to the empirical measurements was calculated using the square of a Gaussian function. FIG. 18F: Representative adaptive optical correction to the SLM/optogenetic stimulation path as represented by Zernike polynomials. Application of the superposition of these polynomials as a compensatory phase mask results in the optimization of the optical PSF. The most significant aberrations are associated with astigmatism and possibly compensating for deformations across the face of the large-format SLMs. FIG. 18G: Optogenetic excitation of manually-selected targets with no known functional association, segregated by anatomical layer (L2/3 only, L4 only, L5 only, L2/3+L5), demonstrate positively responding neurons localized only in the anatomical layers associated with viral expression under the AAV8-CaMKIIa-GCaMP6m-p2a-ChRmine-TS-Kv2.1-HA construct. Averaged and normalized $\Delta F/F$ results from n=5 randomized trials across all four cases are presented in the lower row. The imaging conditions sample six planes, uniformly separated by 65 μm intervals across L23 to L5, and were held constant across all four stimulation conditions (which were randomly interleaved). Note that since little expression was localized to L4, the targets for that stimulation condition are generally not localized to cell bodies, but are used as a control for modulation of neighboring layers by the excitation light. FIG. 18H: To measure to axial localization of the photostimulation response across the entire sampled volume, fluorescence modulations where quantified from every exclusive set of 8×8 pixel ROIs throughout the image acquisition volume. They are then organized according to sample depth during image acquisition and then aligned by the conditions in FIG. 18G. Optogenetic modulation is measured by the d' (the difference in the mean number of counts acquired during photostimulation versus baseline, divided by the average of the standard deviation in counts of both time epochs) of each 8×8 pixel ROI. Supporting evidence that the optogenetic targeting is axially/anatomically localized is seen in the first, third and fourth columns where significant responses are isolated to L2/3, L5 and L2/3+L5, respectively. Conversely, when the same amount of optogenetic stimulation light is delivered to L4, no significant modulation is observed in the layers above or below. Whatever modulation is observed in L4 may be attributable to fluorescence modulation in the apical dendrites from L5.

Figure 19:
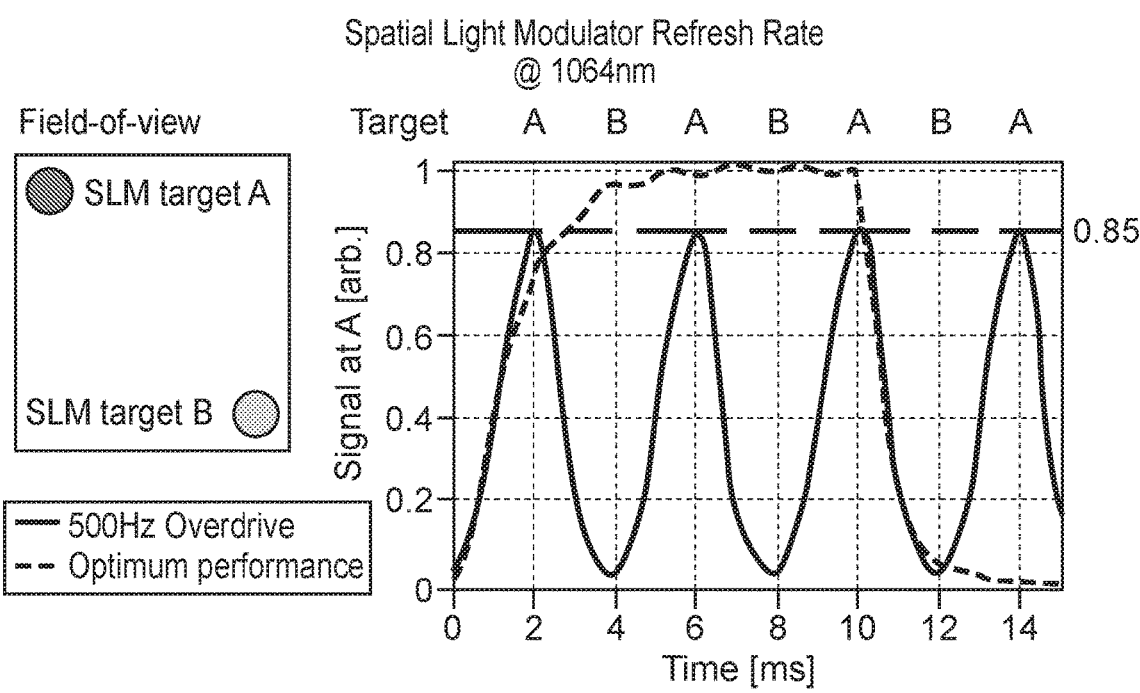
Figure 19:
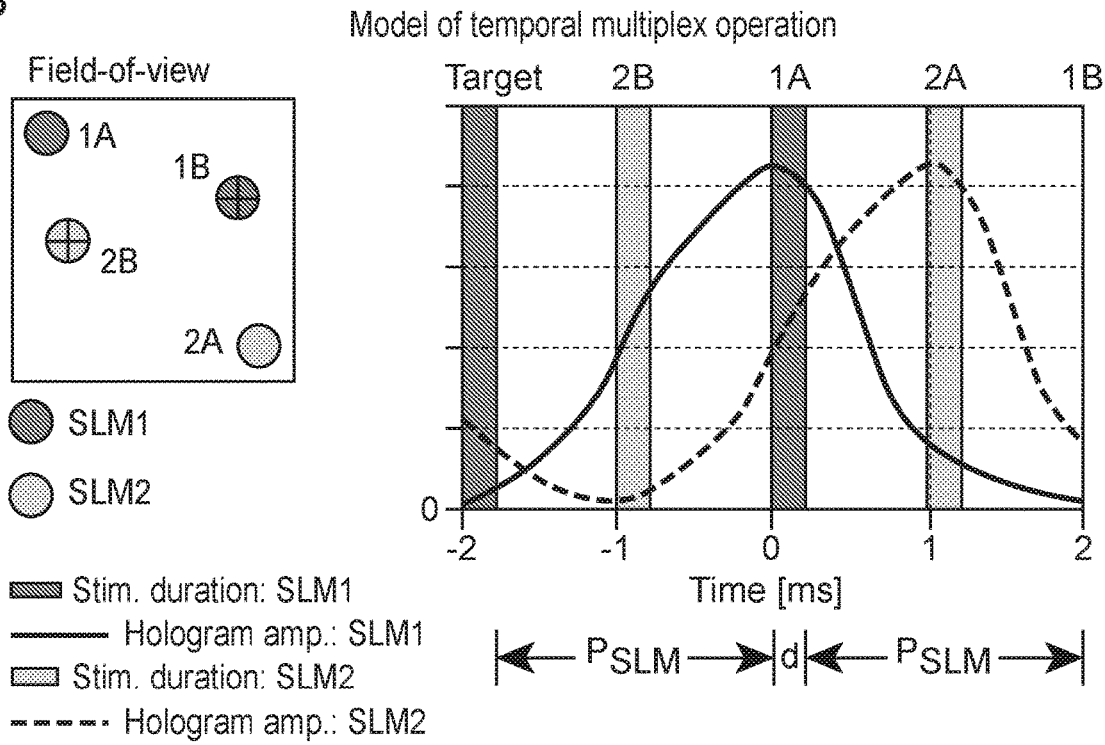
Figure 19:
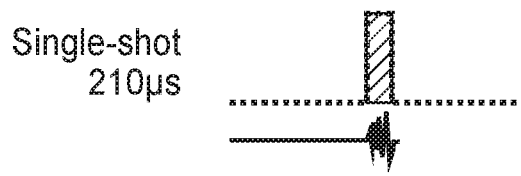
Figure 19:
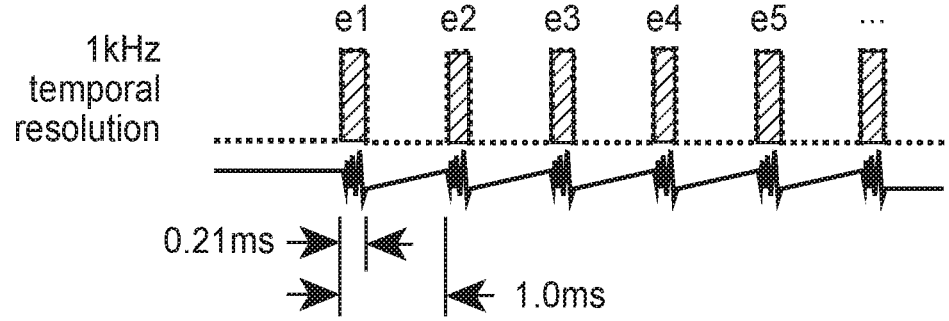
Figure 19:
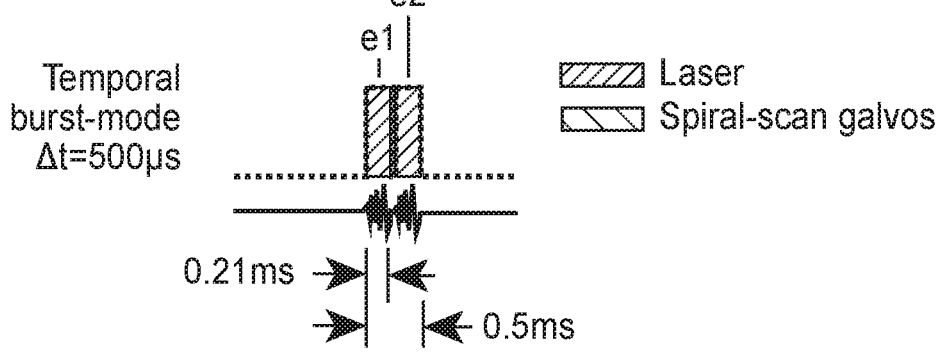
Figure 19:
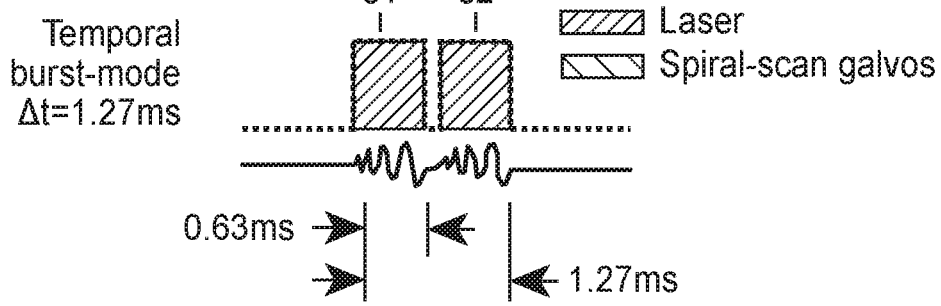

FIG. 19, A-F depicts temporal precision of the MultiSLM. FIG. 19A: The maximum refresh rate of the large-format SLM is benchmarked at optimum diffraction efficiency (and slow refresh rate, red) in comparison to the operation using software overdrive at 500 Hz (blue) by placing a photodiode at the target A position. Alternating between holograms which alternatively place a spot at position A and alternative positions (e.g., position B) reveals that 85% of the optimum performance can be realized at a 500 Hz switching rate. Note, the measurement is at $\lambda$=1064 nm, in the wavelength range where we plan to operate, since LC response is often more than 3× faster at visible wavelengths. FIG. 19B: A diagrammatic description of the temporal interleaving sequence using multiple SLMs. As each target/group hologram is exposed (e.g. solid bar SLM1/target 1A@t=0 ms), the alternate SLM is already constructing the next hologram (e.g. dashed-line SLM2/target 2A@t=0 ms). The maximum temporal resolution of a single SLM is limited by the sum of the SLM rise time ($P_{SLM}$) and optogenetic exposure time (d; see Supplementary Text). FIG. 19C: The MultiSLM with ChRmine technology allows significantly faster ensemble stimulation paradigms than previous studies. For example, a single hologram must be maintained for 5 ms duration to drive a spike. We report exposures driving spikes in cell ensembles (i.e. e1) at 0.21 ms durations with spiral-scanning galvanometers across the cell membrane. FIG. 19D: Exploiting the fast optogenetic exposure and SLM dynamics, as well as temporal interleaving of multiple SLMs, results in a lower practical limit of 1.79 ms rise times and 0.21 ms exposures for a 1 kHz temporal resolution spike train for neuron ensembles e1-eN. (FIGS. 19E, 19F) For a multiple SLM system, the system may run in a burst-mode where the interval between two successive ensembles, addressed by SLM1 and SLM2 respectively, can be continuously variable, down to the switching time of the Pockels cell (<50 μs). Note that all behavior optogenetic stimulation protocols in FIG. 3-6 were operated using condition FIG. 19F: with a switching time of 100 μs.

Figure 20:
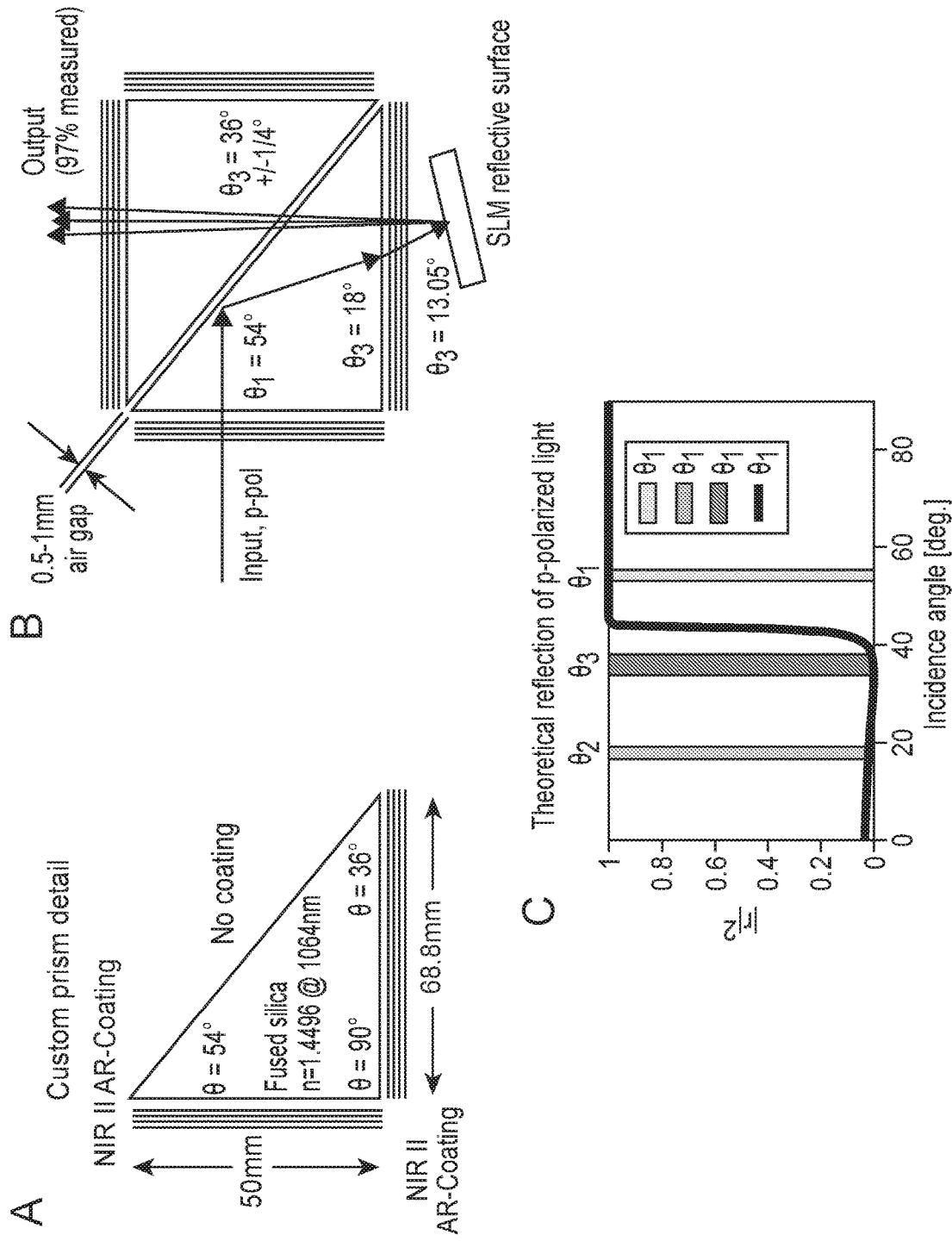
Figure 20:
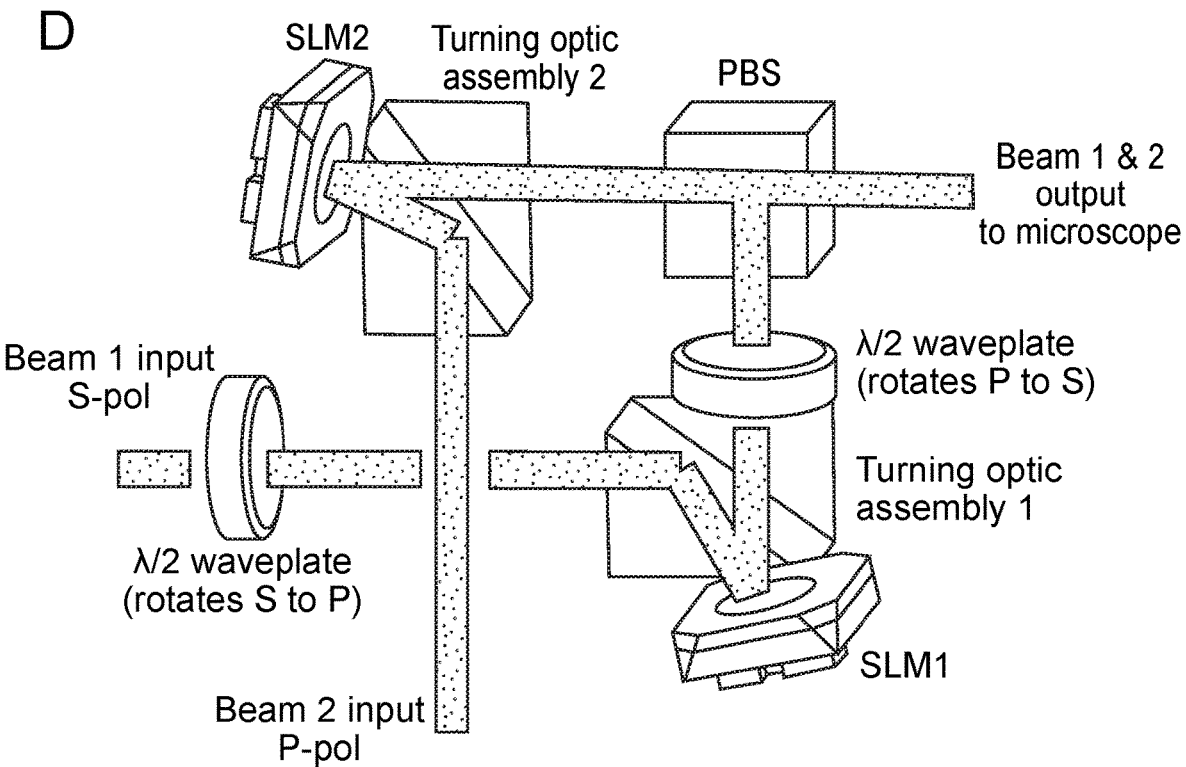
Figure 20:
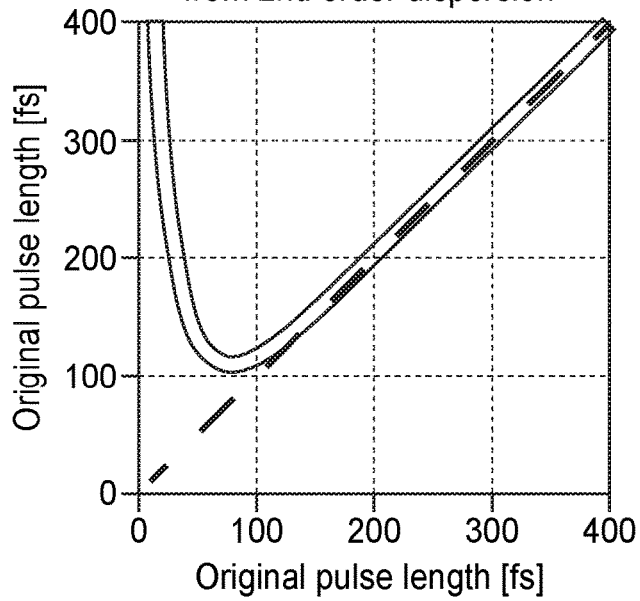
Figure 20:
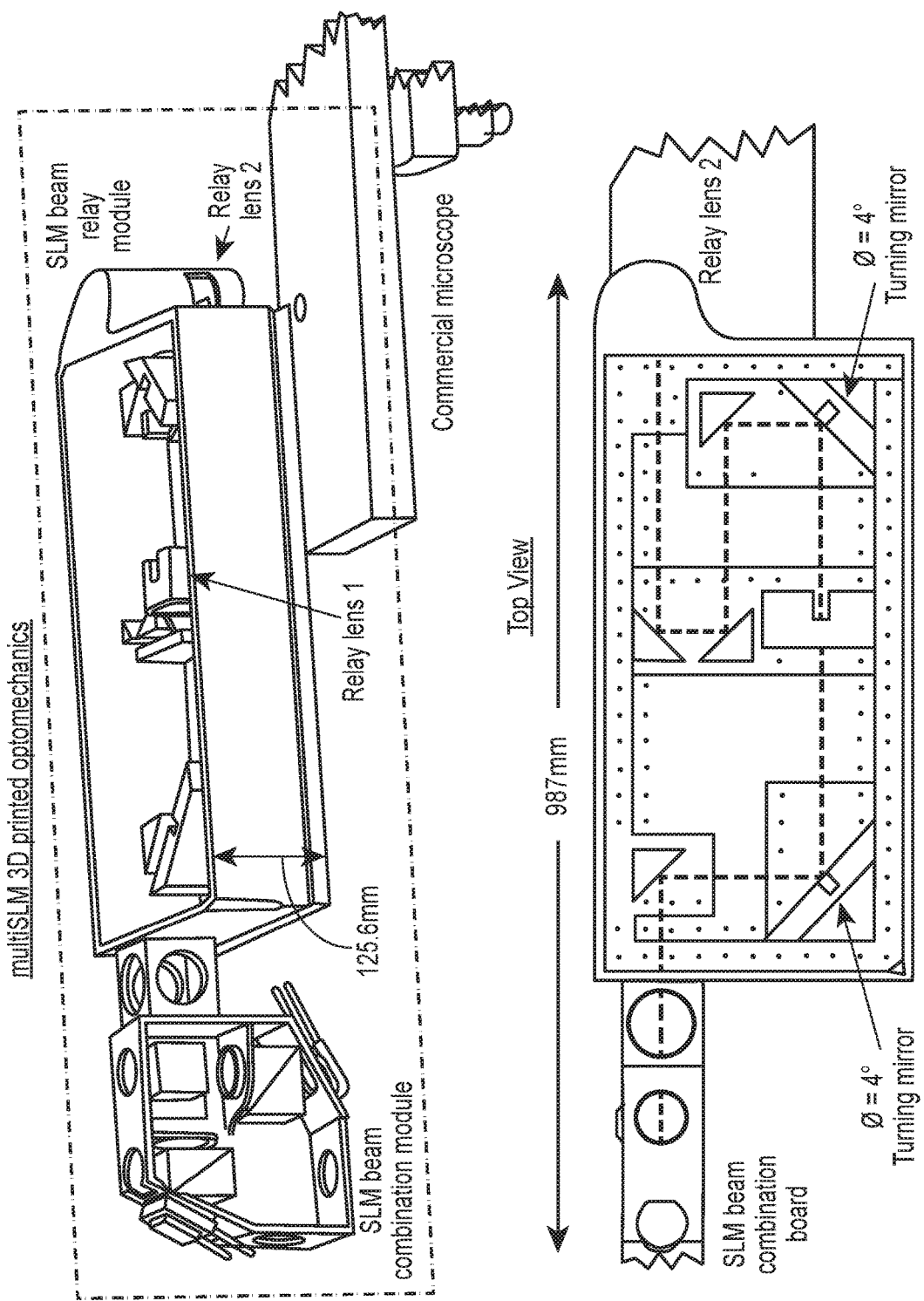

FIG. 20, A-F depicts optomechanics for MultiSLM. The MultiSLM microscope utilizes a novel beam folding approach and 3D printed optomechanics to minimize size and promote mechanical stability. FIG. 20A: A custom 36°-54°-90° prism was manufactured (Edmund Optics) of fused silica and anti-reflection (AR) coated on two faces to minimize air-to-glass interface reflections. FIG. 20B: A pair of prisms, separated by an air gap, are used to redirect a P-polarized input beam to an SLM and to have the SLM output beam exit at a 90° angle, with minimal optical loss (97% throughput measured using a mirror as a proxy for SLM backplane). Note the three specified angles ($\theta_1$, $\theta_2$ and $\theta_3$) are all related to the angle of the beam when propagating from the fused silica into the associated air interface. FIG. 20C: The specific angles of the prism were chosen to allow beam propagation through the turning prism assembly which is aligned to the peak and minimum Fresnel reflection coefficients ($|r|^2$=0 is total transmission, $|r|^2$=1 is total reflection) in order to allow maximum photon efficiency. The specific angles highlighted with a gray-scaled bar are associated with the angles identified in FIG. 20B. $R_{fs\text{-}air}$ is the theoretical scalar coefficient of reflected intensity (e.g., the reflection coefficient of the first interface $\theta_1$, from the fused silica to the air-gap, is 1—indicating total reflection). FIG. 20D: Two turning optic assemblies are utilized, along with beam polarization optics, to co-linearly combine the SLM outputs from a pair of input beams. Half-waveplates are utilized to control the light polarization for maximum transmission through the system. FIG. 20E: Pulse propagation through di-electric material (e.g. glass) can induce a chromatic phase delay which leads to pulse broadening, and therefore less efficient multi-photon excitation. Theoretical modeling of femto-second pulses from the light source as it propagates through these turning prisms (118.8 mm of fused silica, blue curve) indicates that while sub-100 fs pulses would experience significant pulse broadening, minimal pulse broadening is expected using the current optogenetic stimulation light source (nominally between 250 and 300 fs). FIG. 20F: 3D printed optomechanics are used to mount and align the MultiSLM optogenetic path to the commercial microscope. Two distinct optomechanic groups represent the complete set of 3D fabricated parts—the SLM beam combination module and the SLM beam relay module. The SLM beam combination module provides convenient reference points to align and secure the SLMs as well as the beam turning prisms and polarization optics. The MacroSLMs were designed to use the mechanical face of the external SLM mount as a flush and parallel mount to the combination module using 4-40# cap screws. The prism pair are kept parallel to each other and normal to the incident beam by reference groves in the seating of the 3D printed module. The SLM combination module mounts to the beam relay module by use of cap screws and/or Thorlabs cage railings in order to provide a reliable alignment. Within the beam relay module, the optical path is folded by use of 50 mm leg right-angle mirrors and 100 mm circular mirrors to ensure that zero beam vignetting occurs on this smaller footprint. Each 50 mm leg right-angle mirror has guide-points along each leg for precise placement on the 3D printed footings which directly bolt to a 12"×24" Thorlabs breadboard using the 1" hole-spacing. The custom beam relay lenses were aligned and mounted in custom 3D printed optomechanics within the module. By referencing to the 1" grid system of the breadboard, and keyed to other 3D printed components on the board, the relative positions of the two lenses could be readily optimized to ensure precise alignment and telecentricity. Note, both the relay lenses could be rapidly removed from the system to test or verify alignment using these custom opto-mechanics.

Figure 21:
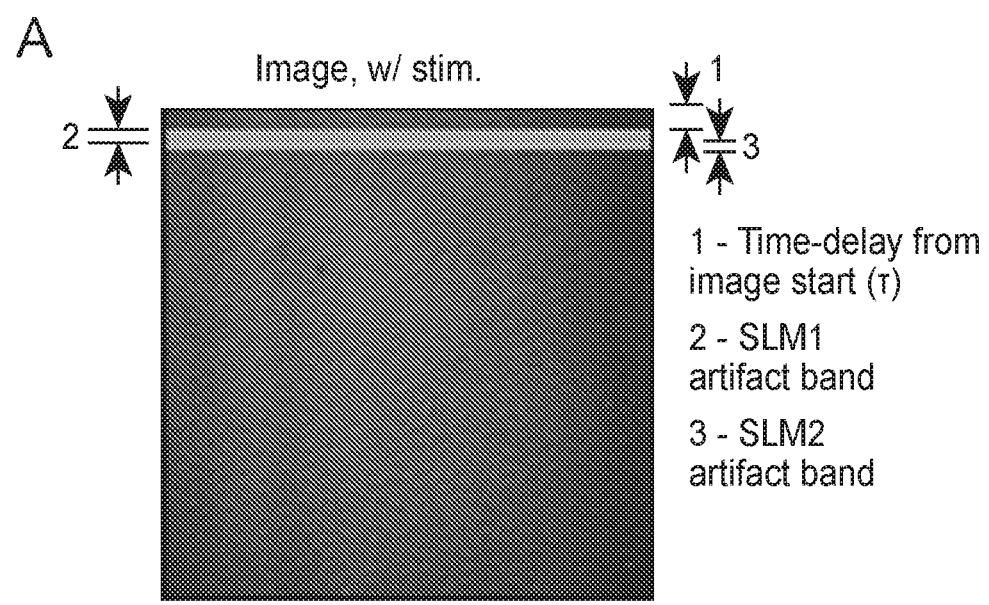
Figure 21:
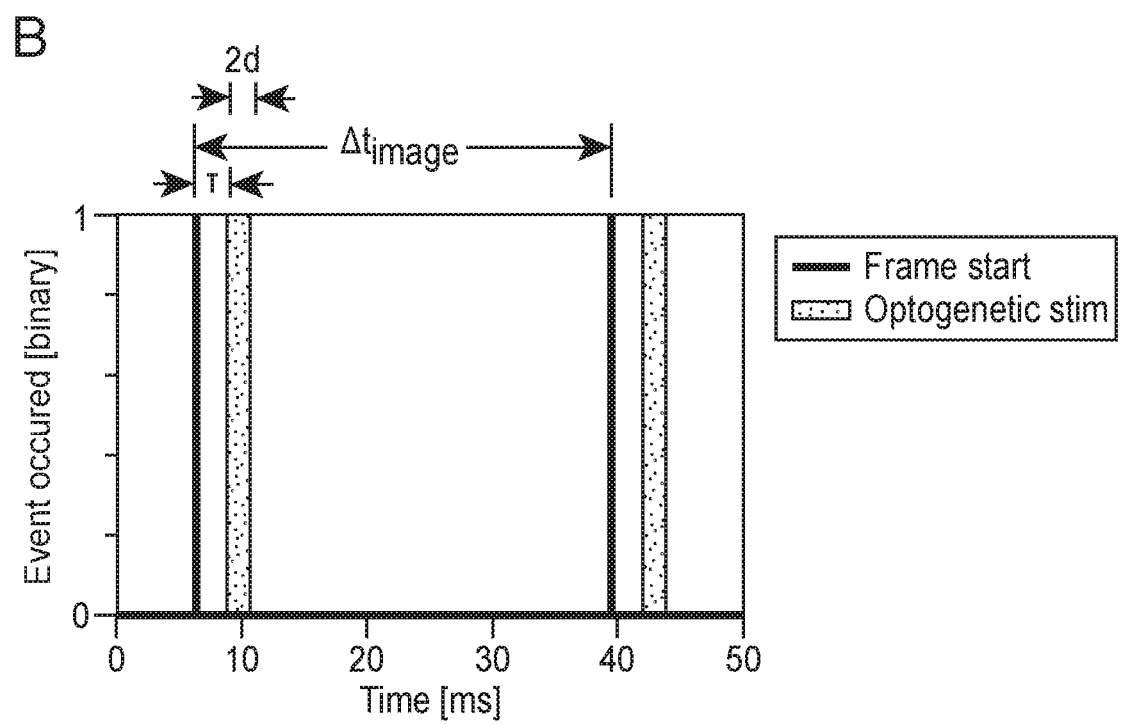
Figure 21:
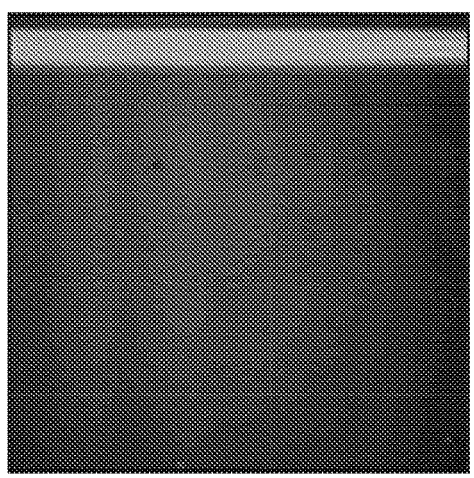
Figure 21:
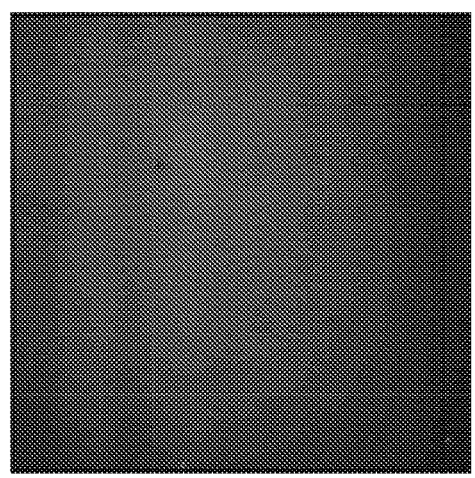
Figure 21:
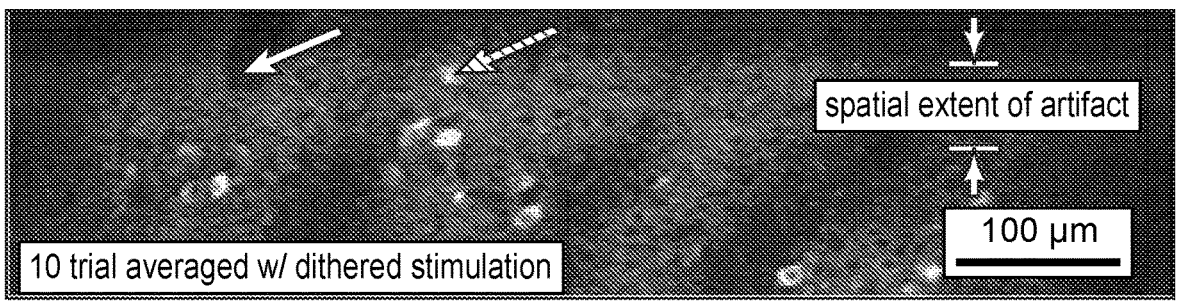
Figure 21:
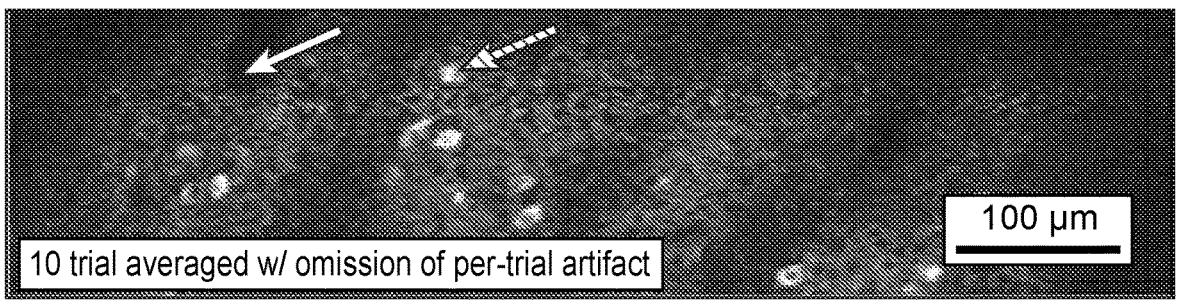
Figure 22:
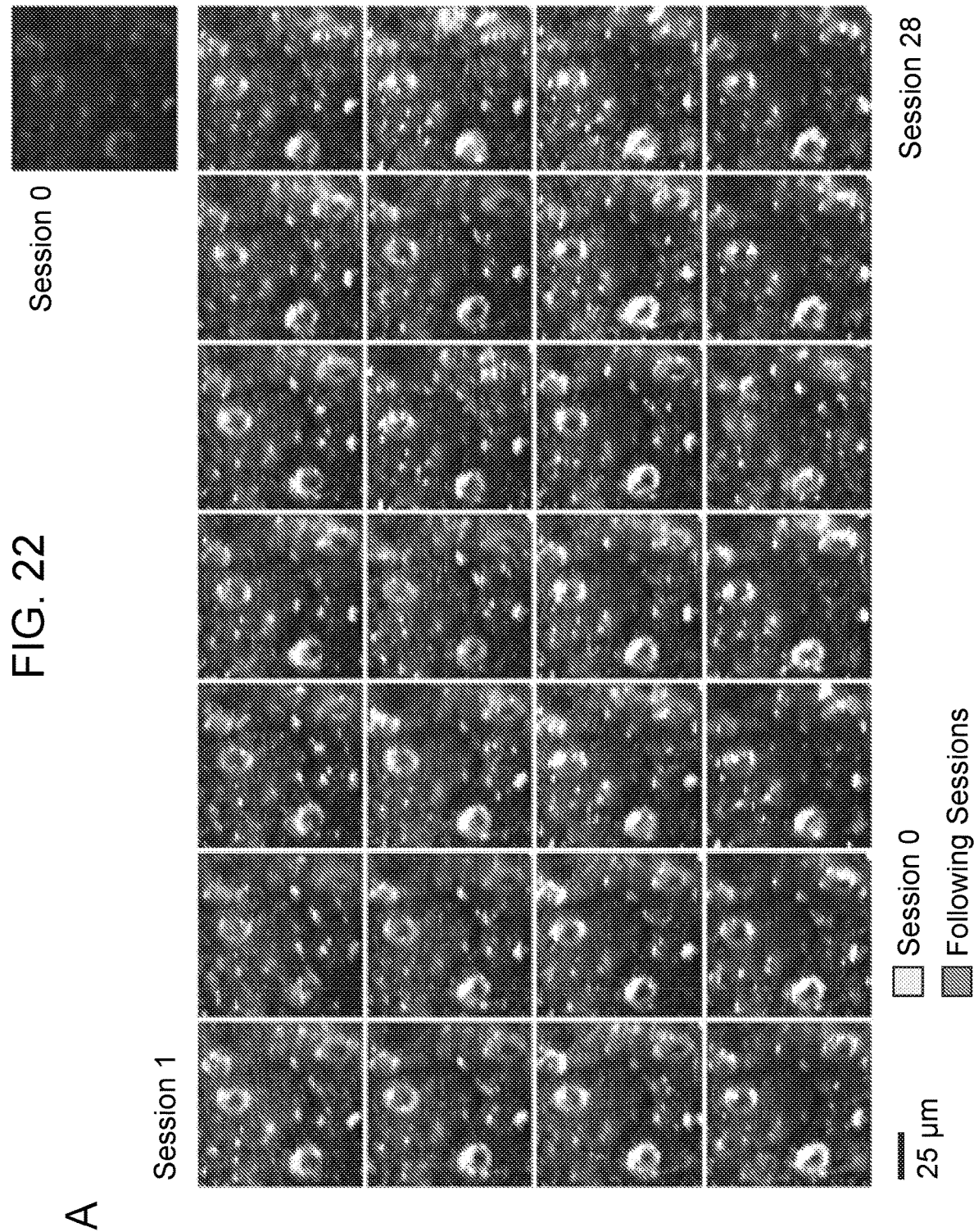
Figure 22:
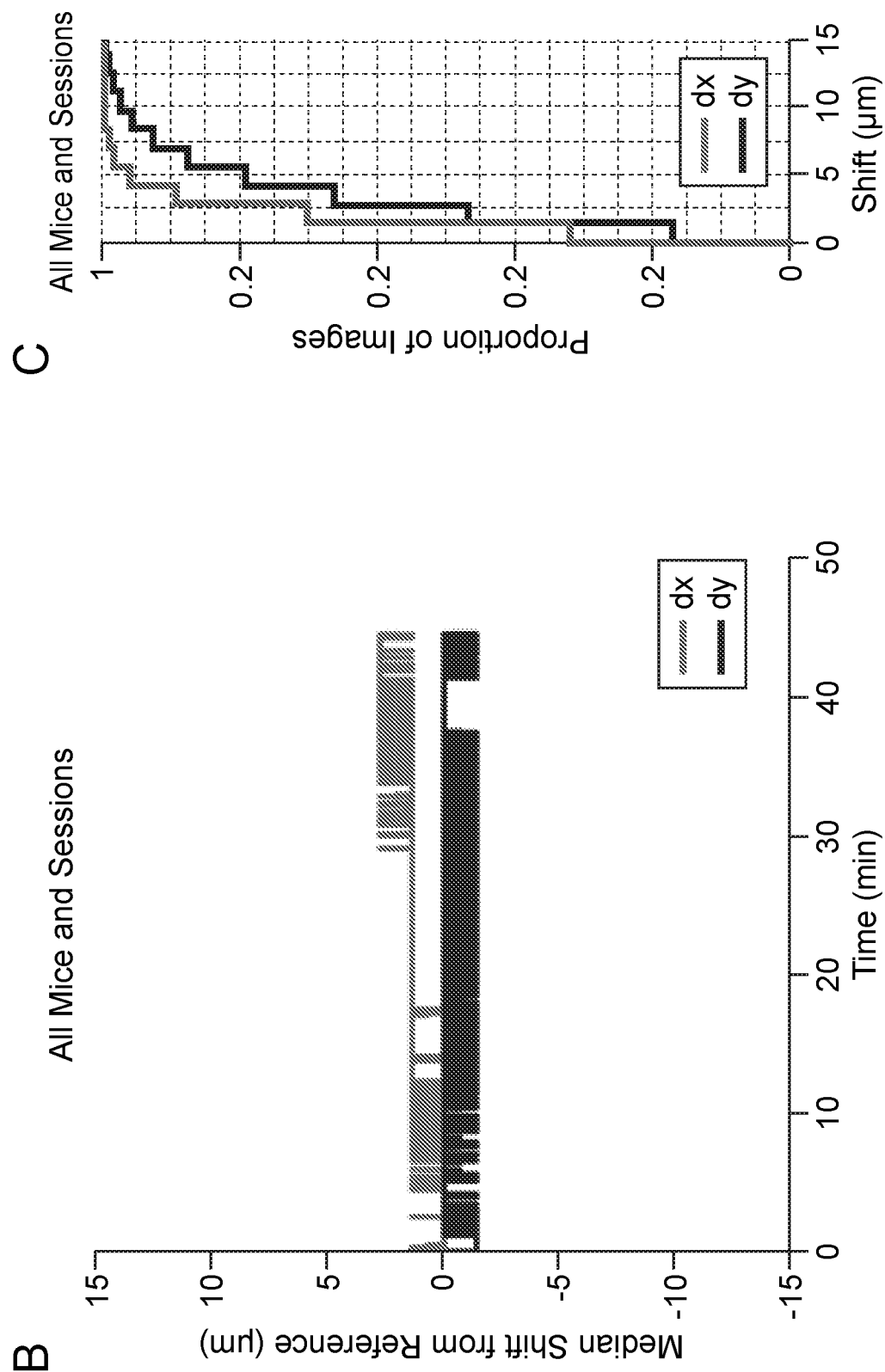

FIG. 21, A-E depicts removal of photostimulation artifact in imaging channel of MultiSLM. FIG. 21A: Targeted excitation of the opsin-fluorophore expressing neurons at $\lambda=1035$ nm results in a spatial block of pixels with increased background signal from co-excitation of the GCaMP6m reporter (here a bulk fluorescent slab serves as a phantom proxy), where the width of the artifact block is directly related to the excitation duration width. Note that optogenetic stimulation of each ensemble will result in an individual artifact band of width proportional to the ratio of the photostimulation duration (here 0.63 ms) to the imaging line-scan time (here, typical is 64.9 μs). Shown here are two ensemble stim artifacts, $e_1$ (SLM1) and $e_2$ (SLM2), analogous to FIG. 19F and the protocol applied in vivo. FIG. 21B: Random offsets of the trial time ($\tau$), where $\tau \in \{-d, 0, +d\}$ and d is the optogenetic exposure duration, diversifies which image pixels which will have a photostimulation artifact. Representative recording of the optogenetic stimulation onset and frame start (where $\Delta t_{image}$ is frame acquisition time) which is used to track the relative timing and therefore the pixels which are contaminated by the artifact. FIG. 21C: Trial mean intensity image taken from 10 trials of 30 Hz stimulation with trial-to-trial temporal shifting (dithering) of the onset ($\tau$). The randomized onset shift broadens the artifact on average but the diversity provides artifact-free access to every pixel for at least ⅓ of trials. FIG. 21D: Result from artifact removal in the trial mean intensity image by omitting all pixels with artifact from the average on a per trial basis. FIG. 21E: Comparison of this artifact removal in vivo. Top: Mean intensity image (one time-point averaged from 10 trials) when including the temporally shifted photostimulation artifact. Bottom: Mean intensity image (same time-point as above) when omitting the pixels associated with photostimulation artifact on a per trial basis. Areas representative of the increased contrast as a result of removing the additive photostimulation artifact are highlighted (cyan and red arrows). Note a Kalman filter (gain=0.8, noise=0.05) was applied to the time-series data after the artifact removal. All stimulation artifact fluorescence was completely removed from analyses of visual experiments by excluding artifact-contaminated pixels FIG. 22, A-C depicts targeting the same ensembles across weeks with cellular resolution. FIG. 22A: The same population of neurons is revisited for many weeks (29 sessions spanning 54 days) by precisely aligning the MultiSLM imaging/optogenetic volumetric stimulation systems to the original field of view (shown is a region of interest in layer 5 with 4 labeled cell bodies; overlay: green, original imaging session, magenta, each subsequent session of imaging and optogenetics). (FIGS. 22B, 22C) Alignment is maintained online during the experiment using a real-time cross-correlation algorithm to compensate for the shift between the instantaneous image and the reference image (from day 0) for each slice through the volume (Materials and Methods). FIG. 22B: Shift relative to the reference image over the duration of the experiment (dx, blue; dy, red; median data are plotted across 9 mice, optical z slices and sessions). FIG. 22C: Shifts relative to reference image for all images (dx, blue, dy, red; 95% of all shifts were <8.34 μm (dx) and <4.17 μm (dy); ~2.5 million image shifts from reference across 9 mice from all optical z slices and sessions).

Figure 23:
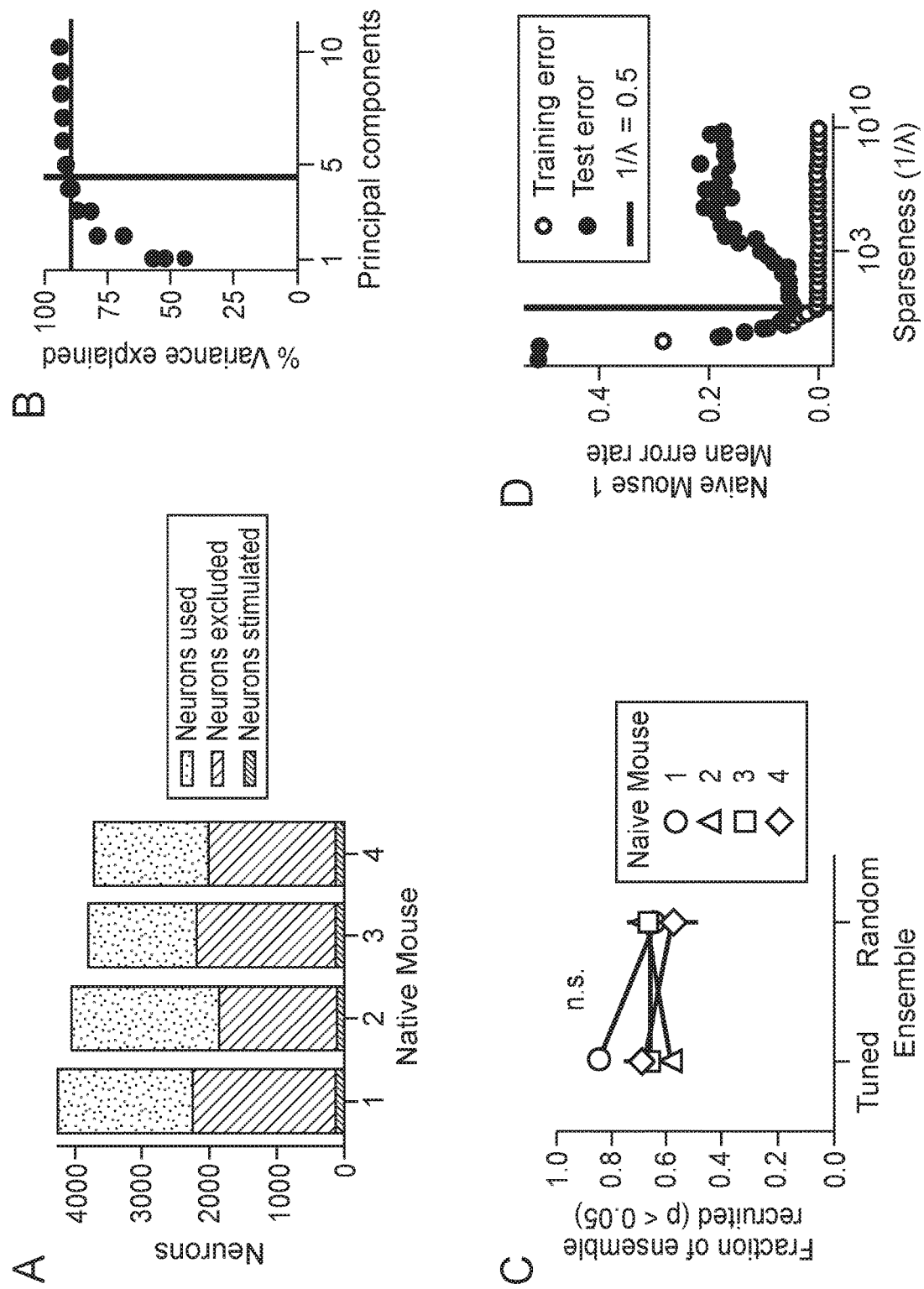
Figure 23:
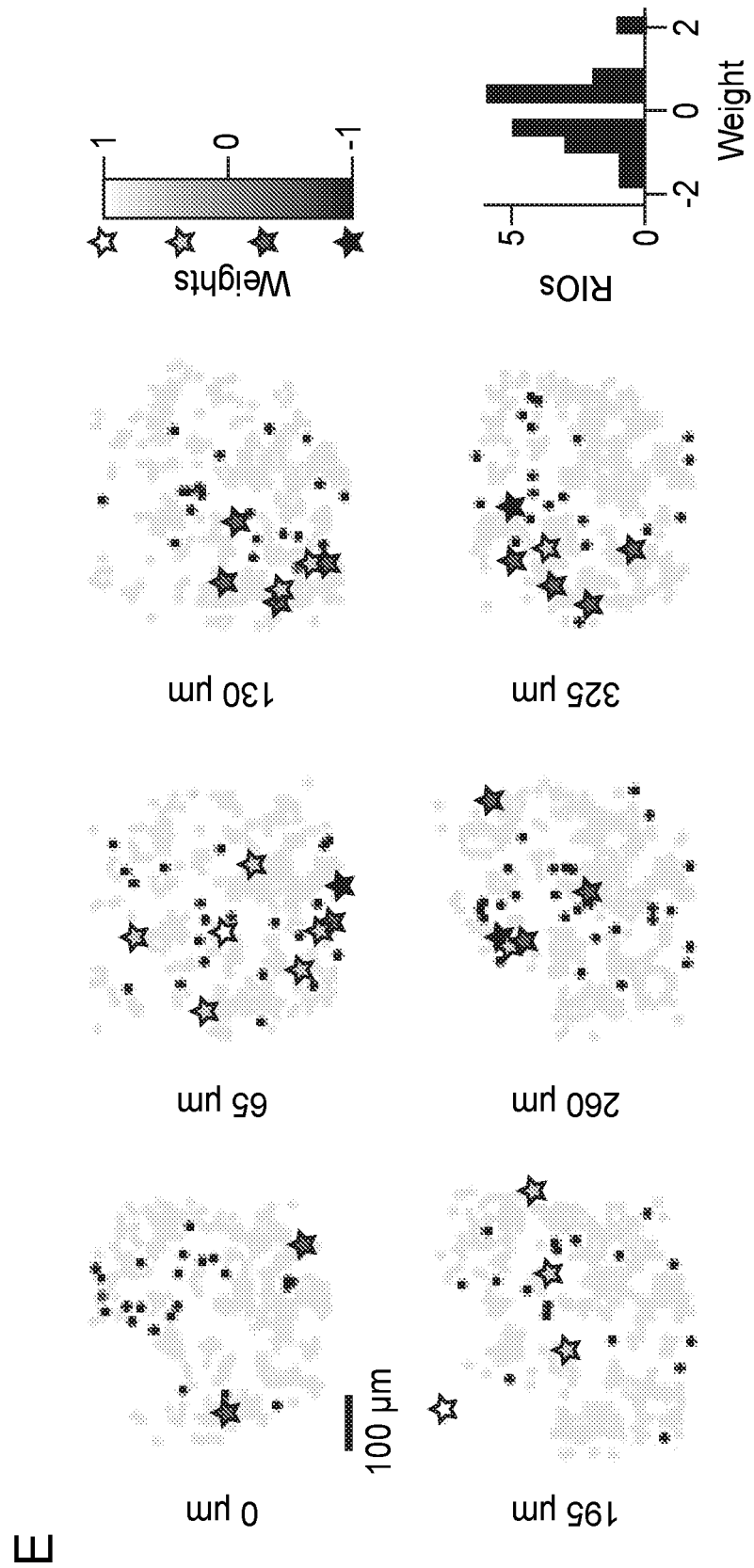
Figure 23:
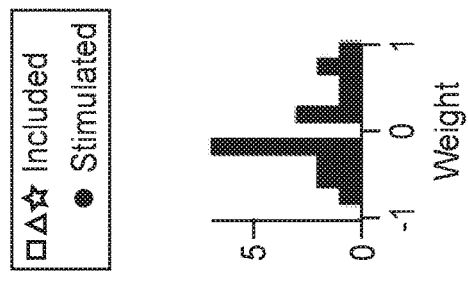
Figure 23:
Figure 23:
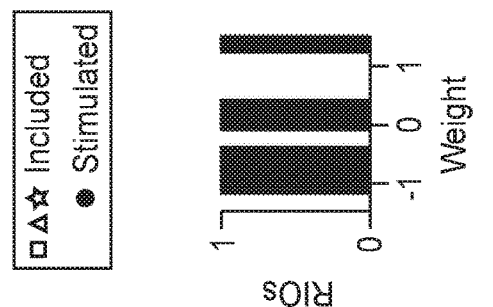
Figure 23:
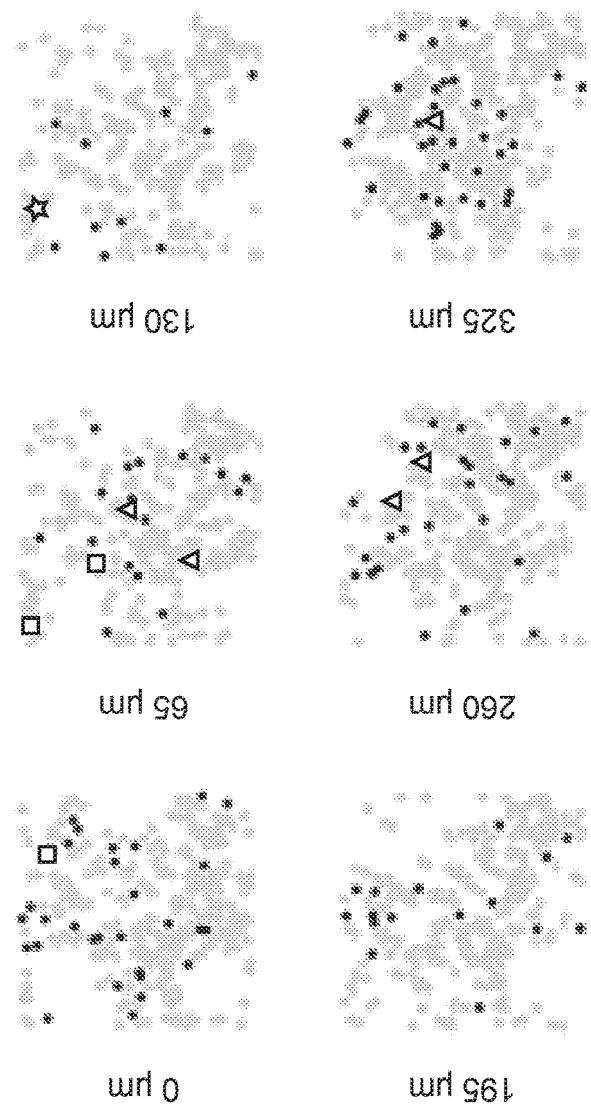

FIG. 23, A-K depicts parameter estimation for classifier analysis of behaviorally naïve mice. FIG. 23A: Bar graph indicating the fraction of all imaged neurons that were used for classifier and neural trajectory analyses (neurons used are termed "unstimulated neurons"). FIG. 23B: Plot indicating cumulative variance explained by increasing numbers of principal components as applied to the unstimulated neuronal traces during visual stimulus presentation. Results shown for four mice. Horizontal red line is at 90%. The vertical red line indicates that five principal components are necessary to explain at least 90% of the variance in all four mice. FIG. 23C: The fraction of optogenetically stimulated tuned (left) and random (right) neurons that were significantly modulated by light is shown for n=4 naïve mice using 60 stimulation trials/neuron (using conservative metrics; see Materials and Methods). A paired t-test pooling across mice revealed no significant difference between these two distributions (p=0.48). FIGS. 23D, 23F, 23H, 23J: Classifier performance shown for four behaviorally naïve mice as a function of the number of neurons with classifier regression weights equal to zero increases (which increases as a function of the parameter $1/\lambda$). A constant value ($1/\lambda=0.5$) was used across all four mice. We found that this value approximately minimized each model's prediction error on held-out test data (that was not used for training). FIGS. 23E, 23G, 23I, 23K: Spatial map of all ROIs extracted across six cortical depths shown for four naïve mice. Black dots (targets) were excited by 2P illumination in at least one experimental condition. Excluded ROIs (not shown, but counted in Panel A) were within 20 microns of a target ROI at some depth or were contaminated by a 2P-induced stimulus fluorescence artifact and were excluded from the classifier analysis. Remaining ROIs (colors) were used for classifier analysis. Right histograms show weight values for ROIs that had weights>10% of the maximum weight obtained by any ROI. Scale bar is 100 μm.

Figure 24:
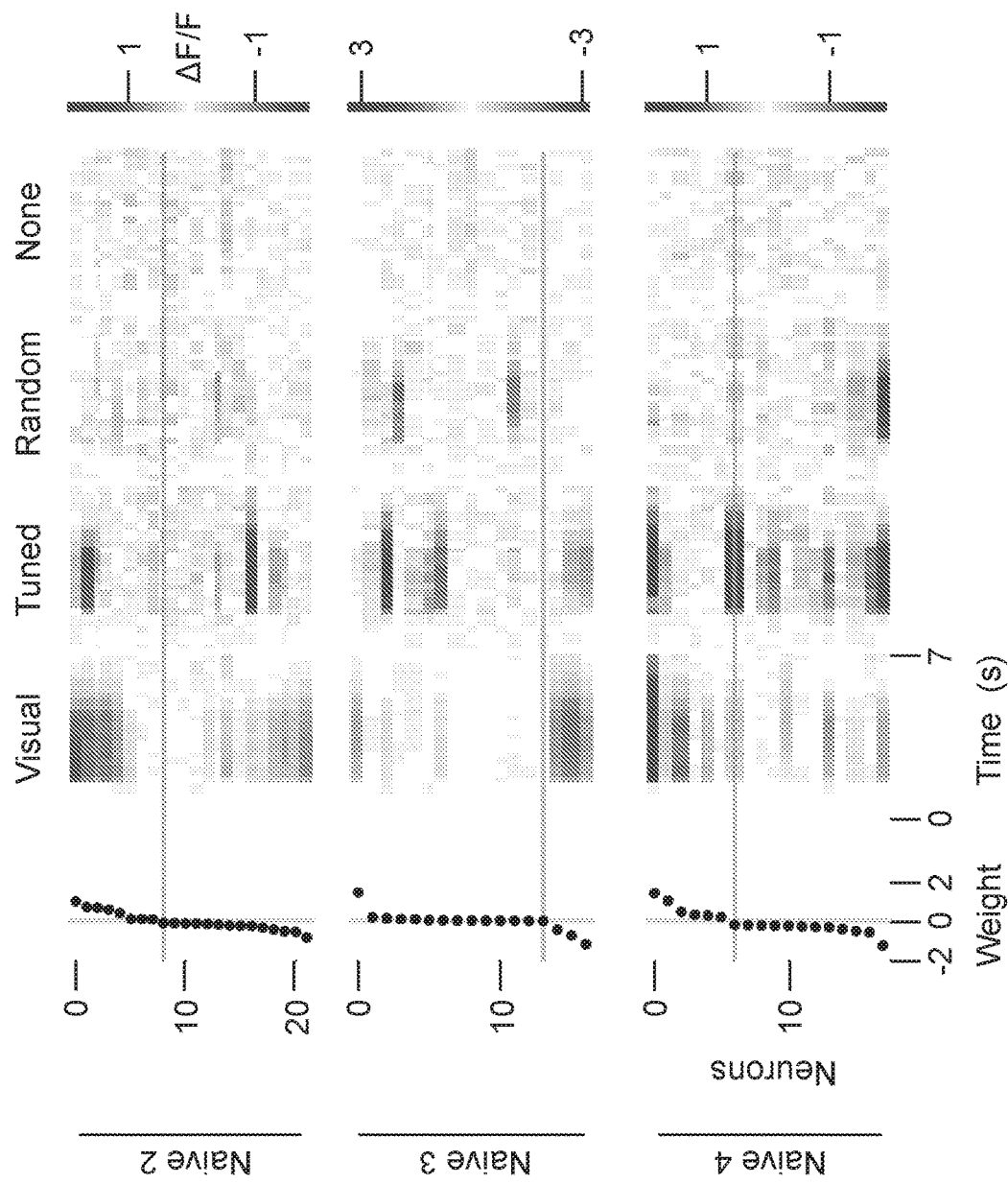

FIG. 24 depicts neural selectivity of additional behaviorally naïve mice. Each row shows the trial-averaged fluorescence response of a neuron during the 0° visual stimulus minus its response during the 90° visual stimulus (or matched optogenetic stimulus) for all neurons with large classifier weights (defined as abs(weight)>99th percentile). This analysis is shown here for three naïve mice not shown in the main text. Dots on the left-hand side of each row indicate the classifier weight of each neuron. Blue indicates neural responses preferential to the 0° condition, red responses were stronger for the 90° condition.

Figure 25:
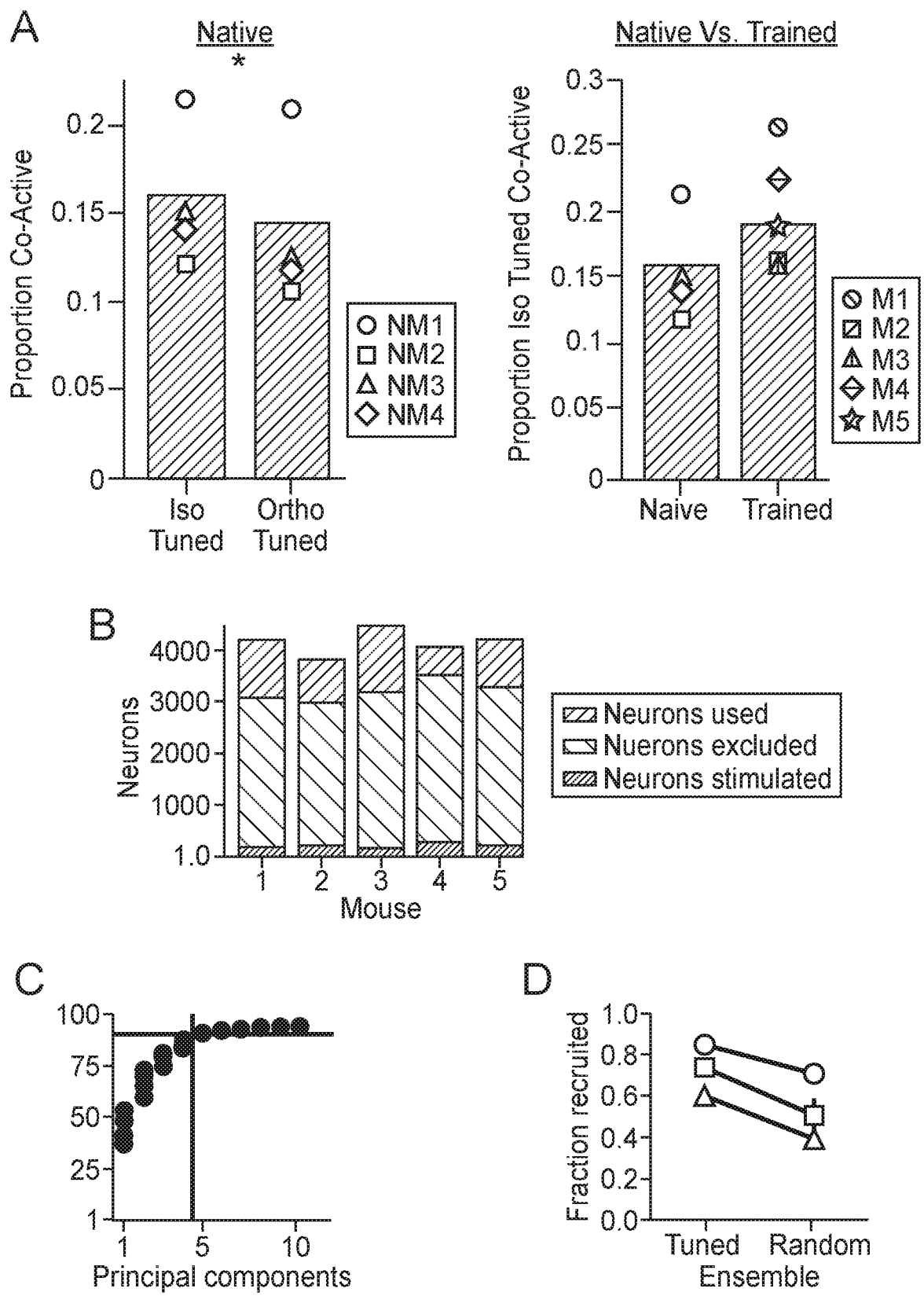
Figure 25:
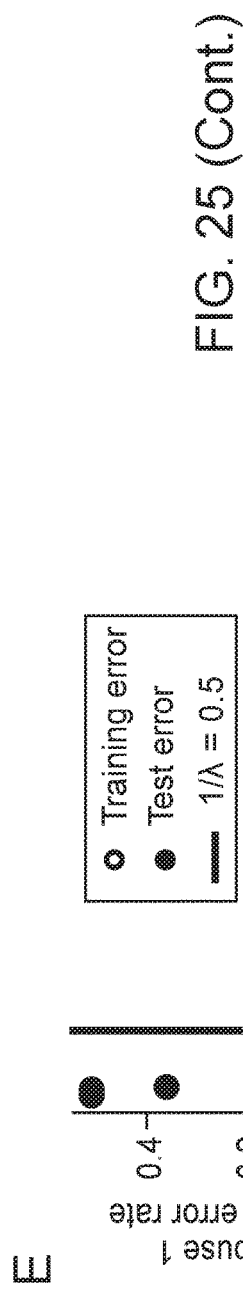
Figure 25:
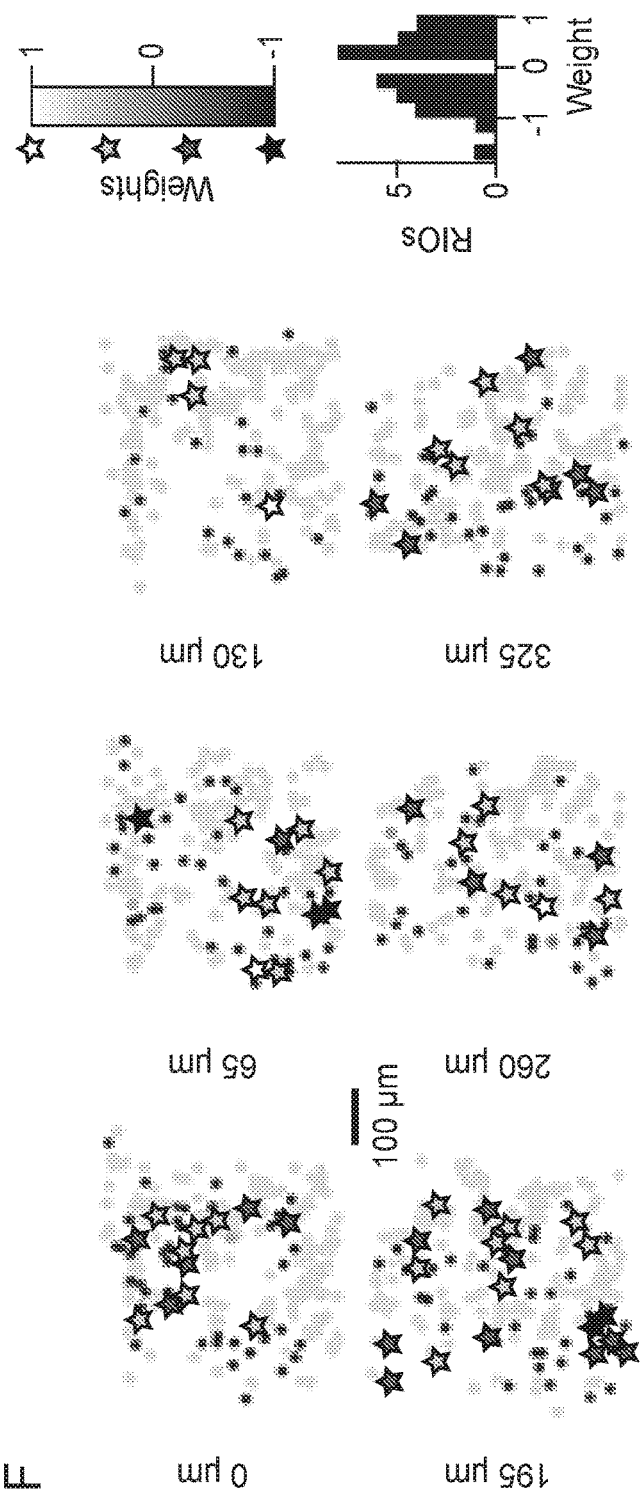
Figure 25:
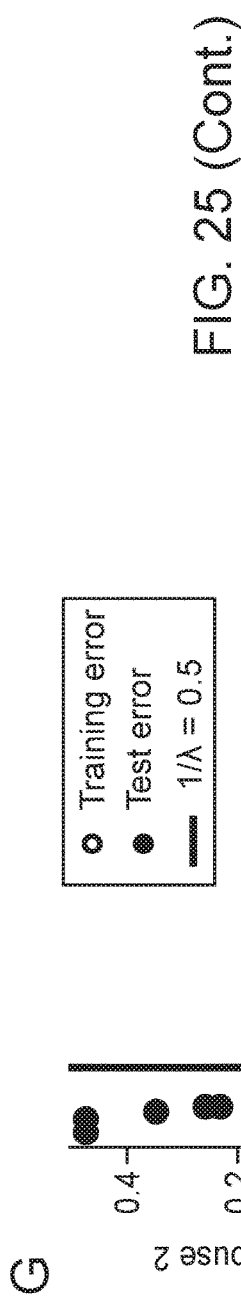
Figure 25:
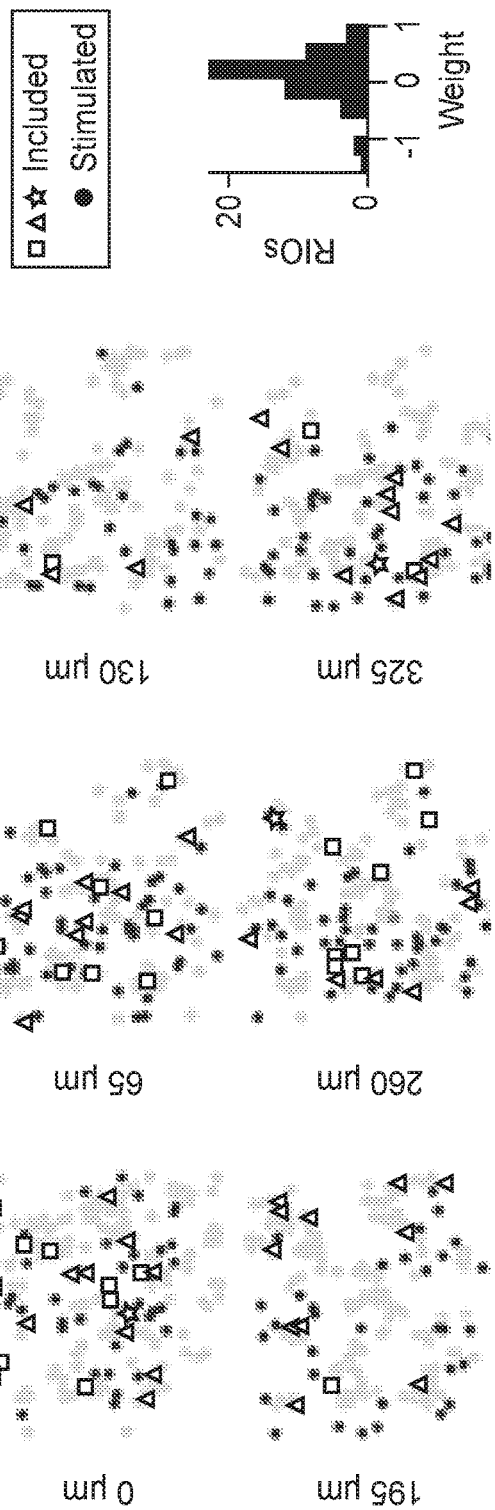
Figure 25:
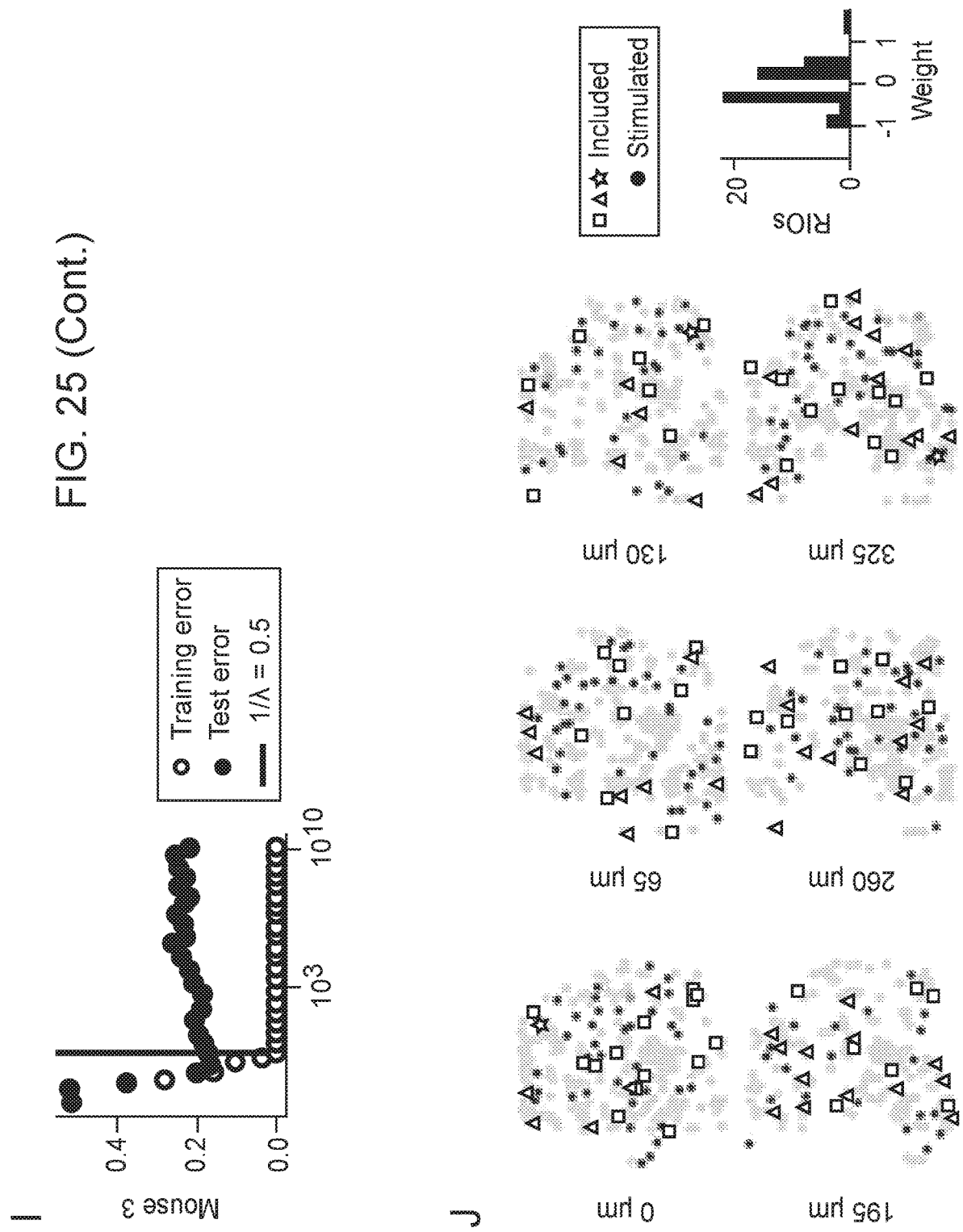
Figure 25:
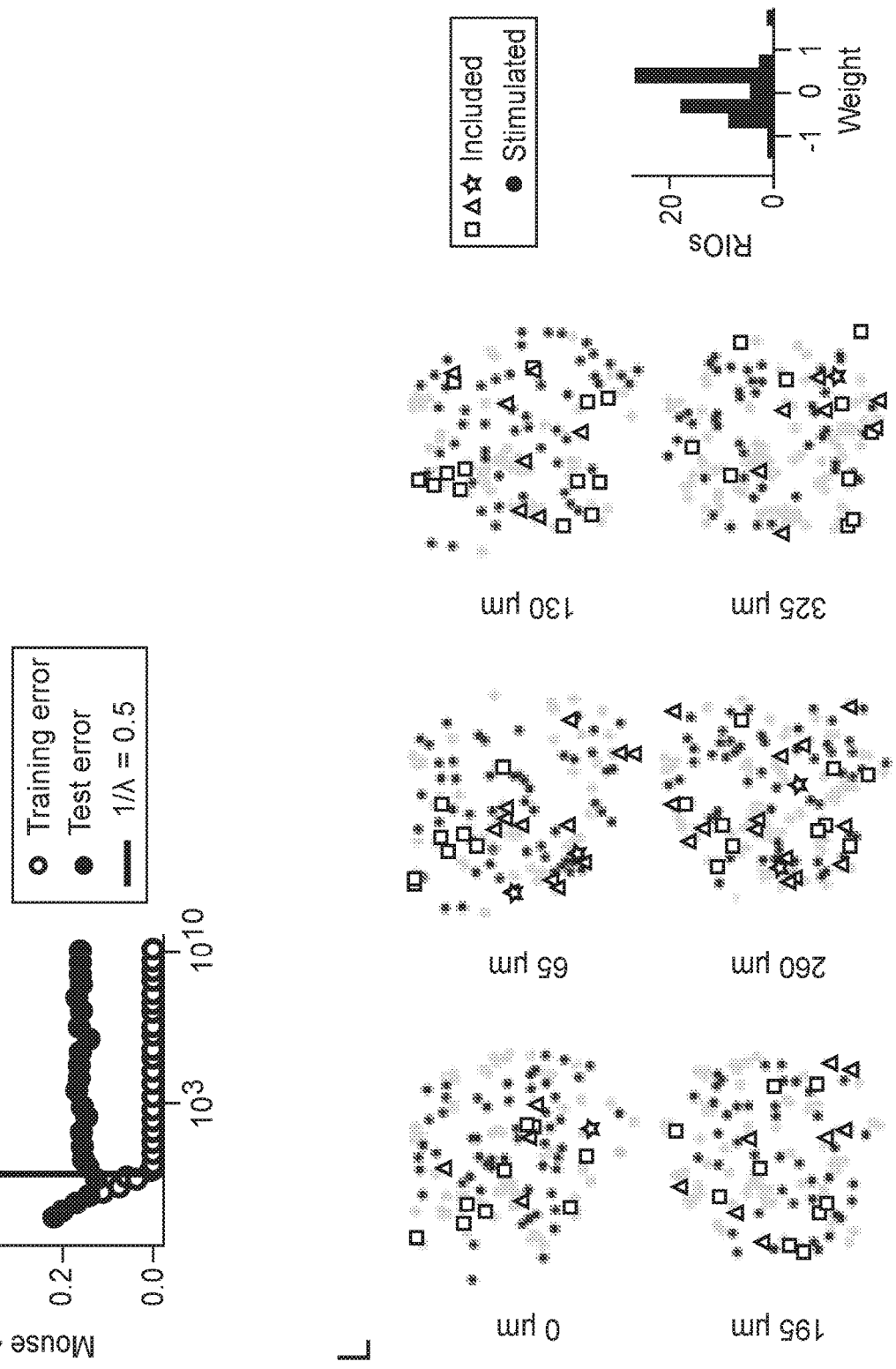
Figure 25:
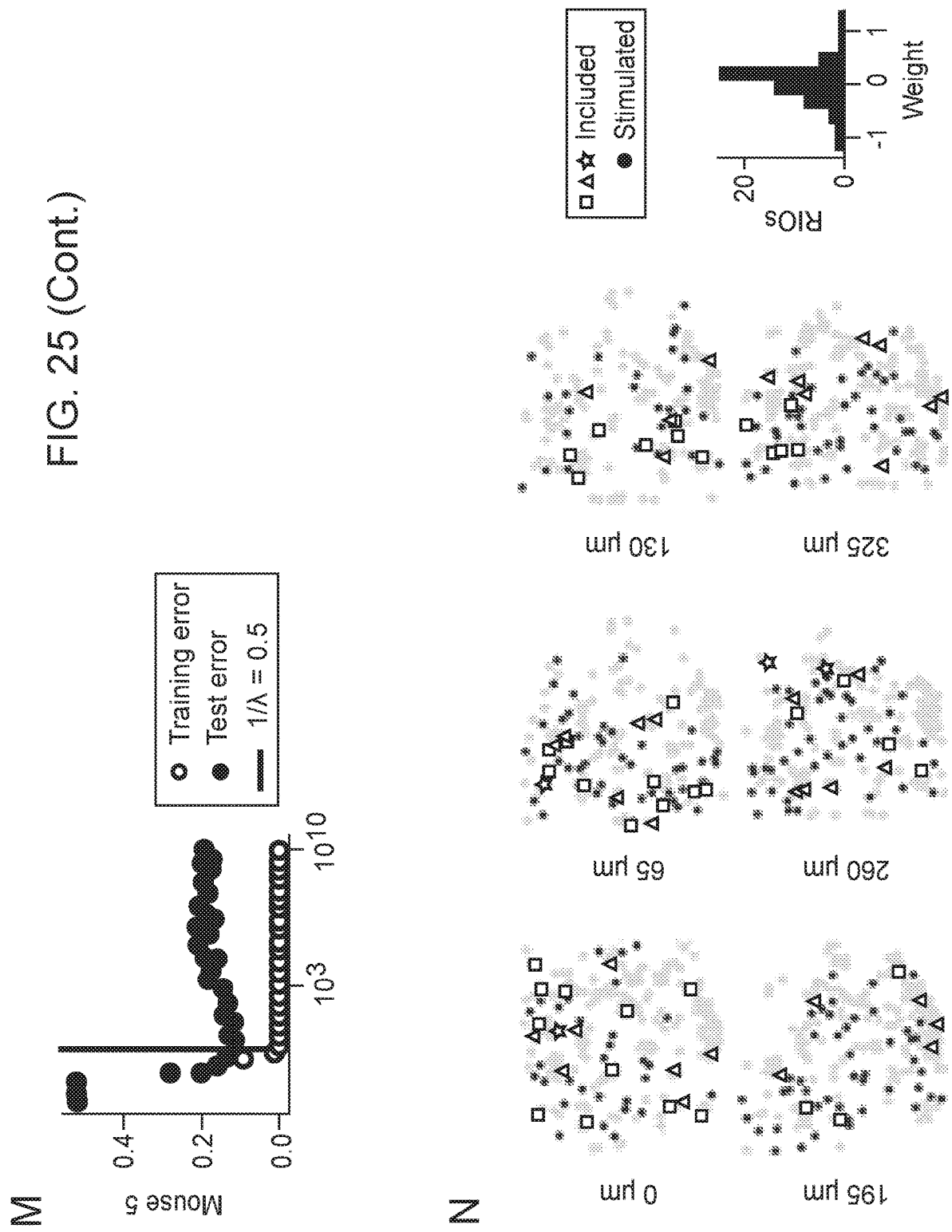

FIG. 25, A-N depict parameter estimation for classifier analysis and tuned visual network recruitment in behaviorally trained mice. (FIG. 25A, left) Among the non-targeted cells in naïve mice, both iso-tuned and orthogonally-tuned neurons are secondarily recruited during tuned ensemble optogenetic stimulation, with a modest preference for iso-tuned in the absence of visual stimuli, (p<0.05, $\chi^2$ two tailed test). Data are pooled across sessions and mice for bars and statistics (n=25 sessions in 5 mice; co-active neurons are found by two-tailed Wilcoxon signed-rank tests, p<0.05, sample window vs. baseline, Materials and Methods). (FIG. 25A, right) Recruitment of iso-tuned populations is enhanced with training on the visual discrimination task (p<0.05, $\chi^2$ two tailed test, trained vs. naïve cohorts). Data for each mouse in each cohort are shown as shaded or color dots corresponding to stratified Cochran-Mantel-Haenszel (CMH) tests controlling for mouse identity (Materials and Methods, see legends: NM is Naïve Mouse, M corresponds to a trained mouse consistent with main figures and numbering throughout this figure). FIG. 25B: Bar graph indicating the fraction of all imaged neurons that were used for classifier and neural trajectory analyses (neurons used are termed "unstimulated neurons"). The number of unstimulated neurons was 929±250 [mean±SD], or 21±5% of all neurons in each of the 5 mice in this cohort. FIG. 25C: Plot indicating cumulative variance explained by increasing numbers of principal components as applied to the unstimulated neuronal traces during visual stimulus presentation. Results shown for five trained mice. Horizontal red line is at 90%. The vertical red line indicates that five principal components are necessary to explain at least 90% of the variance in all five mice. FIG. 25D: The fraction of optogenetically stimulated tuned (left) and random (right) neurons that were significantly modulated by light is shown for n=3 trained mice that had at least 40 stimulation trials/ neuron (using conservative metrics; line color corresponds legend in FIG. 25A; see Materials and Methods). FIGS. 25E, 25G, 25I, 25K, 25M: Classifier performance shown for five trained mice as a function of the number of neurons with classifier regression weights equal to zero increases (which increases as a function of the parameter $1/\lambda$). A constant value ($1/\lambda=0.5$) was used across all five mice. We found that this value approximately minimized each model's prediction error on held-out test data (that was not used for training). FIGS. 25F, 25H, 25J, 25L, 25N: Spatial map of all ROIs extracted across six cortical depths shown for five mice. Black dots (targets) were excited by 2P illumination in at least one experimental condition. Excluded ROIs (not shown, but counted in panel (A)) were within 20 microns of a target ROI at some depth or were contaminated by a 2P-induced stimulus fluorescence artifact and were excluded from the classifier analysis. Remaining ROIs (colors) were used for classifier analysis. Right histograms show weight values for ROIs that had weights>10% of the maximum weight obtained by any ROI. Scale bar is 100 μm.

Figure 26:
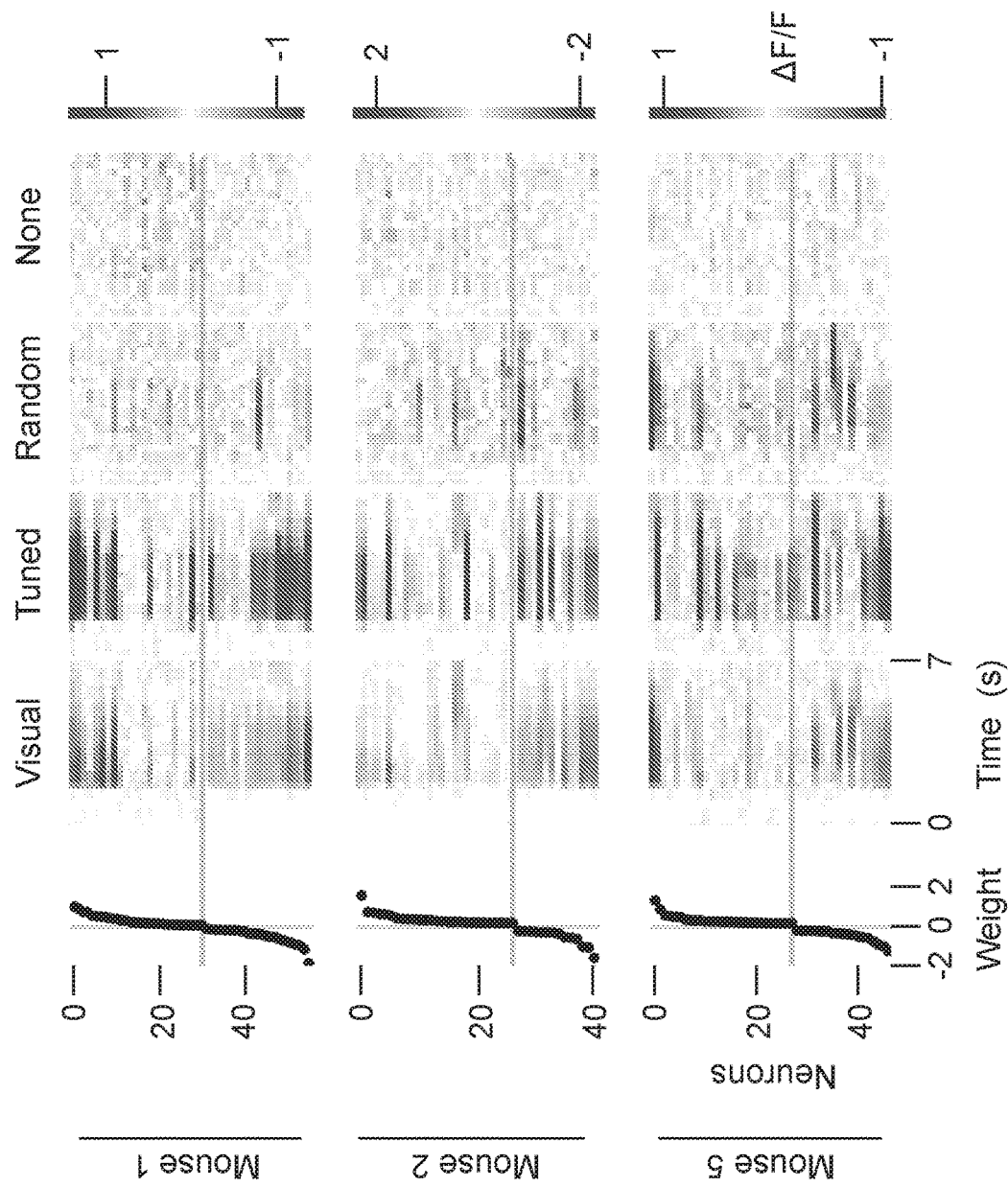

FIG. 26 depicts neural selectivity of additional behaviorally trained mice. Each row shows the trial-averaged fluorescence response of a neuron during the 0° visual stimulus minus its response during the 90° visual stimulus (or matched optogenetic stimulus) for all neurons with large classifier weights (defined as abs(weight)>95$^{th}$ percentile). This analysis is shown here for three trained mice not shown in the main text. Dots on the left-hand side of each row indicate the classifier weight of each neuron. Blue indicates neural responses preferential to the 0° condition; red responses were stronger for the 90° condition.

Figure 27:
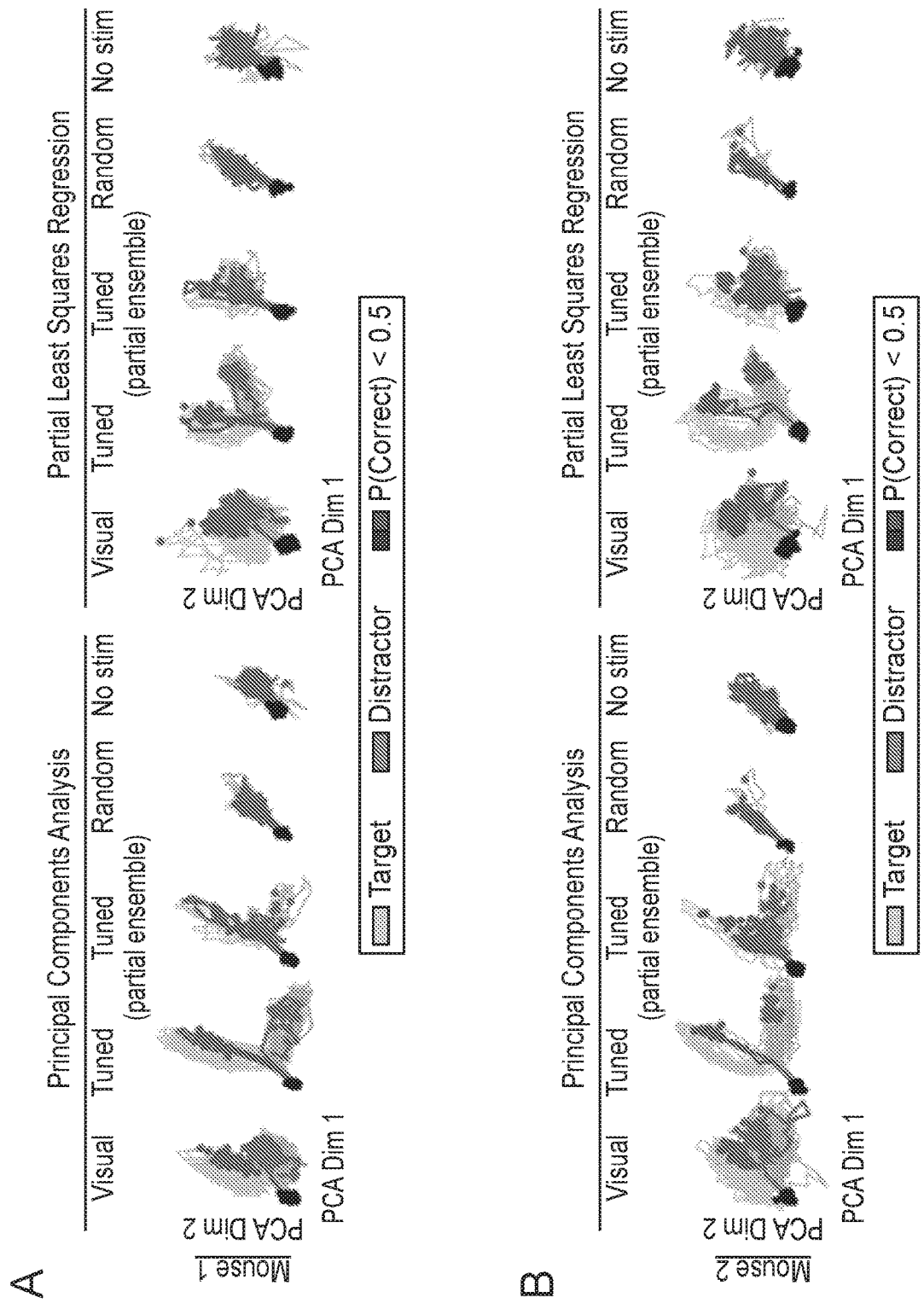
Figure 27:
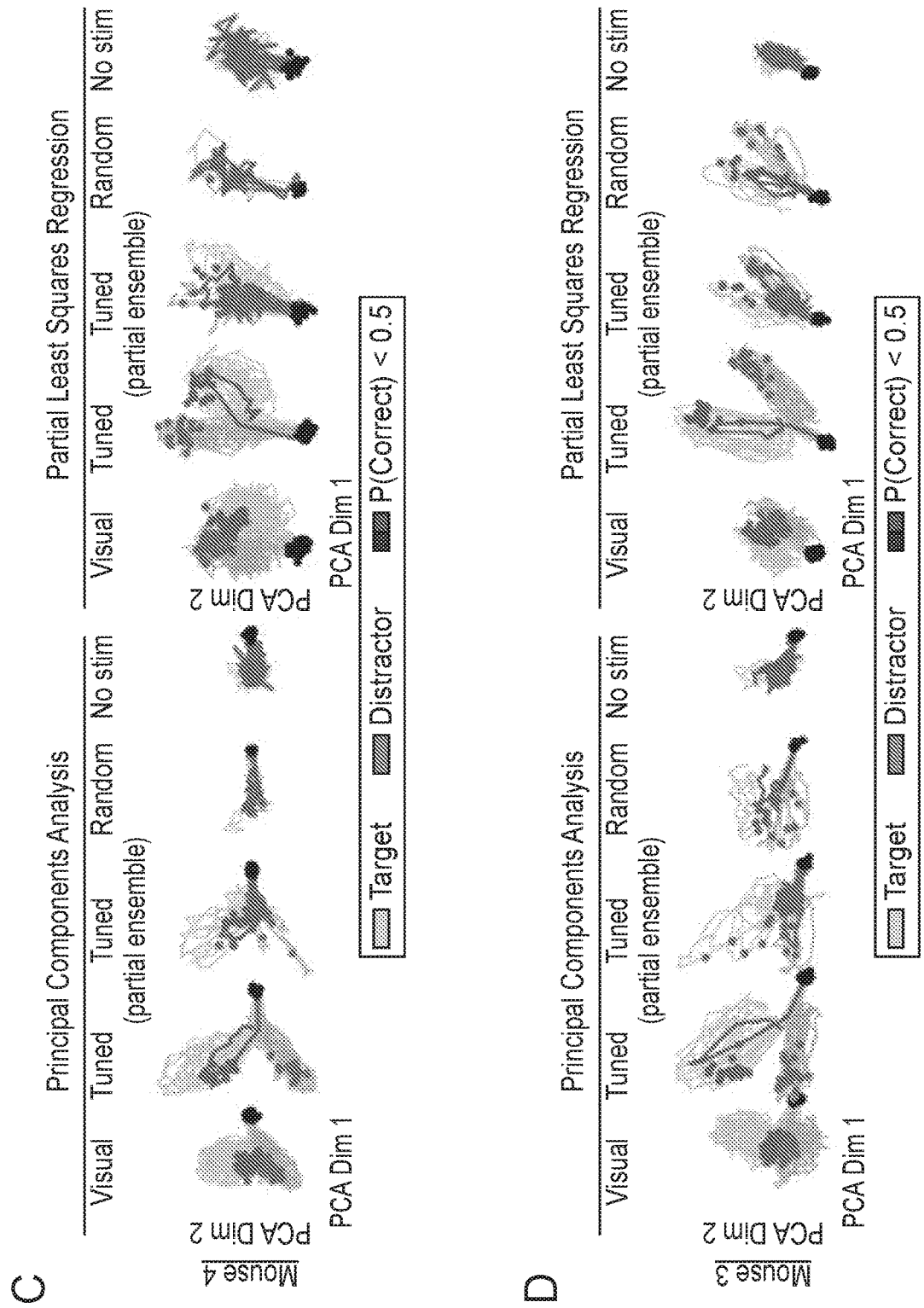
Figure 27:
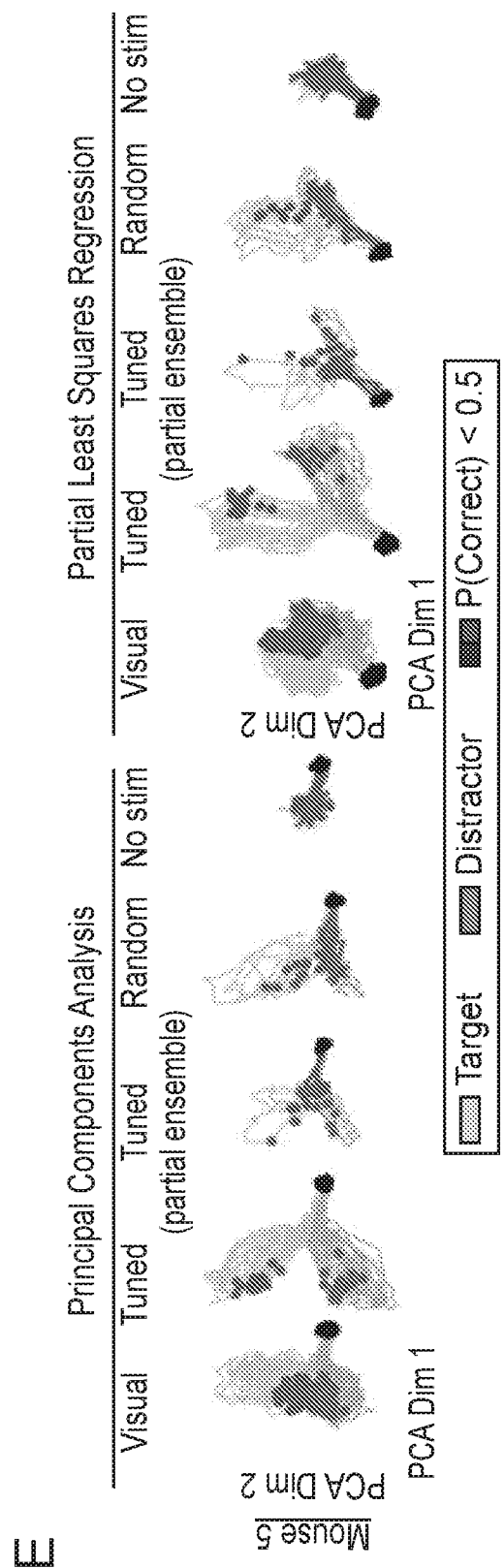

FIG. 27, A-E depicts visually evoked population activity is more similar to that evoked by stimulation of tuned ensembles than by random stimulation. FIGS. 27A-27E: Neural trajectories were computed individually for each experimental condition on each experimental day. The basis vectors were computed for each mouse with the visual only data, using either Principal Components Analysis (PCA, left column) or Partial Least Squares Regression (PLS, right column). Light blue trajectories represent data obtained during target conditions and light red trajectories represent distractor conditions. Dark blue and red trajectories denote target or distractor conditions that the mouse performed with mean performance less than 50% (meaning fewer than half of the trials on that condition and day elicited the correct behavioral response). Each trajectory is composed of neurons that were never optogenetically stimulated and that lie at least 20 microns away from any stimulated neuron. Principal component dimensions were computed using the visual data. Black dots represent the start of each trajectory. Red and blue dots mark the first frame following visual or optogenetic stimulus onset and are superimposed onto each trajectory. All but the tuned partial-ensemble panels from Mouse 3 and Mouse 4 were shown in FIG. 14, and are reproduced here for completeness. If motor behavior plays a role in the shape of these neural trajectories, it would be expected that in the case of the mouse making a large number of behavioral errors, those trajectories would look distinct from trajectories constructed from data where high behavioral performance was observed. Instead we see that the highlighted red and blue trajectories (where mean performance was <50%) look qualitatively indistinguishable from other red and blue trajectories from conditions where few errors were observed.

Figure 28:
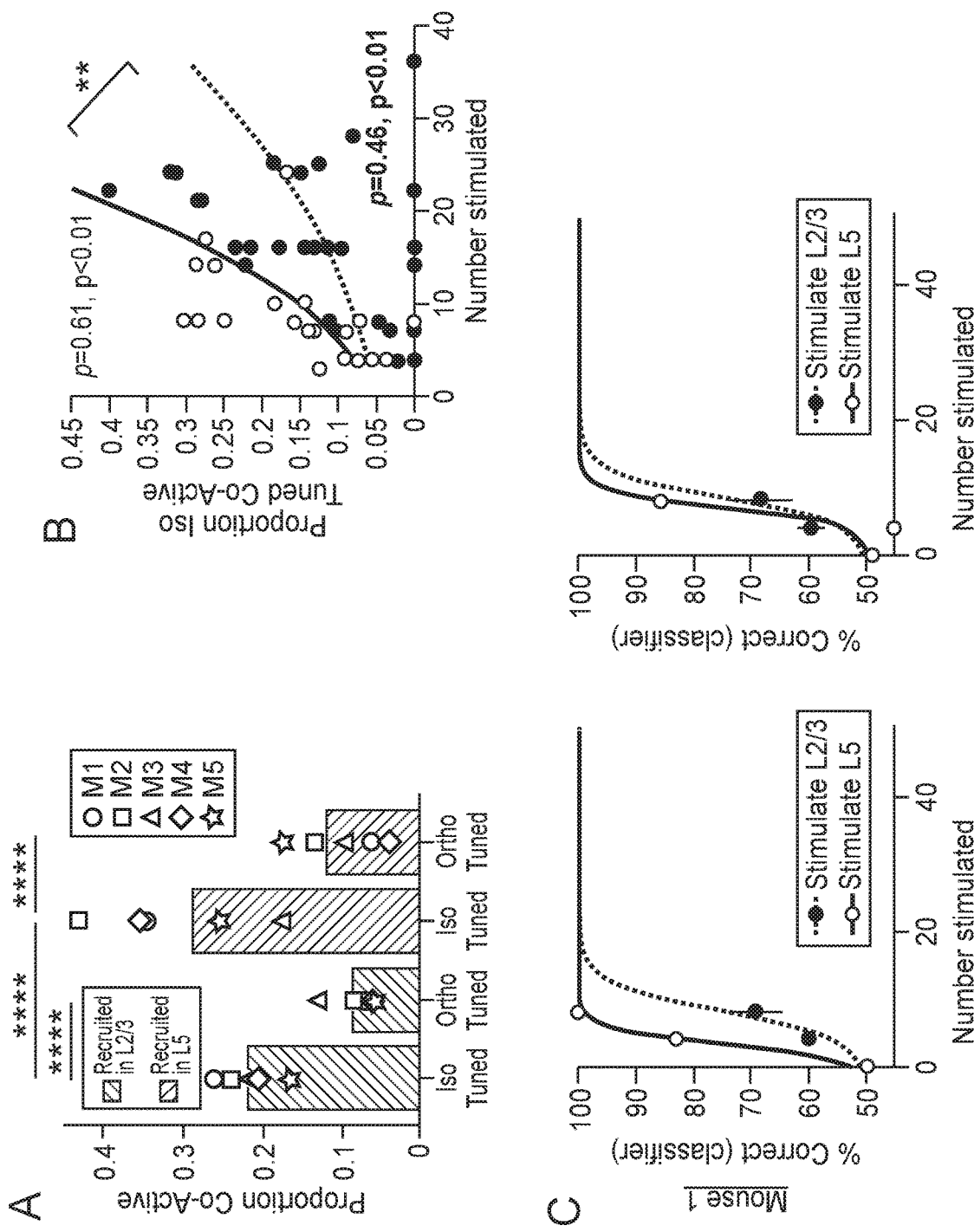
Figure 28:
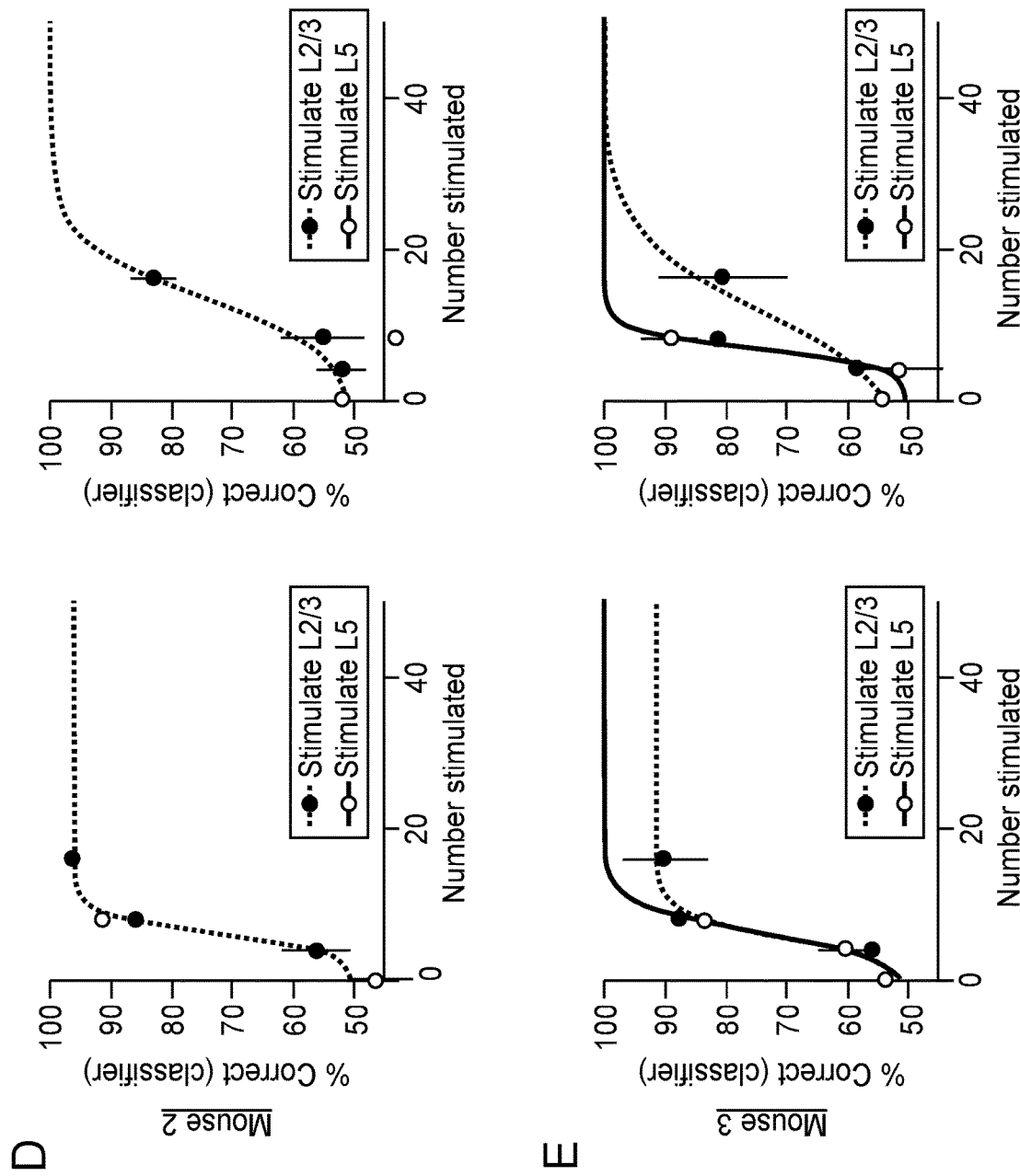
Figure 28:
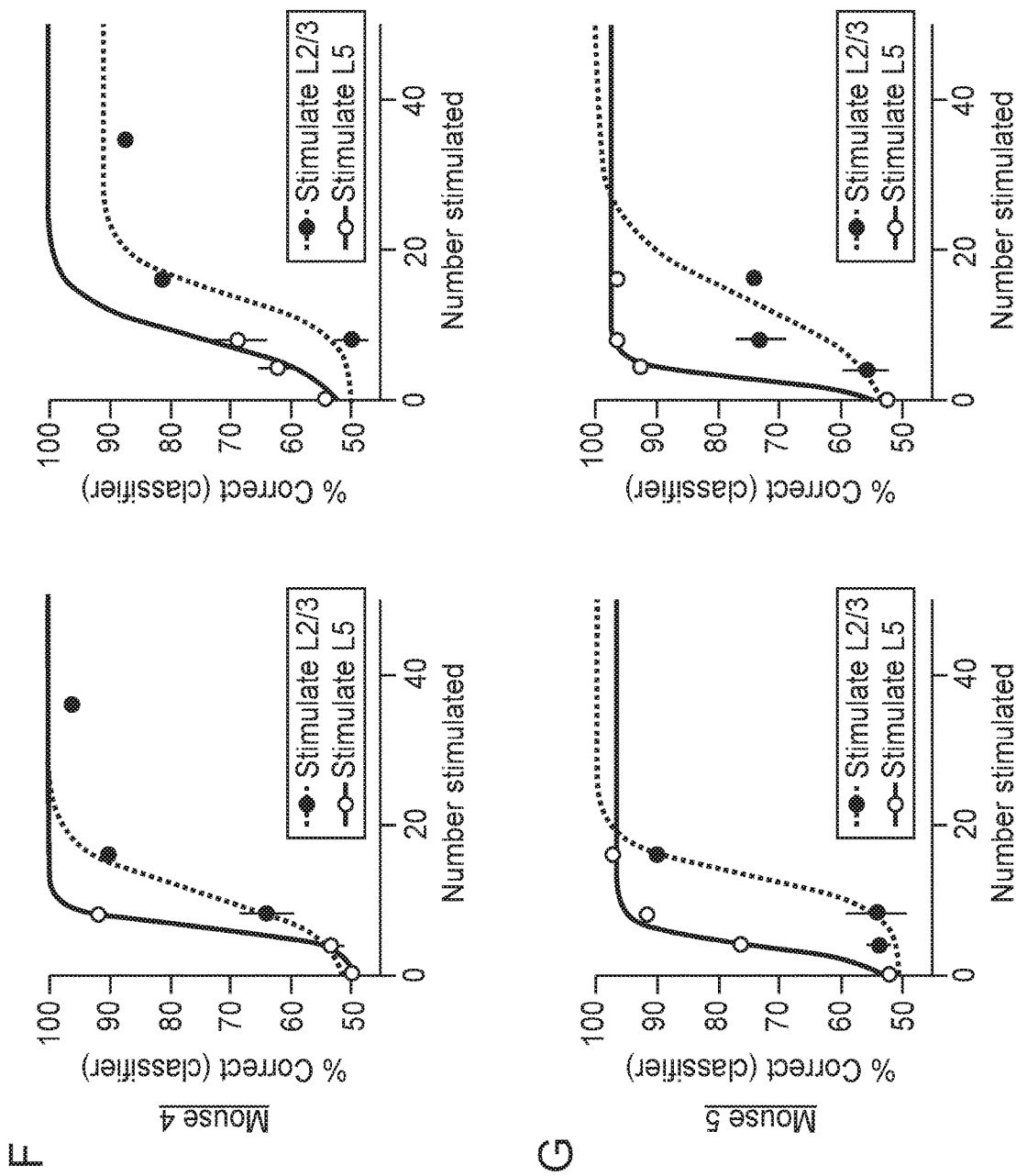

FIG. 28, A-G depicts selective laminar recruitment and ignition threshold visualized for five individual mice. FIG. 28A: Stimulation of full tuned ensembles involving both layers 2/3 and 5 preferentially recruited iso-tuned neurons in both layer 2/3 and layer 5 (p<0.0001, $\chi^2$ two tailed test, iso vs. ortho in each layer; co-active neurons are found by two-tailed Wilcoxon signed-rank tests, p<0.01, sample window vs. baseline, Materials and Methods). A greater proportion of layer 5 iso-tuned neurons was recruited compared to layer 2/3 (p<0.0001, $\chi^2$ two tailed test, n=58 experiments in 5 mice). Data were pooled across sessions and mice for each colored bar and reported with Pearson's $\chi^2$ square test results; pooled data across sessions for each mouse shown as colored dots (see legend, per FIGS. 13H, 14D, 15A; Materials and Methods: stratified CMH tests controlling for mouse identity). p<0.01, p<0.0001 throughout. FIG. 28B: Data from FIGS. 15B, 15D showing direct comparison of iso-tuned recruitment within each stimulated layer. Stimulation of layer 5 neurons recruits a greater fraction of layer 5 iso-tuned neurons more rapidly than layer 2/3 stimulation recruits iso-tuned layer 2/3 cells (p<0.01, ANCOVA controlling for the covariate of number stimulated; Spearman's ρ=0.46, p<0.01, n=46 data points, within layer 2/3 and Spearman's ρ=0.61, p<0.01, n=24 data points for layer 5 recruitment). FIG. 28C: Logistic psychometric functions (solid lines) fit to predictions derived from a classifier trained on either neural (left column) or behavioral data (right column) taken from a single mouse. Each curve relates the mouse's performance to the stimulation of a specific number of neurons. Individual points represent averages across the one or more days where a particular experimental condition was run +/- the SEM Each plot shows fits to data for only conditions where ensembles resided in individual layers. FIGS. 28D-28G: Results shown for four additional mice. FIG. 28**C: No psychometric function was fit to the layer 5 data from Mouse 2 because of insufficient data (there were not many targetable layer 5 neurons in that mouse). Target and Distractor ensembles stimulated in each mouse differ in size by at most 1 neuron. Importantly, the parameters underlying the psychometric function fits were not used for any quantitative statistical analysis and are presented only for illustrative purposes.

DETAILED DESCRIPTION

Methods for selectively stimulating a plurality of light-responsive neurons in a sample are provided. Methods according to certain embodiments include irradiating a sample comprising a plurality of light-responsive neurons with a plurality of holographic images that are each configured to stimulate one or more light-responsive neurons in the sample, wherein the holographic images are created by light projection system that includes a plurality of light sources; a plurality of optical adjustment components; a plurality of spatial light modulators; a controller; a processor; and a computer-readable medium comprising instructions that, when executed by the processor, cause the controller to operate the light sources, optical adjustment components and spatial light modulators to generate and display a plurality of holographic images; direct each of the holographic images to a projection location; and project the holographic images onto the sample at a rate greater than 1 kHz. Light projection systems for irradiating a sample having light-responsive neurons with holographic images are also described.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods for Selectively Stimulating a Plurality of Light-Responsive Neurons in a Sample Aspects of the present disclosure include methods for selectively stimulating a plurality of light-responsive neurons in a sample. Methods of the present disclosure according to certain embodiments are directed to a volumetric imaging and controlled approach that allows for kHz manipulation of any of a plurality (e.g., thousands) of neurons in a 3D volume accessible with a single objective using multiphoton stimulation, while imaging the neural activity of the same population with high spatial resolution (e.g., during a behavioral task). In these embodiments, a plurality (e.g., thousands) of diffraction limited spots, in precise locations and simultaneously, using 3D holograms generated by a light projection system that includes a plurality of light sources; a plurality of optical adjustment components and a plurality of spatial light modulators. The light in the light projection system can be separated into a plurality of distinct channels (e.g., with beam splitters and non-overlapping wavelengths of light, temporal delay in light pulses as described in greater detail below) and may be recombined after propagating through spatial light modulators (e.g., with a 50/50 beam splitter). In embodiments, by staggering refresh times of each individual spatial light modulator (e.g., a 333 Hz refresh rate) across an array of spatial light modulators, the effective temporal resolution of the subject light projection systems may be 1 kHz or greater, such as 1.1 kHz or greater, such as 1.25 kHz or greater, such as 1.5 kHz or greater, such as 1.75 kHz or greater, such as 2 kHz or greater and including 2.4 kHz or greater. In certain embodiments, the subject systems are configured with a 100% duty cycle. In some embodiments, the subject methods provide for accessibility to any and all neurons in a three dimensional field of view of a sample (e.g., 15,000 neurons in a sample). In these embodiments, natural patterns of activity can be precisely measured and/or replayed into a neural network, for example to create artificial perceptions or to artificially reinforce learning. In certain instances, the subject methods provide for an improvement in temporal precision of neural activation patterns.

In embodiments, methods include generating a holographic image by irradiating a spatial light modulator with a light source. The light source may be any suitable broadband or narrow band source of light. In some embodiments, the light source is a narrow band light source configured to emit a wavelength of light ranging from 200 nm to 1800 nm, such as from 250 nm to 1750 nm, such as from 300 nm to 1700 nm, such as from 350 nm to 1650 nm, such as from 400 nm to 1600 nm, such as from 450 nm to 1550 nm, such as from 500 nm to 1500 nm and including from 550 nm to 1450 nm. In some embodiments, the fixed wavelength light source has a wavelength that ranges from 200 nm to 800 nm, for example 480 nm, 532 nm or 800 nm. In other embodiments, the fixed wavelength light source has a wavelength that ranges from 800 nm to 1200 nm, for example 1035 nm, 1060 nm or 1080 nm. In yet other embodiments, the fixed wavelength light source has a wavelength that ranges from 1200 nm to 1800 nm, for example 1700 nm. In certain embodiments, the light source includes a light source emitting light having wavelengths from 1000 nm to 1200 nm. (e.g., 1035 nm, 1040 nm, 1060 nm, 1080 nm, etc.). The number of wavelengths produced by the light source may be any suitable number of wavelengths. In some cases, the light source produces light with 1 or more, e.g., 2 or more, 3 or more, including 4 or more, distinct wavelengths of light, and produces light with 10 or fewer, e.g., 9 or fewer, 8 or fewer, 7 or less, 6 or fewer, including 5 or fewer distinct wavelengths of light. In some embodiments, the light source produces light in the range of 1 to 10, e.g., 1 to 8, 2 to 6, 2 to 5, including 2 to 4 distinct wavelengths.

In some embodiments, methods include irradiating a sample with a hologram generated by a light projection system that includes one or more lasers. Lasers of interest may include pulsed lasers or continuous wave lasers. The type and number of lasers used in the subject methods may vary and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the laser is a dye laser, such as a stilbene, coumarin or rhodamine laser. In yet other instances, the laser is a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the laser is a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof. In still other instances, the laser is a semiconductor diode laser, optically pumped semiconductor laser (OPSL), or a frequency doubled- or frequency tripled implementation of any of the above mentioned lasers.

In some embodiments, the plurality of light sources in the light projection system are pulsed lasers. Depending on the resolution desired, the laser may have a pulse width which varies and may be 0.001 μs or more, such as 0.005 μs or more, such as 0.01 μs or more, such as 0.05 μs or more, such as 0.1 μs or more, such as 0.5 μs or more, such as 1 μs or more, such as 5 μs or more, such as 10 μs or more, such as 25 μs or more, such as 50 μs or more, such as 100 μs or more, such as 250 μs or more, such as 500 μs or more, such as 750 μs or more, such as 1000 μs or more and including 1500 μs or more. In some embodiments, the laser pulse width of each laser varies ranging from 0.001 μs to 1000 μs, such as from 0.005 μs to 900 μs, such as from 0.01 μs to 800 μs, such as from 0.05 μs to 700 μs, such as from 0.1 μs to 600 μs, such as from 0.5 μs to 500 μs, such as from 1 μs to 400 μs and including from 300 μs to 400 μs, for example 375 μs. In some embodiments, one or more lasers are ultra-short pulsed lasers, such as lasers which have femtosecond pulses ranging from 25 fs to 500 fs, such as from 50 fs to 450 fs, such as from 75 fs to 400 fs and including from 100 fs to 250 fs. The frequency of laser pulse may vary for each laser, ranging from 0.01 MHz to 100 MHz, such as from 0.05 MHz to 95 MHz, such as from 0.1 MHz to 90 MHz, such as from 0.25 MHz to 80 MHz, such as from 0.5 MHz to 75 MHz and including from 1 MHz to 50 MHz.

The present method may employ any suitable frequency of light pulses. In some cases, the frequency of the light pulses is 0.1 Hz or more, e.g., 1 Hz or more, 5 Hz or more, 10 Hz or more, 15 Hz or more, 20 Hz or more, including 25 Hz or more, and is 1,000 kHz or less, e.g., 500 kHz or less, 200 kHz or less, 100 kHz or less, 80 kHz or less, including 60 kHz or less. For example, the frequency of the light pulses is 50 Hz or more, 100 Hz or more, 200 Hz or more, including 250 Hz or more and is 1000 Hz or less, e.g., 900 Hz or less, 800 Hz or less, 700 Hz or less, 600 Hz or less, including 500 Hz or less. In certain embodiments, the frequency of the light pulses is in the range of 0.1 to 1,000 Hz, e.g., 1 to 500 Hz, 1 to 200 Hz, 5 to 80 Hz, 10 to 60 Hz, including 15 to 60 Hz. Each light source may be any suitable power. In some cases, each light pulse has a power of 0.5 μW or more, e.g., 1.0 μW or more, 2.0 μW or more, 3.0 μW or more, 5 μW or more, 10 μW or more, 15 μW or more, including 20 μW or more, and has a power of 500 μW or less, e.g., 250 μW or less, 200 μW or less, 150 μW or less, 100 μW or less, 50 μW or less, including 30 μW or less. In some cases, a light pulse for exciting a whose cellular electrical activity has a power in the range of 0.5 to 500 μW, e.g., 1.0 to 250 μW, 1.0 to 200 μW, 2.0 to 100 μW, 3.0 to 50 μW, including 3.0 to 30 μW. In some cases, each light pulse has a power of 0.5 mW or more, e.g., 1.0 mW or more, 2.0 mW or more, including 5.0 mW or more, and has a power of 10 mW or less, e.g., 8.0 mW or less, 6.0 mW or less, 4.0 mW or less, including 3.0 mW or less.

In embodiments, light from the plurality of light sources (e.g., lasers) is propagated through a plurality of optical adjustment components. The term "optical adjustment" is used herein in its conventional sense to refer to any device that is capable of changing one or more characteristics the light source, such as for example, irradiation direction, polarization, wavelength, beam profile, beam width, beam intensity, focal point and pulse width. In some embodiments, light from the plurality of light sources (e.g., lasers) is propagated through a beam splitter. In other embodiments, light from the plurality of light sources is propagated through a beam polarizer. In yet other embodiments, light from the plurality of light sources is propagated through a polarizing beam splitter.

Light from the light source may also be modulated, such as by rotating the polarization of the light. Any suitable light modulation protocol may be employed to rotate the polarization and/or optical power of the light. In some embodiments, methods include rotating the polarization of the light by propagating the light from the light source (e.g., from a beam splitter, polarizing beam splitter, etc.) through an electro-optic light modulator, such as a Pockels cell, and power can be modulated by other techniques such as using an acousto-optic modulator (AOM). Depending on the number of light sources and beam splitters employed, light projection systems according the subject methods may include 2 or more light modulator components, such as 4 or more, such as 6 or more, such as 8 or more, such as 10 or more, such as 12 or more, such as 16 or more and including 24 or more light modulator components. In certain embodiments, the electro-optic light modulator is a Pockels cell, and light projection systems include 2 or more Pockels cells, such as 4 or more Pockels cells, such as 6 or more Pockels cells, such as 8 or more Pockels cells, such as 10 or more Pockels cells, such as 12 or more Pockels cells, such as 16 or more Pockels cells and including 24 or more Pockels cells.

In some embodiments, light from the plurality of light sources is propagated through optical adjustment components such as a polarizing beam splitter and electro-optic light modulator to a spatial light modulator to generate a holographic image. In some instances, to reduce or eliminate interference and light irradiation overlap (e.g., laser pulse overlap), irradiation by the light source may be staggered, such that there is temporal delay between pulses from each light source. In these embodiments, the light sources (e.g., lasers) are pulsing out of phase such that the temporal delay between each light source is 0.1 µs or more, such as 0.5 µs or more, such as 1 µs or more, such as 2 µs or more, such as 5 µs or more, such as 10 µs or more, such as 25 µs or more, such as 50 µs or more, such as 100 µs or more, such as 250 µs or more and including 500 µs or more. In some embodiments, the light sources are synchronized, but laser pulses are maintained out of phase from one another using temporal delay lines, for example, to eliminate interference. In other instances, to reduce or eliminate interference, each light source has a different polarization. In yet other instances, interference is reduced or eliminated by having each light source irradiate at a different wavelength.

In embodiments, methods include propagating the light to a plurality of spatial light modulators. Any convenient spatial light modulator protocol may be employed, where in certain embodiments, spatial light modulators of interest include spatial light modulators based on liquid crystal on silicon (LCOS), for example, reflective LCOS or transmissive LC. The wavelength range of spatial light modulators of interest may vary, ranging from 200 nm to 1800 nm, such as from 250 nm to 1750 nm, such as from 300 nm to 1700 nm, such as from 350 nm to 1650 nm, such as from 400 nm to 1600 nm, such as from 450 nm to 1550 nm, such as from 500 nm to 1500 nm and including from 550 nm to 1450 nm. Depending on the number of light sources and spatial light modulators employed in the subject methods, the active area of spatial light modulators of interest may vary, having a length that varies, ranging from 1 mm to 75 mm, such as from 2 mm to 70 mm, such as from 3 mm to 65 mm, such as from 4 mm to 60 mm and including from 5 mm to 50 mm, for example 30 mm. The width of the active surface may also vary ranging from 1 mm to 75 mm, such as from 2 mm to 70 mm, such as from 3 mm to 65 mm, such as from 4 mm to 60 mm and including from 5 mm to 50 mm, for example 30 mm. In embodiments, depending on the shape of the spatial light modulator, the active surface may have a surface area of from 1 mm$^2$ to 500 mm$^2$, such as from 2 mm$^2$ to 450 mm$^2$, such as from 3 mm$^2$ to 400 mm$^2$, such as from 4 mm$^2$ to 350 mm$^2$, such as from 5 mm$^2$ to 300 mm$^2$, such as from 6 mm$^2$ to 250 mm$^2$, such as from 7 mm$^2$ to 200 mm$^2$, such as from 8 mm$^2$ to 150 mm$^2$ and including from 10 mm$^2$ to 100 mm$^2$. The refresh rate of spatial light modulators of interest also varies and may be 30 Hz or more, such as 60 Hz or more, such as 120 Hz or more, such as 180 Hz or more, such as 240 Hz or more, such as 300 Hz or more, such as 500 Hz or more, such as 750 Hz or more, such as 1000 Hz or more, such as 2500 Hz or more and including 5000 Hz or more. In certain embodiments, the refresh rate of spatial light modulators is 333 Hz or more. Light from the spatial light modulator may be propagated to the sample through one or more optical adjustment components. In certain embodiments, light from the spatial light modulator is combined, such as with beam combining beam splitters, polarizers and dichroic mirrors. Optical adjustment components may further include polarization switches, mirrors and one or more lenses, such as a beam expander, a scan lens, a tube lens and an objective lens. Suitable lenses may have a numerical aperture as appropriate such as a numerical aperture of 0.3 or more, e.g., 0.4 or more, 0.5 or more, including 0.6 or more, and has a numerical aperture of 1.6 or less, e.g., 1.4 or less, 1.2 or less, 1.0 or less, 0.9 or less, including 0.8 or less. In some cases, the combined light from the spatial light modulators has a numerical aperture in the range of 0.3 to 1.6, e.g., 0.3 to 1.4, 0.4 to 1.2, 0.5 to 1.0, including 0.5 to 0.9.

In certain embodiments, the holographic images from the spatial light modulators are propagated to a resonant scanner two photon microscope, such as those described in Prakash et al. Nature Methods (2012) Vol. 9; pp. 1171-1179; Packer et al. Nature Methods (2012) Vol. 9; pp. 1202-1205; Tsien et al. (1995) Video-Rate Confocal Microscopy. In: Pawley J. B. (eds) Handbook of Biological Confocal Microscopy. Springer, Boston, Mass.; Fan, et al. Video-Rate Scanning Two-Photon Excitation Fluorescence Microscopy and Ratio Imaging with Cameleons, Biophysical Journal, Vol. 76(5), 1999; pp. 2412-2420, the disclosure of which are herein incorporated by reference.

In some embodiments, the holographic image produced is moved, such as in a pattern, to scan the sample. Any suitable protocol may be employed to move the holographic image in the desired pattern, such as with a galvanometer mirror. Any suitable shape may be formed using the holographic image, such as points, spirals, a rectilinear pattern, e.g., squares, rectangles, trapezoids, triangles, hexagons, etc., curvilinear patterns, e.g., circles, ovals, as well as asymmetric patterns, irregular patterns, e.g., a parabolic bottom portion coupled to a planar top portion. In other embodiments, methods include forming a holographic image in the shape of a spiral. In yet other embodiments, methods include forming a holographic image in the shape of a neuron (e.g., with cell body and/or neural processes such as dendrites/spines/axons).

The holographic image may be projected onto the sample for a duration that varies depending on the pulse staggering and laser power, where excitation durations of interest may be 1 µs or longer, such as 2 µs or longer, such as 3 µs or longer, such as 5 µs or longer, such as 10 µs or longer, such as 25 µs or longer, such as 50 µs or longer, such as 100 µs or longer, such as 250 µs or longer, such as 500 µs or longer, such as 750 µs or longer, such as 1000 µs or longer, such as 2500 µs or longer, such as 5000 µs or longer and including an excitation duration of 10000 µs or longer.

In embodiments, method according to certain embodiments include projecting the holographic images on the sample at a rate that is 1 kHz or greater, such as 1.5 kHz or greater, such as 2 kHz or greater, such as 2.5 kHz or greater, such as 3 kHz or greater, such as 3.5 kHz or greater and including 5 kHz or greater. In certain embodiments, the subject light projection systems are configured to provide for an effective temporal resolution that is 1 kHz or greater, such as 1.5 kHz or greater, such as 2 kHz or greater, such as 2.5 kHz or greater, such as 3 kHz or greater, such as 3.5 kHz or greater and including 5 kHz or greater, for example an effective temporal resolution of 2.4 kHz. In other words, the subject methods include creating and projecting a holographic image onto a sample having a plurality of light-responsive neurons with a refresh rate of 1 kHz or greater, such as 1.5 kHz or greater, such as 2 kHz or greater, such as 2.5 kHz or greater, such as 3 kHz or greater, such as 3.5 kHz or greater and including 5 kHz or greater, for example a refresh rate of 2.4 kHz.

In embodiments, methods also include detecting a light signal from the sample. Light signals may be detected with any convenient light detection protocol. Detectors of interest may include, but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light from the sample is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors.

In some embodiments, light from the sample is detected with a photodetector array, such as an array of photodiodes, CCDs or CMOS sensors. In these embodiments, the photodetector array may include 4 or more photodetectors, such as 10 or more photodetectors, such as 25 or more photodetectors, such as 50 or more photodetectors, such as 100 or more photodetectors, such as 250 or more photodetectors, such as 500 or more photodetectors, such as 750 or more photodetectors and including 1000 or more photodetectors. The photodetectors may be arranged in any geometric configuration as desired, where arrangements of interest include, but are not limited to a square configuration, rectangular configuration, trapezoidal configuration, triangular configuration, hexagonal configuration, heptagonal configuration, octagonal configuration, nonagonal configuration, decagonal configuration, dodecagonal configuration, circular configuration, oval configuration as well as irregular patterned configurations. The photodetectors may be oriented with respect to the other (as referenced in an X-Z plane) at an angle ranging from 10° to 180°, such as from 15° to 170°, such as from 20° to 160°, such as from 25° to 150°, such as from 30° to 120° and including from 45° to 90°. embodiments, the photodetector array has a rectangular-shaped active surface.

Each photodetector may have an active surface with a width that ranges from 5 µm to 250 µm, such as from 10 µm to 225 µm, such as from 15 µm to 200 µm, such as from 20 µm to 175 µm, such as from 25 µm to 150 µm, such as from 30 µm to 125 µm and including from 50 µm to 100 µm and a length that ranges from 5 µm to 250 µm, such as from 10 µm to 225 µm, such as from 15 µm to 200 µm, such as from 20 µm to 175 µm, such as from 25 µm to 150 µm, such as from 30 µm to 125 µm and including from 50 µm to 100 µm, where the surface area of each photodetector (e.g., photodiode) in the array ranges from 25 to $\mu m^2$ to 10000 $\mu m^2$, such as from 50 to $\mu m^2$ to 9000 $\mu m^2$, such as from 75 to $\mu m^2$ to 8000 $\mu m^2$, such as from 100 to $\mu m^2$ to 7000 $\mu m^2$, such as from 150 to $\mu m^2$ to 6000 $\mu m^2$ and including from 200 to $\mu m^2$ to 5000 $\mu m^2$.

Photodetectors of interest are configured to measure light from the sample at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, photodetectors are configured to measure collected light over a range of wavelengths (e.g., 200 nm-1000 nm). In certain embodiments, photodetectors of interest are configured to collect spectra of light over a range of wavelengths. For example, systems may include one or more detectors configured to collect spectra of light over one or more of the wavelength ranges of 200 nm-1000 nm. In certain embodiments, photodetectors may be configured to be paired with specific fluorophores, such as those having neural activity-dependent fluorescence.

In embodiments, the detector is configured to measure light from the sample continuously or in discrete intervals. In some instances, detectors of interest are configured to take measurements of the collected light continuously. In other instances, the light detection system is configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

In embodiments, the sample contains excitable cells, e.g., light-responsive neurons. The light responsive neurons may contain one or more cellular electrical activity-dependent fluorescent moieties, e.g., neural activity-dependent fluorescent moieties, such as a genetically-encoded calcium indicator. Thus, the cells labeled with a cellular electrical activity-dependent fluorescent moiety may emit fluorescent when stimulated by a light stimulus of an appropriate wavelength and intensity, wherein the intensity of the fluorescence depends on the electrical activity of the cell. In some cases, an electrically active cell, e.g., a more depolarized cell, labeled with a cellular electrical activity-dependent fluorescent moiety will emit a stronger fluorescence when stimulated by a light stimulus at the excitation wavelength of the activity-dependent fluorescent moiety and having sufficient intensity compared to a cell that is not electrically active, e.g., a more hyperpolarized cell, labeled with the activity-dependent fluorescent moiety and stimulated by the same light stimulus. Depending on the wavelength of the light pulses, the region may emit fluorescence that is activity-dependent, or activity-independent.

The sample in methods of the present disclosure includes light-responsive neurons. In some embodiments, the neurons have a neural activity-dependent fluorescent moiety, such as a light-activated polypeptide. The light-activated polypeptide may be a depolarizing or hyperpolarizing light-activated polypeptide. The light-activated polypeptide may be an ion channel or an ion pump. In certain embodiments, the light-activated polypeptide is selected from: ChR2, iC1C2, C1C2, GtACR2, NpHR, eNpHR3.0, C1V1, VChR1, VChR2, SwiChR, Arch, ArchT, KR2, ReaChR, ChiEF, Chronos, ChRGR, CsChrimson, bReaCh-ES, and variants thereof. In other embodiments, the neural activity-dependent fluorescent moieties include a genetically-encoded indicator dye, such as where the sample includes genetically modified neurons expressing the one or more activity-dependent fluorescent moieties.

In some cases, the neurons are defined by a known functional classification. Any convenient functional classification may be used to define the neurons in the sample. In some cases, the light-responsive neurons include excitatory neurons, inhibitory neurons, sensory neurons, motor neurons, interneurons, etc. In some cases, the light-responsive neurons include dopaminergic, cholinergic, GABAergic, glutamatergic, or peptidergic neurons. In some cases, the collection of neurons includes Purkinje cells, pyramidal cells, golgi cells, Lugaro cells, basket cells, candelabrum cells, granule cells, stellate cells, unipolar brush cells, medium spiny neurons, Renshaw cells, spindle cells, etc. The different functional cells may be labeled specifically with a cellular electrical activity-dependent fluorescent moiety using any suitable method. In some cases, a cell-specific promoter, or a combination of different cell-specific promoters, may be used to control expression of a genetically-encoded cellular electrical activity-dependent fluorescent moiety, e.g., a genetically-encoded calcium indicator.

The sample is, in certain embodiments, a human target tissue (e.g., an in vivo, in vitro, or ex vivo target tissue). The target tissue can be a non-human animal target tissue (e.g., an in vivo, in vitro, or ex vivo target tissue). Non-human animals include non-human primates, murines (e.g., rats, mice), lagomorphs (e.g., rabbits), ungulates, felines, canines, and the like. The target tissue can be in a live human or non-human animal. The target tissue can be in a freely-moving human or non-human animal.

The present method may include irradiating any suitable region of the target tissue, e.g., the brain. In some cases, the method includes irradiating a functionally and/or anatomically defined region of a brain, e.g., a amphibian brain, a reptile brain, a bird brain, a marsupial brain, mammalian brain, etc. In some cases, the method includes irradiating at least of portion of the ventral tegmental area (VTA), prefontal cortex (PFC), nucleus accumbens (NAc), amygdala (BLA), substantia nigra, ventral pallidum, globus pallidus, dorsal striatum, ventral striatum, subthalamic nucleus, hippocampus, dentate gyrus, cingulate gyrus, entorhinal cortex, olfactory cortex, sensory cortex, thalamus, primary motor cortex, and cerebellum, etc., of a mammalian brain. Any other suitable functionally and/or anatomically defined region of a mammalian brain may be irradiated in the present method.

In some cases, the method includes irradiating a region of the brain where the cell body of light-responsive neurons is present. In some cases, the method includes irradiating a region of the brain where the neuronal projections, e.g., axonal projections, dendritic projections, etc., of labeled neurons are present.

Systems for Selectively Stimulating a Plurality of Light-Responsive Neurons in a Sample Aspects of the disclosure also include systems for practicing the subject methods. Embodiments according to certain embodiments include a light projection system configured for stimulating a plurality of light-responsive neurons in a sample by projecting a holographic image onto the sample at a rate greater than 1 kHz, where the light projection system includes a plurality of light sources; a plurality of optical adjustment components; a plurality of spatial light modulators; a controller; a processor; and a computer-readable medium comprising instructions that, when executed by the processor, cause the controller to: operate the light sources, optical adjustment components and spatial light modulators to generate and display a plurality of holographic images; direct each of the holographic images to a projection location; and project the holographic images onto the sample at a rate greater than 1 kHz.

As summarized above, light projection systems suitable for practicing the methods described herein include a plurality of light sources. The light source may be any suitable broadband or narrow band source of light. In some embodiments, the light source is a narrow band light source configured to emit a wavelength of light ranging from 200 nm to 1500 nm, such as from 250 nm to 1250 nm, such as from 300 nm to 1000 nm, such as from 350 nm to 900 nm and including from 400 nm to 800 nm. For example, the light source may include a light source emitting light having wavelengths from 1000 nm to 1200 nm. (e.g., 1035 nm, 1040 nm, 1060 nm, 1080 nm, etc.). The number of wavelengths produced by the light source may be any suitable number of wavelengths. In some cases, the light source produces light with 1 or more, e.g., 2 or more, 3 or more, including 4 or more, distinct wavelengths of light, and produces light with 10 or fewer, e.g., 9 or fewer, 8 or fewer, 7 or less, 6 or fewer, including 5 or fewer distinct wavelengths of light. In some embodiments, the light source produces light in the range of 1 to 10, e.g., 1 to 8, 2 to 6, 2 to 5, including 2 to 4 distinct wavelengths.

In some embodiments, one or more of the plurality of light sources is a laser. Lasers of the subject systems may include pulsed lasers or continuous wave lasers. The type and number of lasers in light projection systems may vary and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the laser is a dye laser, such as a stilbene, coumarin or rhodamine laser. In yet other instances, the laser is a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the laser is a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof. In still other instances, the laser is a semiconductor diode laser, optically pumped semiconductor laser (OPSL), or a frequency doubled- or frequency tripled implementation of any of the above mentioned lasers.

In some embodiments, the plurality of light sources in the light projection system includes pulsed lasers. Each laser may have a pulse width which varies and may be 0.001 µs or more, such as 0.005 µs or more, such as 0.01 µs or more, such as 0.05 µs or more, such as 0.1 µs or more, such as 0.5 µs or more, such as 1 µs or more, such as 5 µs or more, such as 10 µs or more, such as 25 µs or more, such as 50 µs or more, such as 100 µs or more, such as 250 µs or more, such as 500 µs or more, such as 750 µs or more, such as 1000 µs or more and including 1500 µs or more. In some embodiments, the laser pulse width of each laser varies ranging from 0.001 µs to 1000 µs, such as from 0.005 µs to 900 µs, such as from 0.01 µs to 800 µs, such as from 0.05 µs to 700 µs, such as from 0.1 µs to 600 µs, such as from 0.5 µs to 500 µs, such as from 1 µs to 400 µs and including from 300 µs to 400 µs, for example 375 µs.

The light source may have a pulse frequency that is 0.1 Hz or more, e.g., 1 Hz or more, 5 Hz or more, 10 Hz or more, 15 Hz or more, 20 Hz or more, including 25 Hz or more, and is 1,000 Hz or less, e.g., 500 Hz or less, 200 Hz or less, 100 Hz or less, 80 Hz or less, including 60 Hz or less. In certain embodiments, the light source may have a pulse frequency in the range of 0.1 to 1,000 Hz, e.g., 1 to 500 Hz, 1 to 200 Hz, 5 to 80 Hz, 10 to 60 Hz, including 15 to 60 Hz. Each light source may be any suitable power. In some cases, each light pulse has a power of 0.5 µW or more, e.g., 1.0 µW or more, 2.0 µW or more, 3.0 µW or more, 5 µW or more, 10 µW or more, 15 µW or more, including 20 µW or more, and has a power of 500 µW or less, e.g., 250 µW or less, 200 µW or less, 150 µW or less, 100 µW or less, 50 µW or less, including 30 µW or less. In some cases, a light pulse for exciting a whose cellular electrical activity has a power in the range of 0.5 to 500 µW, e.g., 1.0 to 250 µW, 1.0 to 200 µW, 2.0 to 100 µW, 3.0 to 50 µW, including 3.0 to 30 µW. In some cases, each light pulse has a power of 0.5 mW or more, e.g., 1.0 mW or more, 2.0 mW or more, including 5.0 mW or more, and has a power of 10 mW or less, e.g., 8.0 mW or less, 6.0 mW or less, 4.0 mW or less, including 3.0 mW or less. In yet other cases, each light pulcse has a power of 0.05 W or more, such as 0.1 W or more, such as 0.5 W or more, such as 1 W or more and including 2 W or more.

The subject systems may be configured to irradiate with the light sources simultaneously or sequentially, or a combination thereof. For example, the light sources may be configured to illuminate simultaneously. In other embodiments, the light sources are configured to irradiate sequentially. Where the plurality of light sources is employed to irradiate sequentially, the time each light source irradiates may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. Each light source may be configured to irradiate for a duration that is the same or different from each other.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. The delay between irradiation by each light source may be the same or different.

Each light source may be configured to irradiate continuously or in discrete intervals. In some instances, the light source is configured to irradiate continuously. In other instances, the light source is configured to irradiate in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

The subject light projection systems also include a plurality of optical adjustment components such as for example components which alter the irradiation direction, polarization, wavelength, beam profile, beam width, beam intensity, focal point and pulse width of light from the light source. In some embodiments, systems include beam polarizers, beam splitter, polarizing beam splitters, beam combining optics such as dichroic mirrors and lenses.

In some embodiments, systems include a plurality of light modulators for rotating the polarization of light from the light source. In some embodiments, the light modulator is an acousto-optic modulator (AOM). In other embodiments, the light modulator is an electro-optic modulator, such as a Pockels cell. Systems may include 2 or more light modulators, such as 4 or more, such as 6 or more, such as 8 or more, such as 10 or more, such as 12 or more, such as 16 or more and including 24 or more light modulators. Where the light modulators are Pockels cells, systems may include 2 or more Pockels cells, such as 4 or more, such as 6 or more, such as 8 or more, such as 10 or more, such as 12 or more, such as 16 or more and including 24 or more Pockels cells.

Systems also include a plurality of spatial light modulators, such as spatial light modulators based on liquid crystal on silicon (LCOS), for example, reflective LCOS or transmissive LC. The wavelength range of spatial light modulators of interest may vary, ranging from 200 nm to 1800 nm, such as from 250 nm to 1750 nm, such as from 300 nm to 1700 nm, such as from 350 nm to 1650 nm, such as from 400 nm to 1600 nm, such as from 450 nm to 1550 nm, such as from 500 nm to 1500 nm and including from 550 nm to 1450 nm. Depending on the number of light sources and spatial light modulators employed in the subject methods, the active area of spatial light modulators of interest may vary, having a length that varies, ranging from 1 mm to 75 mm, such as from 2 mm to 70 mm, such as from 3 mm to 65 mm, such as from 4 mm to 60 mm and including from 5 mm to 50 mm, for example 30 mm. The width of the active surface may also vary ranging from 1 mm to 75 mm, such as from 2 mm to 70 mm, such as from 3 mm to 65 mm, such as from 4 mm to 60 mm and including from 5 mm to 50 mm, for example 30 mm. In embodiments, depending on the shape of the spatial light modulator, the active surface may have a surface area of from 1 $mm^2$ to 500 $mm^2$, such as from 2 $mm^2$ to 450 $mm^2$, such as from 3 $mm^2$ to 400 $mm^2$, such as from 4 $mm^2$ to 350 $mm^2$, such as from 5 $mm^2$ to 300 $mm^2$, such as from 6 $mm^2$ to 250 $mm^2$, such as from 7 $mm^2$ to 200 $mm^2$, such as from 8 $mm^2$ to 150 $mm^2$ and including from 10 $mm^2$ to 100 $mm^2$. The refresh rate of spatial light modulators of interest also varies and may be 30 Hz or more, such as 60 Hz or more, such as 120 Hz or more, such as 180 Hz or more, such as 240 Hz or more, such as 300 Hz or more, such as 500 Hz or more, such as 750 Hz or more, such as 1000 Hz or more, such as 2500 Hz or more and including 5000 Hz or more. In certain embodiments, the refresh rate of spatial light modulators is 333 Hz or more.

In some embodiments, systems further include optical components for combining light propagated from the spatial light modulators, such as beam combining optics (e.g., beam splitters, polarizers, dichroic mirrors) as well as beam expanders, as well as lenses (e.g., scanning lenses, tube lenses and objective lenses) In certain embodiments, systems further include a resonant scanner two photon microscope.

To produce holographic images of a desired shape and size, systems may further include an optical component sufficient to move the holographic image, such as a galvanometer mirror.

Figure 1:
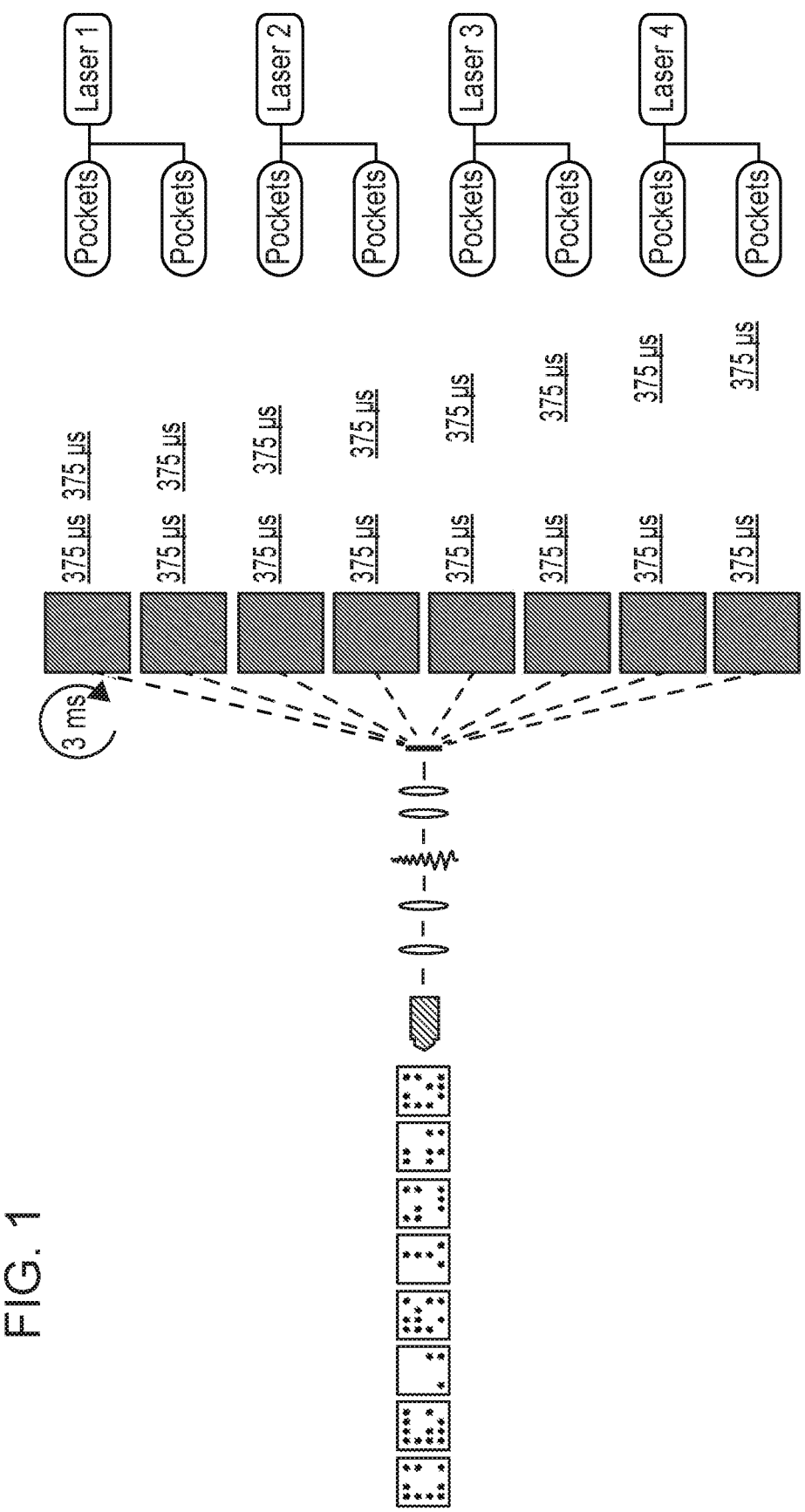
FIG. 1 depicts an illustration of a light projection system according to certain embodiments.

FIG. 1 depicts the setup of a light projection system according to certain embodiments. Light projection system 100 includes a plurality of light sources 101 (lasers 1-4) and optical adjustment components (polarizing beam splitters 102a, 102b, 102c, 102d) that split each laser beam into two separate beams which are propagated through electro-optic modulators 103a, 103b, 103c, 103d, 103f, 103g, 103h and 103i (Pockels Cells). To prevent overlap of laser pulses, the lasers are synchronized and temporal delays are added so that the lasers pulse out of phase with each other. Light from the light modulators is propagated to an array of spatial light modulators (104a, 104b, 104c, 104d, 104e, 104f, 104g, 104h and 104i). Holographic images from the spatial light modulators are combined with beam combining optics (105, beam splitter, polarizers and dichroics) and passed through a beam expander (106), scan lens (107), tube lens (108) and through an objective lens (109). A galvanometer mirror (110) provides for continuous motion of the holographic images to produce spot holograms 109a, 109b, 109c, 109d, 109e, 109f, 109g and 109h.

In embodiments, systems may include one or more detectors. Detectors of interest may include, but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the subject systems include one or more charge-coupled devices (CCD), semiconductor charge-coupled devices (CCD), active pixel sensors (APS), complementary metal-oxide semiconductor (CMOS) image sensors or N-type metal-oxide semiconductor (NMOS) image sensors.

In some embodiments, systems include a photodetector array, such as an array of photodiodes, CCDs or CMOS sensors. In these embodiments, the photodetector array may include 4 or more photodetectors, such as 10 or more photodetectors, such as 25 or more photodetectors, such as 50 or more photodetectors, such as 100 or more photodetectors, such as 250 or more photodetectors, such as 500 or more photodetectors, such as 750 or more photodetectors and including 1000 or more photodetectors. The photodetectors may be arranged in any geometric configuration as desired, where arrangements of interest include, but are not limited to a square configuration, rectangular configuration, trapezoidal configuration, triangular configuration, hexagonal configuration, heptagonal configuration, octagonal configuration, nonagonal configuration, decagonal configuration, dodecagonal configuration, circular configuration, oval configuration as well as irregular patterned configurations. The photodetectors may be oriented with respect to the other (as referenced in an X-Z plane) at an angle ranging from 10° to 180°, such as from 15° to 170°, such as from 20° to 160°, such as from 25° to 150°, such as from 30° to 120° and including from 45° to 90°. embodiments, the photodetector array has a rectangular-shaped active surface.

Each photodetector may have an active surface with a width that ranges from 5 μm to 250 μm, such as from 10 μm to 225 μm, such as from 15 μm to 200 μm, such as from 20 μm to 175 μm, such as from 25 μm to 150 μm, such as from 30 μm to 125 μm and including from 50 μm to 100 μm and a length that ranges from 5 μm to 250 μm, such as from 10 μm to 225 μm, such as from 15 μm to 200 μm, such as from 20 μm to 175 μm, such as from 25 μm to 150 μm, such as from 30 μm to 125 μm and including from 50 μm to 100 μm, where the surface area of each photodetector (e.g., photodiode) in the array ranges from 25 to $\mu m^2$ to 10000 $\mu m^2$, such as from 50 to $\mu m^2$ to 9000 $\mu m^2$, such as from 75 to $\mu m^2$ to 8000 $\mu m^2$, such as from 100 to $\mu m^2$ to 7000 $\mu m^2$, such as from 150 to $\mu m^2$ to 6000 $\mu m^2$ and including from 200 to $\mu m^2$ to 5000 $\mu m^2$.

Photodetectors of interest are configured to measure light from the sample at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, photodetectors are configured to measure collected light over a range of wavelengths (e.g., 200 nm-1000 nm). In certain embodiments, photodetectors of interest are configured to collect spectra of light over a range of wavelengths. For example, systems may include one or more detectors configured to collect spectra of light over one or more of the wavelength ranges of 200 nm-1000 nm.

In some embodiments, one or more of the components of the subject light propagation system (e.g., light sources, optical adjustment components, light modulators, spatial light modulators, optical combining optics, etc.) may be computer controlled where each component may be configured for complete automation or partial automation. In some embodiments, the subject systems include a computer having a computer readable storage medium with a computer program stored thereon, where the computer program when loaded on the computer includes instructions for modulating one or more of the light sources, optical adjustment components, light modulators, spatial light modulators or detectors.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for modulating one or more of the light sources, optical adjustment components, light modulators, spatial light modulators or detectors. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, MATLAB, LabVIEW, Python, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction therewith.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Custom written computer programs and hardware interfaces control and synchronize all devices during an experiment for online, closed-loop and pre-computed control and timing. For example, phase holograms are calculated to produce light patterns desired by the user and/or experiment. These phase holograms are generated and sent to the light modulators, by downloading onto the device memory storage system (with an index address for each hologram such that it can be specifically called by the program later), or by directly loading to the modulator device and bypassing memory for complete, real time, closed-loop control. The phase hologram generation algorithms are based on Fourier and inverse Fourier transform computations of the target patterns (e.g., Gerchberg-Saxton algorithm), and/or deterministic algorithms that provide both prism and lens phase for full three-dimensional control of light within the object space (see Quirin, Peterka & Yuste 2013 Optics Express), including terms for calibration of the imaging and stimulation systems in lateral (x,y) and axial (z) coordinates at different objective positions. Adaptive optics algorithms (based on Zernike polynomials and coefficients) are applied to correct for aberrations in the system and achieve near ideal optical performance in the sample. Control software thus includes coordinates for positions (cells) of interest in three dimensions, calibrated to the imaging system used to record those positions and ongoing functional activity.

The control software also synchronizes device outputs such as laser pulse timing and intensity (including waveforms to modulate Pockels cells and/or AOMs), as well as galvanometer mirror positions to create excitation patterns (e.g., spiral scanning for optogenetics). The software also calibrates the targeted three-dimensional positions accounting for the instantaneous position of the objective while the objective is in motion driven by a piezo-electric motor. This allows the same positions in the sample's coordinates to be targeted regardless of objective position. The SLM-system is synchronized in software and hardware to the imaging system to the microsecond or better level.

Online software reads imaging data as it is collected (near real time, <5 ms) such that targeting can be maintained on the targets of interest with micron resolution, regardless of any drift in the system (online motion correction and drift estimation are calculated, for example using cross-correlation analysis of images at the beginning of a session versus real time images). Online software analyzes incoming imaging data and summarizes ongoing activity patterns for the neurons and cell segments of interest such that hologram generation, hologram selection (from pre-computed or stored holograms), and optogenetics can be performed in a closed-loop fashion based on ongoing activity patterns, or other measurements (such as behavioral measurements).

All of the above software and hardware-control components are built into a software package that is readily loaded all at once (including calibrations, or software exists for running calibration routines to determine new calibration parameters) and includes a graphical-user interface. This experiment interface allows experiments to be flexibly created such that several ensembles of neurons can be defined as different conditions of an experiment, with different parameters, such as stimulation timing, frequency, laser power, excitation parameters (such as different spiral scan patterns), etc. A trial structure can be created to repeat and randomize the order of each condition into a trial structure, and all holograms and voltage outputs (used for hardware synchronization and control) can be pre-computed. Conditions and trial orders can also be loaded into the software in a predetermined fashion in the form of simple files (text files, simple data files), for example, as the result of a specific analysis of imaging data to find neurons of interest for stimulation. Additional software is synchronized to the system to control imaging timing and parameters, and other experimental manipulations, such as sensory and behavioral manipulations of the animal.

Biological Sample

The present methods and systems may be used to irradiate a variety of biological samples. The biological sample may be a multicellular organism or a portion thereof, such a tissue, e.g., animal tissue, or organ. The tissue or organs may be whole or part of a brain, eye, heart, liver, pancreas, muscle, bone, kidney, prostate, breast, cervix, lung, and/or ovary. The biological sample may be a healthy sample, e.g., a healthy tissue from a healthy individual, or may be a pathological sample, e.g., a pathological tissue from an individual suspected of having or known to have a disease. The disease may be any suitable disease, including, but not limited to, cancer, inflammation, diabetes, etc. The biological sample may be a live sample, a processed sample (e.g., a clarified sample, as described above; a labeled sample, etc.), or a fixed sample. In some cases, the biological sample is an animal, such as a living animal. In some cases, the biological sample is a genetically modified sample (e.g., a genetically modified organism or tissue).

In some embodiments, the biological sample is labeled or stained with a detectable label. In some cases, the biological sample contains one or more cells that are associated with a detectable label, e.g., a fluorescent label, colorimetric label, etc. A fluorescent label may be a fluorescent dye or a fluorescent protein that enables the cells to emit fluorescence in response to an appropriate light sheet illumination (e.g., light sheet illumination having the appropriate wavelength and intensity of illumination). In some embodiments, the cells of the biological sample, e.g., neurons, include a fluorescent moiety, e.g., a fluorescent dye or a fluorescent protein, that enables the cells to emit fluorescence in response to light irradiation. The cells of the biological sample may be made to associate with the fluorescent moiety by any suitable method, including being labeled directly or indirectly with a fluorescent dye or fluorescent protein, or expressing a genetically encoded fluorescent protein. Any suitable method may be used to indirectly label cells of the biological sample with a fluorescent moiety. In some cases, a binding member, e.g., an antibody, that specifically binds to a cellular component, e.g., a cell surface marker on the cells, may be conjugated with a detectable label, e.g., a fluorescent dye or protein, and the labeled binding member may be used to label the cells indirectly. In some cases, the binding member is a nucleic acid that includes a sequence that hybridizes with a target sequence in cells of the biological sample, and the nucleic acid may be conjugated to a detectable label.

The biological sample may be labeled with a detectable label at any suitable density. In some cases, substantially all cells of the sample are labeled with a detectable label. In some cases, substantially all cells of a cell type (e.g., substantially all neurons) are labeled with a detectable label. In some cases, where a detectable label is encoded genetically and expressed by cells of the biological sample, the detectable label is expressed under a promoter that drives expression in specific subsets of cells in the biological sample. In some cases, the promoter is a tissue-specific promoter. In some cases, the promoter is specific for cell types within a tissue.

Fluorescent dyes of interest include, but are not limited to, fluorescein, fluorescein isothiocyanate (FITC), rhodamine, tetramethylenerhodamine isothiocyanate (TRITC), sulforhodamine 101 acid chloride (Texas Red®), phycoerythrin (PE), allophycocyanin, phycoerythrin-Texas Red® (PETR), 4-methylumbelliferone, etc. Fluorescent proteins of interest, which may be genetically encoded, include green fluorescent protein, yellow fluorescent protein, cyan fluorescent protein, etc., and variants thereof.

In certain embodiments, the detectable label is a small molecule dye such as DAPI (4',6-diamidino-2-phenylindole), acridine orange, hydroethidine, etc. Other detectable labels may include Acid Fuchsin, Acridine Orange, Alcian Blue 8GX, Alizarin, Alizarin Red S, Alizarin Yellow R, Amaranth, Amido Black 10B, Aniline Blue Water Soluble, Auramine O, Azure A, Azure B, Basic Fuchsin Reagent A.C.S., Basic Fuchsin Hydrochloride, Benzo Fast Pink 2BL, Benzopurpurin 4B, Biebrich Scarlet Water Soluble, Bismarck Brown Y, Brilliant Green, Brilliant Yellow, Carmine, Lacmoid, Light Green SF Yellowish, Malachite Green Oxalate, Metanil Yellow, Methylene Blue, Methylene Blue Chloride, Methylene Green, Methyl Green, Methyl Green Zinc Chloride Salt, Methyl Orange Reagent A.C.S., Methyl Violet 2B, Morin, Naphthol Green B, Neutral Red, New Fuchsin, New Methylene Blue N, Nigrosin Water Soluble, Nigrosin B Alcohol Soluble, Nile Blue A, Nuclear Fast Red, Oil Red O, Orange II, Orange IV, Orange G, Patent Blue, 4-(Phenylazo)-1-naphthalenamine Hydrochloride, Phloxine B, Ponceau G R 2R, Ponceau 3R, Ponceau S, Procion Blue HB, Prussian Blue, Pyronin B, Pyronin Y, Quinoline Yellow SS, Rhodamine 6G, Rhodamine B Base Alcohol Soluble, Rhodamine B O, p-Rosaniline Acetate Powder, Rose Bengal, Rosolic Acid, Saffron, Safranine O, Stilbene Yellow, Sudan I, Sudan II, Sudan III, Sudan IV, Sudan Black B, Sudan Orange G, Tartrazine, Thioflavine T TG, Thionin, Toluidine Blue O, Tropaeolin O, Trypan Blue, Ultramarine Blue, Victoria Blue B, Victoria Blue R, Xylene Cyanol FF, Xylene Cyanol FF, Alizarin, Alizarin red S (sodium monosulfonate) monohydrate, Alum carmine, Amaranth, Arsenazo III, Basic red 2 (Cotton red; Gossypimine; Safranin A or O or Y), Bismark brown, Bromocresol green, Bromocresol purple, Bromophenol blue, Bromophenol red, Bromothymol blue, Calcein, Calcon (Eriochrome black B), Clayton yellow (Thiazole yellow), Coomassie blue (Brilliant blue), Cotton Red (Basic red 2; Gossypimine; Safranin A or O or Y), Cresol red sodium salt, Cupferron, 2',7'-Dichloro fluorescein, Dicyanobis (1,10-phenanthroline)Iron, Diethyldithiocarbamic acid silver salt, 4,7-Diphenyl-1,10-phenanthroline-x.x-disulfonic acid diNa salt, Diphenylthiocarbazone, Dithizone, Eosin bluish, Eosin Y, Eriochrome black B (Calcon), Eriochrome black T, Eriochrome blue, Eriochrome blue black R, Eriochrome blue SE, Eriochrome gray SGL, Eriochrome red B, Erionglaucine (A), Erythrosin B, Fast Green FCF, Fuchsin acid, Fuchsin basic (Pararosaniline HCl), Gentian Violet, Gossypimine (Basic red 2; Cotton red; Safranin A or O or Y), Hematoxylin, Hydroxy Naphthol blue, Indigo blue pigment, Janus green B, Methyl orange, Methyl orange, Methyl red, Methyl thymol blue, Methyl violet B (Aniline violet; Dahlia violet B), Methyl violet base (Solvent violet 8), Methylene blue, Murexide indicator, Neutral red, Orange G, Orange IV, Owen's blue, Patent blue (Acid blue 1), Pararosaniline HCl (Basic fuchsin), Phenolphthalein, Phenol red, Phlorglucinol dihydrate, Pyronine Y (or G), Safranin, Safranin A or O or Y (Basic red 2; Cotton red; Gossypimine), Solvent violet 8 (Methyl violet base), Sudan III, Sudan IV, Thiazole yellow (Clayton yellow), Thymol blue, Thymolphthalein pH indicator 9.4-10.6, Wright's stain, Xylene cyanole FF, Chromotrope 2B, Chromotrop 2R, Clayton Yellow; Cochineal Red A, Congo Red, Coomassie® Brilliant Blue G-250, Coomassie® Brilliant Blue R-250, Cotton Blue, Crocein Scarlet 3B, Curcumin, Diazo Blue B, Eosin B, Eosin B Water Soluble, Eosin Y, Eriochrome Black A, Eriochrome Black T Reagent A.C.S., Eriochrome Blue Black R, Eriochrome Cyanine R, Erioglaucine, Erythrosin B, Ethyl Eosin, Ethyl Violet, Evans Blue, Fast Garnet GBC Base, Fast Garnet GBC Salt, Fast Green FCF, Fluorescein Alcohol Soluble U.S.P., Fluorescein Alcohol Soluble, Fluorescein Water Soluble, Hematoxylin, 8-Hydroxy-136-pyrenetrisulfonic Acid Trisodium Salt; Indigo Synthetic, Indigo Carmine, Indophenol Blue, Indulin Water Soluble, and Janus Green B. In other embodiments, the detectable label may include labeled or unlabeled antibodies specific for a particular protein or antigen such p53, p38, p43, fos, c-fos, jun, NF-κB, anillin, SC35, CREB, STET3, SAMD, FKHD, D4G, calmodulin, calcineurin, actin, microtubulin, ribosomal proteins, receptors, cell surface antigens such as CD4, etc.

In some cases, the biological sample contains cells that contain an indicator dye, such as a functional indicator dye. The indicator dye may be a genetically encoded indicator dye. The genetically encoded indicator may be configured to be expressed in specific subsets of cells in the biological sample using specific promoters to drive expression of the indicator dye, as described above. The indicator dye may be adapted to emit fluorescence in response to cellular electrical activity, e.g., neuronal activity, muscle contraction, etc. Fluorescent moieties whose fluorescence properties are sensitive to cellular electrical activity include genetically encoded ratiometric/non-ratiometric dyes and fluorescent proteins. Fluorescent moieties whose fluorescence properties are sensitive to cellular electrical activity may be a fluorescence resonance energy transfer (FRET)-based reporter. Fluorescent moieties whose fluorescence properties are sensitive to cellular electrical activity may be sensitive to changes in intracellular concentration of ions such as calcium, sodium and protons or to changes in membrane potential. In such cases, fluorescent dyes of interest include, but are not limited to, calcium indicator dyes (Indo-1, Fura-2, and Fluo-3, Calcium Green®, Fluo-4, etc.); sodium indicator dyes (sodium-binding benzofuran isophthalate (SBFI), Sodium Green™, CoroNa™ Green, CoroNa™ Red, etc.); and proton indicator dyes (2',7'-bis-(carboxyethyl)-5-(and-6)-carboxyfluorescein (BCECF), etc.). Cellular electrical activity-sensitive fluorescent proteins of interest include, but are not limited to, calcium indicators (Cameleon, GCaMP1, GCaMP2, GCaMP3, GCaMP6 and derivatives thereof, as well as those cited in U.S. Pat. No. 8,629,256, and Tian et al. 2012 *Prog Brain Res.*, 196:79, the disclosures of each of which are incorporated herein by reference); and voltage indicators (QuasAr1, QuasAr2, VSFP, and derivatives thereof, as well as those cited in U.S. App. Pub. No. 2013/0224756, Hochbaum et al., *Nat Methods*, 2014, 11:825, Baker et al. *Brain Cell Biol.*, 2008, 36:53; and Mutoh et al., *Exp Physiol.*, 2011, 96:13, the disclosures of each of which are incorporated herein by reference). In some cases, the fluorescent moiety may be sensitive to biochemical changes in the excitable cell, such as changes in enzymatic activity (e.g., activation of kinases); changes in binding interactions (e.g., binding of transcription factors to DNA); changes in subcellular localization of proteins; etc. Exemplary fluorescent moieties are further described in, e.g, Mehta et al., *Annu Rev Biochem.*, 2011; 80: 375, the disclosure of which is incorporated herein by reference.

In some embodiments, the biological sample contains cells that are adapted to hyperpolarize and/or depolarize in response to an extrinsic stimulus, e.g., a laser light stimulus applied to the sample. In some embodiments, the biological sample may contain a photo-sensitive caged compound, e.g., a caged neurotransmitter, that, when uncaged by a light stimulus, binds to a receptor on an excitable cell nearby and contributes to hyperpolarizing or depolarizing the excitable cell, depending on the neurotransmitter and the receptor. In some cases, the caged neurotransmitter may be glutamate, dopamine, serotonin, GABA, etc., available from, e.g., Tocris, as well as those caged neurotransmitters described in, e.g., U.S. Pat. No. 8,178,496, the disclosure of which is incorporated herein by reference. Suitable methods of using caged neurotransmitters to stimulate neurons is described in, e.g., Noguchi et al., *J Physiol.*, 2011, 589:2447, the disclosure of which is incorporated herein by reference.

In some embodiments, the biological sample contains cells that are genetically modified to express a light-responsive polypeptide that, when stimulated by an appropriate light stimulus, hyperpolarizes or depolarizes the cell, e.g., excitable cell, such as a neuron or muscle cell. In some instances, the light-responsive polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the cell when activated by light of an activating wavelength. In some embodiments, the light-responsive polypeptide hyperpolarizes the cell when activated by light of an activating wavelength. Suitable hyperpolarizing and depolarizing polypeptides are known in the art and include, e.g., a channelrhodopsin (e.g., ChR2), variants of ChR2 (e.g., C128S, D156A, C128S+D156A, E123A, E123T), iC1C2, C1C2, GtACR2, NpHR, eNpHR3.0, C1V1, VChR1, VChR2, SwiChR, Arch, ArchT, KR2, ReaChR, ChIEF, Chronos, ChRGR, and the like. Hyperpolarizing and depolarizing opsins have been described in various publications; see, e.g., Berndt and Deisseroth (2015) *Science*, 349:590; Berndt et al. (2014) *Science*, 344:420; and Guru et al. (Jul. 25, 2015) *Intl. J. Neuropsychopharmacol.*, pp. 1-8 (PMID 26209858).

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Development of a Fast, High-Resolution Spatial Light Modulator (SLM): MacroSLM

Figure 2:
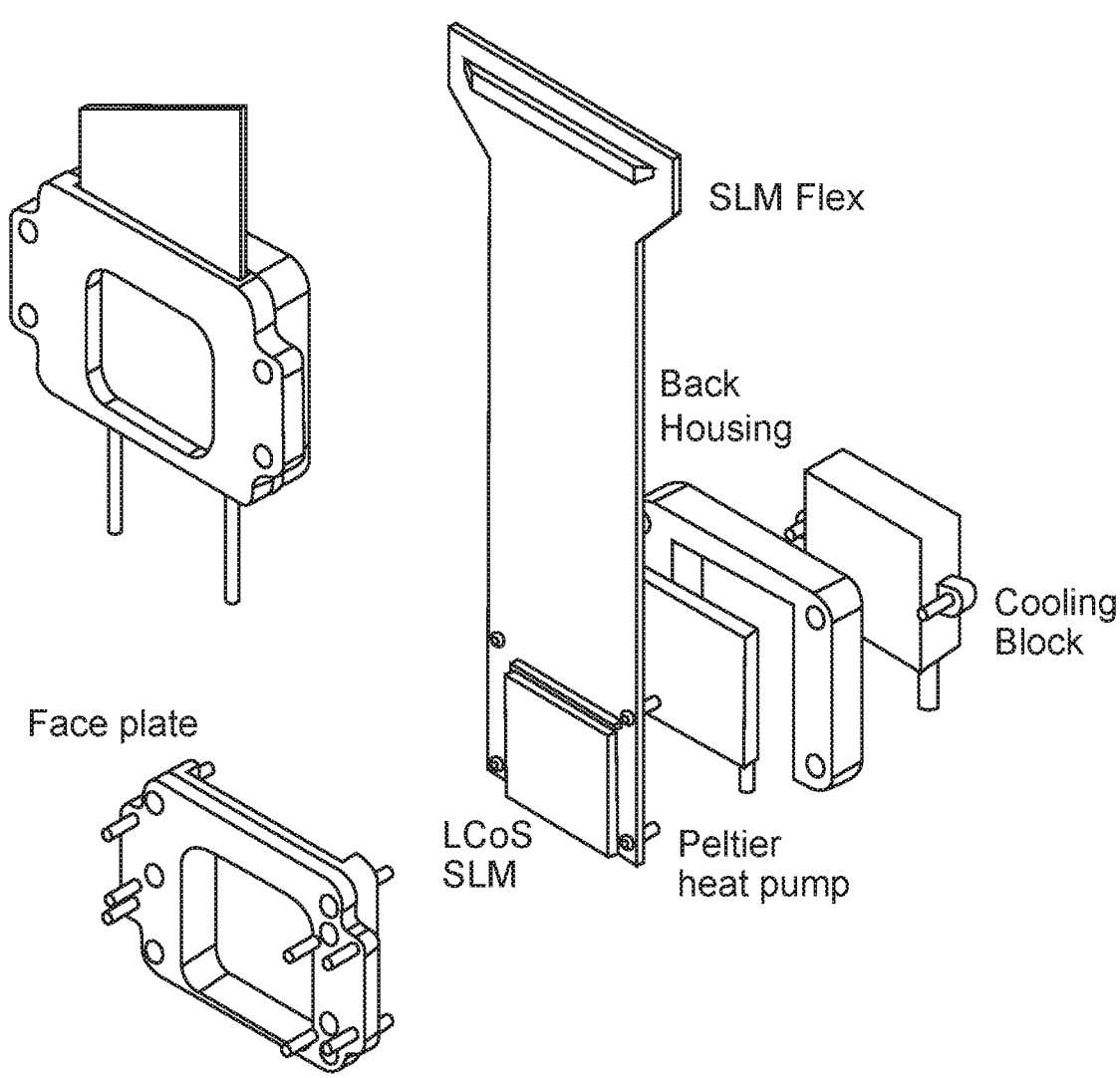
FIG. 2, A-F depicts a light projection system according to certain embodiments.
Figure 2:
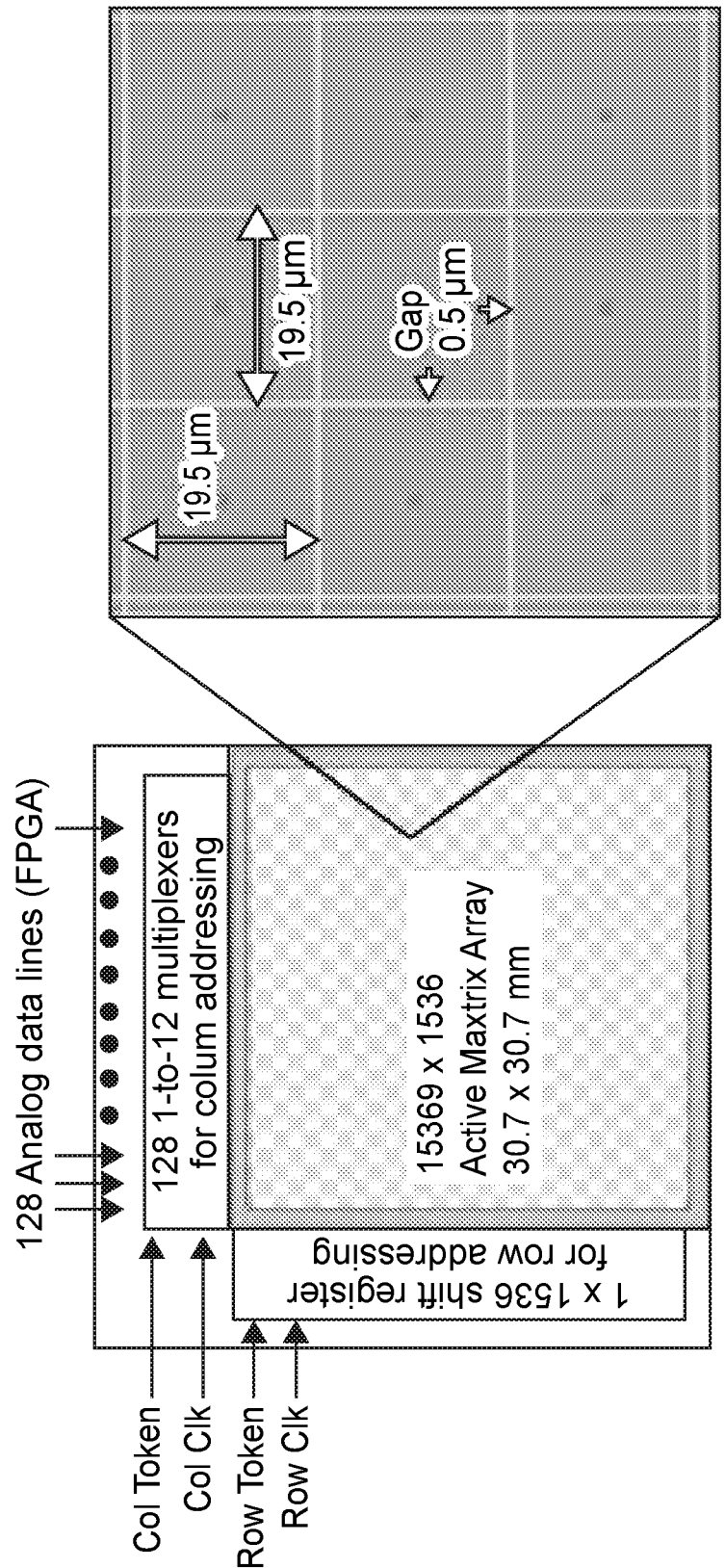
Figure 2:
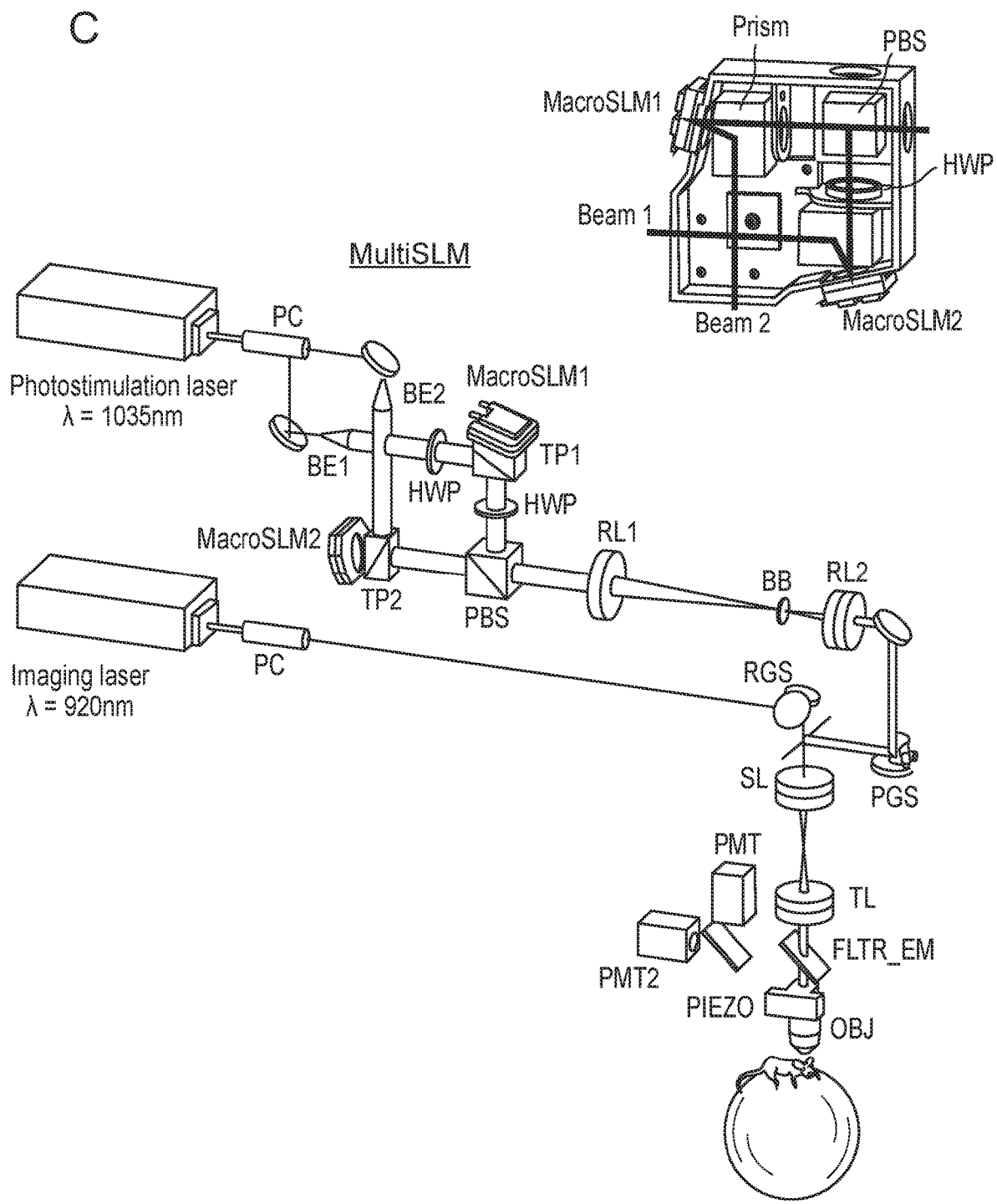
Figure 2:
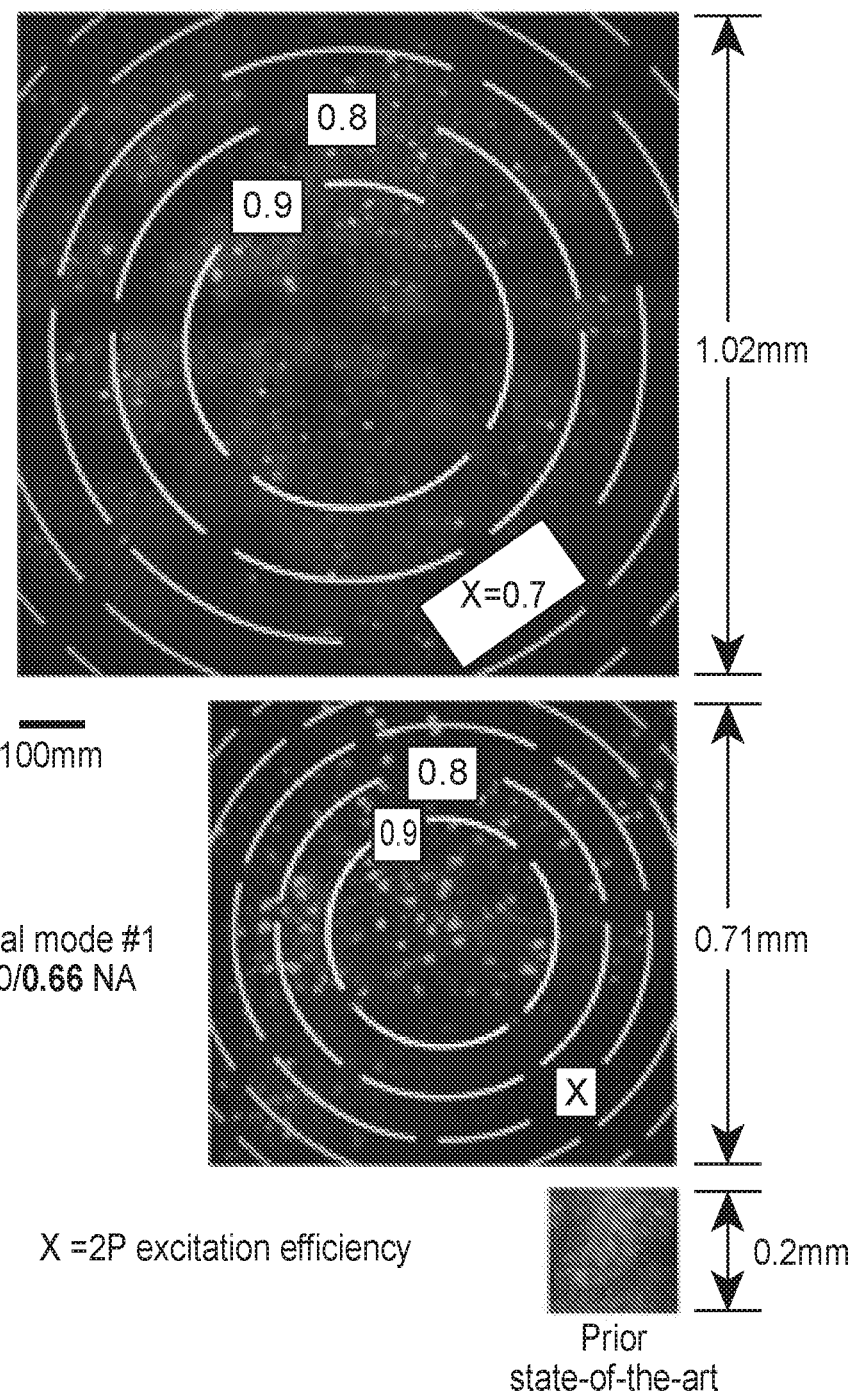
Figure 2:
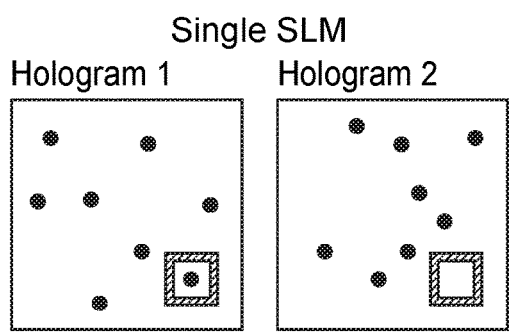
Figure 2:
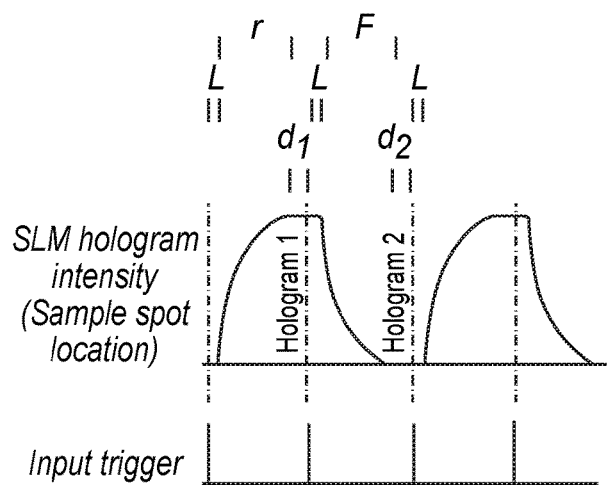
Figure 2:
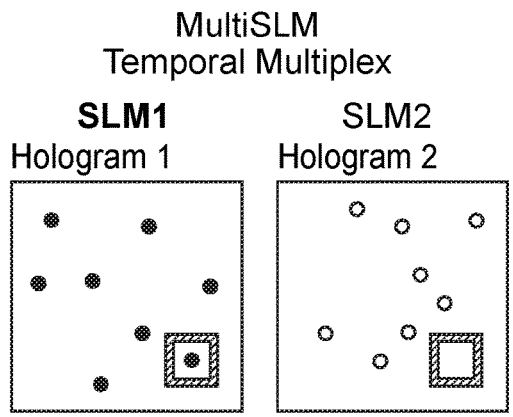
Figure 2:
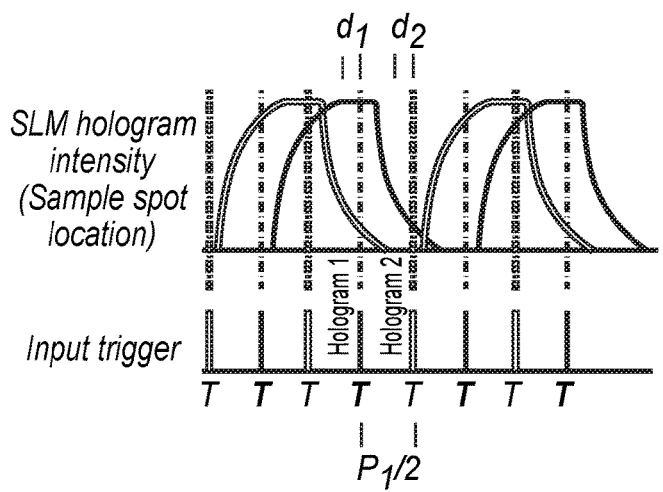
Figure 2:
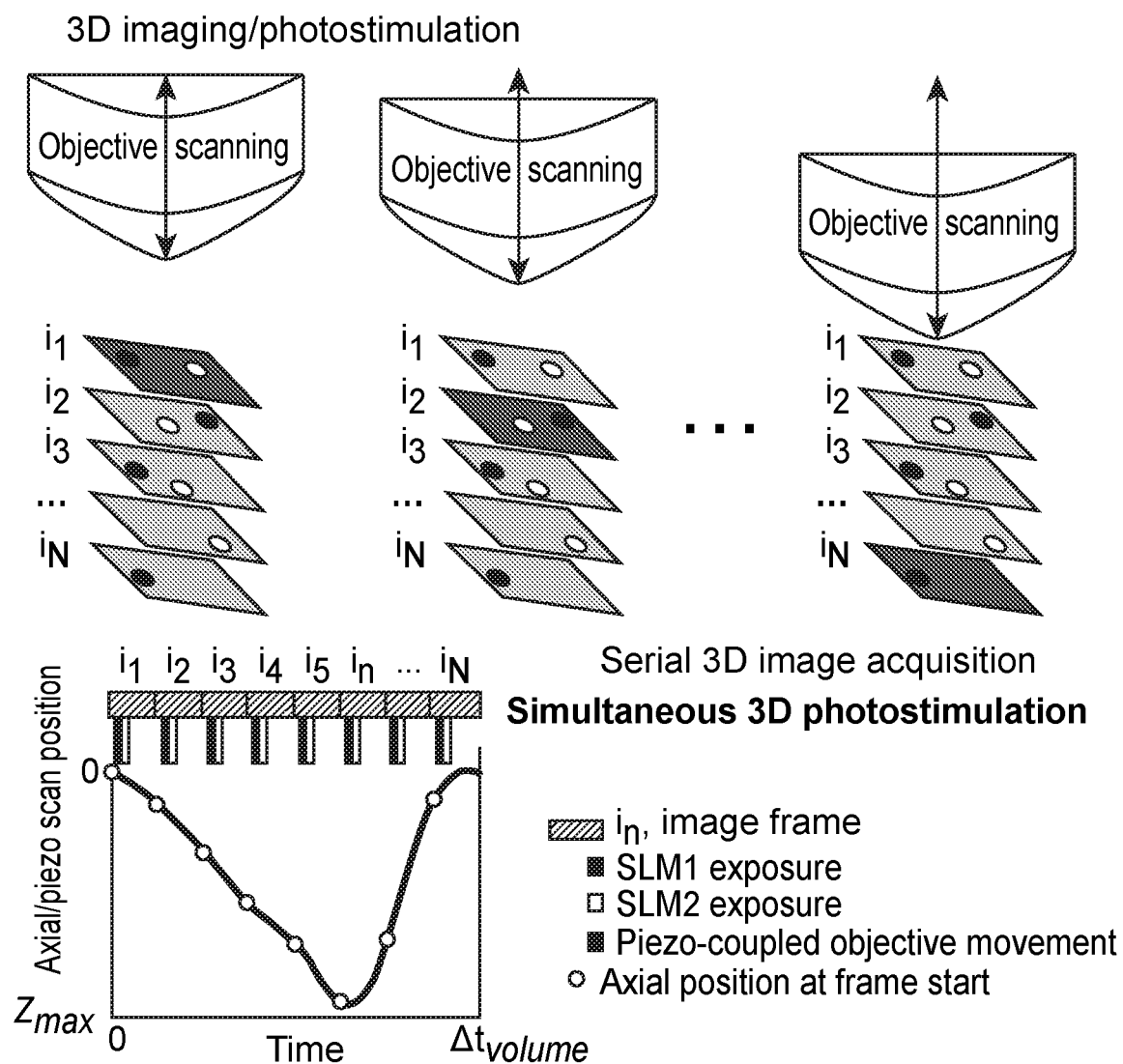
Figure 5:
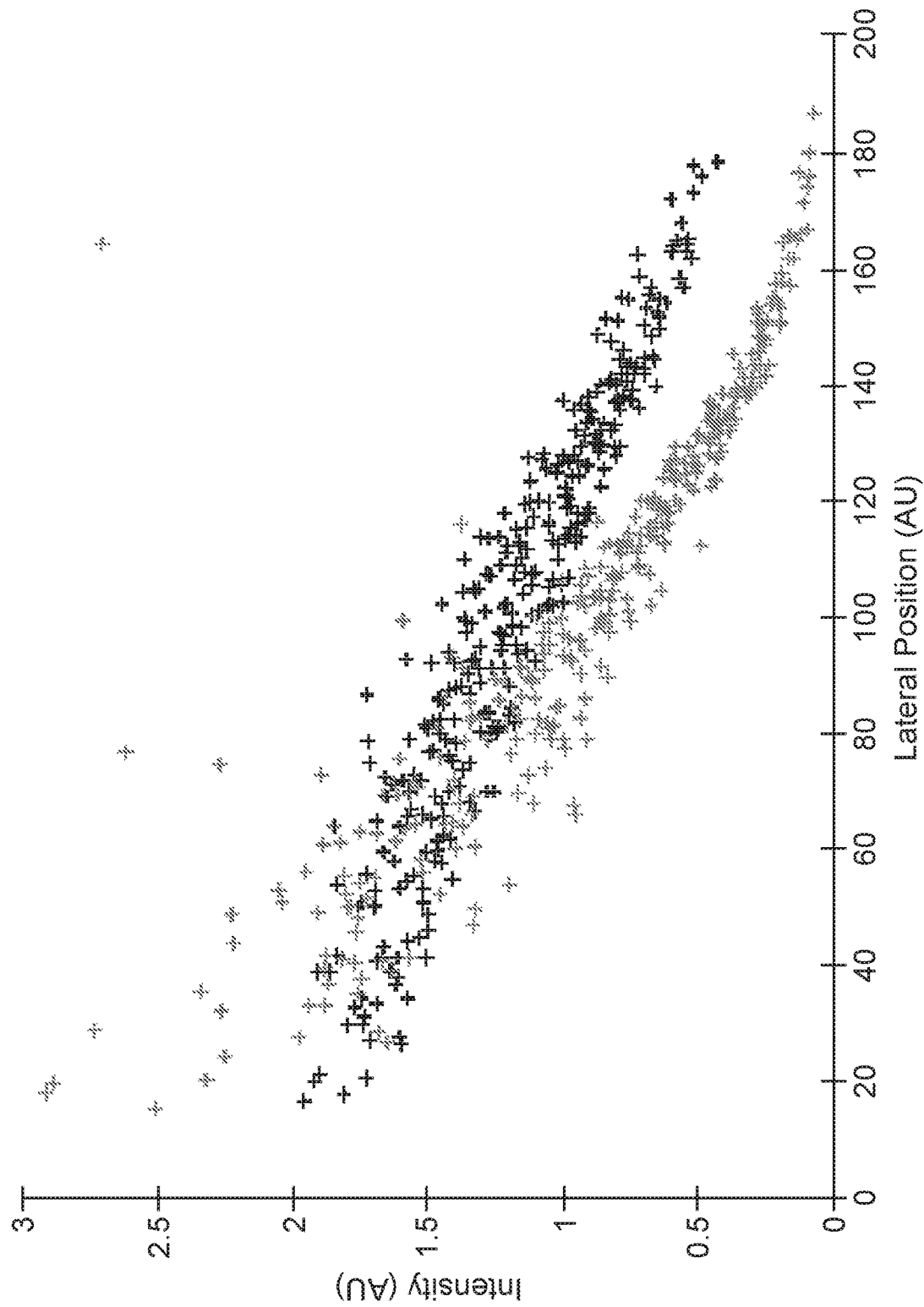
FIG. 5 depicts the effect of dielectric mirror coating on spot uniformity according to certain embodiments. The same 400 spot hologram was displayed on two comparable 512×512 SLM devices using a 1064 nm laser, with the difference being the use of dielectric mirror (red) or not (blue). The spot pattern is more uniform across the field of view for the SLM without a dielectric mirror.

A MacroSLM was optimized along several design dimensions. SLM pixel resolution directly translates to addressable field of view, and diffractive optics inherently lose efficiency as light is steered away from the central, zero order. The highest pixel count possible was targeted while satisfying several other design criteria focused on high fidelity and high-speed operation optimized for in vivo two photon optogenetics, as well fabrication reliability and overall size of the SLM. The result of these optimizations yielded a 1536×1536 active pixel SLM, with a large pixel pitch (20 µm) that enabled high voltage (12V), high storage capacitance (178 fF), and high fill factor (>94% measured, 96% based on pixel design) (FIG. 2a,b). This SLM has a theoretical diffraction limited field of view of 1.6×1.6 mm at 0.5 NA (the resolution needed for optimized single cell stimulation). The large pixel pitch: 1) enables large voltage swings, which in turn increases hologram transition speed; 2) is sufficient to store enough charge (capacitance) to hold the electric field across the liquid crystal while it is switching patterns; and 3) provides an extremely high fill factor since the active pixel (19.5 µm width) is much larger than the gap between the pixel pads needed to prevent shorting (0.5 µm). Fill factor determines the diffraction efficiency (DE) of the device, with DE=(fill factor)*2×pixel reflectivity, or theoretically for this device (0.96)*2×0.95=0.88. The high diffraction efficiency improves overall efficiency of the system and also minimizes potential artifacts from non-diffracted light. A high DE is achieved based fundamentally on our high fill factor, obviating the need for a dielectric mirror coating, typically used to increase DE. Commercially available SLMs demonstrated that dielectric mirror coatings increased artifacts (ghost spots), strongly affected spot uniformity by increasing pixel crosstalk (reducing effective SLM resolution and therefore addressable field of view), and reduced the electric field across the liquid crystal, which in turn lengthened response time (FIG. 5). The large pixel pitch had other advantages. Increasing pixel pitch decreases the corresponding deflected angle to achieve the same field of view in the image plane (maximum deflection angle is 1.4 degrees for the MacroSLM), reducing the diameter of downstream optics (which practically improves system feasibility and performance), and minimizes the lateral chromatic aberration inherent to a diffractive optic when addressing large fields-of-view. Finally, the large pixel pitch and high pixel count results in a larger SLM capable of higher power handling, important for stimulating large ensembles of neurons simultaneously.

To achieve high-speed hologram transition, a driver system based on multiplexed field-programmable gate arrays (FPGAs) was developed to drive the full array of over 2.3 million pixels in 799 µs (128 channels at 25 MHz). The hologram display algorithm used to display the completed hologram on the liquid crystal device was optimized by 'overdriving' the pixels with extreme voltages before settling on the target hologram. 'Phase wrapping' was implemented for each pixel to shorten the distance in phase between adjacent phase values in time. Furthermore, the SLM backplane was heated and maintained at 45° C. with a closed-loop Peltier heat pump with water-cooled cooling block to increase liquid crystal responsiveness and reliability. Since phase depth decreases with increased temperature, the SLM was built with at least $3.5\pi$ of phase stroke at 1064 nm so that the necessary full $2\pi$ of phase stroke needed for full phase modulation would be achieved at high temperatures, while also reducing the possible phase difference between adjacent phases in time with any 'excess' phase stroke depth available. For integration into precisely timed and synchronized experiments, a high-speed triggering system was implemented that instructed the SLM to transition to the next commanded hologram with low latency and jitter. Holograms were preloaded into onboard memory on the FPGA driver system such that specific holograms could be called with a simple index value and a trigger that nearly instantaneously began the hologram refresh on the SLM. Under these conditions, the trigger and transition between different holograms was at 330-500 Hz with 90-100% target hologram efficiency.

Figure 6:
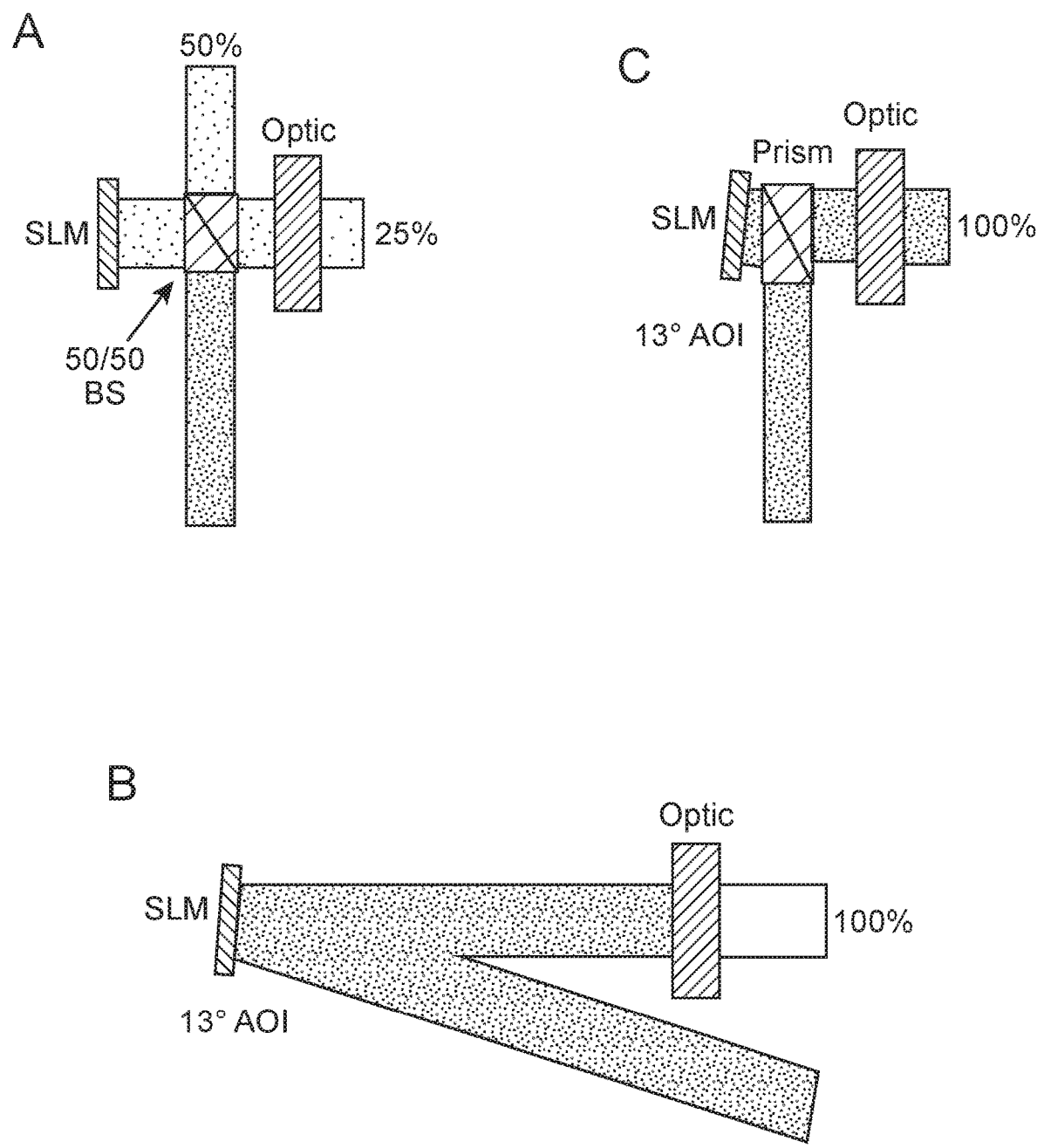
FIG. 6, A-C depicts SLM illumination strategies for confined optical footprint and closer optical elements to the SLM according to certain embodiments.
Figure 7:
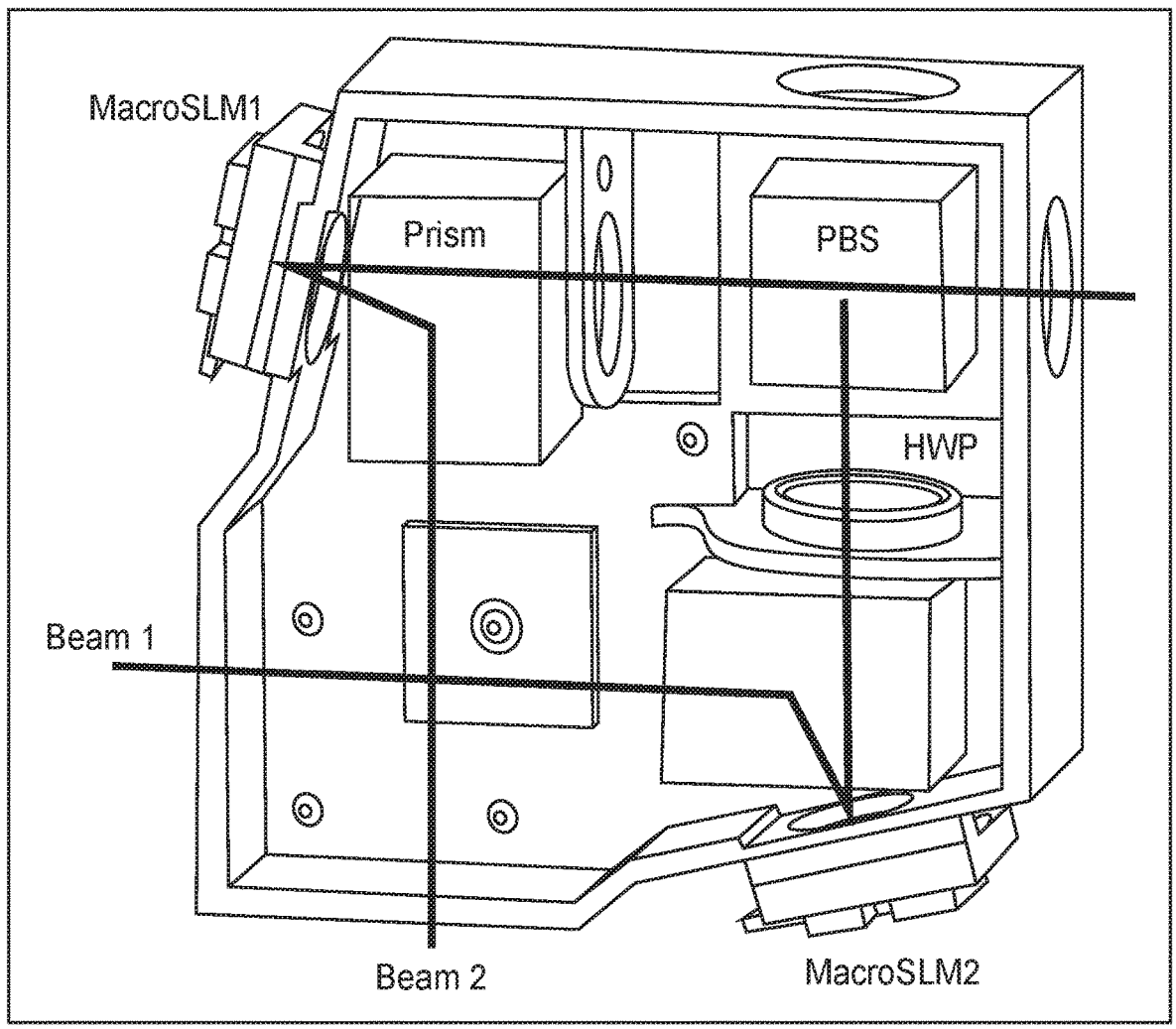
FIG. 7, A-D depict 3D printed breadboards for MultiSLM integration into a microscope according to certain embodiments.
Figure 7:
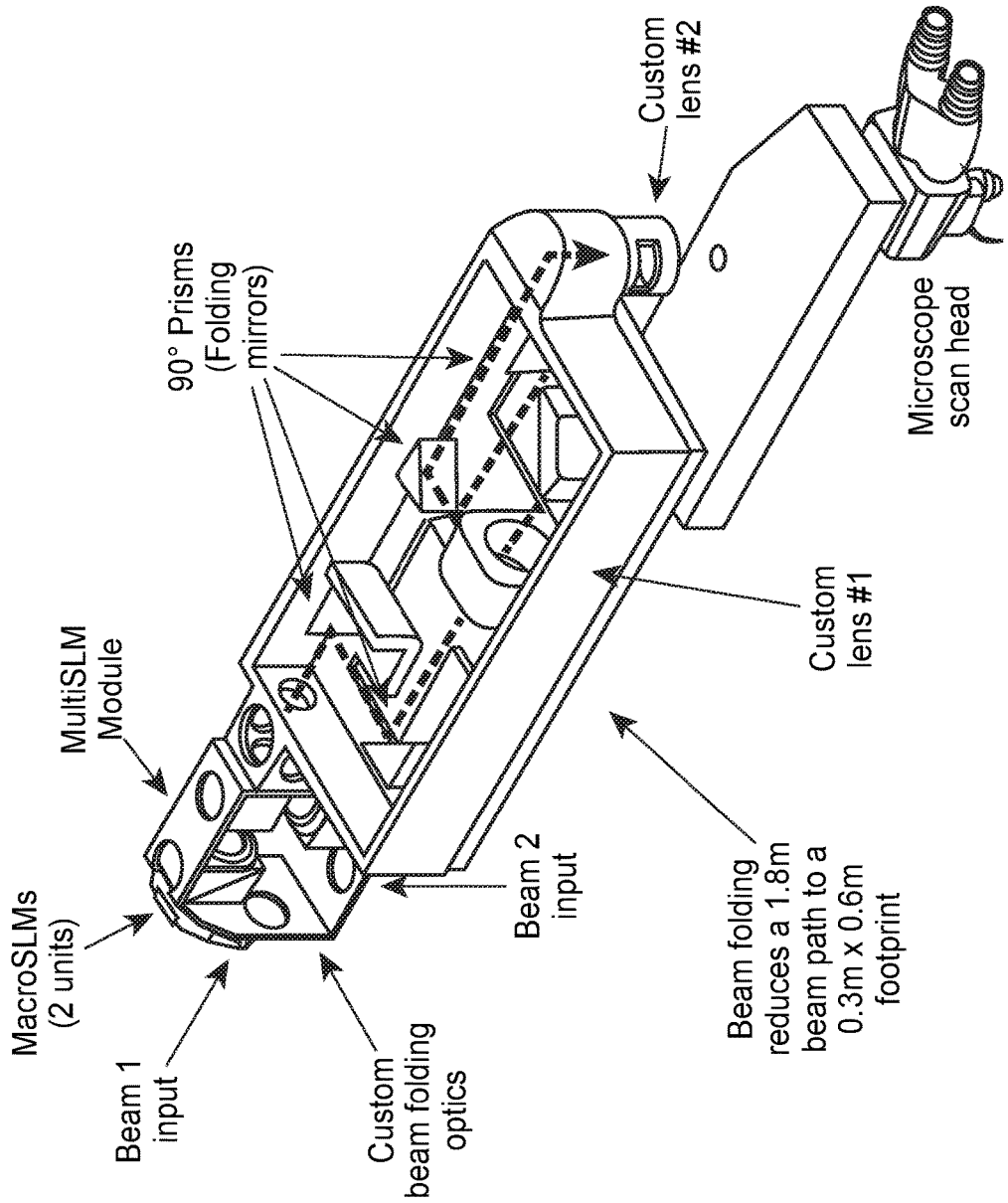
Figure 7:
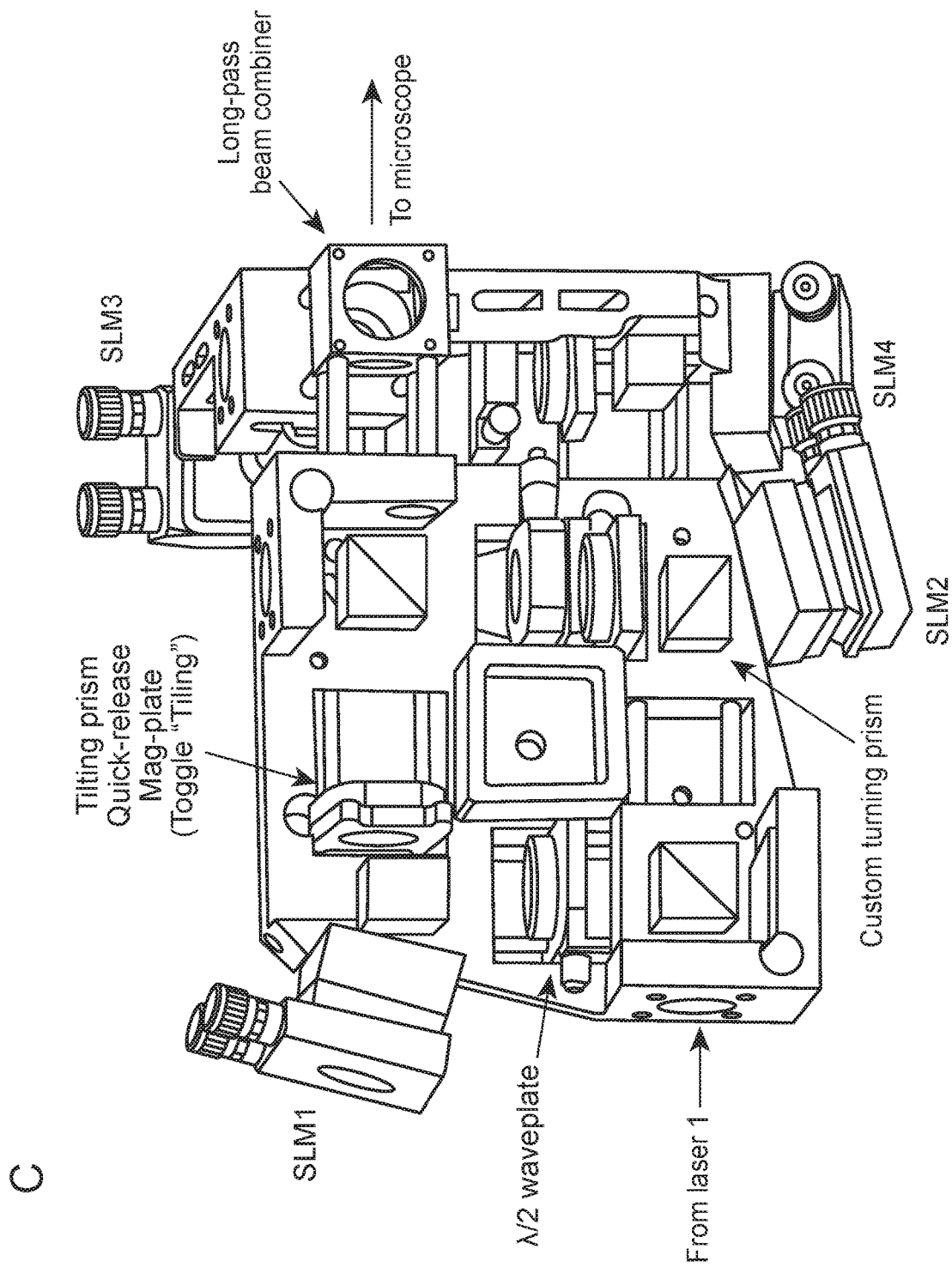
Figure 7:
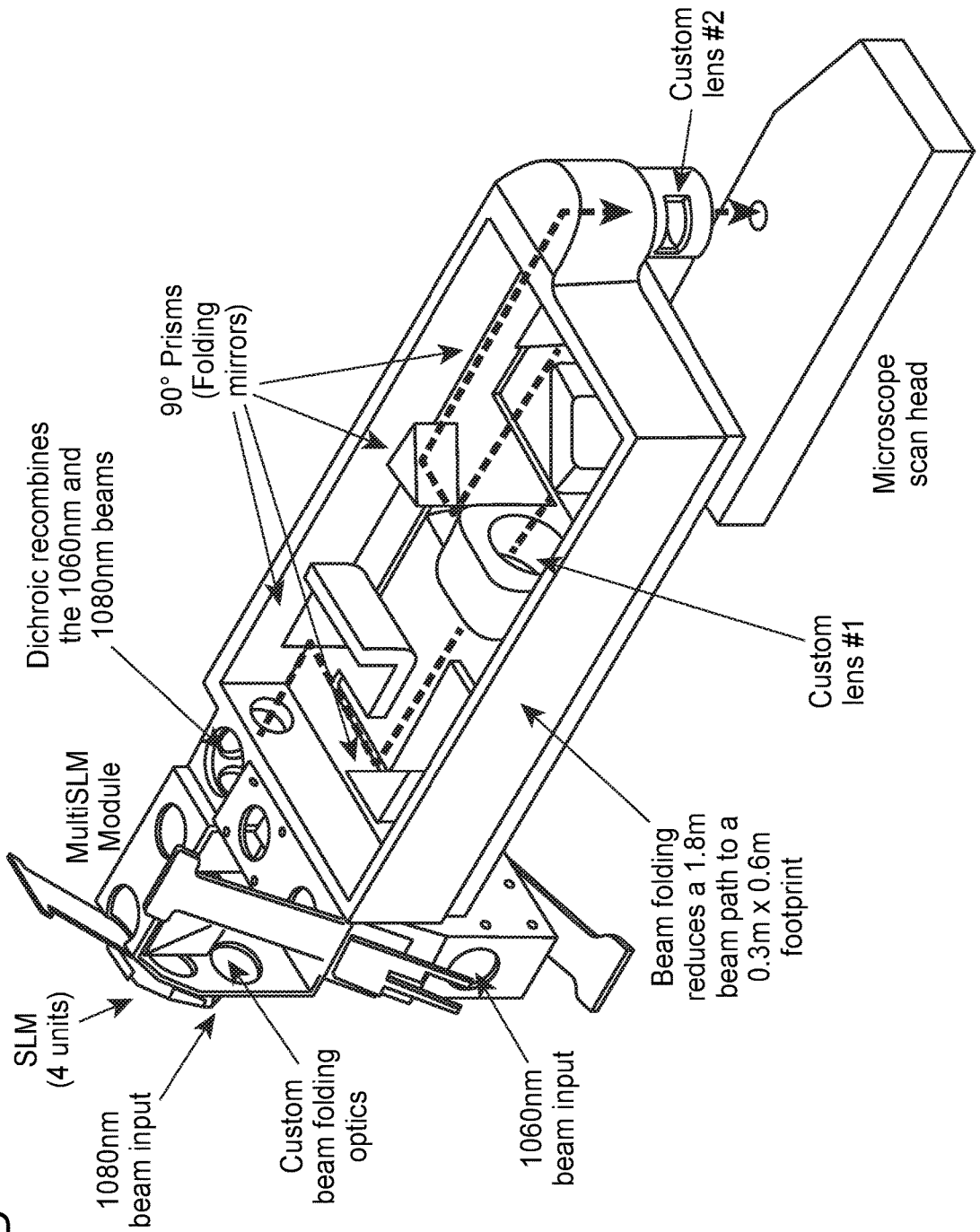

Multiplexed Spatial Light Modulator System for High-Speed Light Control at High Resolution Over a Large Field of View: MultiSLM A custom optical path to integrate the MacroSLM described above into a resonant scanner multiphoton microscope as developed. A custom, high efficiency prism was used to direct an expanded laser beam to the SLM face (13° angle of incidence (AOI) on SLM), allowing shorter focal length lenses to be used for the subsequent telescope relay to the sample by achieving essentially orthogonal optical paths. In a typical setup, the focal length is long enough such that the incoming beam can pass by the first downstream telescope lens with the smallest angle of incidence on the SLM possible to improve its performance; or, a 50/50 beamsplitter is used to create an orthogonal path at the cost of losing at least half of the SLM-modulated light in addition to half of the incoming laser beam (FIG. 2c and FIG. 6). The telescope relay following the SLM was folded upon itself to reduce the overall footprint and custom breadboards integrating the optical and optomechanical elements were 3D printed to simplify robust integration into the multiphoton microscope (FIG. 2c and FIG. 7a,b). Combined with commercially available, high NA, low magnification multiphoton objectives, high two-photon excitation efficiency was achieved across at least a 1 mm×1 mm field of view, while maintaining high NA for stimulation (FIG. 2d). Switching between two such objectives, a 16× 0.8 NA and a 10× 0.6 NA objective, yielded 0.71 mm×0.71 mm (Spatial Mode #1, FIG. 2d) and 1.02 mm×1.02 mm (Spatial Mode #2, FIG. 2d) imaging fields of view with the resonant scanner system, and provided options in terms of imaging/excitation NA and objective characteristics. This represents an increase in addressable field of view by at least 26 fold compared to previously published, in vivo all optical methods. Notably, these fields of view are sufficient to encompass one or several cortical areas (e.g., multiple visual, auditory, or somatosensory barrel columns). Larger fields of view are possible with these objectives and can be supported by the MacroSLM given its 1.6 mm×1.6 mm theoretical maximum FOV, if the base microscope (i.e., galvanometer system, lenses and apertures) accommodate larger scan angles. Effective NA for excitation was determined by the relative fill of the back aperture of each objective (determined by our telescope de-magnification factor of the relayed SLM image) and was 0.66 NA or 0.41 NA for each spatial mode, respectively.

The optical paths from two MacroSLMs were combined using orthogonal polarizations, which physically cannot interfere with one another given orthogonality (FIG. 2c, the incident polarization was optimized for SLM performance, and a half waveplate was used to rotate one beam such that a polarization beamsplitter combined the two independent beams onto a common optical path). Different lengths of each optical path from the laser shift each beam's femtosecond pulses out of phase, providing another mechanism to fully prevent interference between beams. Using high speed power modulation (200 kHz analog control, acousto optic modulator, AOM) and polarization-switching Pockels cell system (also 200 kHz control), stimulation timing and duration were controlled on the microseconds level, as well as polarization (and thus which SLM path was enabled) to coincide with periods when the corresponding SLM was at its peak hologram performance (FIG. 2e). This multiplexing strategy (MultiSLM) allowed us to at least double the time resolution of the stimulation system relative to the hologram switching speed of a single SLM, taking advantage of otherwise unusable time when an SLM is forming a specific hologram (including the time to deliver the hologram pattern from the driver to the SLM pixels and the time the liquid crystal takes to realize the desired hologram phase pattern), using a single laser source (FIG. 2c,e). A single SLM could not attain kilohertz hologram switching rates. A multiplexed SLM system as described herein achieved kilohertz ensemble control using 2 multiplexed, high-speed Macro-SLMs and twice as many neurons could be excited in time.

Kilohertz Ensemble Stimulation of Hundreds of Neurons in 3D

Figure 3:
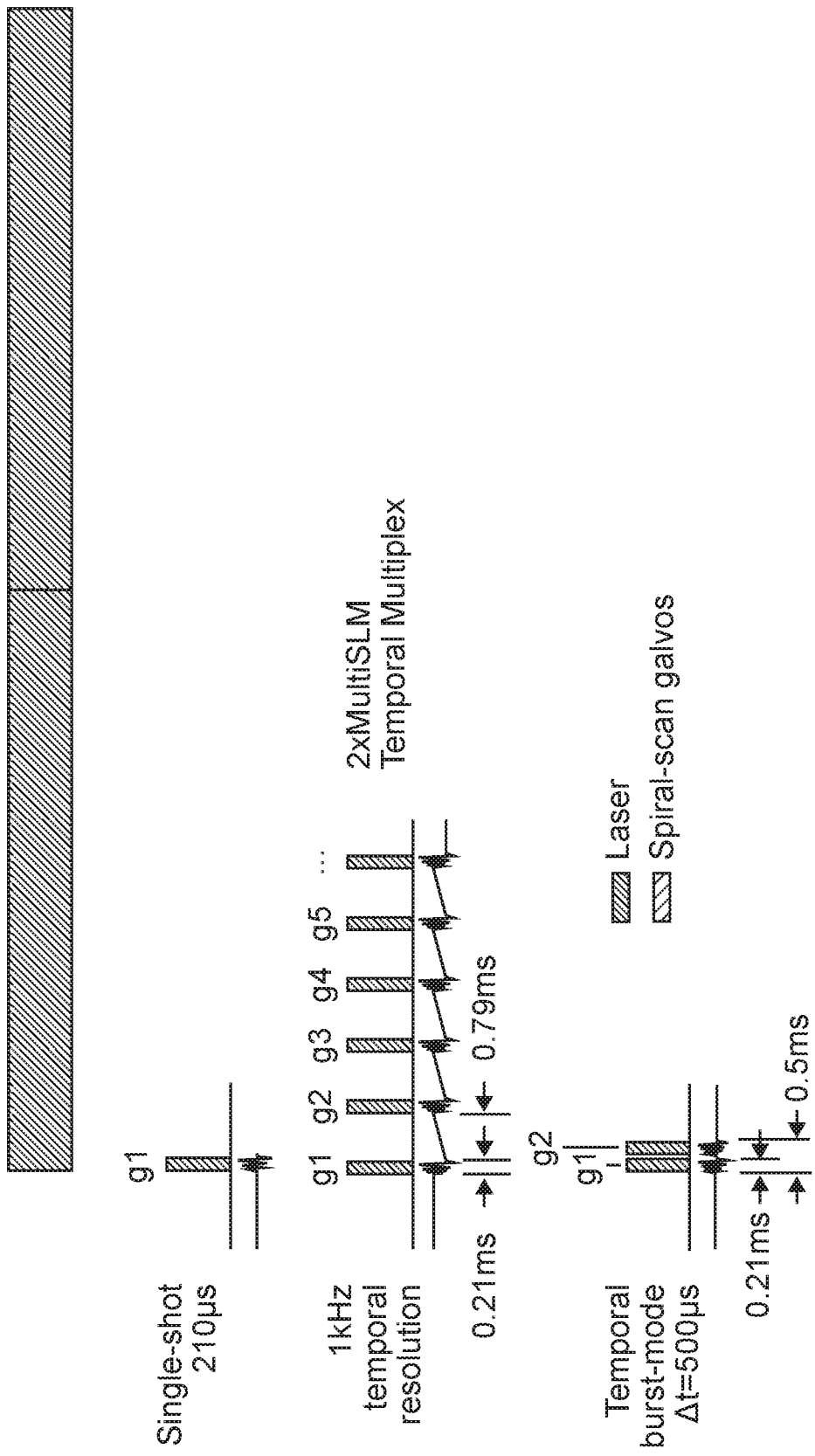
FIG. 3, A-J depicts optically addressing sequences of unique neuronal ensembles composed of a plurality of neurons at kHz temporal resolution in 3D, and over 1 mm$^2$ according to certain embodiments.
Figure 3:
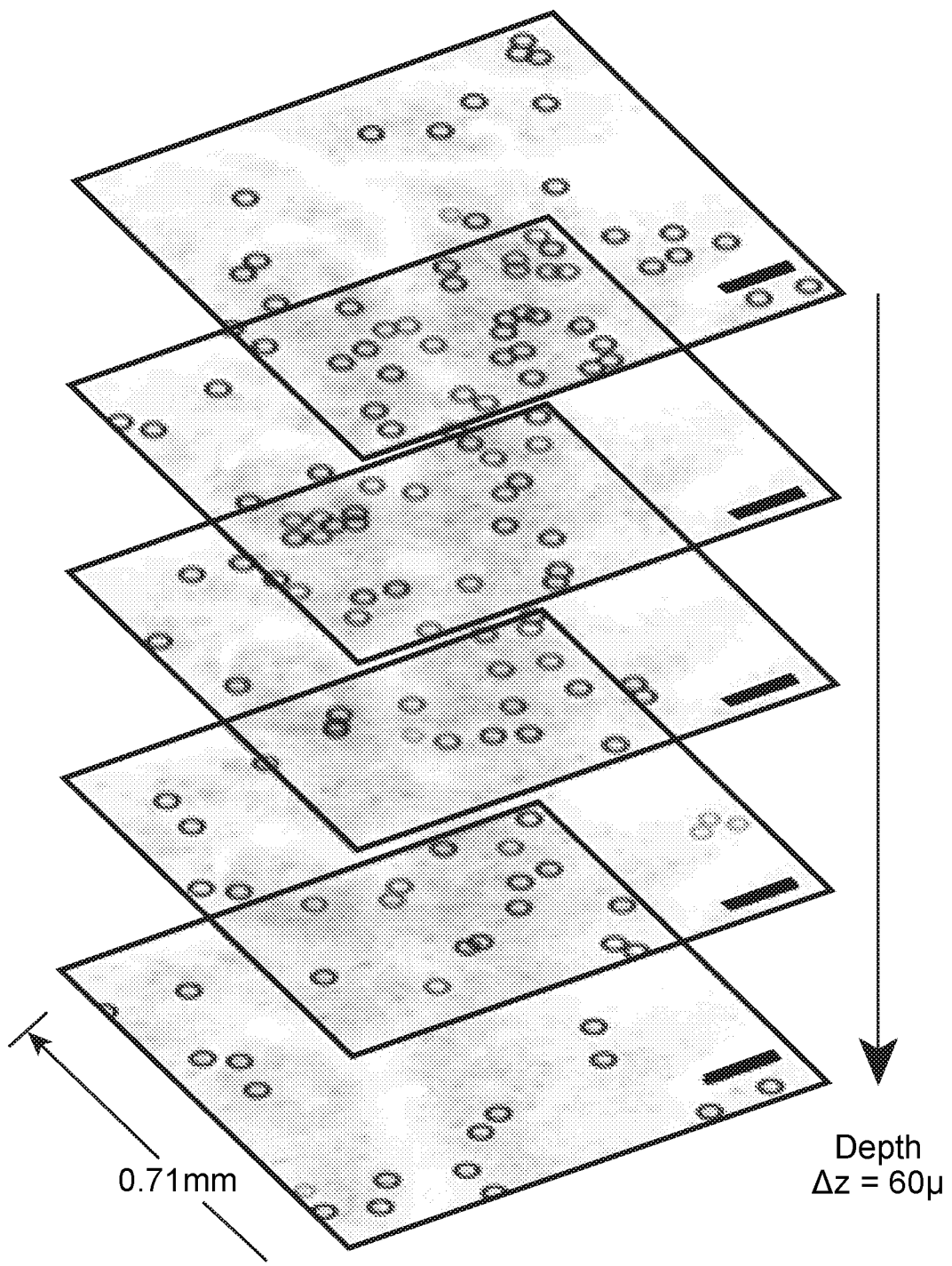
Figure 3:
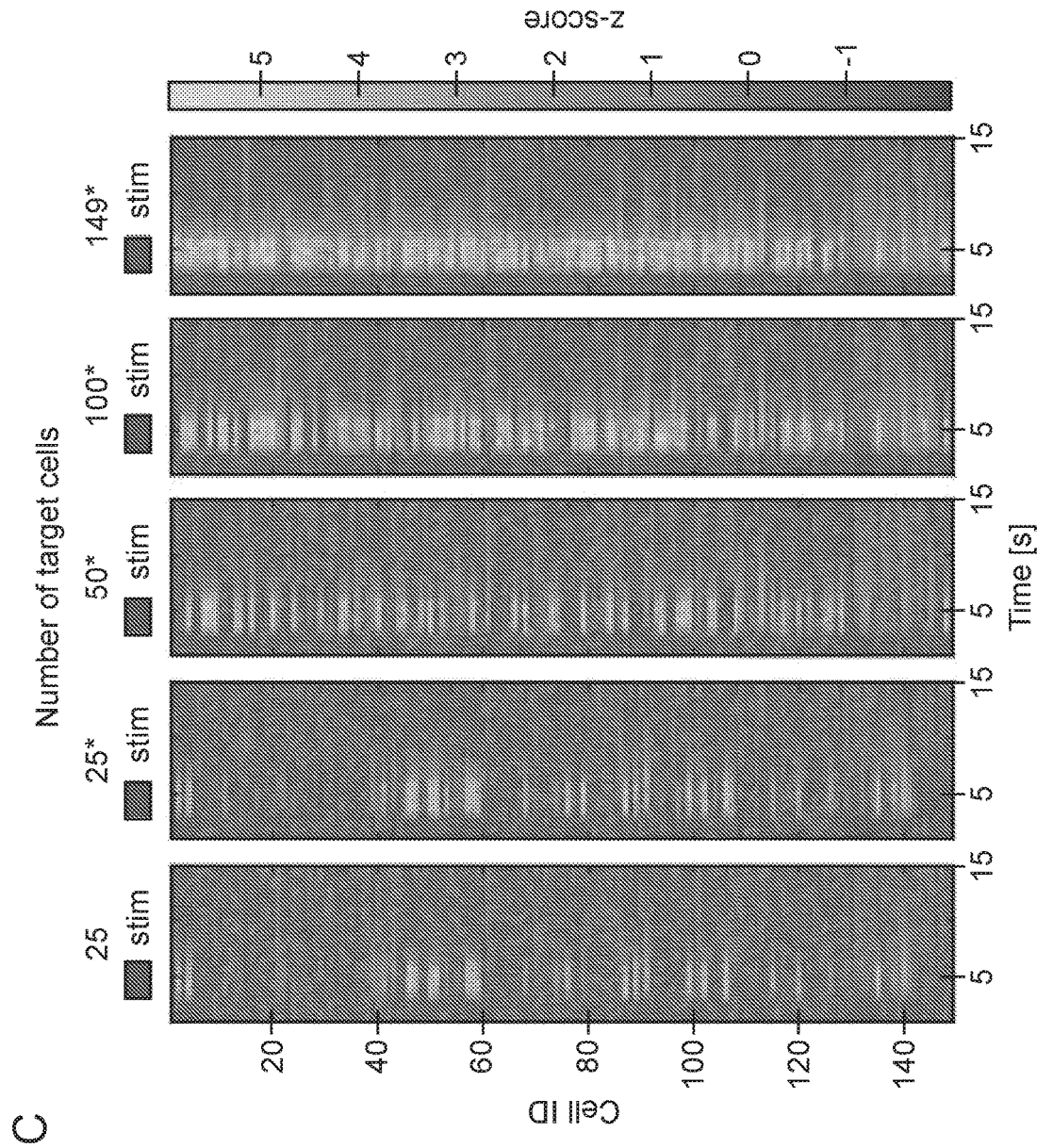
Figure 3:
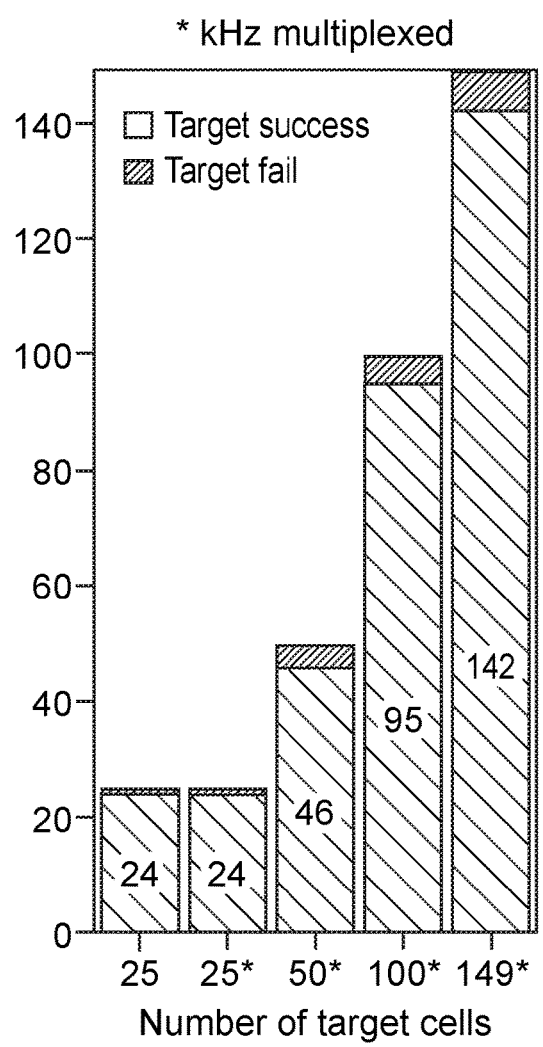
Figure 3:
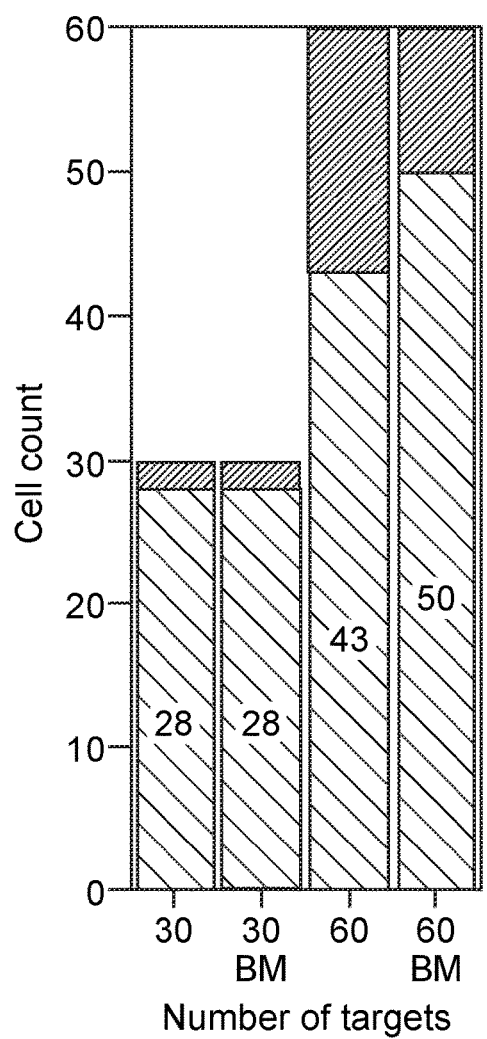
Figure 3:
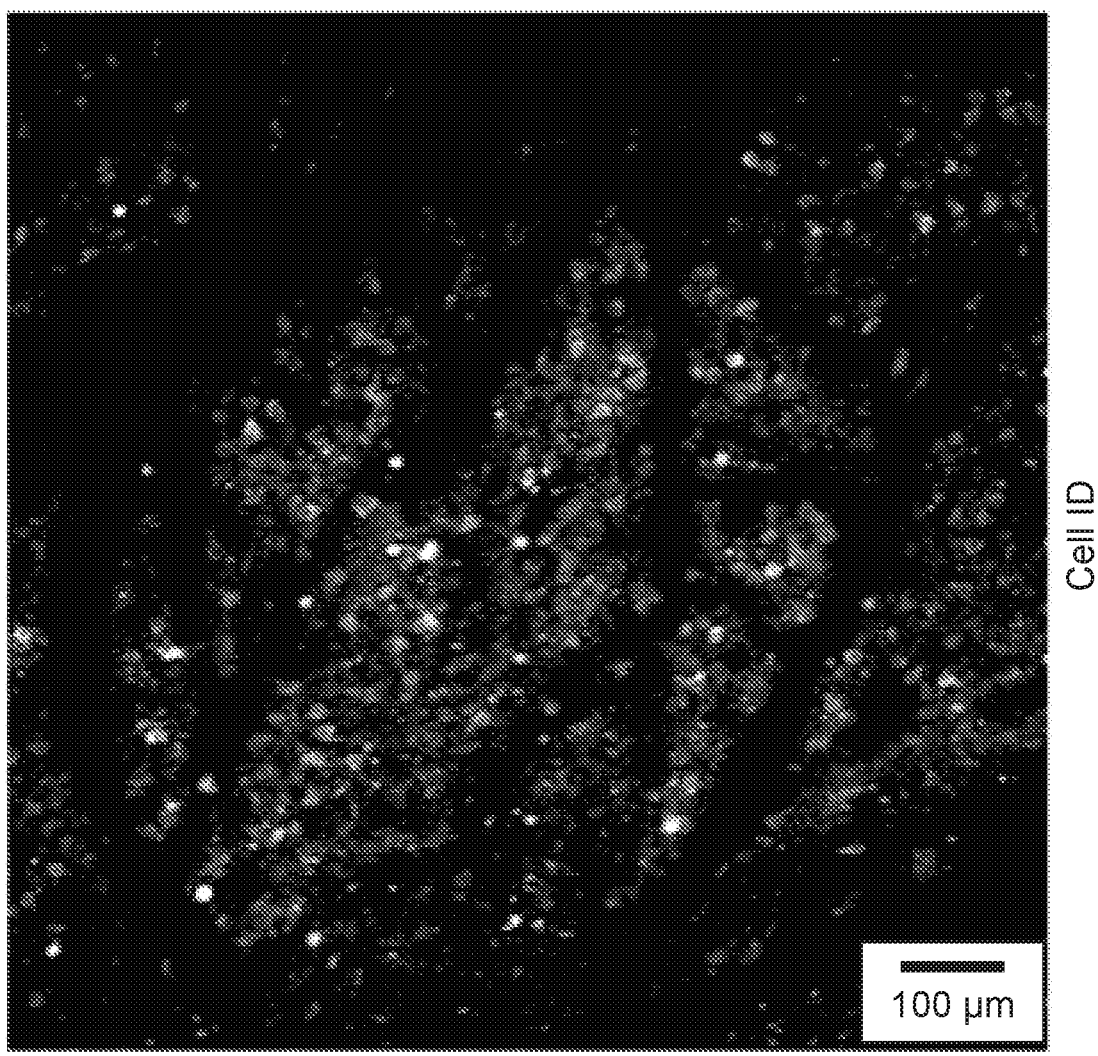
Figure 3:
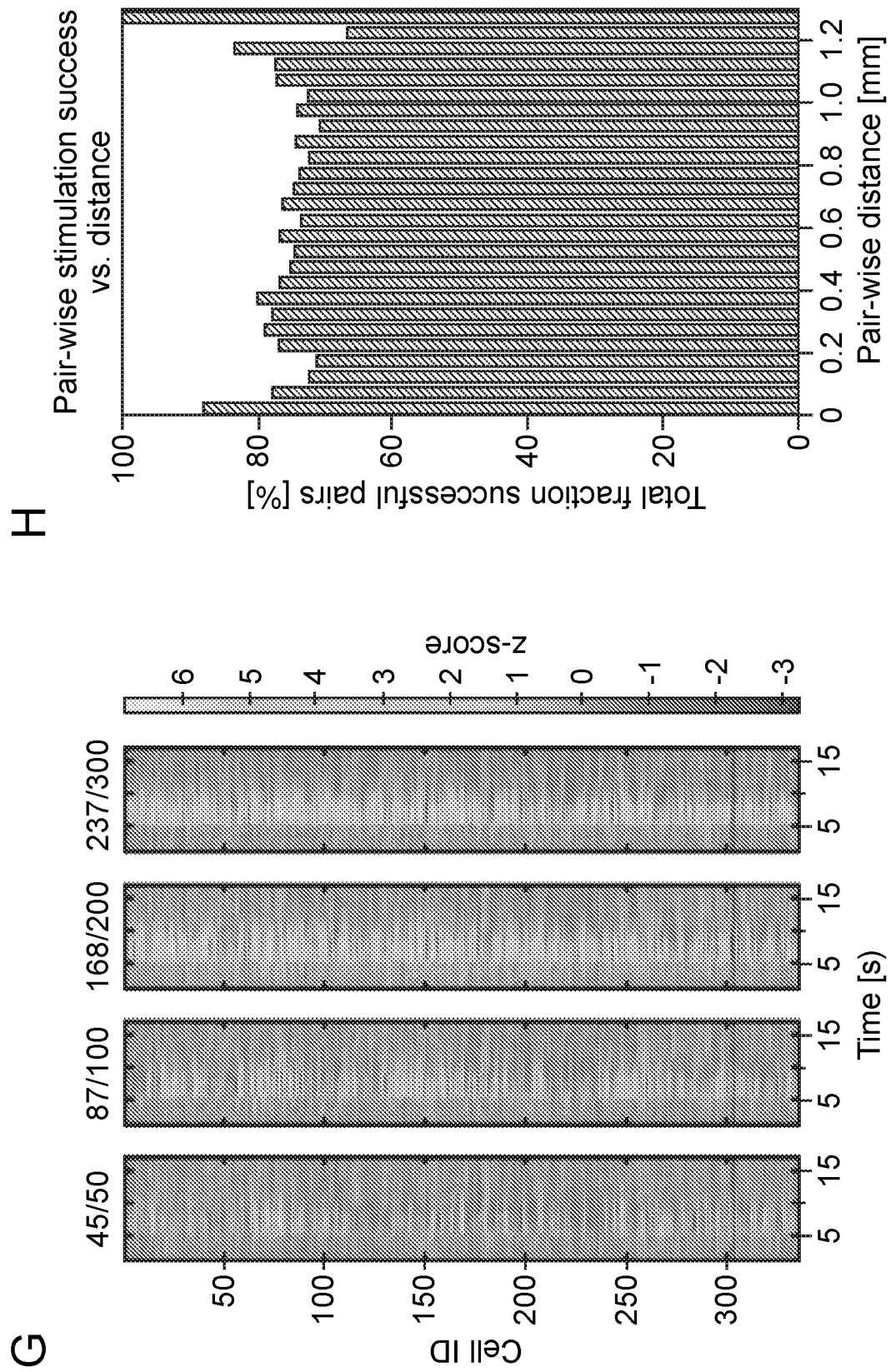
Figure 3:
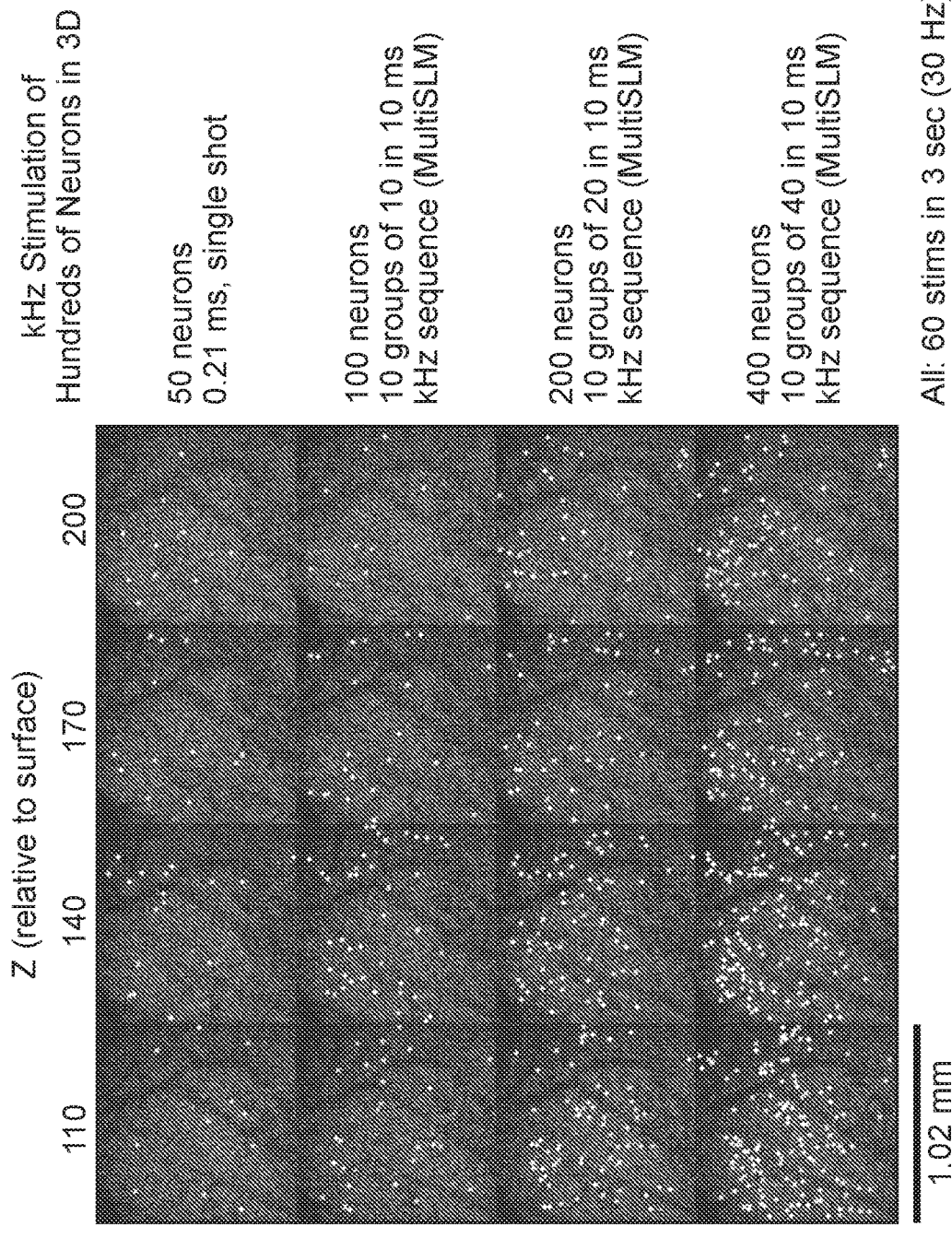
Figure 4:
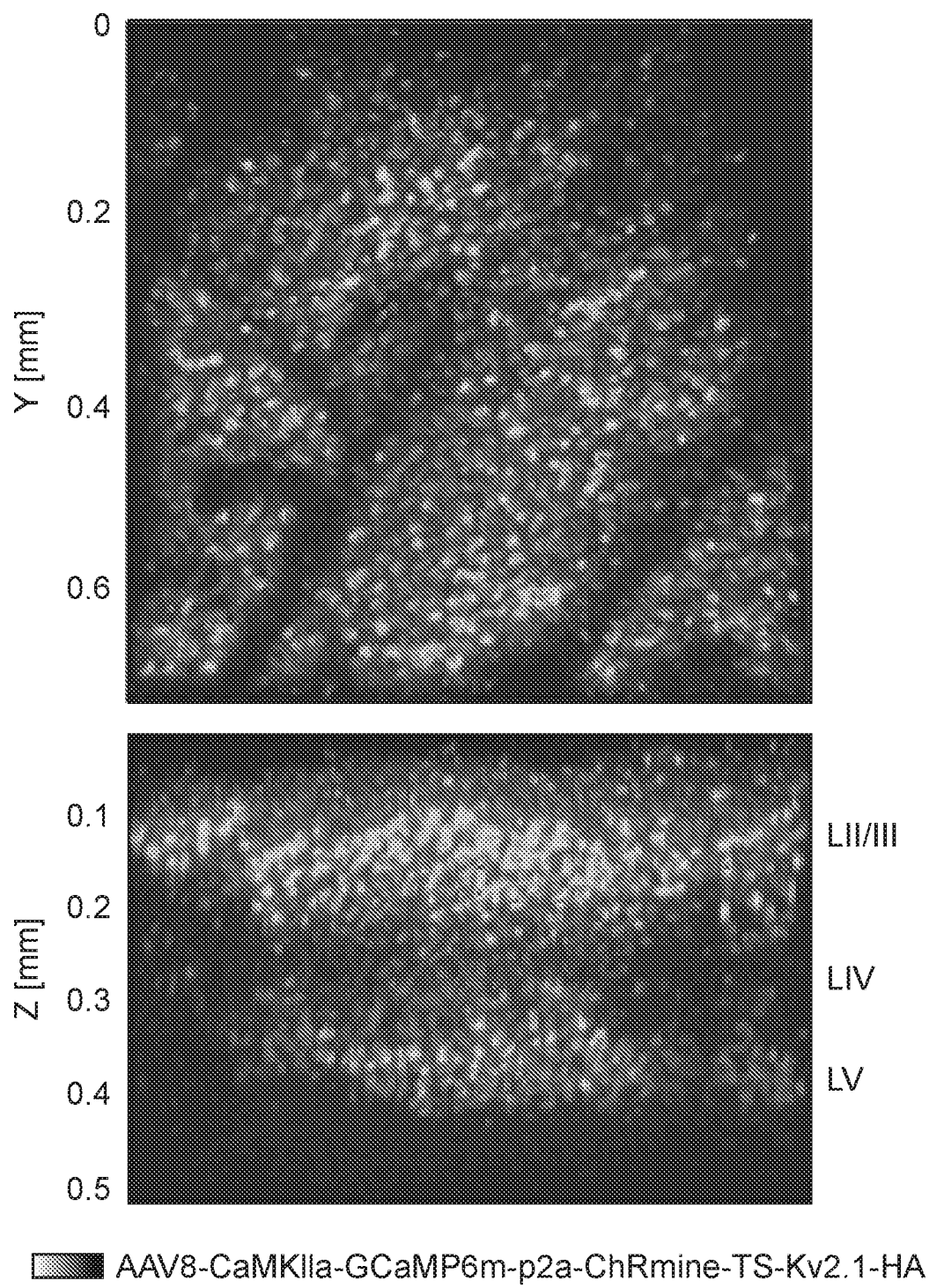
FIG. 4, A-F depicts inter-laminar read-out with simultaneous write-in of neural activity in primary visual cortex (V1) according to certain embodiments.
Figure 4:
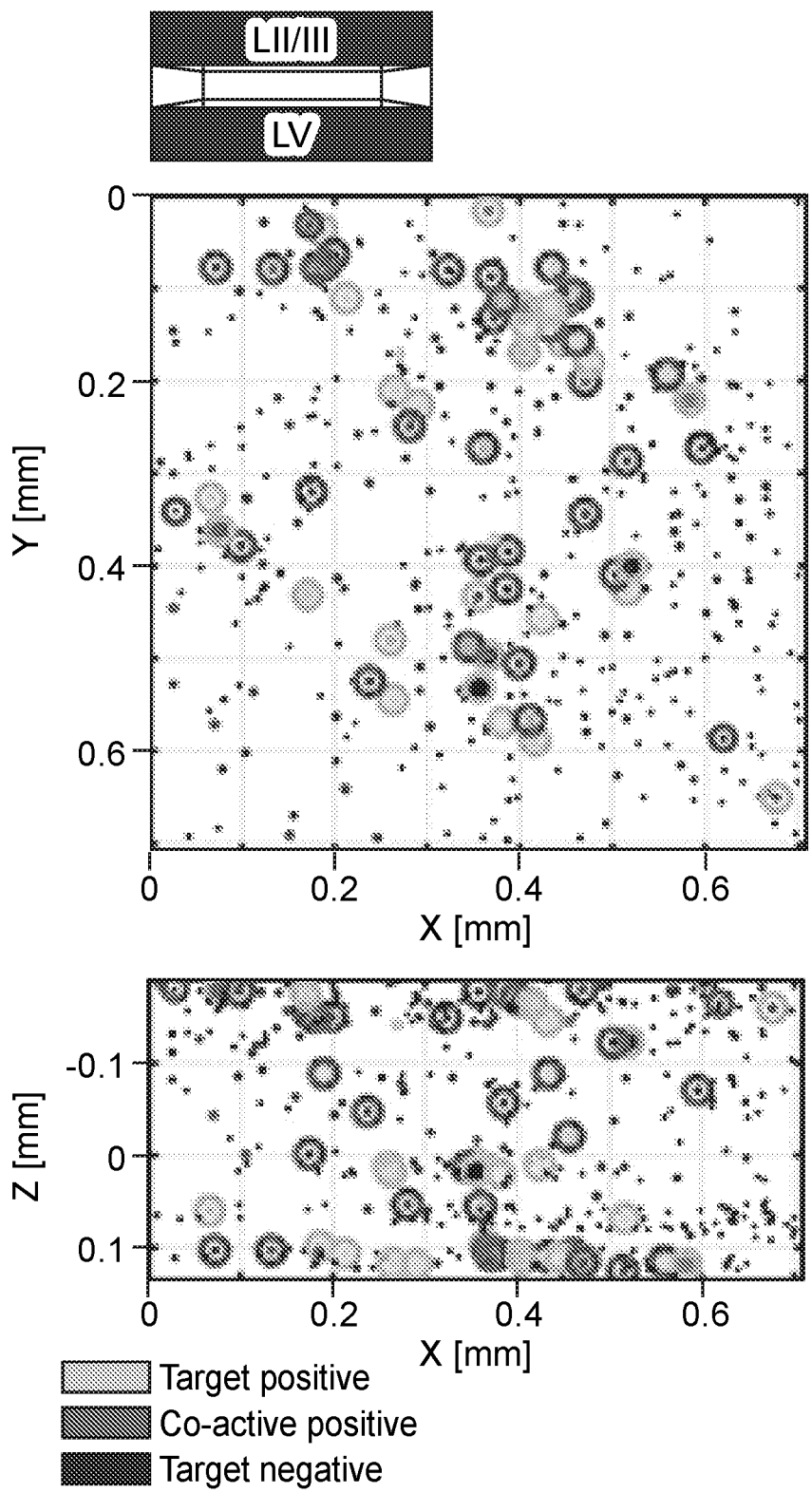
Figure 4:
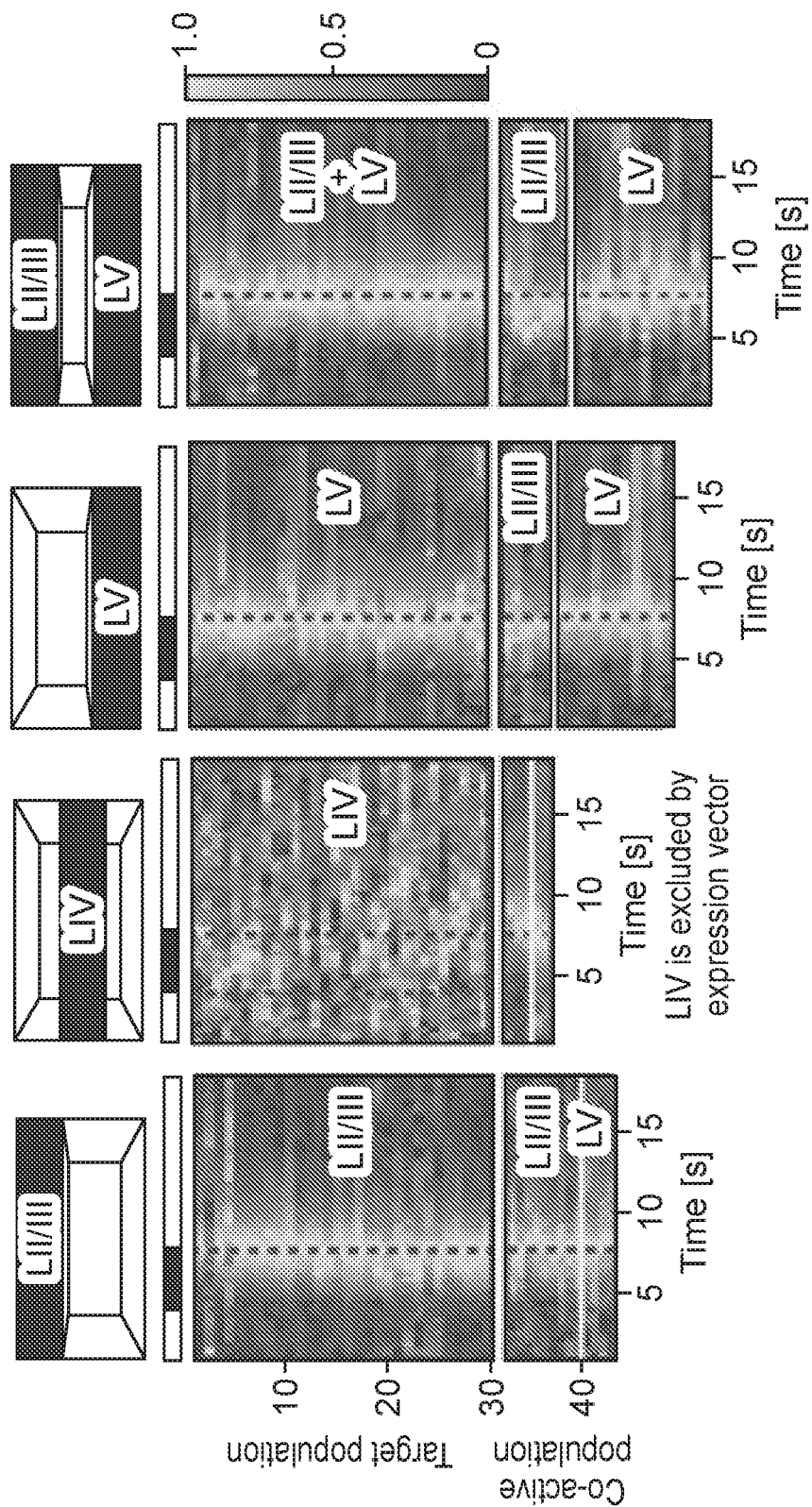
Figure 4:
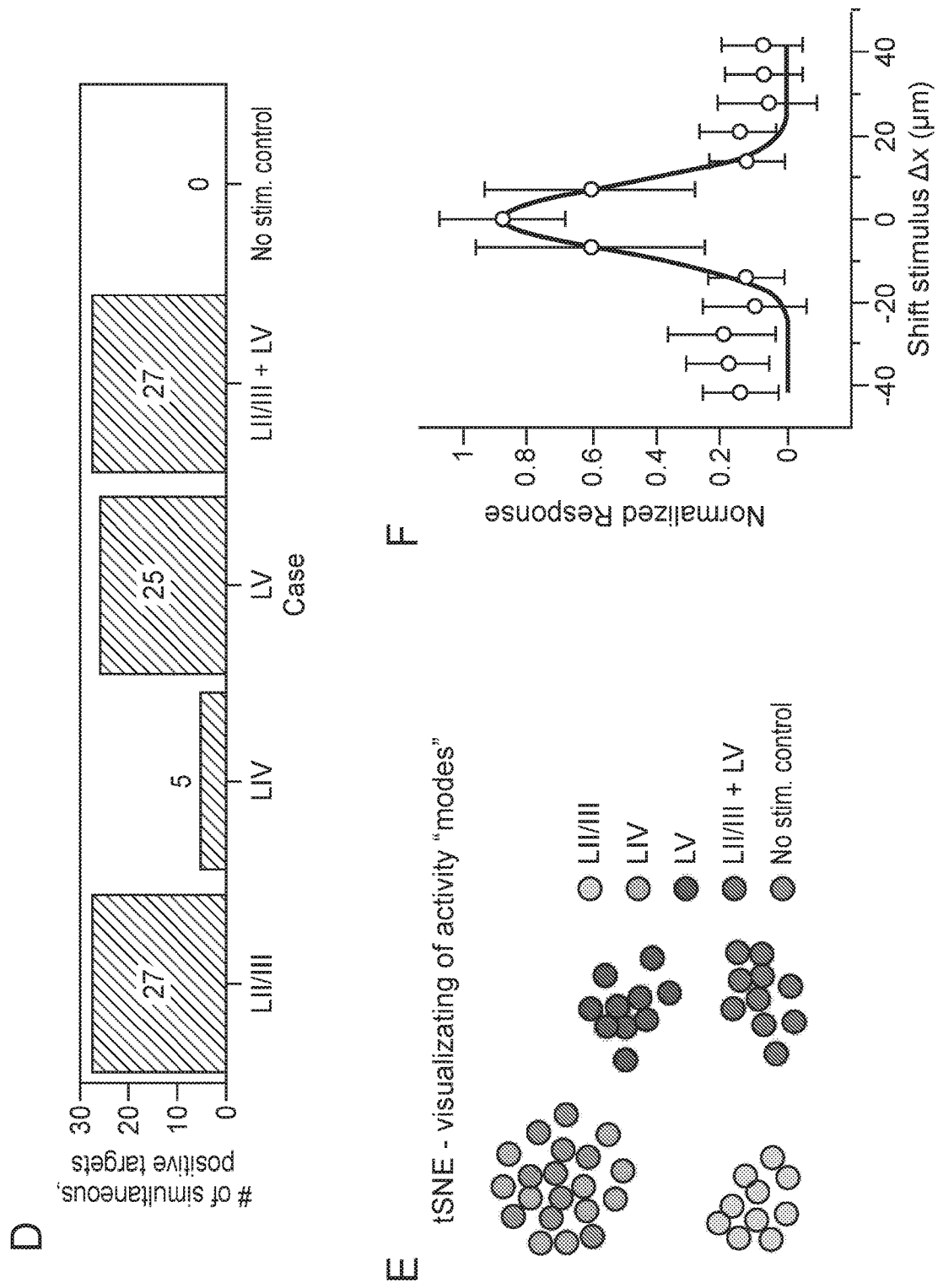

In order to accomplish kilohertz stimulation of sequences of unique ensembles, a multiplexed SLM approach was taken to allow each SLM to form each of its target holograms in a sequence with a 2 ms period (500 Hz for each SLM, 1 kHz for the 2×MultiSLM system). Stimulation timing and duration was targeted to the final 210 μs of the hologram formation in order to target peak efficiency of hologram formation (FIG. 2e). The 210 μs stimulation duration was determined by testing a variety of modified spiral stimulation protocols (e.g., different spiral diameters and numbers of spiral rotations, while keeping spiral scan velocity constant at the fastest supported setting for the galvanometer mirrors). A novel red-shifted opsin was developed, with extremely high photocurrents (4 nA, 594 nm excitation), fast kinetics and high spike fidelity, even when driven with extremely short light pulses (with 0.5 ms pulses of 594 nm light). Implementing a reduced diameter (10 μm, Spatial Mode #1; 15 μm, Spatial Mode #2) spiral scan with 5 total rotations, and using the highly-sensitive, fast, high-photocurrent opsin ChRmine resulted in high reliability of stimulation in vivo (FIG. 3). A random set of 25 neurons was selected from a layer 2/3 visual cortical volume for stimulation with the 210 μs spiral stimulus, repeated at 30 Hz for 3 seconds, while calcium activity in the targeted neurons and neurons in the surrounding volume were imaged with a synchronized piezoelectric 3D imaging system (FIG. 3a-c, FIG. 2f; the motion of the piezo was compensated by the SLM stimulation system software). Expression of GCaMP6m and ChRmine was driven in the population by a cocktail of adeno-associated viruses. GCaMP6m activity reliably and significantly increased during the stimulation duration (24/25 neurons confirmed reliable activation, FIG. 3c, leftmost panel). In the same experiment, randomly interleaved trials tested the kilohertz ensemble stimulation rate capability of the MultiSLM system. In one condition, the same 25 neurons were divided into 6 subgroups (4-5 neurons per group), and they were stimulated in a rapid kHz sequence (5.21 ms total stimulation duration for all groups, with each group stimulated 1 ms apart), with the full sequence repeated at 30 Hz for 3 seconds (FIG. 3c, second from left panel). Responses in the targeted neurons were virtually indistinguishable from the single-shot experiment (FIG. 3c, leftmost panel), indicating that kilohertz ensemble stimulation was effective at driving reliable activity in the ensembles. Increasing subgroup size in the 6 ensemble, kHz sequence allowed stimulation of 46/50, 95/100 and 142/149 targeted neurons in the same 5.21 ms total duration, kHz sequences (FIG. 3c-d). Enhanced temporal resolution of the MultiSLM approach was tested, running the system in a 'burst mode'. In this mode, rather than stimulating with an equally-spaced, kHz sequence period (1 ms), the phase of stimulation was shifted by the second SLM to occur nearly instantaneously after the first SLM in each sequence. This doubles the number of neurons targetable in a ~0.5 ms time window, and facilitates determining the effects of precise spike timing in larger ensembles. Applying this approach, more neurons were driven using the burst mode vs single-shot approach (50/60 vs 43/60 neurons reliably activated, FIG. 3e).

To expand the field of view and number of targetable neurons even further, the system in the lower magnification configuration was tested (Spatial Mode #2, FIG. 2d). Furthermore, a single viral construct was developed to drive expression of both the GCaMP6m and the ChRmine, with the addition of a soma-targeting kv2.1 motif and an HA tag (AAV8-CaMKIIa-GCaMP6m-p2A-ChRmine-TS-Kv2.1-HA). This new construct yielded several millimeters of homogeneous expression from a single injection (FIG. 3f). The capability of the system in this mode was tested, randomly selecting 50 neurons in a 1.02 mm×1.2 mm×120 µm volume of layer 2/3 visual cortical neurons for single-shot stimulation (210 µs spiral stimulus), repeated at 30 Hz for 3 sec. A high success rate of reliable stimulation-induced activity in targeted neurons (FIG. 3g, leftmost panel) was found. The capability of kilohertz ensemble stimulation was tested, increasing subgroup size from 10 groups of 10 neurons, to 10 groups of 40 neurons, all stimulated in a kilohertz sequence with a total stimulation duration of 10.21 ms, repeated at 30 Hz for 3 sec. Stimulation-induced activity was highly reliable in all cases (FIG. 3g). Furthermore, this success rate was essentially equivalent regardless of the distance between stimulated neurons (FIG. 3h). These results demonstrate the capability of the system to stimulate at least 50 neurons/ms with true simultaneity (0.21 ms stimulus), in kilohertz ensemble activation sequential patterns in 3D and over a 1 mm$^2$ field of view (also see FIG. 3i and FIG. 3j).

Read/Write Across Cortical Layers: Layer 2/3 Through Layer 5

The high resolution of the above-described SLM system provides for large fields of view in the lateral dimension as well as high efficiency in the axial dimension. Large volumes were tested with the system, with an axial dimension sufficient to span several cortical layers. Expression of the same AAV8-CaMKIIa-GCaMP6m-p2A-ChRmine-TS-Kv2.1-HA drove dense, homogeneous expression in layer 2/3 and layer 5 of visual cortex (FIG. 4a). The imaging volume was addressed by a piezoelectric motor to span layer 2/3-layer 5, and selected random sets of 30 neurons for simultaneous stimulation (600 µs stimulation of all 30 neurons in single-shot mode, repeated at 30 Hz for 3 seconds) distributed throughout layer 2/3, layer 5, or across both layers. A control of 30 target spot locations essentially randomly located throughout layer 4, where little cell body labeling was found, but that contained axons and dendrites coursing through originating from neurons labeled in other layers. All 4 conditions, in addition to a control with the same imaging parameters but without any optogenetic stimulation, with 10 repetitions per condition, were randomly interleaved in time. Reliable stimulation-induced activity was detected in all cell-body stimulation cases, and minimally for the layer 4 and no stimulation controls, regardless of position throughout the volume (FIG. 4b-d). Populations of neurons in layer 2/3 and layer 5 were coactive with stimulation of neurons in layer 2/3, layer 5, or both layer 2/3 and layer 5, but to a much lesser extent (and lacking the same time-locked nature of activity even in cells which did pass statistical thresholds for activity simultaneous with stimulation) with stimulation of non-cell-body locations in layer 4 (FIG. 4c,d). Generally, recruitment was stronger within layer than across layers for the layer 2/3 stimulation condition and layer 5 stimulation condition, but both included recruitment of many neurons in the opposite layer. The greatest recruitment occurred when the same overall number of neurons (n=30) was stimulated in populations spanning both layer 2/3 and layer 5 (FIG. 4b,c). Different activity modes generated by these stimulation conditions using a dimensionality reduction analysis of the full experiment, including all trials of all conditions, but not providing the analysis with any information about the correspondence of specific trials and conditions. In this analysis, the activity over time of each neuron is treated as a vector in a multidimensional space. Applying t-distributed stochastic neighbor embedding (tSNE) dimensionality reduction analysis revealed 4 main clusters of trials, representing different activity modes. After the analysis was completed, the corresponding condition labels as assigned for each trial. Viewing the result of this analysis revealed that 3 activity modes corresponded to the three conditions involving layer 2/3, layer 5 or both layer stimulation, and a 4th activity mode representing the layer 4 non-cell-body stimulation and no stimulation controls intermingled (FIG. 4e). These results, combined with the single-cell resolution of spiral stimulation (FIG. 4f), reveal that stimulation of 30 neurons simultaneously in vivo is sufficient to drive neurons within and across layers via circuit mechanisms. The ability to study these circuit effects across cortical layers (including the corticortical output layers of the cortex as demonstrated here) in wide fields of view potentially spanning multiple cortical areas, forms the foundation for a powerful experimental paradigm for studying encoding, information propagation and circuit mechanisms, underlying cortical circuit computations in vivo with single cell, single-spike and ensemble-level resolution.

Scaling of the MultiSLM Approach

Figure 8:
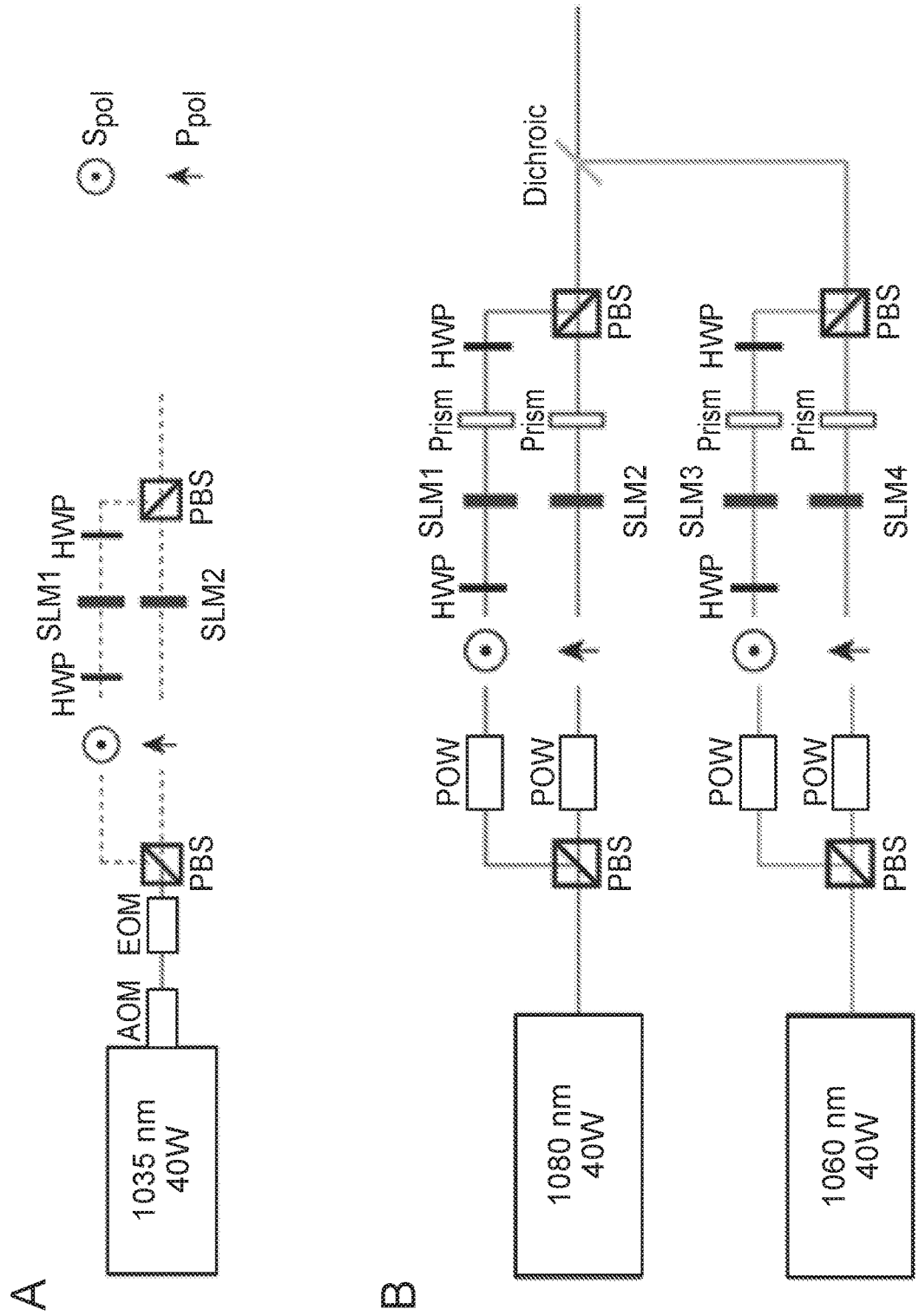
FIG. 8, A-C depict multiplexed spatial light modulator light projection systems according to certain embodiments.

Expanded multiplexed SLM designs with further capabilities (i.e., larger field of view, improved timing and size of ensembles, FIG. 8) were developed. The utility of expanding the field of view of commercially available SLMs (512×512 resolution) by a factor of ~4 fold (FIG. 7c,d, 7b, 9) was demonstrated. In this approach 4 SLMs are illuminated with 4 laser beams which are independent in wavelength and/or polarization permitting combination of beams simultaneously using orthogonal polarization (as above) and using distinct wavelengths combined with a dichroic mirror (FIG. 7c,d, 8b). Further ensuring zero interference between beams, even when all 4 SLM paths are illuminated simultaneously, all 4 laser beams are synchronized to each other at the femtosecond pulse level, and the phase of each beam is shifted by inherently different optical path lengths (delay lines to sufficiently shift phase are created essentially automatically when laying out slightly different optical paths for each SLM). Each SLM-modulated path is further modulated with a prism placed immediately after the SLM in the optical path, which applies a constant tilt to the beam. Selecting the appropriate tilt angle and direction, when relayed into the sample, each of the 4 SLMs ultimately addresses a different quadrant of the image. This directs the center of an SLM FOV to a different location in the sample image space, conceptually similar to previous demonstrations using galvanometer mirrors conjugate to the SLM, but permits truly simultaneous addressability of all 4 quadrants when applied in the 4× MultiSLM tiling system. Applying this approach with 4× tiled MacroSLMs would yield of a combined field of view with a fundamental diffraction efficiency limit of 3.2×3.2 mm, and would require larger, custom lens relay systems (and benefit from a larger imaging field of view). Removing the tilting prisms converts the system to a 4× multiplex of the same addressable volume, permitting 4× multiplexing in the time domain and/or 4× multiplied simultaneous stimulation, to overcome inherent limitations of single SLMs (e.g., timing, power handling, spatial frequency limitations for complex holograms involving large numbers of spots, etc.).

In terms of further scalability of the MultiSLM approach, while additional wavelengths and dichroic mirrors could be added to the system allowing more SLMs to be combined, a fully scalable approach while maintaining wavelength within a narrow bandwidth, can rely on the same high speed polarization switching approach (FIG. 8c), scaled further by additional polarization switches to split the beam onto more independent paths, and after the SLMs to combine those paths back together using the same logic. This design is fully scalable, and allows up to 2 independent SLM paths to be illuminated simultaneously, while all of the paths can be multiplexed fully in time. This could be applied to achieve 100% duty cycle stimulation limited in time only by the duration of stimulation, here demonstrated to be as short as 210 µs for reliable optogenetic stimulation in vivo, setting the maximum to ~16-20 combinable SLMs into a single system, using a single or multiple laser sources, to maximize excitation potential at 100% duty cycle.

Notably, synchronizing the imaging beam to the same repetition rate (possible with commercially-available Ti:Sapphire lasers for example) could further separate all laser lines in time at the femtosecond or nanosecond scales, eliminating any potential interference effects and permitting stimulation artifacts to be completely removed with gigahertz gating, and taking advantage of the short fluorescence lifetime of fluorescent indicators (e.g., green fluorescent protein, which GCaMP is based on, has a fluorescent lifetime of 3 ns, whereas Ti:Sapphire lasers used for two-photon imaging typically pulse with 12.5 ns inter-pulse interval, or 80 MHz). Similar high speed pulse interleaving and separation of independent paths on the nanosecond scale have been demonstrated to allow multiple fields of view to be imaged simultaneously (defined as simultaneous on the >ns scale), and fully separated into independent images, suggesting the validity of these concepts as well as potentially pointing to further applications of MultiSLM in the imaging domain.

Temporal and Spatial Multiplexing of Spatial Light Modulators (MultiSLM) for High-Speed, Precise Imaging and Control of Thousands of Neurons in the Living Brain A volumetric imaging and control approach is termed the MultiSLM, which allows arbitrary >kHz optogenetic control of any of the thousands of neurons in a three dimensional (3D) volume accessible with a single objective using multiphoton stimulation, while imaging the neural activity of the same population with high spatial resolution (<1 µm lateral) during a head-fixed behavioral task. In this fast MultiSLM approach, we generate hundreds of diffraction limited spots, in precise locations and simultaneously (within <1 ms), using 3D holograms generated by combining high peak power lasers with an array of several customized, high-resolution spatial light modulators (SLMs) controlled by custom computational hardware and software.

The MultiSLM separates laser light originating from 1 or more lasers into at least 2 distinct channels (1 module) utilizing an array of strategies for beam separation across multiple channels simultaneously, or directed to different channels (SLMs) in rapid sequence, with precision on the order of microseconds. Additional SLM array modules can be added by a number of strategies to yield 4 or more SLMs in one system, and/or for combined imaging and photostimulation (optogenetics) using two or more wavelengths. These channels are recombined after reflecting off the SLMs by using custom dichroic mirrors, polarization beam splitters, high speed polarization switches (or electro-optic modulators) and/or 50/50 beamsplitters, which will be carefully aligned with angle and polarization tuning.

In "Sequential Mode", staggering the refresh times of each individual SLM (>500 Hz refresh rate each) across the array of SLMs, the effective temporal resolution can exceed 1 kHz, and no time will be lost waiting for holograms to be loaded on subsequent SLMs such that there will be the potential for 100% duty cycle of light stimulation at >1 kHz, or lower duty cycle with higher temporal precision of stimulation and lower average power. This approach also guards against any possibility of unwanted effects of interference between the laser beams since illumination of each channel is independent in time. In the case of simultaneous illumination of multiple SLMs simultaneously, or of combined imaging and optogenetic photostimulation with different lasers, interference is mitigated due to orthogonal polarization, the low duty cycle of the pulsed lasers, and/or differences in wavelength. Furthermore, path lengths for the lasers can be optimized to prevent any chance of overlap of the pulses, especially in the case of a single seed laser line source, or multiple synchronized laser sources. Synchronizing imaging and photostimulation lasers also permits photostimulation to occur out of phase with imaging at the level of laser pulse times, such that light and fluorescence artifacts caused by optogenetic photostimulation can be removed with a lock-in amplifier, chopper circuit operating on the MHz or GHz scale (depending on the laser source repetition rates).

Temporal precision and stimulation duration (<600 µs) is tightly controlled with custom software and electro-optic modulators (Pockels cells and/or polarization switches) to cause a single spike in each targeted neuron in the stimulation case, or high signal to noise at high imaging rates in the imaging case. The SLM modulated light reflects off a set of high-speed galvanometer mirrors which move the SLM generated hologram rapidly in the volume, for example, to create a spiral motion spanning the size of a typical neuron, or could be divided into multiple "mini-spirals" to span the majority of the neuron cell body more rapidly, and with greater efficiency. This motion moves the spot around the cell body of the neuron using empirical parameters for velocity and spatial resolution to reliably yield a spike in the neuron (reaching saturating photocurrent in the best case, or at least enough photocurrent to reliably elicit a spike). It should be noted that, alternatively, a disc of light can be created using SLM-based holography to stimulate an entire neuron cell body (perhaps employing temporal focusing techniques to reduce axial blur), or other part of a neuron, such as a dendritic spine, without the need to move the galvanometer mirrors. Or, a grid of dots or other arbitrary pattern of light can be created to match the features (i.e., neuron cell body locations) in the volume for imaging or stimulation. The galvanometer mirrors are part of a modified two-photon microscope, which has two additional sets of galvanometer mirrors, including a resonant scanner dedicated to imaging at up to 100 Hz.

The wavelengths for SLM optogenetic stimulation are chosen to potentially excite an array of excitatory and inhibitory opsins and pumps (e.g., MO20, bReaChES, C1V1$_{T/T}$, Chrimson, eArch, ChRmine) at or near their peak excitation wavelengths, while minimally exciting neural activity sensors, such as calcium sensitive indicators (e.g., GCaMP) and voltage sensitive indicators expressed in cell-type specific fashion in the brain by engineered viruses or other genetic targeting strategies. This allows simultaneous opsin stimulation and neural activity imaging from the same population of neurons. Thus, the effects of stimulated patterns of activity on local dynamics cam be read out in real time with neural activity imaging at greater than single cell resolution. Any and all neurons in the three dimensional field of view accessible with a single two-photon objective (>1000 um$^3$) will be accessible to fire with high precision. Thus, natural patterns of activity could be precisely replayed into the network, for example, to create artificial perceptions, or to artificially reinforce learning using neuromodulators coupled with spike-timing dependent plasticity protocols. Furthermore, the generated pattern of activity could be altered in precise ways, or combined with other experimental manipulations, to help understand the necessity and sufficiency of quantifiable features of the pattern on neural coding robustness, perception and behavior. In these ways, this novel device and experimental strategy may open fundamental new insights into the complexities of the brain.

MultiSLM Sequential Mode

The MultiSLM design allows for the overall hologram generation rate of the system to surpass the hologram generation rate of any single SLM in the system, by staggering the triggering of individual SLMs in the system, each running at maximum hologram generation rate (plus dwell time on a given hologram). The following equations describe the design and limits on the sequential mode of operation.

$$P_{SLM} = L + r_{SLM} + (2*\sigma_L) + (2*\sigma_r)$$

Where $P_{SLM}$ is the period in time that the SLM takes to reach complete formation of a hologram (including time to load phasemask onto the SLM and time for the liquid crystal to respond and reach desired phase level to successfully generate the hologram), $r_{SLM}$ is the mean hologram generation time of the SLM from start to completion, L is the mean latency from input trigger to beginning of hologram generation by the SLM, $\sigma_L$ is the standard deviation of latency from trigger input to the time the SLM begins transitioning to the next hologram, and $\sigma_r$ is the standard deviation of $r_{SLM}$. Assuming a normal distribution of L and $r_{SLM}$, this achieves an estimate of $P_{SLM}$ that is true 95% of the time. If the distributions are not normally distributed, then the distribution of $P_{SLM}$ can be sampled and determined to the ≥95% level (or any desired level up to 100% if the full time ranges are used).

Following from this, the hologram refresh rate of a given SLM in the system is:

$$R_{SLM} = \frac{1}{P_{SLM}}$$

The hologram refresh rate of the MultiSLM system in sequential mode, $R_{seq}$, that is the rate at which new holograms can be created, is:

$$R_{seq} = \frac{N_{SLM}}{P_{SLM} + d}$$

Where d is the duration that a formed hologram is displayed (e.g., to illuminate the sample for a desired period of time typically on the order of microseconds), and $N_{SLM}$ is the number of SLMs in the MultiSLM system.

So far, this assumes that $P_{SLM}$ and d are each the same for all SLMs in the system. More generally, periods, durations, latencies and jitters can be determined for each SLM in the system and summed to determine $R_{seq}$:

$$R_{seq} = \sum_{i=1}^{N_{SLMs}} \frac{N_{SLM}}{P_{SLMi} + d_i}$$

The period of the MultiSLM system, $P_{seq}$, is:

$$P_{seq} = \frac{1}{R_{seq}}$$

The duty cycle of stimulation, D, is defined as:

$$D = \frac{d * N_{SLM}}{P_{seq}}$$

assuming equal interval in time between illumination of each SLM in the MultiSLM system. 100% duty cycle is achieved for all:

$$P_{seq} \leq d * N_{SLM}$$

The maximum hologram refresh rate of the MultiSLM system, MAX($R_{seq}$), occurs with 100% duty cycle when $$P_{seq} = d * N_{SLM}$$

and laser pulse times for each SLM in the MultiSLM system, LaserPulse$_{Time}$, are spaced sequentially in time such that:

$$LaserPulse_{Time_{i+1}} = LaserPulse_{Time_i} + \left(\frac{P_{seq}}{N_{SLM}}\right)$$

and the laser pulse duration, LaserPulse$_{Duration}$, equals d:

$$LaserPulse_{Duration} = d$$

and triggers to a given SLM, $T_i$, repeat with period $P_{trig}$, such that:

$$P_{trig} = P_{seq}$$

assuming that all SLMs in the system have equal $P_{SLM}$ (otherwise, timings should account for the different periods of each SLM to achieve the same effect). MAX($R_{seq}$) increases as d approaches zero.

Furthermore, the improvement in hologram refresh rate of the MultiSLM compared to the hologram refresh rate of a single SLM in the system, $R_{SLM}$, is:

$$\text{MAX}(R_{seq}) = (R_{SLM} + d) * N_{SLM}$$

Increased temporal precision [beyond that afforded by the MAX($R_{seq}$) at 100% duty cycle] can by generated for all:

$$P_{seq} > d * N_{SLM}$$

leading to lower than 100% duty cycle. This also has the effect of lowering the average power delivered to the sample proportional to the reduction in duty cycle (see below). Higher temporal precision could be applied in a burst mode (that is the array SLMs are illuminated in rapid sequence at or near 100% duty at the higher rate and overall in less time than $P_{seq}$, followed by a time period to allow the completion of $P_{seq}$) or the higher temporal precision can be achieved while maintaining equal, sequential spacing between SLMs as described above for the 100% duty cycle implementation.

The maximum temporal precision, MAX(p), that is the precision in stimulation time that can be guaranteed by the system, is ultimately limited by the Pockels Cell response time (or more generally whatever device is used to modulate the laser beam such as electo-optic modulator, acousto-optic modulator, polarization switch, shutter, etc), $r_{PC}$ $$\text{MAX}(p) = r_{PC}$$

assuming Pockels Cell driver electronics with equal or better temporal precision as $r_{PC}$ (if this assumption is not met, then the limiting factor is driver signal sample rate). Furthermore, it is assumed that:

$$r_{PC} << d$$

A pulse of laser power to illuminate the hologram is calibrated in intensity depending on the hologram generated (e.g., calibrated to achieve equal hologram spot intensity for any spot in any hologram generated regardless of number or location of spots in a hologram), is created by a calibrated signal sent by the driver electronics to the Pockels Cell, which in conjunction with a polarizing beam splitter and beam dump, achieves the desired power level for the hologram after the light has passed through all optics and biological tissue. Additional software corrections in the hologram generation code normalize the intensity of spots across the field of view (FOV) to account for diffraction efficiency fall off from the center of the FOV. The timing of the laser pulse for a given SLM should have duration d and be synchronized to start with the completion time of the hologram generation by an SLM, such that:

$$\text{LaserPulse}_{Time_i} = T_i + P_{SLM_i}$$

In sequential mode, the overall laser power stimulated at one time corresponds to the laser power of the laser pulse generated, $\text{LaserPulse}_{Power}$, at that time to illuminate a single hologram generated by a single SLM in the system, without overlap with illumination of other SLMs. Thus, the maximum pulse power, MAX($\text{LaserPulse}_{Power}$), is limited to the maximum power allowable for any one SLM ($\text{SLM}_{damagethresh}$) or hologram ($\text{Hologram}_{noisethresh}$). For example, damage thresholds for a single SLM or noise level dependent on hologram complexity (e.g., artifacts in the hologram worsened by large numbers of spots in the hologram, or noise increased by increased scattering due to high power stimulation of the biological tissue) may limit the amount of power that any one hologram or SLM can tolerate to avoid unwanted noise or damage. The power may be further limited based on the peak power allowable into the biological tissue, $\text{PeakPower}_{biothresh}$, which may depend on the duration of d.

Thus:

$$\text{LaserPulse}_{Power} < \text{SLM}_{damagethresh}(d)$$

and $$\text{LaserPulse}_{Power} < \text{Hologram}_{noisethresh}$$

and $$\text{LaserPulse}_{Power} < \text{PeakPower}_{biothresh}(d)$$

Furthermore, an allowable average power limit may further constrain the allowable $\text{LaserPulse}_{Power}$, for example, in the case when accumulated heating over a longer period of time must be avoided, such as over the full period of the system, $P_{seq}$ (but other time durations can be used depending on the application). Depending on empirically determined limits of power into biological tissue, a limit may be set taking the form of:

$$\sum_{i=1}^{N_{SLM}} \frac{\text{LaserPulse}_{Power_i}}{P_{seq}} * D < \text{AveragePower}_{biothresh}$$

where lower duty cycle (D) can increase the allowable $\text{LaserPulse}_{Power}$, up to peak power limitations.

MultiSLM Simultaneous Mode

In some configurations, the MultiSLM system can be run in synchronized mode, such that independent holograms generated across all of the SLMs are illuminated by laser pulses at the same time, such that $$\text{LaserPulse}_{Time_i} = \text{LaserPulse}_{Time_{i+1}} = \ldots = \text{LaserPulse-Time}_{NSLM}$$

In this configuration, the damage threshold of a single SLM can be overcome by distributing more power onto more than one SLM.

$$\text{MAX}(\text{Power}_{simul}) \leq \text{SLM}_{damagethresh}(d) * N_{SLM}$$

As in the case of sequential mode, power limits will still remain in place regarding peak and average power into the biological tissue, and would be summed across laser power used for each SLM in the system:

$$\sum_{i=1}^{N_{SLM}} \text{LaserPulse}_{Power_i} < \text{PeakPower}_{biothresh}(d)$$

$$\sum_{i=1}^{N_{SLM}} \frac{\text{LaserPulse}_{Power_i}}{P_{seq}} < \text{AveragePower}_{biothresh}$$

Some sources of noise depending on the stimulation pattern (hologram) could benefit from distributing the pattern generation across multiple SLMs, instead of a single SLM. For example, complex holograms involving generation of many spots, or complex shapes may be achieved with fewer artifacts (e.g., higher intensity spots or pattern with lower background and/or lower speckle). This is because since the laser source(s) can produce synchronized pulses across multiple optical paths (corresponding to each optical path in the MultiSLM system), and because temporal delay lines can be added to each path (as will occur easily given the extremely low duty cycle of the pulsed laser source and the typical length differences between optical paths on an optical table), the holograms are not generated simultaneously at the femtosecond timescale, but would be synchronized at the microsecond timescale. This design removes any chance of interference between the holograms generated on each SLM in the MultiSLM system.

In simultaneous mode, duty cycle would be lower than sequential mode; and depends on d and the period of the slowest SLM in the system:

$$D_{simul} = \frac{d}{MAX(P_{SLM})}$$

Since all SLMs are illuminated at the same time, the maximum period is limited by the period by the period of the slowest SLM in the system:

$$P_{simul} = MAX(P_{SLM}) + d$$

The refresh rate in simultaneous mode is comparable to the refresh rate of a single SLM:

$$R_{simul} \approx MAX(R_{am})$$

and is equal to the inverse of $P_{simul}$:

$$R_{simul} = \frac{1}{P_{simul}}$$

Example 2

Perceptual experiences may arise from neural circuit activity patterns in the mammalian cortex. To probe physical substrates of visual percept-guided behavior at the cellular level, we integrated a new class of red-shifted opsin (ChRmine) discovered via crystal structure-guided gene mining, with the subject multiplexed multiphoton holography technology (MultiSLM) for reading and writing cellular-resolution large-ensemble activity across cortical layers and regions with millisecond precision. We found that stimulating ensembles containing a number of neurons selectively ignited widespread population responses involving functionally-related neurons and could elicit correct and selective visual discrimination behavior even in the absence of sensory input. Population activity following ignition selectively propagated from layer 2/3 to layer 5. Smaller ensembles of directly-driven layer 5 neurons were as effective at driving ignition and behavior as larger numbers of layer 2/3 neurons. Ignition did not require task learning or performance, but was powerfully enhanced with learning, revealing percept-specific network plasticity. Similarities between natural neural representations of visual stimuli and observed population dynamics following optogenetically-evoked ignition were found which dynamics predicted the elicited behaviors, revealing cortical network dynamics supporting animal behavior.

To investigate V1 circuit elements and dynamics that may underlie behaviorally-potent detection of visual percepts, we developed an integrated experimental paradigm to test the role of specific activity patterns, delivered to large numbers of individually-specified V1 neurons defined by their natural response properties (a tuned ensemble), in guiding the dynamical responses of the local circuit and the elicited perception-driven behavior. We developed an optical read-write system capable of kilohertz speed, three-dimensional (3D) access to tens to hundreds of individually-specified neurons across superficial to deep layers of cortex, and millimeter-scale spatial scope across the V1 region thought to be involved in visual perception; this system was developed alongside and integrated with a new biological intervention capability derived from microbial opsin crystal structure-based genome mining, which allowed identification of a naturally-evolved optogenetic tool with unprecedented properties crucial for this biological question—through the conjunction of red-shifted light sensitivity, extremely large photocurrents alongside millisecond spike-timing fidelity, and compatibility with simultaneous two-photon $Ca^{2+}$ imaging via a green light-emitting fluorescent activity reporter. Using this system, we were able to measure naturally-occurring large-scale 3D ensemble activity patterns during visual experience, and then replay these patterns at the level of many individually-specified cells. In this way, we were able to recruit the broader network with dynamics corresponding to those elicited by actual visual stimuli (a phenomenon we refer to as ignition), as well as to elicit the correctly selective behaviors, even in the absence of visual input. This approach allowed mapping of the cell numbers, layers, network dynamics, and plasticity dynamics underlying generation of behaviorally-potent percepts in neocortex, by enabling precise control over naturally-occurring, widely-distributed, and finely-resolved temporal and cellular elements of the corresponding neural representations.

Materials and Methods

In Silico Opsin Screening, Molecular Cloning, and Imaging

For the purpose of finding new classes of opsin genes, in silico screening was performed on the data of the Marine Microbial Eukaryote Transcriptome Sequencing Project. Transcript sequences were obtained via tblastn search against the eukaryotic transcriptome data using known opsin sequences as a query with the threshold of e-value 0.1; duplicated sequences and sequences shorter than 750 bp were excluded. Then, phylogenetic analysis was performed to search for putative functionally-novel opsin genes; to find channelrhodopsins with high cation conductance, we focused on sequences with more negatively charged amino acids in the transmembrane domains 1, 2, 3, and 7 comprising our structure-resolved ion-conducting pathway and guided by our structure-derived pore surface electrostatic model (as described in greater detail below).

The amino acid sequence was human codon optimized and synthesized by Genscript in pUC57 vectors, the gene was subcloned into an adeno-associated viral vector fused with enhanced YFP (EYFP) along with the trafficking sequence (TS) and ER export signal and under control of either the CaMKIIα promoter for neuron expression or the Ef1α promoter for HEK293 cell expression. For confocal images of opsin-expressing neurons, coverslips of transfected neurons were fixed for 15 minutes in 4% paraformaldehyde and mounted with PVA-DABCO. Images were acquired with a Leica DM600B confocal microscope.

The opsin sequence described herein and discovered via this workflow (from *Tiarina fusus* strain LIS, SEQ_ID=MMETSP0472-20121206|19186), which we named ChRmine, was edited and used for subsequent functional analysis. The edited sequence was deposited in the database (accession number TBD). All transcriptome data used in this study are available in the Marine Microbial Eukaryote Transcriptome Sequencing Project (MMETSP).

Histology, immunohistochemistry and confocal imaging: Mice were anaesthetized with isoflurane and Beuthanasia-D, and transcardially perfused in cold 4% paraformaldehyde perfusion fix solution (Electron Microscopy Services, Hatfield, Pa., USA). Brains were extracted and kept in the fixation solution for 24 hours at 4° C. and then transferred to 30% sucrose in PBS to equilibrate for 2 days at 4° C. 40 μm slices were cut on a freezing microtome and stored in cryoprotectant at 4° C. Sections were washed three times for 10 minutes each in 1× phosphate buffered saline (Thermo Fisher Scientific) then incubated for 60 mins in blocking buffer (PBS+0.3% TritonX and 3% normal donkey serum), all at room temperature, while rocking. Sections were incubated with primary antibodies diluted 1:500 in blocking buffer overnight at 4° C. The two primary antibodies used were rabbit anti-GFP (Fisher Scientific A11122) and mouse monoclonal anti-HA tag (Fisher Scientific A26183). Sections were then washed in PBST and incubated in secondary antibodies against rabbit conjugated to Alexa Fluor® 488 (A21206, Thermo Fisher Scientific) and against mouse conjugated to Alexa Fluor® 647 (A-31571, Thermo Fisher Scientific) for three hours at room temperature, diluted 1:500 in blocking buffer. This was followed by three washes of ten minutes each in PBST. The nuclei were stained by DAPI (4',6-diamidino-2-phenylindole) diluted 1:50000 in PBS for 30 min at room temperature, then washed again and mounted on slides with PVA-DAPCO.

Confocal imaging of GFP fluorescence (for GCaMP expression), HA antibody staining for localization of the opsin, and DAPI for cytoarchitecture was performed using a Leica TCS SP5 confocal scanning laser microscope with a 20× or 40× oil objective. Co-localization was performed using 40× images (5-6 z slices through each section) by annotating GCaMP6m-expressing cell body locations and then overlaying these annotations and verifying expression in the anti-HA image. Images are displayed in the figure with 1% pixel saturation.

In Vitro Characterization with One-Photon Electrophysiology

The hippocampi of Sprague-Dawley rat pups (Charles River) were removed at postnatal day 0 (P0), and CA1/CA3 regions were digested with 0.4 mg/ml papain (Worthington, Lakewood, N.J.) and plated onto 12 mm glass coverslips pre-coated with 1:30 Matrigel (Beckton Dickinson Labware). Cells were plated in 24-well plates, at a density of 65,000 cells per well. The cultured neurons were maintained in Neurobasal-A medium (Invitrogen) containing 1.25% FBS (Fisher Scientific), 4% B-27 supplement (Gibco), 2 mM Glutamax (Gibco) and 2 mg/mL fluorodeoxyuridine (FUDR, Sigma), and kept in a humid culture incubator with 5% $CO_2$ at 37° C.

Primary neuronal cultures were transfected 6-10 days in vitro (DIV). For each well to be transfected, a DNA-$CaCl_2$ mix containing with the following reagents was prepared: 2 μg of DNA (prepared using an endotoxin-free preparation kit (Qiagen)) 1.875 μl 2M $CaCl_2$, and sterile water added for a total volume of 15 μl. An additional 15 μl of 2× filtered HEPES-buffered saline (HBS, in mM: 50 HEPES, 1.5 $Na_2HPO_4$, 280 NaCl, pH 7.05 with NaOH) was added, and the resulting 30 μl mix was incubated at room temperature (20-25° C.) for 20 minutes. Meanwhile, the neuronal growth medium was taken out of the wells and kept at 37° C., and was replaced with 400 μl pre-warmed minimal essential medium (MEM). The DNA-$CaCl_2$-HBS mix was then added dropwise into each well, and the plates were transported to the culture incubator for 45-60 minutes. Each well was then washed three times with 1 mL of pre-warmed MEM, after which the MEM was removed and the original neuronal growth medium was added back into the wells. The transfected neuronal culture plates were placed in the culture incubator for another 6 days.

Recordings in hippocampal cultured neurons were performed 4-6 days after transfection in Tyrode's solution: 150 mM NaCl, 4 mM KCl, 2 mM $CaCl_2$, 2 mM $MgCl_2$, 10 mM glucose and 10 mM HEPES-NaOH pH 7.4. Tyrode was perfused at a rate of 1-2 ml $min^{-1}$ and was kept at room temperature. Intracellular solution contained 140 mM K-gluconate, 10 mM HEPES-KOH pH 7.2, 10 mM EGTA and 2 mM $MgCl_2$. Signals were amplified and digitized using the Multiclamp 700B and DigiData1400 (Molecular Devices, Sunnyvale, Calif., USA). The Spectra X Light engine (Lumencor) served as a light source and was coupled into a Leica DM LFSA microscope. Borosillicate patch pipettes (4-6 MOhm) were pulled using a P2000 micropipette puller (Sutter Instruments, Novato, Calif., USA). HEK293 cells were cultured. Cells were transfected using Lipofectamine 2000 (Life Technologies). Recordings in HEK293 cells were performed 12-36 hours after transfection in extracellular and intracellular solution as described above.

Voltage clamp recording was performed in the presence of bath-applied tetrodotoxin (TTX, 1 μM; Tocris). For initial screening of action spectra, cells were held at resting potential of −70 mV, with 0.7 $mW/mm^2$ light delivery for 1 second at wavelengths (in nm) of 390, 438, 485, 513, 585 and 650, which were generated using filters of corresponding peak wavelengths and 15-30 nm bandpass. Liquid junction potentials (LJPs) were corrected using the Clampex build-in LJP calculator by subtracting 15 mV from measured values. For reversal potential measurement, HEK293 cells expressing opsins were held at resting potentials from −70 mV to +60 mV (after LJP correction) in steps of 10 mV, with 585 nm, 0.7 $mW/mm^2$ light delivered for 1 s.

Current clamp measurements were performed in the presence of glutamatergic synaptic blockers: 6-cyano-7-nitroquinoxaline-2,3,-dione (CNQX; 10 μM, Tocris) for AMPA receptors and D(−)-2-amino-5-phosphonovaleric acid (APV; 25 μM, Tocris) for NMDA receptors. For light-sensitivity measurements, light was passed through a 585/29 nm filter (Thorlabs) and delivered through a 40×, 0.8 NA water immersion objective. For light pulse-width experiments, 585 nm light with 5 Hz frequency and 0.7 $mW/mm^2$ intensity was used at varying pulse-width values (in ms) of 0.1, 0.5, 1, 2, 5 and 10. For light sensitivity experiments, 585 nm light with 5 Hz frequency and 5 ms pulse-width was used at varying light power densities (in $mW/mm^2$) of 0.002, 0.014, 0.08, 0.28, 0.7, 1.4 and 2.8. For spike fidelity experiments, 585 nm light with 0.7 $mW/mm^2$ power density was used, with 1 ms pulse-width for ChRmine and 5 ms for bReaChES and CsChrimson. For all experiments, 5-7 cells were tested, and data collection across opsins was randomized and distributed to minimize across-group differences in expression time, room temperature, and related experimental factors.

In Vitro Characterization Preparatory to All-Optical Set-Up

Dissociated hippocampal neurons were cultured and transfected with both red opsin variants and GCaMP6m. Coverslips of cultured neurons were transferred from the culture medium to a recording bath filled with Tyrode's solution containing (in mM, 129 NaCl, 5 KCl, 30 glucose, 25 HEPES-NaOH, pH 7.4, 1 $MgCl_2$ and 3 $CaCl_2$) supplemented with 10 μM CNQX and 25 μM APV to prevent contamination from spontaneous and recurrent synaptic activity. Optical stimulation and imaging were performed using a 40×/0.6-NA objective (Leica), sCMOS camera (Hamamatsu, ORCA-Flash4.0) and LED light source (Spectra X Light engine, Lumencor), all coupled to a Leica DMI 6000 B microscope. GCaMP6m was excited by 488 nm (Semrock, LL01-488-12.5) with the Spectra X Light engine.

GCaMP6m emission was reflected off a dual wavelength dichroic mirror (Chroma, ZT488/594rpc) for orange light stimulation or another mirror (ZT488/640rpc) for red light stimulation, and passed through a 535-30-nm emission filter (Chroma, ET535/30 nm). Red-responsive opsins were activated with a Spectra X Light engine filtered either with 585 nm orange light (Semrock, FF01-585/29-25, 0.2 or 2.0 mW/mm$^2$) or 635 nm red light (Semrock, FF01-635/18-25, 0.2 or 2.0 mW/mm$^2$).

We used low-intensity 488-nm laser light (12 μW/mm$^2$) for imaging GCaMP fluorescence without substantially activating red-responsive opsins. Images were acquired at 20 Hz using MicroManager (http://micro-manager.org). Light for stimulation was controlled by LabVIEW (National Instruments) and applied every 20 sec at an exposure time of 5, 25, 100, 400 and 800 msec. Imaging data were analyzed in MATLAB (MathWorks). Circular regions of interest (ROIs) were drawn manually based on the averaged image. We performed background subtraction before calculating Ca$^{2+}$ signal. ΔF/F response was calculated to normalize the signal in each ROI by dividing by its mean value of total fluorescence intensity and subtracting 1. Noise was calculated as the standard deviation of the total ΔF/F fluctuation before the first stimulation. S.D. response was then computed as ΔF/F response divided by noise. Peak amplitude was calculated from the maximum value between the stimulus onset and 2 sec after the stimulus cessation. To compare red-responsive opsins to triggered GCaMP6m kinetics, we calculated 400 ms exposure-triggered Ca$^{2+}$ transients. Rise time ($t_{peak}$) was defined as the time-to-peak from the beginning of the light stimulus to the time point at which maximal-amplitude fluorescence was reached. The decay constants (tau) were determined by single exponential fit from the peak of the fluorescence response for 15 sec after stimulation.

In Vitro Characterization in Two-Photon Electrophysiology

All two-photon electrophysiology experiments were conducted on a commercial microscope (Bruker Ultima running PrairieView v5.4) using a Nikon 16x/0.8 NA (CFI75) long-working-distance objective for light delivery. For two-photon stimulation, spiral scanning was performed through a defined spiral ROI with 25 μm diameter, with 12 rotations per spiral, and 4 ms total exposure duration with 80 MHz laser repetition rate (Coherent Chameleon Ultra II). For imaging, a second 80 MHz laser (Coherent Chameleon Ultra II) was relayed through a resonant galvo path for 30 Hz imaging rates, to match the imaging characteristics present for the in vivo experiments. As each plane in the behavior in vivo imaging experiments was recorded at ~2.7 Hz, the imaging rate was appropriately modified by acquiring a new image every 370 ms such that the patched cell was sampled at ~2.7 Hz.

The two-photon stimulation and imaging light paths shared a common objective, tube lens and scan lens—but in contrast to the in vivo behavior imaging datasets, for the in vitro characterization data, the photostimulation galvanometer pair was smaller than the imaging galvanometer pair (3 mm vs. 6 mm). This effectively scaled down the actualized NA for photostimulation from the stated microscope objective values. Experiments were performed with cultured hippocampal neurons expressing ChRmine-EYFP through AAV transfection, and the same intracellular and extracellular solutions for one-photon electrophysiology characterization were used for recording.

For two-photon action spectra and power spectra characterization, recordings were done in voltage clamp mode at holding voltage of −70 mV. Action spectra were measured in randomized trial order at wavelengths (in nm) of 800, 860, 920, 980, 1035, 1080, at the laser power of 20 mW. Power spectra were measured in randomized trial orders at powers (in mW) of 0, 5, 10, 15, 20, 25, 30, at the two-photon wavelength of 1035 nm. All measurements were normalized by the maximum value of the single recording session. Experiments were done in 6 different cells.

For spike fidelity and imaging laser cross-stimulation experiments, recordings were done in current clamp mode, under the membrane potential at −65 mV to −70 mV. Spike fidelity was estimated by stimulation of cells at frequencies (in Hz) of 5, 10, 20, 30, with 1035 nm laser at 20 mW. For cross-stimulation experiments, membrane voltage was observed during image acquisition as a function of imaging power (920 nm, at 2.7 Hz frame-rate) at 0, 20, 40, and 60 mW. Data collection across opsin expressing neurons was randomized.

Electrophysiology Data Analysis pClamp 10.6 (Molecular Devices), and Prism 7 (Graph Pad) software were used to record and analyze data. Statistical analyses were performed with two-tailed unpaired t-test or one-way ANOVA. Data is presented as mean±s.e.m. $P<0.05$ is defined to be statistically significant.

For preparation of phylogenetic trees, opsin sequences were first aligned using Clustal Omega server (https://www.ebi.ac.uk/Tools/msa/clustalo/) and later calculated using AQUAPONY (http://www.atgc-montpellier.fr/aquapony/aquapony.php) and TreeDyn (http://www.treedyn.org/) for circular and rectangular trees, respectively. The homology model of ChRmine was built using the C1C2 crystal structure (PDB ID: 3ug9) as a template, using RosettaCM method. All molecular graphics figures were prepared with Cuemol (http://www.cuemol.org).

Mouse In Vivo Experiments

Viral constructs: The genes for GCaMP6m and soma-targeted ChRmine were cloned in a cis configuration separated by the ribosomal skip motif p2A under the CaMKIIα promoter in an AAV2 backbone. This construct was sequenced for accuracy, tested for in vitro expression in cultured hippocampal neurons and packaged by the Stanford Neuroscience Gene Vector and Virus Core (GVVC) as AAV8/Y733F to create AAV8-CaMKIIa-GCaMP6m-p2a-ChRmine-TS-Kv2.1-HA (used in all mice except for one). AAV8-CaMKIIa-GCaMP6m-p2a-ChRmine-TS-HA was used in the remaining single mouse (mouse 2 in behavioral cohort).

Surgery: All animal procedures followed animal care guidelines approved by Stanford University's Administrative Panel on Laboratory Animal Care (APLAC) and guidelines of the National Institutes of Health. Male C57/BL6 mice (8-12 weeks) were anesthetized with 5% isoflurane for induction and ~1-2% isoflurane during surgery. The skull was exposed, cleaned and coated with a layer of Vetbond (3M). A circular (1 cm diameter, 1 mm height) titanium implant with a counter bore (8 mm outer diameter and 6 mm through hole) was affixed to the skull with Metabond dental cement (Parkell) centered on −2.75 mm (lateral) and −2.25 mm (posterior) from bregma over the lateral portion of primary visual cortex of the left hemisphere (imaging experiments were performed approximately 500 μm medial and posterior from this location, and thus were more centrally located within primary visual cortex). The mouse was transferred to a head clamp device designed to firmly hold the metal implant by an angled groove around its perimeter (this same head clamp device design was used to hold the animal under the two-photon microscope and thus had micron-level stability). A circular craniotomy was performed using a high-speed drill by slowly drilling away bone within the perimeter of the through hole of the implant. Once the bone was as thin as possible, but before drilling all the way through the bone, the remaining intact bone was pulled away with forceps to reveal the underlying cortex with the dura fully intact. A glass pipette injection needle (~25 µm diameter, angled tip) calibrated to the stereotaxic coordinates and filled with the virus was lowered into the cortex to a depth of ~400 µm. 500 nl of virus (typically $4 \times 10^{12}$ vg/ml) was injected over ~5 min and then the pipette was lowered to ~600 µm and another 500 nl was injected over an additional ~5 min. The pipette was left in place in the brain following injection for at least 3 minutes and then slowly retracted. A 4 mm glass coverslip affixed with UV-cured optical glue (Newport) to a titanium cannula of the same diameter (the cannula also had an ~8 mm flange at the top to register with the outer circular implant) was applied the surface of cortex and cemented in place with Metabond. For analgesia up to 72 hours, buprenorphine sustained release (SR) was injected pre-operatively at 0.3-1.0 mg/kg subcutaneously, or buprenorphine (0.05-0.1 mg/kg) was injected by subcutaneous or intraperitoneal injections.

Visual stimulation: Drifting sine wave gratings (0.2 cycles/degree spatial frequency; 2 Hz temporal frequency; 2, 3, 4, 5, 12, 25, or 50% contrast) were generated using custom software in Pyschtoolbox running on MATLAB (code available online adapted from) and presented on a calibrated liquid crystal display monitor placed 15 cm from the mouse's eye, centered on the retinotopically targeted location in V1. The gratings subtended 60 deg of visual space and were surrounded by uniform gray around the rest of the screen. A trial began with a 100 ms, 5 kHz tone cue. 1.25 seconds later, the drifting grating was displayed for 3 seconds. The next trial began ~4.5-9 seconds later depending on whether the mouse made an error during the answer window and received a time out as penalty (no time outs were added for naïve mice or mice in the conditioning phase below). A uniform gray screen was presented between drifting grating presentation.

Behavioral training: Mice were kept on a reverse day/night cycle. Mice were habituated to the experimenter and to a floating Styrofoam ball and behavior apparatus (Phenosys) for approximately 3 days (the setup was either under the microscope or replicated in a behavioral chamber for initial training before imaging experiments; mice were briefly anesthetized with isoflurane prior to head fixation and allowed to fully recover before proceeding). For discrimination behavior training, mice were water restricted and first allowed to lick freely to trigger immediate water delivery from a lickport by triggering an infrared optical lickometer (Sanworks). This was repeated daily until the animal immediately and consistently consumed water once presented with the lickport. Then, mice were presented with visual stimuli (50% contrast 0 and 90° gratings, see below) using the same trial structure as above, without penalties. If the mice licked during the answer window (1-3 seconds after visual stimulus onset) during the 0° (target) stimulus, they immediately received a water reward (~6 µl). During this conditioning phase, mice always received ~6 µl of water at the end of target visual stimulus presentation, in addition to any lick-triggered reward. Once mice reliably licked to the target stimulus before the free water was delivered at the end of the trial (mean 6.8 days), they advanced to the discrimination task in which water was only delivered if they licked during the answer window during target stimulus presentation, and time outs (4.5 sec) were added to the end of error trials (misses/false alarms). If the mice did not show discrimination behavior improvement over the course of 4-5 days, a mild air puff directed toward the mouse's face was added as immediate penalty for false alarms. This air puff was eventually added for all mice for consistency. Training continued until mice had nearly 100% hit rates and discriminated 50% contrast gratings with ≥2 d' for at least 3 days (mean 9 days total). Then, an equal number of 25% contrast gratings trials were added to the protocol and training continued for 3 days. The same criteria were applied until the task included 2, 12, 25 and 50% contrasts (mice generally could not discriminate 2% contrast gratings). If not done so already, mice were additionally trained under the microscope until behavior was stable to all contrasts before advancing to all-optical experiments. d' was defined as norminv(Hit Rate)−norminv(False Alarm Rate) in MATLAB. For the d' calculation, rates equaling 100% or 0% were adjusted to 99% and 1% respectively. Percent correct was computed for a given condition(s) as [(Hits)+(Correct Rejections)]/(Total Trials).

In vivo visual and optogenetic stimulation experiments: Once trained (or in the case of naïve mice, once habituated to the head-fixed floating ball setup under the microscope), mice performed the task (or passively viewed visual stimuli) while volumetric two-photon $Ca^{2+}$ imaging was performed in V1 and visual stimuli were presented to the animal. A series of reference images were collected of the volume to aid in alignment to the same region on subsequent days. Neural $Ca^{2+}$ responses were analyzed as described below in order to identify ensembles for stimulation on subsequent days/experiments.

Mice returned to the microscope each day and the field of view was aligned to the reference images from the reference experiment. This was accomplished using an automated image registration algorithm (based on the same cross-correlation procedure described below for subsequent analysis) that reported the real-time offsets in pixels between the current imaging field of view (streamed from the microscope acquisition pipeline with minimal latency) and the reference images. In addition, a real-time overlay image was presented to allow the experimenter to optimize x, y, z and θ for precise alignment. This was done before beginning the stimulation experiment using several imaging planes throughout the volume. During the volumetric imaging and stimulation experiments, a similar program reported real-time offsets and displayed image overlays (allowing the experimenter to correct for any offsets online using the motorized translation stage), and could be alternated between imaging planes throughout the volume in order to confirm alignment across cortical layers (see FIG. 22).

On randomly interleaved trials, visual stimuli were presented to the animal or ensemble stimulation (tuned or random, target or distractor) ensembles were stimulated with the MultiSLM (see below). For naïve mice, contrasts included 12, 25 and 50%, as well as an equal number of 0% (no visual stimulus), and optogenetic ensemble stimulation occurred on 2/3 of 0% contrast trials (balanced tuned and random ensemble stimulation trials), but was never paired with visual stimulation. Trial order was pseudorandomized for all condition types, and re-randomized if the trial order contained >3 target, distractor, or low contrast (≤5%) conditions in a row. For the behavioral cohort, the same paradigm was used, except optogenetic stimulation could occur alone, or in combination with the visual stimuli (randomly interleaved, balanced trials), and the low contrast condition was exchanged from 0% to 2, 3, 4 or 5% and back to 0% over the course of the contrast ramp experiments. Following the contrast ramp experiments, the low contrast condition was kept at 0% for subsequent experiments (for example, layer-specific ensemble stimulation experiments described below). For the behavior cohort, licking during target stimuli (0° gratings, 0° tuned ensemble or size-matched "0°" designated random ensemble) during the answer window (1-3 sec after stimulus onset) triggered a water reward. Licking during distractor stimuli (90° grating, 90° tuned ensemble or size-matched "90°" designated random ensemble) during the answer window triggered an air puff. Errors (misses or false alarms) resulted in a time out (4.5 sec) at the end of the trial. Importantly, the microscope hardware performed the same operations on every trial, regardless of condition (e.g., galvanometer spiral scanning, laser shutter opening, imaging scanning pattern, spatial light modulator phase mask transition, etc.), with the exception of the laser power applied to the holograms (either 0 power or power calculated to stimulate the ensemble with 5 mW instantaneous power delivered to each cell for 0.63 ms at ~30 Hz, see below), such that all experiment sounds were the same between all conditions. All mice that proceeded through the contrast ramp with layer 2/3 and 5 stimulation experiments and proceeded onto the layer-specific stimulation experiments are included in the manuscript. Three additional mice proceeded only through the contrast ramp experiment, but we increased laser stimulation power beyond the typical protocol (i.e., to attempt to offset weaker stimulation responses). Including these mice in the behavioral analysis yielded comparable statistical results.

All-Optical Physiology Microscope Design and Characterization

As described in detail below, the all-optical (read/write) microscope used in this manuscript was optimized to address neural ensembles distributed over large volumes beyond millisecond temporal precision for the first time. Achieving these biologically-important specifications required development and optimization of several components, including an entirely new, high-pixel-count, fast spatial light modulator (SLM) with new electronics and software interfaces (MacroSLM), new multiplexing strategies (MultiSLM; also see FIGS. 18-20, 27 and 28), and a unique pairing with a three-dimensional (3D) imaging strategy during head-fixed mouse behavior.

In prior work, when realizing all-optical physiology using SLMs at high spatial resolution (e.g., NA>0.4), the addressable targeting volume has thus far been significantly constrained relative to the available imaging volume due to a ceiling on the number and size of available pixels provided with current commercial devices. Furthermore, generation of new ensemble-targeting hologram patterns in near-infrared wavelengths has been limited in overall refresh rate by the SLM response time and the stimulation durations required by previous multi-photon optogenetic opsins and protocols. This has restricted the ability to write in activity patterns at fundamental biological timescales (~1 ms) over volumes spanning several cortical layers and whole brain areas in the mouse (~0.5-1 mm spatial scale). Therefore, we sought a solution where the addressable optogenetic volume meets or exceeds the volume available for imaging, potentially spanning multiple functional areas/volumes across cortical layers—and developed a hardware and biological interface allowing millisecond-level precision of ensemble stimulation during behavior.

MacroSLM: To achieve the frame rates, trigger responsiveness, and 3D field of view used in this work, we designed and built a custom liquid crystal on silicon (LCoS) spatial light modulator (SLM). The MacroSLM achieves 500 Hz hologram-to-hologram frame rate at $\lambda=1064$ nm at 85% diffraction efficiency (FIG. 19A). The square 1536×1536 pixel array assures a uniform numerical aperture is available across the transverse dimensions of the sample and employs high-voltage (0-12V analog) pixel addressing, and carefully-timed transient voltages (also known as overdrive), for increased liquid crystal (LC) response speed, requiring development of complex driving electronics. In addition, built-in temperature control allows the LC to operate at a fixed temperature where LC viscosity is low, while adjusting automatically for illumination- and data-throughput-related heating effects.

MacroSLM optimization for three dimensional fields of view: Achieving a large addressable field of view with high spatial precision was a key driving force behind the design of the MacroSLM, affecting our choice of pixel count and pixel size. Pixel count determines the holographic field of view of the microscope when the magnification of the optical system is designed to image the SLM onto the pupil of the objective lens. The MacroSLM 1536×1536 pixel array provides a theoretically addressable field of view of >>1 mm at high NA (>0.4) when using appropriate relay optics and microscope objectives (FIG. 18A). We designed the SLM with a relatively large 20 µm pixel pitch to achieve several advantages over smaller pixels. The large pixel pitch makes the effect of fringing fields small and minimizes interpixel cross-talk (that would otherwise act like an unwanted low-pass filter on the pattern that the SLM displays). This allows the SLM to maintain high diffraction efficiency (DE) at large steering angles, including when generating large numbers of excitation spots. The resulting large 30.7×30.7 mm array allows the input beam to be spread over a large square area which, along with internal light shielding layers, aids peak power handling. The large pixel pitch was also chosen for several important reasons: it enables large voltage swings (here 0-12 V analog), which in turn increases hologram transition speed; it is sufficient to store enough charge (178 fF) to hold the electric field across the liquid crystal while it is switching patterns; and it provides an extremely high fill factor since the active pixel (19.5 µm width) is much larger than the gap between the pixel pads needed to prevent shorting (0.5 µm). Ultimately, fill factor determines the DE ceiling of the device, with DE=(fill factor)*2×pixel reflectivity, or theoretically for this device (0.96)*2×0.95=0.88. This high DE improves overall efficiency of the system while minimizing potential artifacts from non-diffracted light. Also, achieving this DE value through realizing a high-fill-factor obviates the need for a dielectric mirror coating, which is typically used to increase DE, but dielectric mirrors increase the chances of unwanted optical artifacts. Lastly, larger pixels will be responsible for minimizing the lateral chromatic aberration inherent to using the SLM as a diffractive optic when addressing large fields-of-view (maximum deflection angle is 1.4°) and therefore improve the relative efficiency for multi-photon excitation at the focal spot (128). Indeed, our calculations indicate that when using the fixed-wavelength ultrafast laser source reported herein (Coherent Monaco 1035-80-60 at $\lambda=1035$ nm) at a pulse-width ($sech^2$) of $\Delta t \approx 300$ fs (spectral width of 4.5 nm), a maximum chromatic shift of only +/−0.64 µm would be present when addressing the full-width of the scanned imaged plane (reported herein as 710×710 µm).

MacroSLM liquid crystal speed response: High-voltage (0-12 V analog) pixel addressing makes the LC response fast, along with the use of high transient voltages (also known as overdrive). 'Phase wrapping' was implemented for each pixel to shorten the distance in phase between phase values in time. We also maintain the LC temperature with the use of backplane Peltier heating/cooling, allowing the device to operate at a temperature (45° C.) where LC viscosity is low while also adjusting for the varying heating effects of high-power laser illumination. We optimized the SLM thickness for the use of overdrive at our NIR (~1064 nm) target wavelength, and for maintaining full ≥2π phase modulation.

MacroSLM data handling: Data handling is another significant aspect of increasing speed, since the system must be capable of calculating the required transient voltages to achieve fast LC switching from phase to phase at each pixel, while loading the transient 1536×1536 images onto the SLM pixels at ~1250 Hz continuous frame rate. We use a custom field-programmable gate array (FPGA) solution for handling these high data rates, including on-board storage of 2045 images, on-board application of spatially-varying voltage calibrations, and on-board calculation of individual transient voltages for every pixel. The driver board receives data over PCIe on cable to a Xilinx Kintex-7 primary FPGA. This FPGA distributes the data to 8 secondary Kintex-7 FPGAs using the Xilinx Aurora high-speed serial interface. Each secondary FPGA is capable of performing the overdrive processing for, and supplies the data to, its own section of the SLM (this feature was not yet available for data collected in this manuscript; overdrive frames were precomputed and loaded into the on-board storage for these experiments). The primary FPGA also contains a Microblaze soft microcontroller that performs a number of additional functions, such as loading certain parameters over I2C, temperature monitoring, and automatic safety-shutdown for both the driver board and SLM head. Interruptible image downloads mean that new holograms can be triggered at arbitrary rates exceeding 1 kHz (rather than at integer multiples of the SLM's base refresh rate), without missing triggers. For integration into precisely timed and synchronized experiments, the high-speed triggering system instructs the SLM to transition to the next commanded hologram with low latency and jitter. The latency between a trigger arriving and the voltage changing on the SLM is 6 μs with a range of 3-9 μs, so that the transition to a new hologram can be very predictably initiated. We developed a MATLAB-based software development kit (SDK) to interface with the SLM. Under these conditions, we could trigger and transition between different holograms at 330-500 Hz with 85-100% target hologram efficiency (FIG. S4A).

All-optical physiology microscope design: We developed a custom MultiSLM photostimulation path that was integrated into a commercial multi-photon imaging microscope including a resonant-scanner imaging path and piezo-coupled microscope objective holder (Bruker Nano Surfaces Division, Ultima, Middleton, Wis.). We developed custom optical elements and opto-mechanics, alongside commercial elements when possible, to integrate the optogenetic stimulation path, including the multiple SLMs, into this microscope. The optical path was modeled in both Zemax OpticStudio (Zemax LLC, Kirkland, Wash.) and MATLAB (The Mathworks, Natick, Mass.) and optimized to maximize the field of view at the full available back aperture of the microscope (FIG. 18A). Integration is realized via a two-position drop-down mirror located before the existing uncaging galvanometer unit. For the imaging light path, a tunable-wavelength femtosecond pulsed light source is utilized (Coherent Chameleon Ultra II, $\lambda_{typ.}$=920 nm, Santa Clara, Calif.). For the optogenetic stimulation, a fixed-wavelength ($\lambda$=1035 nm) femtosecond pulsed light source (Coherent Monaco 1035-80-60, Santa Clara, Calif.) is used at a user-selected 10 MHz pulse repetition rate. The integrated gate and power-modulation signals of the optogenetic laser were utilized to guarantee zero residual optogenetic-laser illumination on sample. An optical switch (Conoptics LTA360-80 with 302RM driver) (OS, FIG. 11) is used to selectively direct the optogenetic stimulation light towards two alternative paths at 200 kHz temporal resolution, each path with a dedicated SLM. Each path has a 20× beam expander (Thorlabs GBE20-B) (BE, FIG. 11A) and a custom pair of turning prisms (Edmund Optics, 36°-54°-90° prism, NIRII coated, PN 913418) (TP1 and TP2, FIG. 11A, see also FIGS. 20A-20C, 20E) to maintain a compact footprint, thereby minimizing mechanical drift issues as well as facilitating simple beam alignment by keeping the optics at 90° angles (FIG. 20D). One light path requires a pair of half-wave plates (Thorlabs WPH20ME-1064) (HWP, FIGS. 11A and 20D) in order to maintain optimal polarization alignment through the turning prisms, the SLM liquid crystal alignment layer and the beam combining polarization cube (Thorlabs PBS513) (PBS, FIG. 11A). A custom optical relay (Special Optics 54-44-783 AR-coated doublet and 54-8-750 AR-coated triplet) (RL1 and RL2, FIG. 11A) was designed to de-magnify the SLM active area at a 5:1 ratio, matching the SLM size to the clear aperture of the dedicated optogenetic galvanometers (OGS, 6 mm clear aperture, FIG. 11A) mounted within the commercial multi-photon microscope. This relay was optimized to correct for chromatic aberration, field curvature and distortion. To block residual DC signal from the un-diffracted optogenetic beam off the SLMs, a pair of magnets (D101-N52, K&J Magnetics, Inc, Pipersville, Pa.) are mounted to each side of a glass cover slip (Fisher Scientific, 12-546-2) and placed in the intermediate image plane of the microscope (located between the two lenses of the SLM relay, BB, FIG. 11A). A majority of the optogenetic optical path resides on custom 3D printed opto-mechanics which facilitates alignment and improves compactness as well as total costs (FIG. 20F, for individual mechanical parts the files are available through contacting the authors). The optogenetic galvanometers (OGS, FIG. 11A) are utilized to generate the temporal spiral raster scans which trace the SLM-diffracted beamlets across the neuron cell body membranes. The optogenetic and resonant-imaging beams are combined by a dichroic notch filter (Semrock NFD01-1040) (DC, FIG. 11A). After both beams are combined, they pass through the commercial scan lens, tube lens and emission filter (SL, TL, and FLTR_EM, respectively, FIG. 11A) before reaching the microscope objective. Axial scanning during image acquisition was realized with a 1 mm-throw piezo-coupled microscope objective (objective for 3D scanning: Nikon 16×/0.8NA (16XLWD-PF), whereas the objective for 2D imaging: Olympus 10×/0.6NA). Optical fluorescence emission is collected by the appropriate microscope objective (OBJ, FIG. 11A) and redirected via the emission filter to a pair of PMTs (PMT1 and PMT2, FIG. 11A) which collect the red and green fluorescence channels (523/70 nm and 627/73 nm).

Precise temporal and spatial optogenetic control: To increase temporal resolution beyond that achievable by a single SLM capable of operating at up to 500 Hz (FIG. 19A), we demonstrated alternating optogenetic excitation from either SLM1 or SLM2 in the MultiSLM system (FIGS. 11C-11G and 19B). At the maximum temporal resolution tested, a $\Delta t_e$=210 μs spiral raster scan was designed using a 5-rotation, 10 μm diameter spiral for optogenetic light exposure and validated with the Olympus 10×/0.6 NA physiology objective at 20-30 mW/cell (FIGS. 11C-11G and 19C). This short stimulation-duration is many-fold faster than previously reported for in vivo two-photon optogenetics. Post-exposure, each SLM has 1.79 ms to load the next hologram in the sequence, ensuring that the hologram is nearly fully-formed to maximize fidelity and minimize DC illumination before exposing the sample. Therefore, when each SLM is running at 500 Hz and is temporally interleaved at uniform intervals, full 1 kHz temporal resolution is realized (FIGS. 11C-11G and 19D). This approach realizes efficient targeting precision across a full 1.03×1.03 mm field of view with no apparent roll-off in optogenetic excitation success rate vs position in the field (FIG. 11C, average of 8 randomized trials of the $e_1$-$e_6$ ensemble (FIG. 11F) photostimulation along with control, FIG. 18B). Alternatively, a burst-mode operation is available where both SLM1 and SLM2 are pre-loaded with the necessary holograms and each is sequentially illuminated to expose the sample to an optogenetic illumination pattern, with the sequential temporal difference limited only by the gating time of the Pockels cell (here, $\Delta t$=80 μs is conservatively applied). The burst mode operation was typically employed during all the visual in vivo experiments reported herein as a means to maximize the number of neurons stimulated per unit time. In those experiments all the targets in the ensemble were randomly distributed across two groups, and each group was assigned an individual SLM for the duration of the experiment.

In order to image multiple axial planes, we opted for a lighter microscope objective (Nikon 16×/0.8 NA) to reduce the inertial mass burden on the rapidly scanning piezo to help maintain its lifetime. Notably, this solution using a piezo-scanning objective does allow for rapid scanning across multiple axial layers while maintaining the ideal optical imaging performance of the microscope (FIG. 18C). Despite the temporal lag of acquiring an image from each axial slice (33 ms per slice), the optogenetic photoexcitation can be performed volumetrically, simultaneously. Using the viral vector approach taken here, selective expression is observed in layer 2/3 and layer 5 (FIG. 11B) and three-dimensional, simultaneous optogenetic excitation is realized across the full volume of 0.71×0.71×0.39 mm, capable of targeting layer 2/3 through layer 5 in this preparation (FIGS. 18G and 18H, 30 Hz at 20 mW/cell at the objective, 0.63 ms, 9 rotations, 15 μm spirals). This was also the configuration used for all in vivo visual experiments, except the power was reduced to 10 mW/cell at the objective (see below); thus, the characterization measurements at higher power described here are conservative with regard to stimulation spatial precision.

To assess axial precision of our stimulation system, we selectively targeted optogenetic perturbation only to layer 4, where expression is not present in the cell bodies. We measured all resulting activity in unbiased fashion across the entire imaged volume by subsampling the images into 8×8 pixel bins and reporting the modulation in fluorescence during optogenetic perturbation as a function of the tissue depth from the most superficially sampled image. As expected, based on the axial point spread function of our system (0.48 NA, FIG. 18E), layer 4 stimulation did not yield activity modulation in neighboring layers (FIGS. 18G and 18H). In the same experiments, on randomly interleaved trials, we stimulated neurons in layer 2/3 and/or 5 for comparison, which elicited robust responses. It is also important to note that, as a result of the axial translation of the microscope objective during volumetric imaging, the spiral-scan stimulation will correspondingly be slightly tilted through the cell body, relative to normal. However, this is minimized in our setup due to the short exposure times required with this opsin/optics combination. As an example, the maximum axial slew rate of the objective in our experiments was ~2 μm/ms. Since all individual exposures in the protocols introduced in FIGS. 19C-19F, and used throughout the manuscript, are below 0.63 ms, we expect a maximum axial blur due to microscope objective motion to be ≤1.2 μm. Imaging and Optogenetic beam alignment: Spatial alignment of the targeting and imaging beams was accomplished by using the SLMs and optogenetic galvanometers to burn a constellation of holes into a thick fluorescent slab and then to register them to the collected imaging frame via manual identification of the hole centroids. A rigid, affine transform was defined for each axial position (at up to 7 axial planes) and a linear fit was implemented to characterize how each of the 9 affine transform coefficients would vary as a function of axial plane. This fit was stored and later recalled when generating the hologram patterns to be generated for targeting identified neurons in the sample. The axial localization of the imaging and optogenetic stimulation beams was characterized by measuring the fluorescence signal as a thin fluorescence slab (<5 μm) was translated through the beam (FIG. 18E).

The phase control afforded by the SLMs was exploited in two additional capacities to mitigate inherent optical challenges. First, due to the non-unity fill-factor of the SLM, a fixed amount of light will remain un-diffracted from the SLM and be focused in the sample plane unless mitigating steps are taken. First, we addressed this by placement of a beam block, in the form of a pair of magnets mounted to a cover slip (BB, FIG. 11A) in the intermediate image plane located between relay lens 1 and 2 (RL1 and RL2). This effectively blocked any light from undesirably focusing into our sample plane. To further address any potentially un-blocked, un-diffracted light focusing in the sample, we opted to de-collimate the beam expander (BE, FIG. 11A) such that the native foci of the SLMs were located approximately 300 μm above the native imaging plane of the microscope objective. This axial shift of the native SLM focal plane was compensated by adding a complementary focusing and spherical aberration correction term to the SLM phase mask, such that the un-diffracted illumination focuses ~300 μm above the targeting volume. The second capacity in which the SLMs were exploited to mitigate optical challenges was by employing an optical aberration correction algorithm which accounted for a) slight deviations from phase uniformity across the entire 30.7×30.7 mm face of the SLM and b) potential aberrations from optical misalignment or inherent to the optics. The aberration correction was realized by manually adjusting the weights of a linear summation of Zernike polynomials (up to $Z^{16}$) to account for the phase aberration (FIG. 18F), as measured by the fluorescence signal excited from a thin layer (<5 μm) of fluorescent material on a glass slide. The dominant phase errors were found to be astigmatism and spherical, with an additional defocus term which accounted for making the optogenetic target and the imaging plane effectively co-planar. The astigmatism phase correction likely compensated for any residual surface error not already corrected by the SLM look-up table.

Optical power considerations for all-optical physiology: It is worthwhile to note that in addition to considering instantaneous power, the time-averaged power into the sample (which is most likely related to brain heating) is minimal due to the very low duty cycles of each optogenetic photoexcitation exposure. For example, to target all 160 cells shown in FIGS. 11C-11G required only:

$$\frac{30 \text{ mW}}{\text{cell}} \times 160 \text{ cell} \times \left(\frac{29 \text{ Hz} \times 0.21 \text{ ms}}{1000 \text{ ms}}\right) = 29.2 \text{ mW}$$

of average power during the 3 seconds of optogenetic stimulation. Further reducing time-averaged power into the brain, optogenetic stimulation epochs were generally a fraction of the total trial time (e.g., minimum 3 out of 8 seconds in behavioral trials).

In general, combined time-averaged power including imaging and optogenetic stimulation lasers during visual experiments was <50 mW. Instantaneously during either imaging or optogenetic stimulation (it was exceedingly rare that both occurred simultaneously on the microsecond scale for a given neuron due to raster scanning and very short optogenetic stimulation duration), we estimate that each neuron experienced <20 mW imaging power or ~5 mW optogenetic stimulation power, when laser attenuation into the brain is accounted for (150 µm attenuation constant). Mitigation of photo-stimulation artifact in images: The optogenetic stimulation creates an image artifact due to the excitation of GCaMP in the targeted cells. Here, due to the low-duty cycle of the optogenetic stimulation, this artifact is present in only a small percentage of the imaging pixels (e.g., one 210 µs optogenetic stimulation will create artifact in only 0.6% of the total image). Furthermore, the artifact band is dithered across trials such that when the artifact pixels are excluded from any individual trials (see below), the trial-averaged results will reconstruct a full, artifact-free image (FIG. 21).

Figure 11:
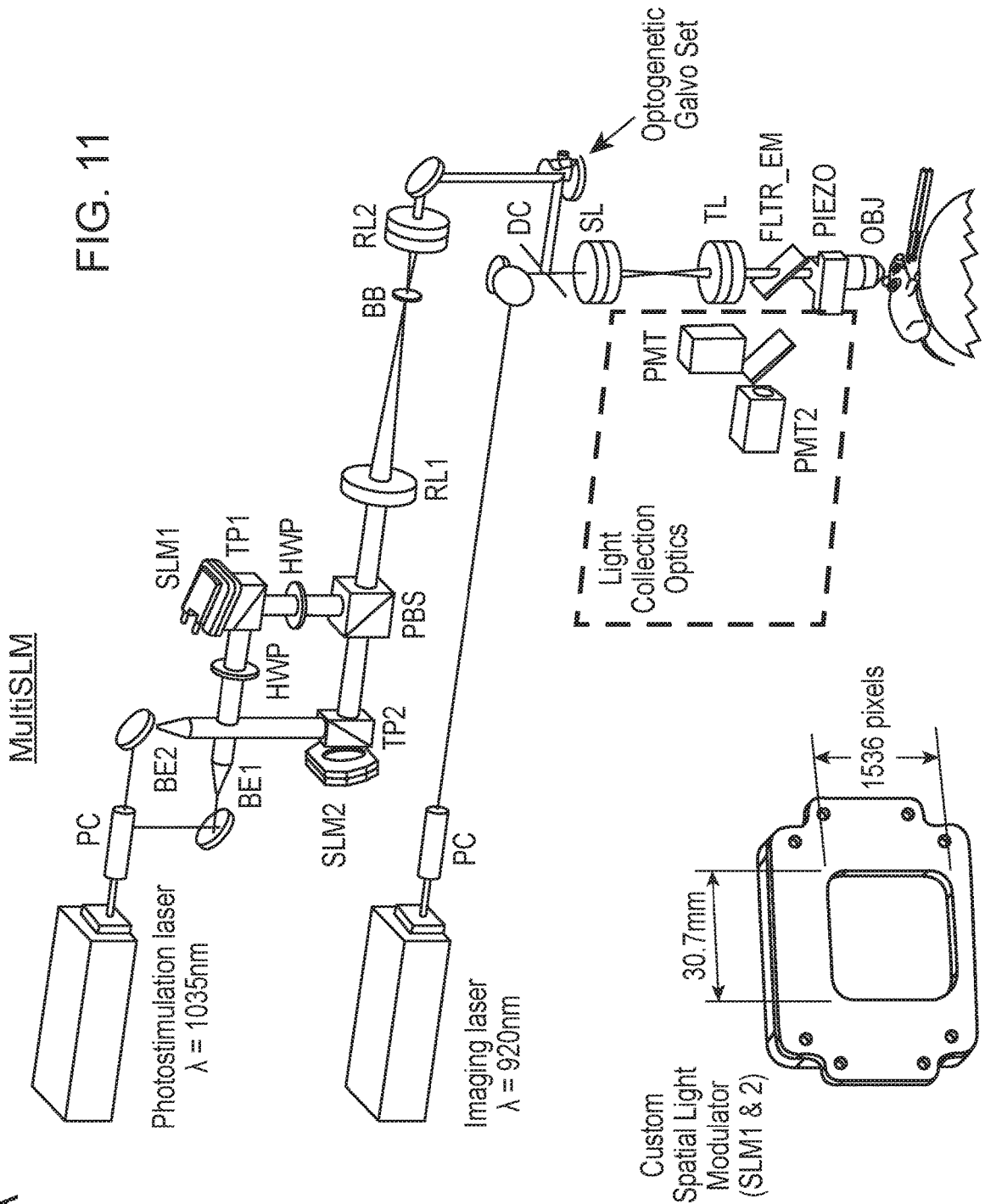
FIG. 11, A-I depicts MultiSLM large-volume temporally-precise all-optical microscope.
Figure 11:
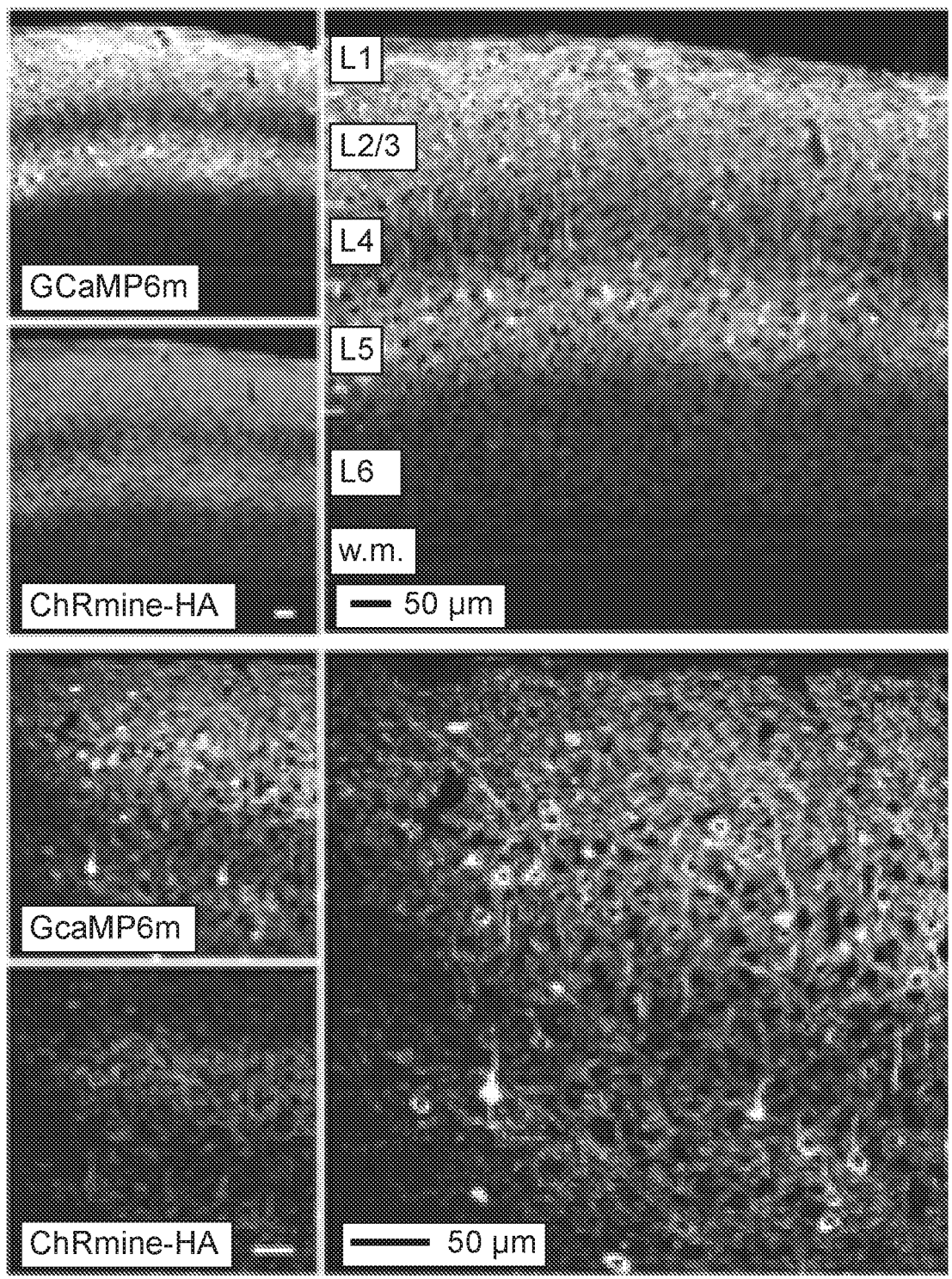
Figure 11:
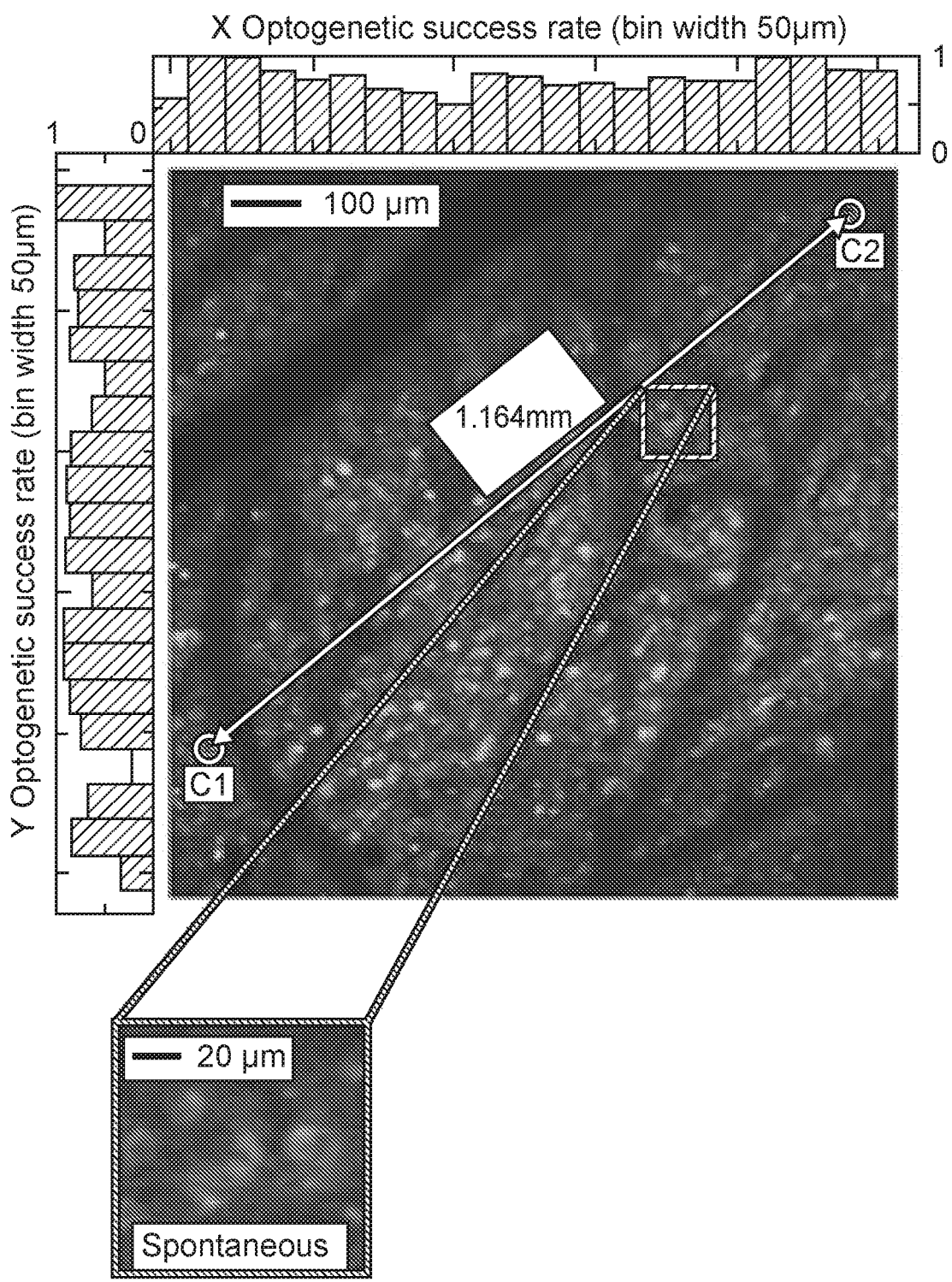
Figure 11:
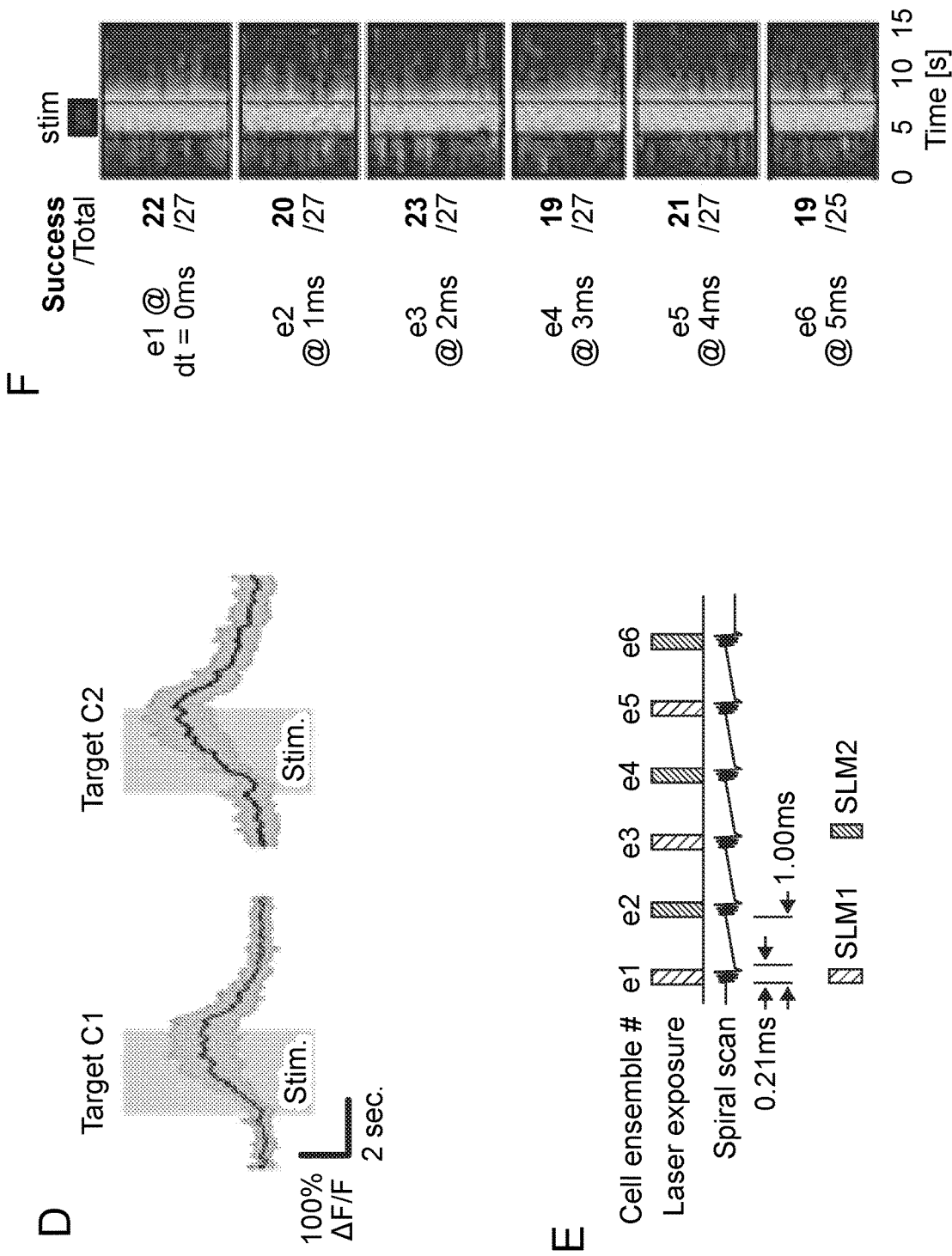
Figure 11:
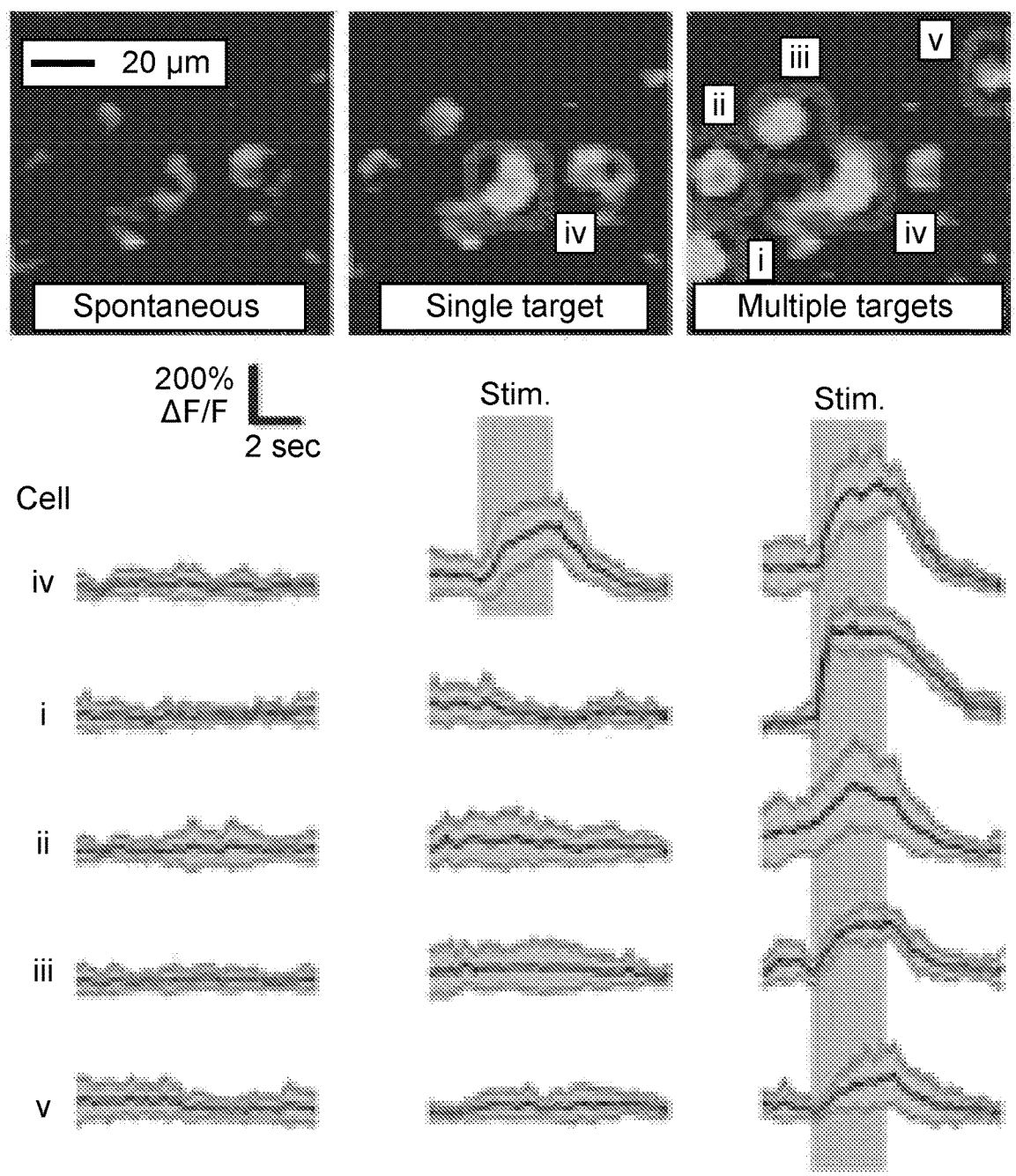
Figure 11:
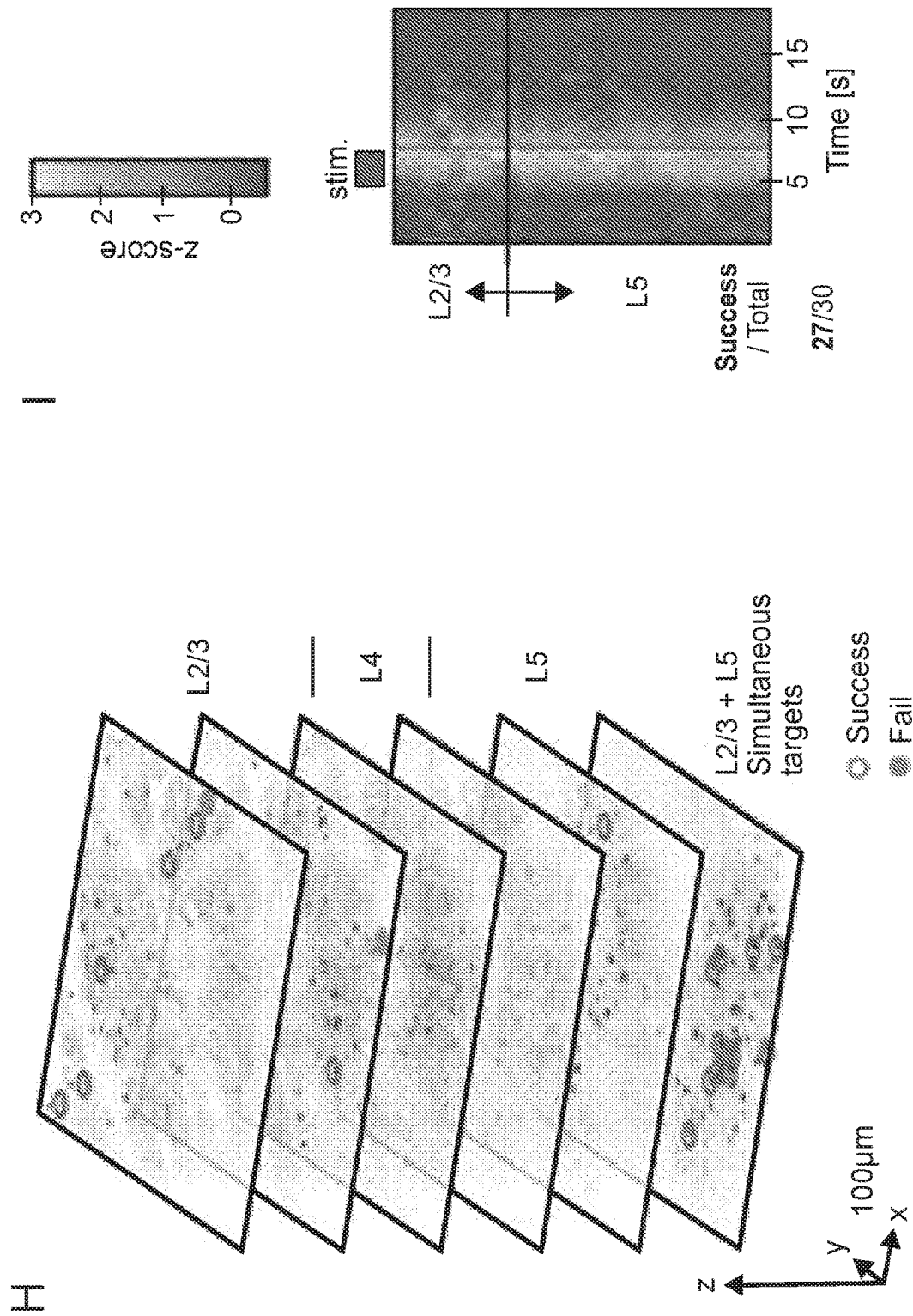

Data analysis of microscope performance: Multi-photon imaging data in FIGS. 11 and 18 were processed in MATLAB (R2017a, The Mathworks, Natick Mass.). Non-overlapping ROIs were defined from manual selection of targets. After defining the regions of interest (ROIs), the image movies were Kalman filtered (gain=0.5, noise=0.05) and data was then extracted by using each ROI as a binary mask and calculating the mean signal for each image frame. From this time-series ROI signal, the ∆F/F was calculated using the mean of the final ⅕ duration of the time-series data as the baseline measurement of each respective ROI. In FIG. 11C, for a neuron ROI to be deemed a positive optogenetic stimulation it must pass the following two criteria: a) the difference of the mean signal from the stimulation signal and the pre-stimulation baseline must be greater than $2\sigma$ ($p \leq 0.025$), and b) the difference of the mean signal and the post-stimulation baseline must be greater than $2\sigma$ ($p \leq 0.025$). Note that the trial-averaged artifact in FIGS. 11C-11G was negligible due to: the phase offset of the image acquisition (30 Hz) and the optogenetic stimulation (29 Hz), which decreased the probability of the artifact being present in the same pixel across sequential frames; the minimal duration/line width of the artifact $$\left(\frac{210 \text{ µs}}{64.9 \text{ µs/line}}\right)$$

group in the stimulus, accounting for 3.8% of the image).

Data Analysis of In Vivo Visual Experiments

Preprocessing of in vivo visual experiment imaging data and selection of stimulated ensembles: Raw imaging data were loaded into MATLAB (R2016a, The Mathworks, Natick Mass.) and analyzed using built in functions, MATLAB Distributed Computing Server, and custom scripts. To reduce processing time by ~6 fold (n slices) and facilitate activity-guided experiments, raw images (~40,000 images per session, per channel) were processed in parallel in a computing cluster in which each optical slice (a defined depth in the volume) was processed by a single multi-core computing node. Data was served to each node by a high-performance data server in RAID 1+0 configuration in a 10-Gigabit network.

Any pixels in the image that were collected during optogenetic stimulation were replaced with "not a number" (NaN), and omitted from all subsequent analyses. Images from a single imaging plane in the volume were aligned to a reference image by determining the highest cross-correlation coefficient between each image and the reference image in a 20-pixel shift-window in X and Y. For the reference visual-only experiment, the reference image was defined as the average image of frames 10-50 from the imaging session. For each subsequent imaging session, the cross-correlation alignment procedure was repeated in the following order. First, the reference image was defined as the average of all images from the aligned, already motion-corrected visual-only experiment. The cross-correlation algorithm was applied to determine the optimal shifts to align Kalman filtered (gain=0.5, noise=0.05) imaging data from the current session to the reference experiment. These shifts were applied to the raw (non-Kalman filtered) data. A new reference image was defined as the mean image across the current, aligned dataset, and used to perform a final cross-correlation based motion correction for the current dataset. In this way, each session's dataset was aligned to the reference experiment using temporally-smoothed data, and further fast-motion corrected using its own reference.

Aligned imaging data from the reference visual-only experiment were input into the constrained nonnegative matrix factorization (CNMF) algorithm. The spatial components estimated by CNMF were alone used to define a single set of cell masks across experimental sessions. Time courses for each cell were defined by averaging pixels within each cell mask for each image frame. Cell time course data were organized by trial, and baseline-normalized (to compute ∆F/F) by the following formula: $(R_i - F)/F$, where $R_i$ is the cell's fluorescence at each time point i, and F is the cell's mean fluorescence during the three frames before a visual or optogenetic stimulus for each trial. The rigid alignment algorithm described above (well-suited for the high-speed imaging data, with minimal warping in each 33 ms frame), and alignment of the imaging volume to the reference experiment during each session (maintained in real-time using online cross-correlation software during image acquisition, see above), allowed us to use the same cell masks across sessions in order to conserve cell identity.

Tuned ensembles were defined as neurons (any mask segments resembling dendrites were removed by visual inspection) which responded robustly and reliably (at least 3 of 8 time points>0.3 ∆F/F, and p<0.05 t-test stimulation epoch versus baseline) to either the 0° or 90° 50% contrast visual stimulus, with an orientation selectivity index (OSI) greater than 0.5. OSI was defined by the following formula: $(R_{pref} - R_{orth})/(R_{pref} + R_{orth})$, where $R_{pref}$ is the response during the visual stimulus to the preferred orientation, and $R_{orth}$ is the response to the orthogonal orientation. For these analyses of the reference visual experiment (but not subsequent analyses), cell time courses were Kalman filtered (gain=0.5, noise=0.05) before computing ∆F/F. Tuned ensemble sizes were 0°: 32, 26, 27, 37 and 90°: 19, 40, 33, 26 for each mouse in the naïve cohort, respectively (Naïve Mouse 1-4). Tuned ensembles sizes were 0°: 55, 42, 33, 53, 33 and 90°: 38, 37, 28, 46, 42 for each mouse in the behavioral cohort, respectively (Trained Mouse 1-5). Random ensembles were randomly selected from the remaining population across the volume to match the number of neurons in the respective tuned ensembles. For stimulation of sub-ensembles in each cortical layer, either all of the neurons from the tuned ensemble from an anatomically-defined layer were used, or a randomly selected subset of those neurons was used, where the number of neurons was defined for each subset tested.

Statistical analysis of co-activity: Stimulated neurons and any neuron masks containing pixels within a 20.85 μm (15 pixels) radius, including any neurons above or below stimulated neurons within a cylinder with the same radius, were excluded from all analyses of co-activity. On each day, high contrast visual trials (50% contrast; no optogenetic stimulation) were used to find reliable (significant two-tailed Wilcoxon signed-rank test, MATLAB function, frames 5 and 6 versus baseline frames 2 and 3), orientation selective (OSI>0.5, calculated as above) neurons. Importantly, frames 5 and 6 occurred during the "Sample Window", that is during the visual or optogenetic stimulus but before any water reward or air puff was delivered. These reliable, orientation-selective neurons, which were distinct from the original tuned ensembles as described above, were used to define the tuned populations for network analyses. Neurons within these tuned populations that reliably increased fluorescence across trials of a specific optogenetic ensemble condition (significant two-tailed Wilcoxon signed-rank test, frames 5 and 6 versus frames 2 and 3) were deemed co-active. To define the fraction of co-active neurons for each condition, the number of co-active neurons was divided by the number of tuned neurons.

For scatter plots, each data point is the result from a single optogenetic ensemble stimulation condition from a single day. Relationships between the number of stimulated neurons and the fraction of co-active neurons were computed using the Spearman's correlation coefficient, with significance defined by a two-tailed test versus no correlation (built in MATLAB function). To statistically compare p values, a two-tailed Fisher's z transformation was performed.

For bar graphs, the number of co-active neurons and tuned neurons neurons were each summed across sessions for each mouse to define each mouse-identified data point plotted on the figure, and across mice for summary data. A two-tailed Pearson's chi square test was used to statistically compare frequencies of co-activity on pooled data across mice between conditions (SPSS). To account for the contribution of mouse identity, additional statistics are presented here using the Cochran-Mantel-Haenszel (CMH) test, in which data are stratified by mouse identity. The CMH tests yielded comparable results to the Pearson's chi squared test in all instances. A Breslow-Day test was run to test the assumption of homogeneity of the odds ratio for each CMH test. The Breslow-Day test rejected the null hypothesis that the odds ratio was equal across mice for the following statistical tests, implying that an interaction may have existed between mouse identity and observed co-activity counts. These included Tuned After Contrast Ramp (FIG. 13L), Random After Contrast Ramp (FIG. 13M), Tuned vs. Random Before Contrast Ramp (FIG. 11N), Tuned vs. Random After Contrast Ramp (FIG. 13N), Iso vs. Ortho (FIG. 14E), Layer 2/3 vs Layer 5 Iso Tuned (FIG. 15C), Layer 2/3 Iso vs. Ortho (FIG. 28A), and Layer 5 Iso vs. Ortho (FIG. 28A). Pearson's chi square tests were run independently for each mouse for each of these instances and were found to be significant to at least p<0.05 for 4/5, 4/5, 4/5, 3/5, 5/5, 3/4, 5/5, and 5/5 mice, with effect directions always matching the pooled data, for each of these comparisons respectively. Layer 2/3 vs. Layer 5 Iso Tuned (FIG. 28A) had 4/5 mice with significant Pearson's chi square tests (p<0.001) going in the direction of increased layer 5 recruitment vs. layer 2/3, and Mouse 3 had greater layer 2/3 recruitment than layer 5 (p=0.046).

Statistical analysis of neuronal dynamics: All classifier and neural decoding analyses were performed in Python 3.6 and used open source libraries listed below. This analysis is presented in parts of FIGS. 12, 14-15 and FIGS. 23-28.

Neural decoding analysis using sparse logistic regression: In order to select cells to include in our neural decoding analysis for a given mouse, we first identified all neurons that were ever optogenetically stimulated on any experimental day or condition. Then we defined a column of exclusion with an approximately 20.85 μm (15 pixel) radius around each of these stimulated neurons to conservatively identify any neuron that might have been erroneously stimulated during our experiments. Other neurons whose fluorescence signals were contaminated by stimulation artifacts were also removed during this process (see above). This neuron selection procedure differs slightly from the one used for the statistical analysis of co-activity (see previous methods section) in that all neurons that were ever stimulated in a mouse (plus surrounding neurons) were excluded on all days to facilitate training regression models that generalize between experiments where different ensembles were optogenetically stimulated.

Our regression models were trained only on experimental trials where mice watched a visual stimulus and no neurons were optogenetically stimulated. Specifically, for each experimental day, we found each condition where a visual stimulus was presented (at any contrast between 12-50%). Then from each one of these trials, we computed the average fluorescence of each neuron across two fluorescence frames after stimulus onset (frames 5 and 6 of 19 total imaging frames/trial; the same frames used for co-activity analyses above). These two frames were specifically chosen to eliminate the frame where fluorescence was rising at the onset of the visual stimulus (frame 4) and to also eliminate the later frames during the stimulus where either a water reward or punishing air puff could have been delivered. This process yielded a vector of length equal to the number of unstimulated neurons in each dataset, for each trial. We concatenated each of these vectors into a matrix of size equal to the number of trials by the number of unstimulated neurons. Importantly, only this visual-stimulus-only data was ever used to train our regression models. The same models were then used to predict condition type (target vs. distractor) on all other kinds of data (i.e. during optogenetic stimulation of different types). This procedure was identically followed in both the behavioral cohort of mice (where reward and airpuff stimuli were present) and the naïve cohort of mice (where neither stimulus existed).

We then took this data matrix and another vector containing the true stimulus type (target, 0° or distractor, 90°) and used them to fit a set of sparse logistic regression models. This procedure was repeated independently for each mouse. To perform the regression model fitting, we used a class in Python's scikit-learn package named LogisticRegression with the penalty argument set to 'L1.' Each of the five models was trained on a distinct random fifth of all of the trials presented (five-fold cross validation). Classifier weights and predictions reported are means across all five of the regression models trained for each mouse. Finally, we found that across all n=5 behavioral mice (FIG. 23) and n=4 behaviorally naïve mice (FIG. 25), setting the sparseness parameter (1/λ) equal to 0.5 approximately minimized the training error in each case. Models generating all results reported had 1/λset to this value.

Across n=4 behaviorally naïve mice (and 2 tuned+2 random ensembles for each mouse; 60 stimulation trials from each neuron were used in this analysis), we tested that the effective size of the tuned and random optogenetically-stimulated ensembles was comparable. This was computed by using a Wilcoxon signed-rank test to compare the average fluorescence in the baseline period (frames 1 and 2) to the average fluorescence after optogenetic stimulus onset (frames 5 and 6) across all individual trials from each targeted neuron. The significantly recruited fraction of tuned ensembles ranged from 0.4-0.92. This fraction for random ensembles ranged from 0.37-0.74. A paired t-test revealed no significant difference between these two distributions, (p=0.48) (FIG. 23C).

This same analysis was also applied to n=3 behaviorally trained mice (40 stimulation trials/neuron were used for this analysis; there were 2 tuned and 2 random ensembles analyzed for each mouse). In contrast to the naïve mice, our conservative metric found that there was a significant difference in stimulation efficacy between the size-matched random and selective ensembles. The significantly recruited fraction for tuned ensembles ranged from 0.58-0.9. For random ensembles it ranged from 0.26-0.75. A paired t-test revealed a significant difference here, p<0.001.

Neural trajectory analysis using PCA: In a similar manner to the procedure described above for our decoding analysis, we used Principal Components Analysis (PCA; scikit-learn class PCA) to visualize the average population response of all trials of an identical experimental condition, on a given experimental day. Principal components were identified using a data matrix composed of the mean fluorescence responses across all neurons to both the target, 0° and distractor, 90° visual stimuli (contrast ranged from 12 to 50%; in the absence of any optogenetic stimulation). Since each trial was 19 frames long, this yields a training matrix of size: (19×2)×number of neurons. The first two principal components estimated from this data matrix were used to plot all neural trajectories for an individual mouse in all experimental conditions.

A similar analysis using Partial Least Squares Regression (scikit-learn function PLS Regression) was performed with the identical data matrices, but also with ground truth visual stimulus information (target, 0° vs. distractor, 90°). This approach yielded nearly identical results to PCA—despite the fact that the latent dimensions were explicitly derived to separate target from distractor conditions, rather than to simply maximize variance explained (FIG. 27).

Psychometric curve fitting: To assess the relationship between either neural or behavioral performance and the size of an optogenetically stimulated ensemble, we used an open-source package called Psignifit-python to fit logistic psychometric curves of the following form:

$$\psi(x) = \gamma + (1 + \lambda - \gamma) S(x; m, w)$$

$$S(x; m, w) = \frac{1}{1 + e^{-2\log\left(\frac{1}{0.05} - 1\right)\frac{x-m}{w}}}$$

We fitted three parameters of the curve: the threshold m, width w, and the lapse rate λ. The lower asymptote parameter, y, was fixed to 50%. Psychometric curves fit in this manner are presented as a visual aid for interpreting the data and were statistically analyzed as described in the text.

Results

Marine Organism-Based Genomic Screen for New Classes of Microbial Opsin

We sought to screen for new excitatory opsins that would jointly exhibit the required properties (all-optical capability, large photocurrents, high light-sensitivity, and robust performance over multiple stimuli) via genomic sequencing of ocean-sourced organisms. Recent structural understanding of ChRs has enabled exploration of a much broader range of sequences than was previously feasible, guided by definitive knowledge that ion conductance is dependent upon certain residues in particular transmembrane (TM) helices (for example, cation-conducting ChRs (CCRs) use carboxylate moieties of TM2), and that ion selectivity depends upon overall surface electrostatic potential in the pore and vestibules of the channel. We used this knowledge to screen ~1000 suitable CCR-like sequences from transcriptome databases spanning >600 marine microbial organisms (FIG. 10A), optimized the sequences for mammalian expression, and performed whole-cell patch clamp in cultured hippocampal neurons (collecting light-evoked action spectra over 390-650 nm, alongside comparisons to CsChrimson and bReaChES). From this screen, we discovered a marine opsin gene (named here ChRmine to reflect both its deep red or carmine responsiveness, and its unique identification by ChR crystal structure-based mining) from *Tiarina fusus*, a ciliate phylogenetically distinct from green algae that have provided most known natural CCRs.

The new gene exhibited little similarity to previously known CCR genes (in fact showing more similarity to anion-conducting ChR (ACR) and proton-pumping proteorhodopsin (PR) genes; FIG. 10B and FIG. 16) but expression in cultured neurons surprisingly gave rise to inward (excitatory) photocurrents driven by red-shifted light (4.1±0.53 nA at 585 nm) that were much stronger than for CsChrimson (0.9±0.05 nA) or bReaChES (1.9±0.36 nA; nanoamp-scale currents were observed even at 650 nm; FIG. 10C). The reversal potential of −5.64±1.39 mV (FIG. 10D) revealed robust $Na^+/K^+$ permeability ideal for driving spikes in neurons under typical physiological ion balance conditions, and recovery from desensitization in darkness (crucial for stationarity of performance over multiple stimuli) was found to be an order of magnitude faster than for other red-shifted opsins (half-recovery time 0.63±0.08 s; FIG. 17A). Along with increased effective power density (EPD50, a measure of light sensitivity for opsin-expressing cells) for ChRmine (0.03±0.01 mW/mm², also many-fold improved compared with the other red-shifted opsins; FIG. 17B), these properties resulted in the capability of ChRmine to drive sustained spiking up to 40 Hz with red-shifted light (FIG. 17C). Finally, in another consequence of fast kinetics, large photocurrents, and high light sensitivity, ChRmine reliably induced spiking even with short red-shifted light pulses (100% spike success rate at 1 ms; FIG. 10E) and at low irradiance values (100% spike success rate at 0.08 mW/mm²; FIGS. 10F, 10G). These properties have not been seen, even in isolation, in other fast red-shifted CCRs; appearing all together in a single opsin, these ChRmine data supported further testing.

Simultaneous Optogenetics and Imaging in Cultured Neurons

To test suitability for all-optical experiments, integrated wide-field one-photon stimulation and imaging was implemented with ChRmine and GCaMP6m in cultured neurons. Consistent with ChRmine photocurrent magnitude, we observed much larger orange light-evoked GCaMP6m fluorescence signals in ChRmine-expressing neurons compared with other ChR-expressing cells at the same light-exposure duration (FIGS. 10H, 10I); moreover, as expected from its large fast photocurrents, ChRmine evoked faster rise and decay of evoked GCaMP6m signals at both orange (585 nm; FIGS. 10H, 10J) and red (635 nm; FIG. 17D) wavelengths. Noting the slower kinetics of CsChrimson-mediated $Ca^{2+}$ signals (FIGS. 10J, 17D) and considering prior biochemical studies suggesting unusual pH-dependence of Chrimson, we imaged opsin-mediated GECI signals at external pH 7.0, 7.2 and 7.4 to test pH dependency across red-shifted opsins. Consistent with prior work, CsChrimson use was associated with pH dependency of evoked $Ca^{2+}$ transients (slower rise-and-decay kinetics at pH 7.4 vs. 7.0), in contrast to ChRmine-evoked transients (FIG. 17E). Together, these remarkable properties of ChRmine as an excitatory opsin may be explained in part by an unusually strong predicted electronegative surface potential, as suggested by homology model-based comparison (FIG. 17F).

Since two-photon (2P) illumination is required for single-cell resolution in vivo, we next performed whole-cell recording during ChRmine recruitment via 2P spiral scanning over the soma. Mapping laser power from 0-30 mW (FIG. 10K) and illumination wavelengths from 800-1080 nm (FIG. 10L) revealed ChRmine photocurrents suitable in magnitude for 2P-driven spiking in all-optical experiments. Indeed, examining elicitation of spike trains with 2P photostimulation of ChRmine, we observed reliable performance in trains up to 30 Hz (FIGS. 10M, 10N). Since a key limitation in all-optical neural control using red-shifted ChRs is persistent blue-light-driven cellular excitation which may occur as a side effect during imaging, we characterized ChRmine responses to blue light. With one-photon illumination, spikes were not elicited by 470 nm light over a broad range of light powers that reliably drove spiking at 585 nm (up to 100 $\mu W/mm^2$; FIG. 10G); likewise, the 2P imaging laser (at 920 nm/80 MHz raster scanned at 90.8 ns/μm) over a broad range of powers from 0-60 mW, did not elicit spiking (FIGS. 10M, 10N), further suggesting suitability for all-optical 2P experiments. Finally, we observed a remarkable property of sub-millisecond spike jitter of 2P light-evoked spikes (0.99±0.26 ms; FIG. 10O). Together these properties supported use of ChRmine as a tool with potentially unprecedented power and precision for 2P single-cell all-optical experiments.

Kilohertz Control and Readout of 3D Ensembles Over $mm^2$ Domains of Neocortex In Vivo The precise temporal response and relatively low irradiance requirements to drive spiking with this high-potency opsin raised the prospect of control of unprecedented numbers of recruited neurons at kilohertz rates using safe illumination powers, potentially enabling new optical hardware designs that could elicit meaningful circuit dynamics and behavior by targeting large, arbitrarily-defined cellular ensembles at speeds consistent with fast neural circuit computations. For example, neocortical ensemble dynamics that are behaviorally potent may involve many cells that are sparsely and widely distributed, both transversely across cortical areas and axially across layers. To gain optical access across large volumes of cortex for single-cell photostimulation with kHz temporal resolution while simultaneously imaging local neural activity dynamics, we designed, fabricated, and optimized a high-pixel-density (1536×1536 pixels) spatial light modulator (SLM) optimized for high-fidelity NIR hologram generation at high-speed (Macro-SLM; ~85% diffraction efficiency in 2 ms at λ=1064 nm) which we paired with custom optical elements and precise temporal sequencing protocols to access large volumes of cortex for single-cell, ensemble-scale photostimulation while simultaneously imaging local neural activity dynamics. To further improve temporal resolution to the kHz regime, we incorporated multiple SLMs along the same photo-stimulation path for multiplexed ensemble stimulation (MultiSLM, FIGS. 11A and 18-21).

To test these new capabilities, mouse primary visual cortex (V1) was transduced with a single integrated ChRmine/GCaMP6m virus (AAV8-CaMKIIa-GCaMP6m-p2a-ChRmine-TS-Kv2.1-HA); this dual GECI/opsin construct achieved large-scale, homogeneous, highly reliable co-expression of reporter and actuator in cell bodies across layers 2/3 and 5, with very little expression in layer 4 (FIG. 11B). To leverage the exquisite temporal properties of ChRmine for high-fidelity timing of elicited spikes within individual neurons, we developed a 210 μs spiral photo-stimulation protocol, which along with our novel high-speed hologram generation technology (termed MultiSLM), allowed realization of kHz ensemble stimulation over 1 $mm^2$ of superficial layer 2/3 in V1, with comparable efficiency across the entire imaging field-of-view (FIGS. 11C, 11D, 18A and 18B). Sequential addressing of neuronal ensembles at 1 kHz resolution was readily feasible with high success rates (FIGS. 11E, 11F and 18-19) and without off-target modulation of neighboring neurons (FIGS. 11G, 18D-18H). This new high-performance SLM technology also allowed addressing of larger axial displacements with 3D holographic patterns; coupling this capability with 3D 2P imaging, all-optical physiology experiments were realized for tens to >100 individually-specified neurons across millimeter spatial scales across cortex and across cortical layers (layer 2/3 to layer 5; FIGS. 11C-11I; 18A, 18B, 18G and 18H).

Selective Visual Network Recruitment by Functional Ensemble Stimulation

Figure 12:
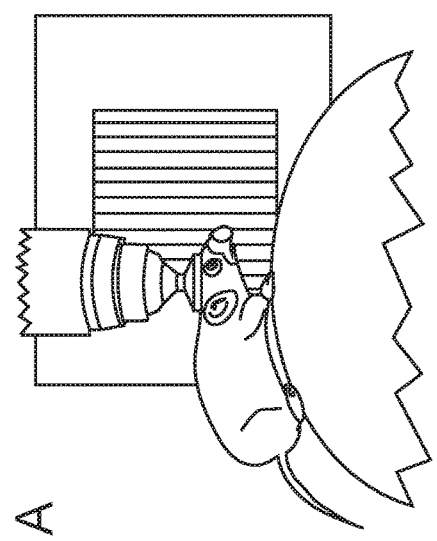
FIG. 12, A-K depicts selective visual network recruitment by functionally-defined-ensemble stimulation.
Figure 12:
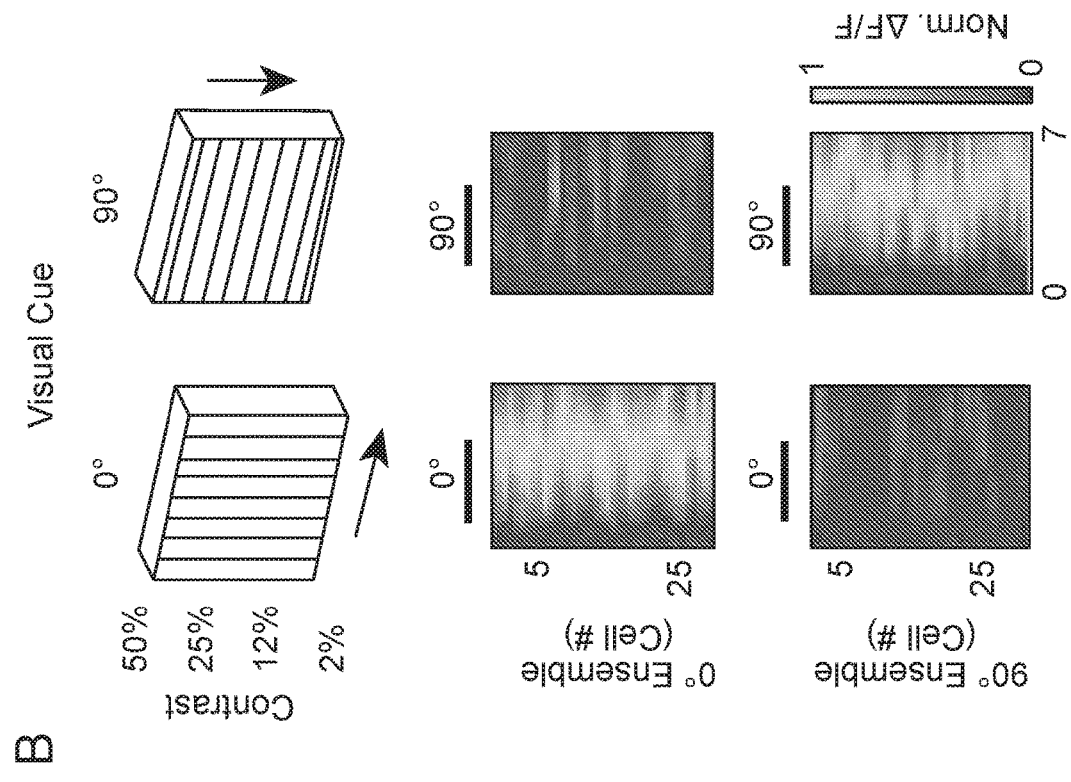
Figure 12:
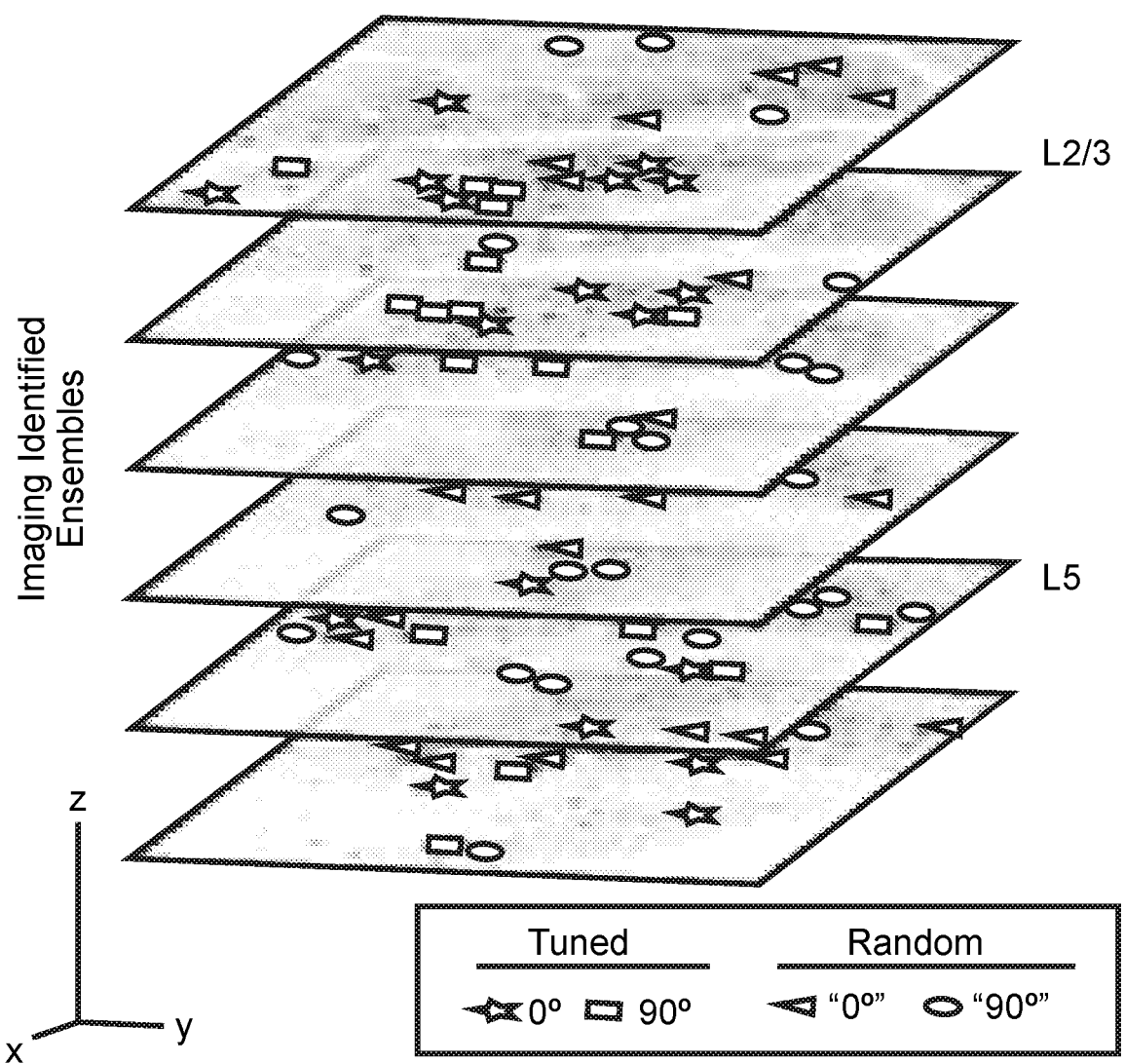
Figure 12:
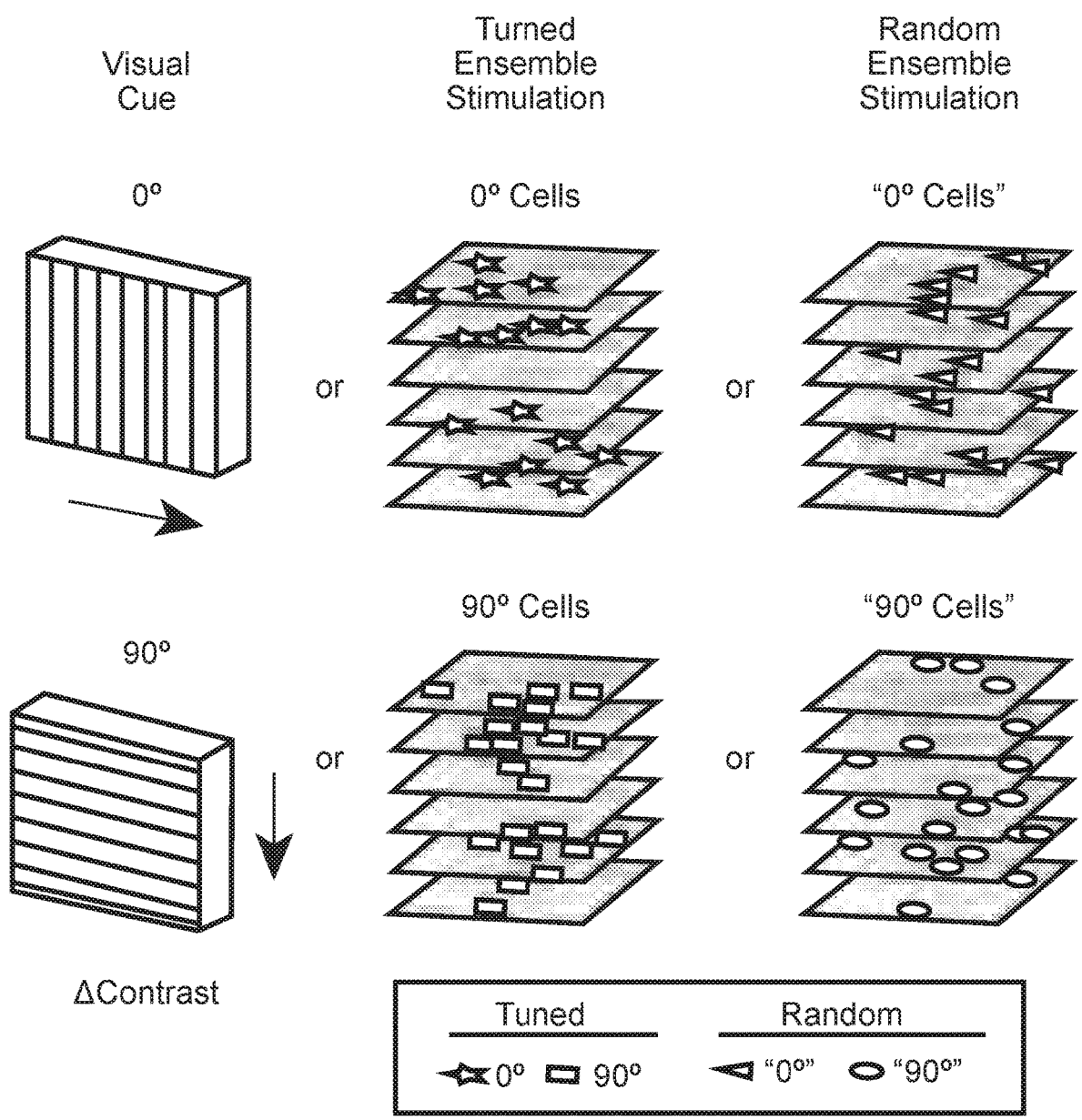
Figure 12:
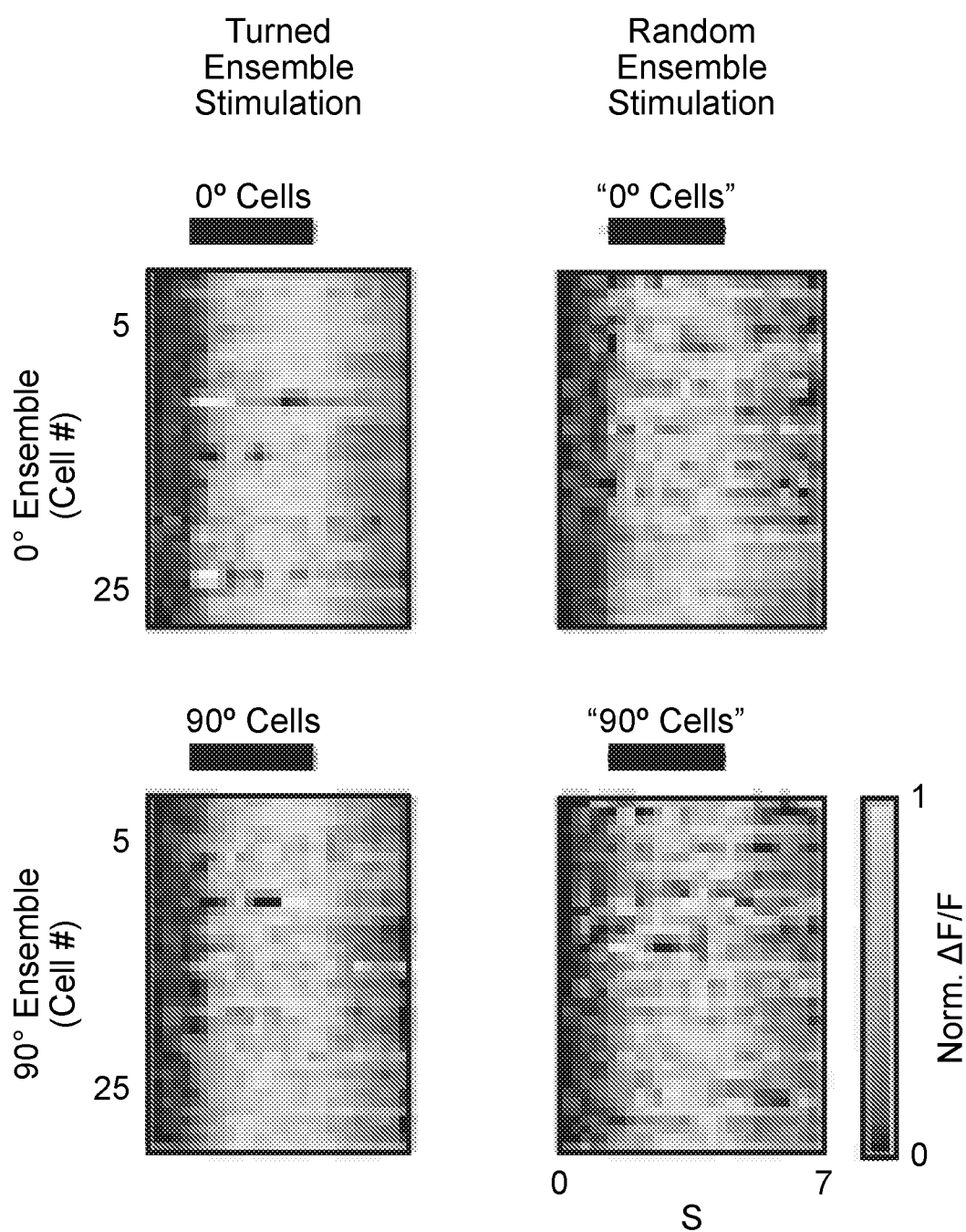
Figure 12:
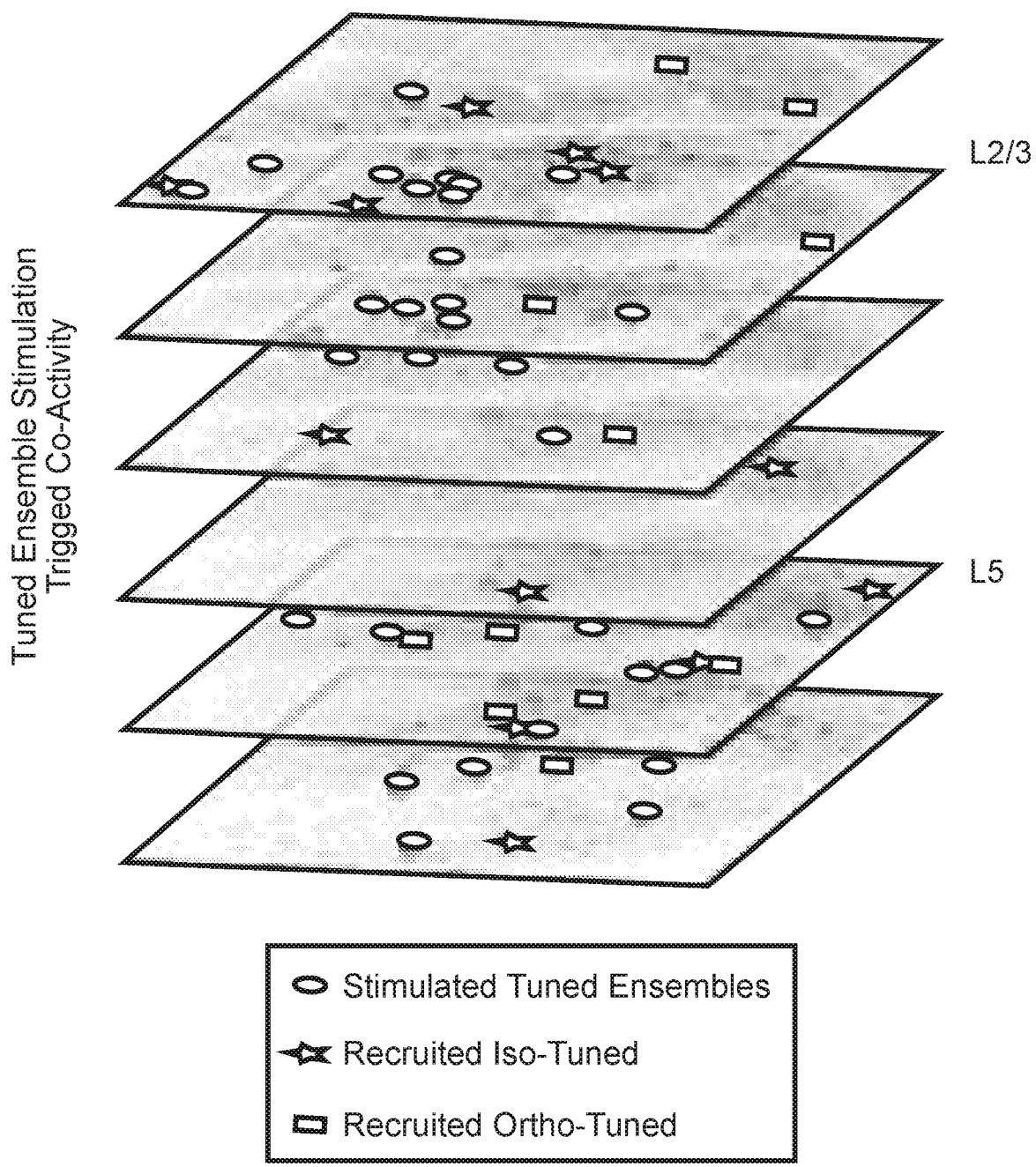
Figure 12:
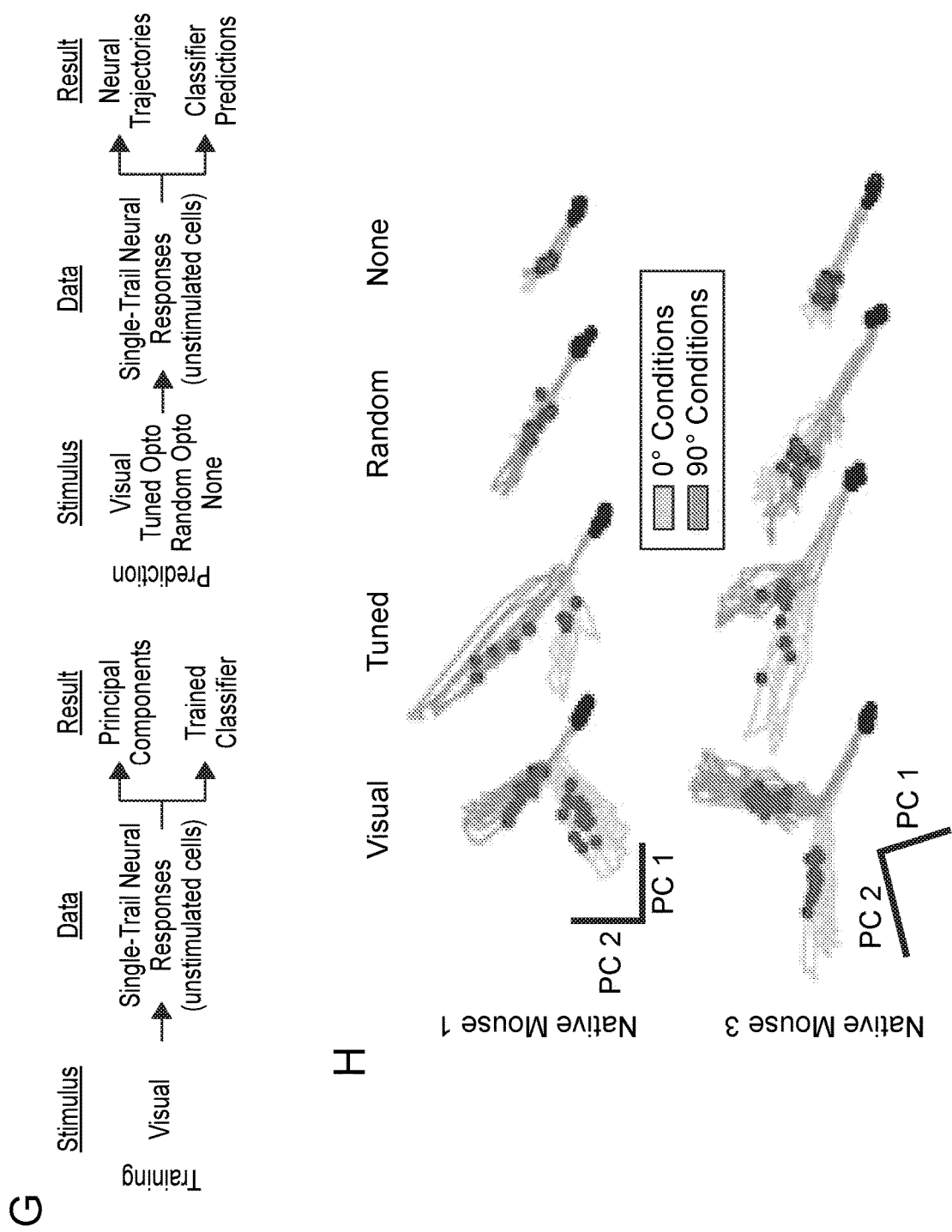
Figure 12:
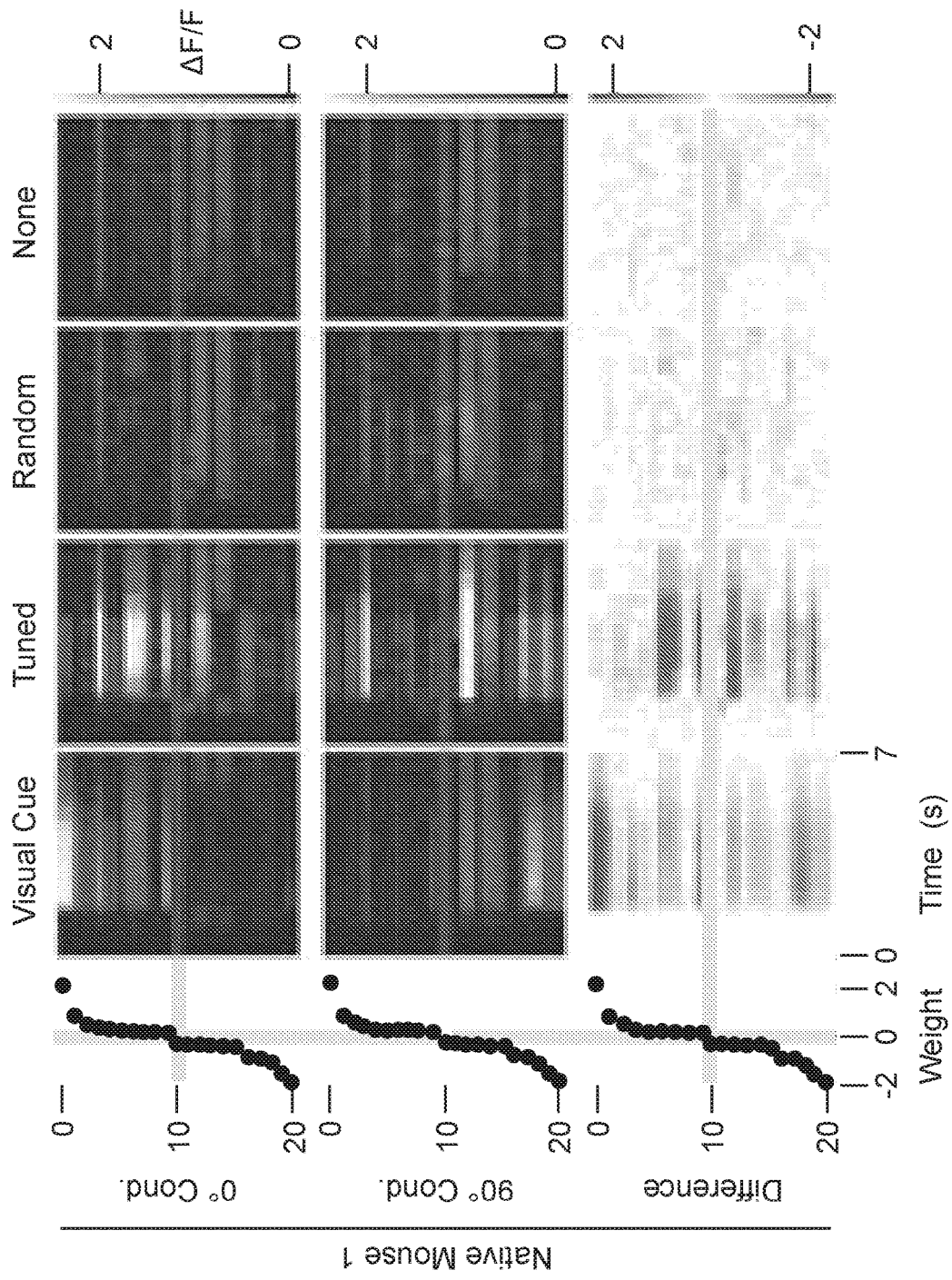
Figure 12:
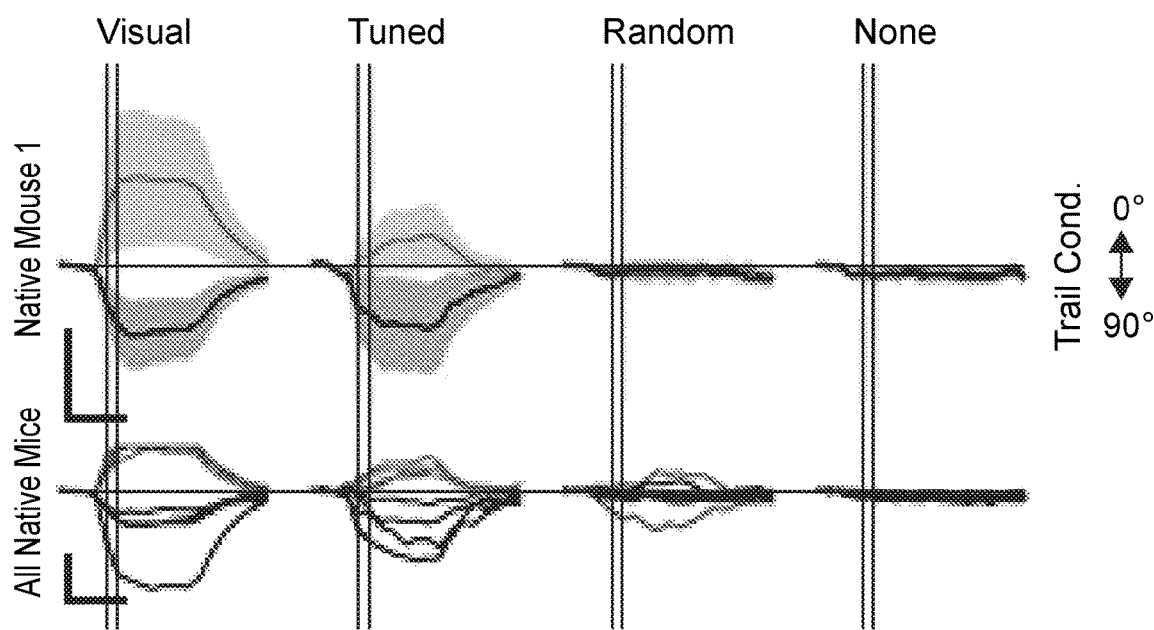
Figure 12:
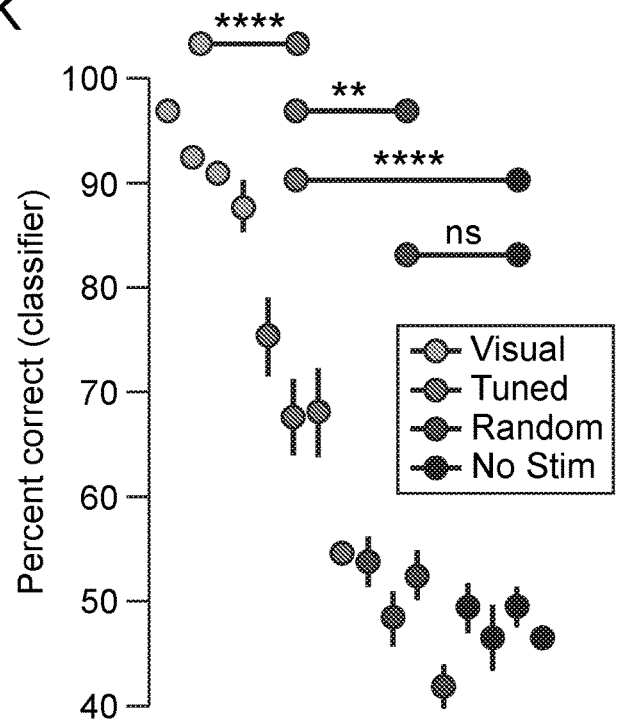
Figure 13:
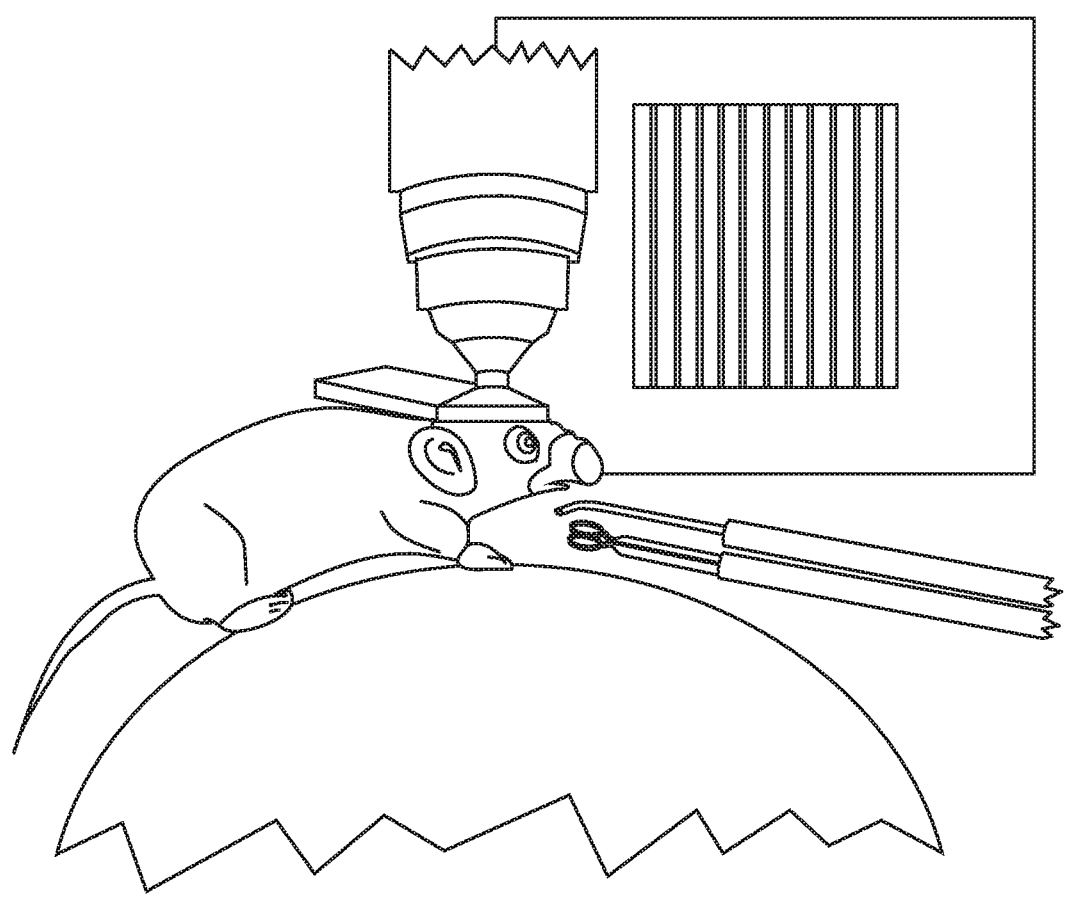
FIG. 13, A-N depict eliciting a specific visual percept through targeting individually-identified neurons.
Figure 13:
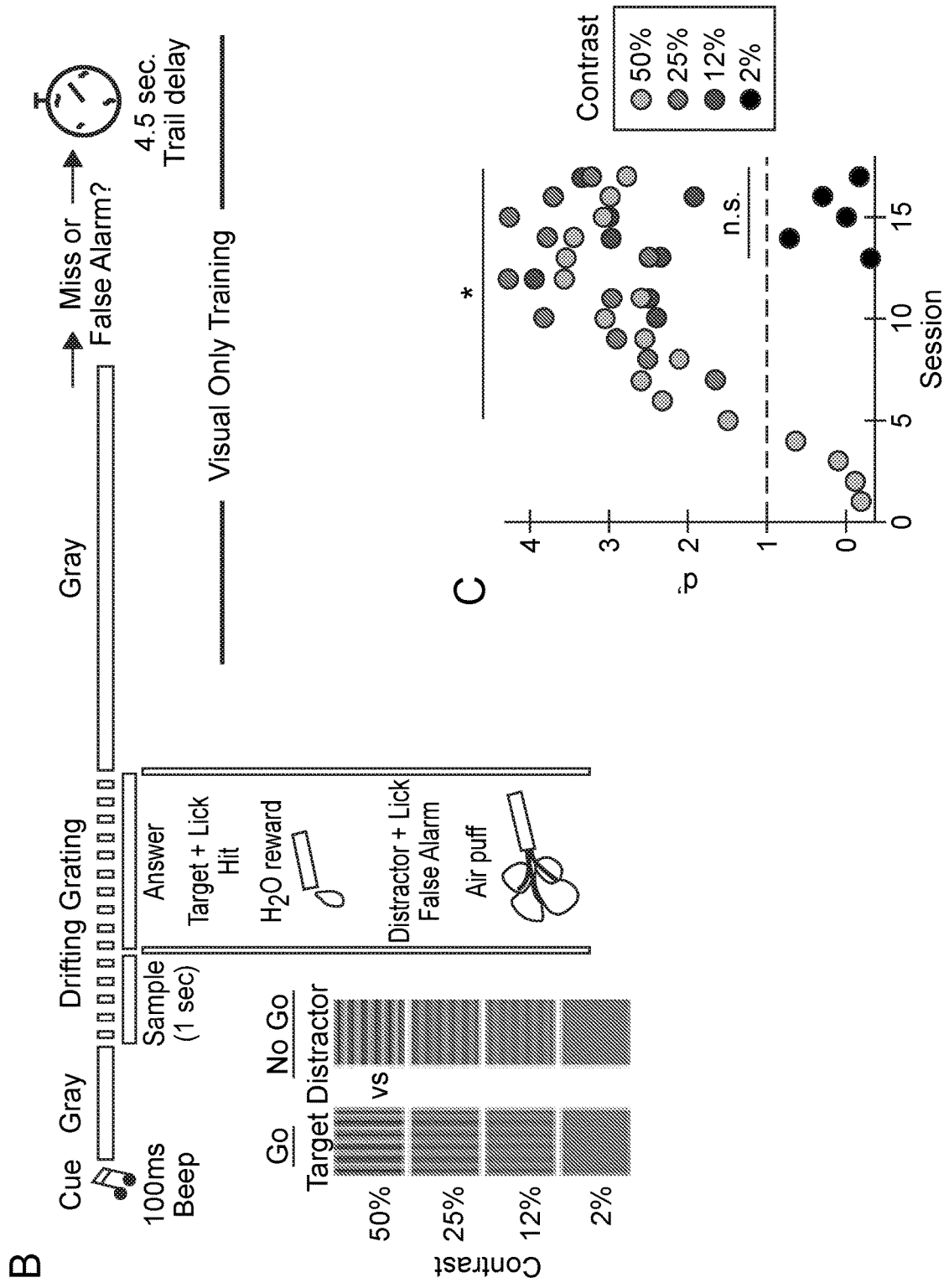
Figure 13:
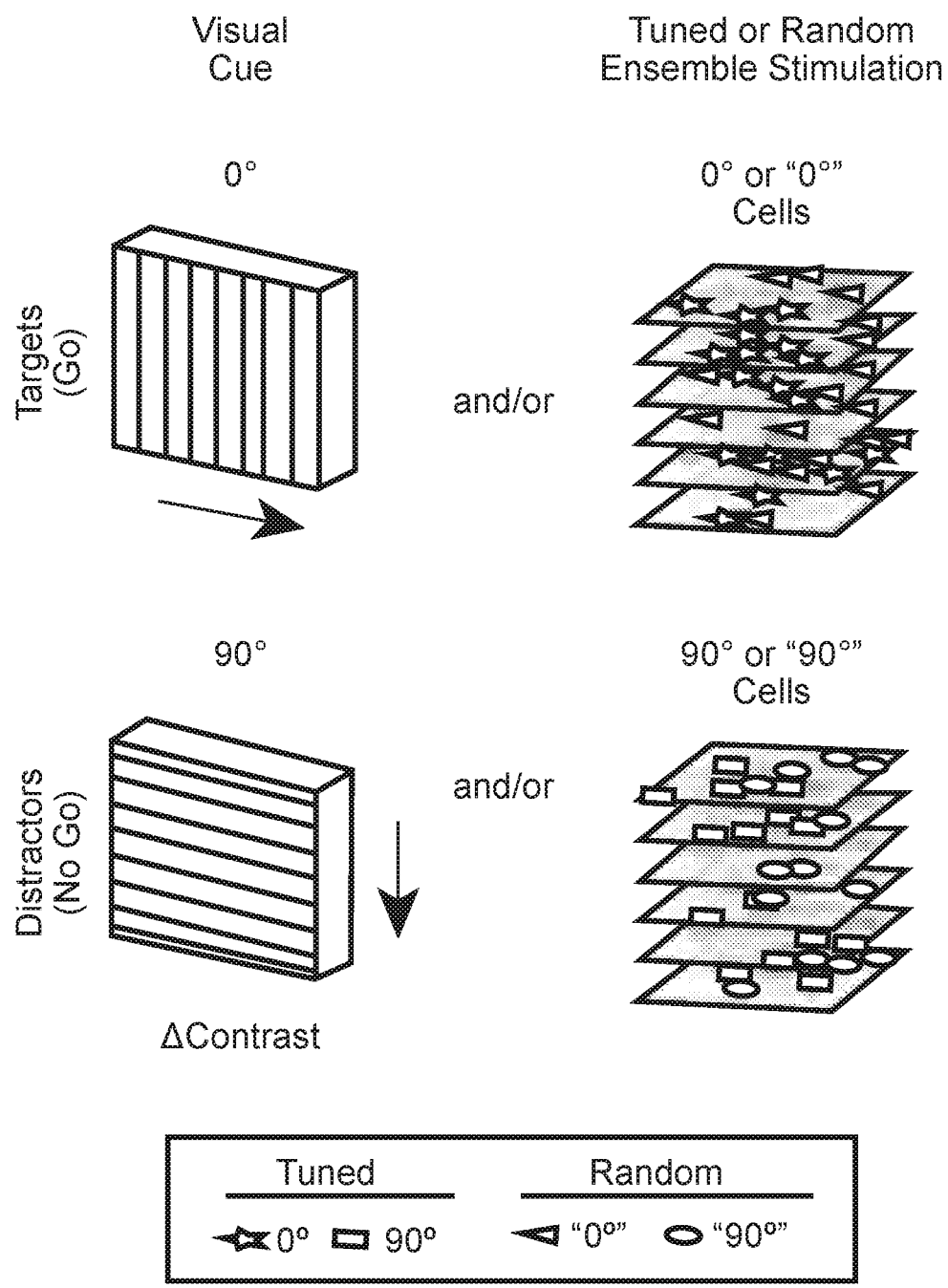
Figure 13:
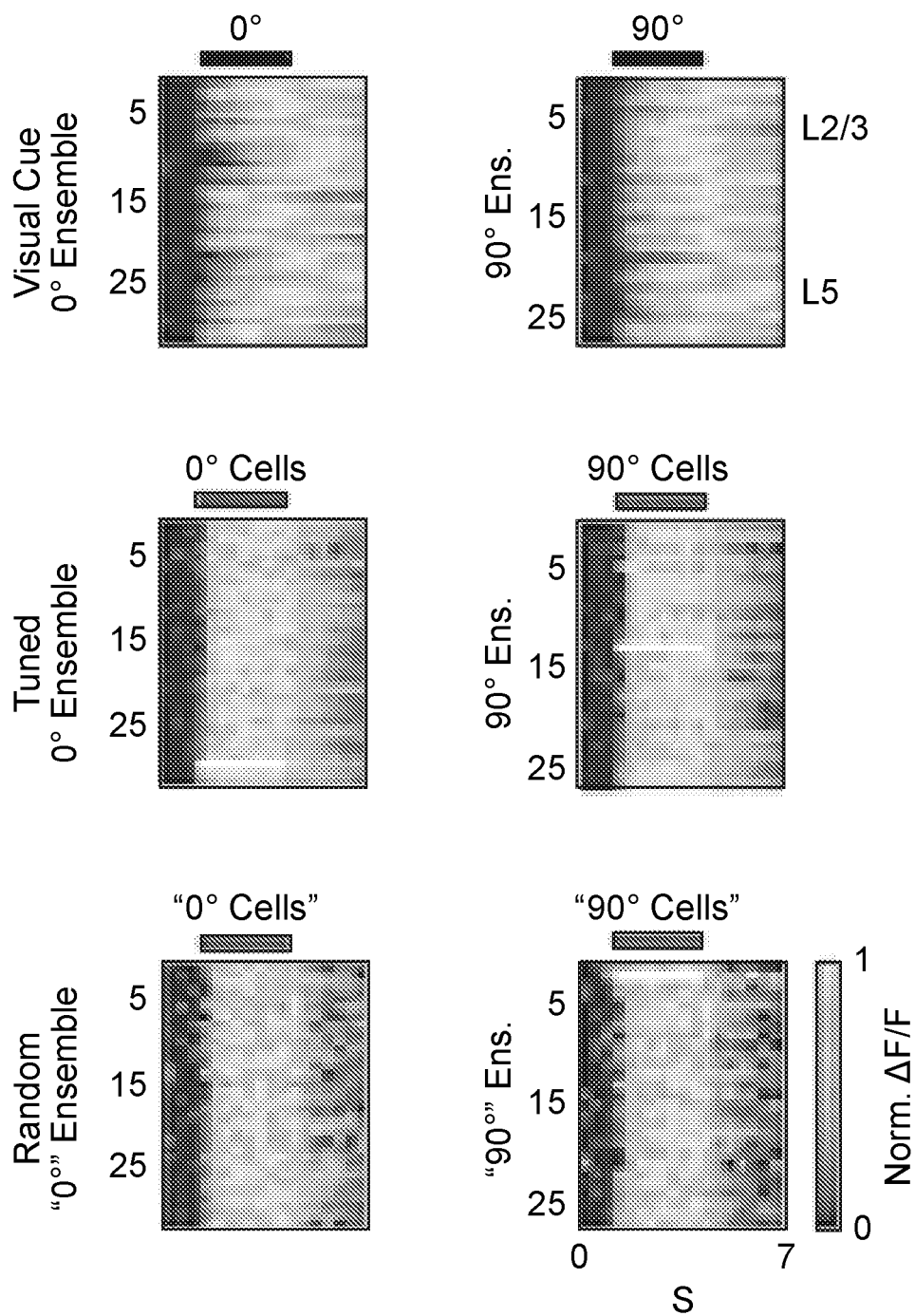
Figure 13:
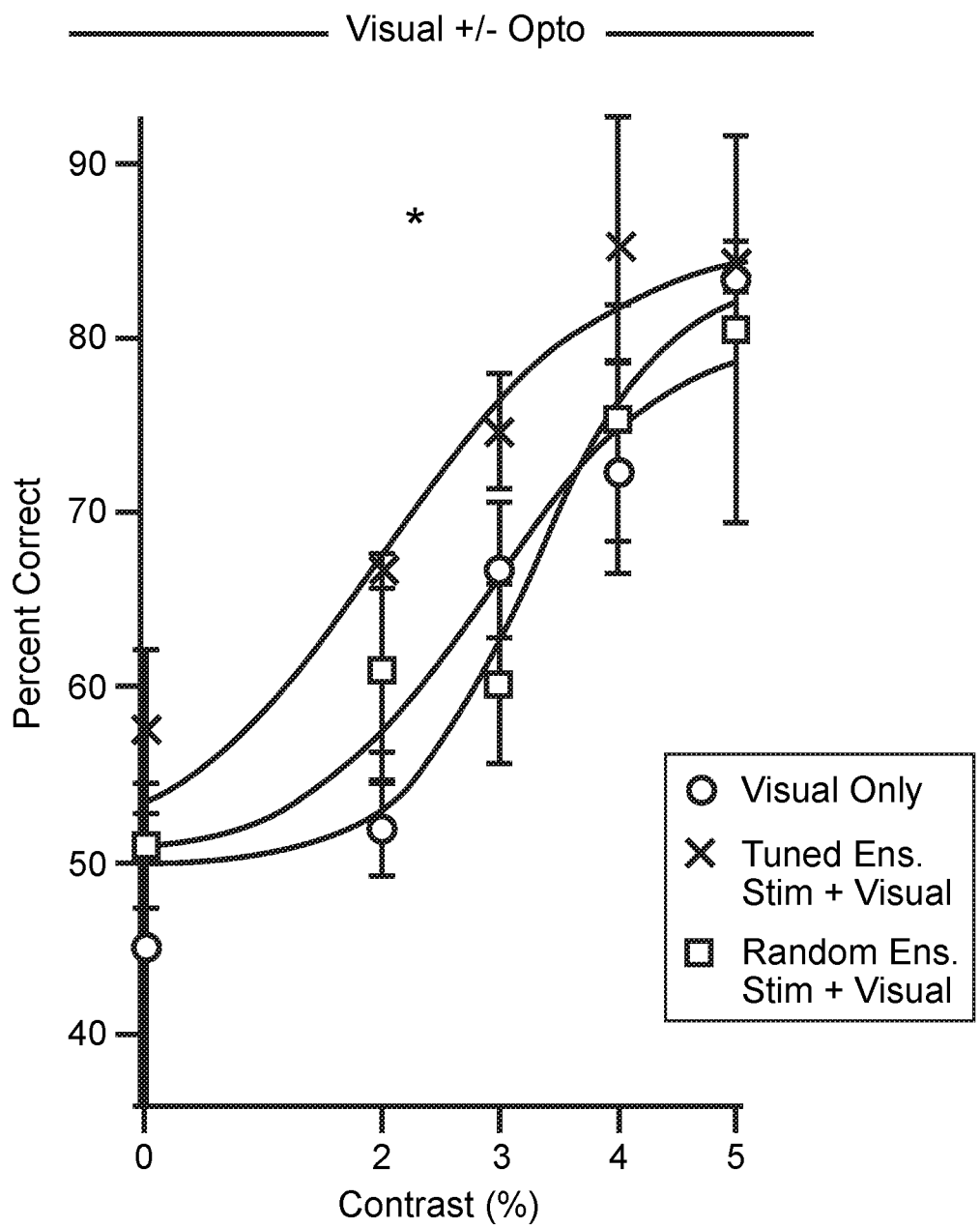
Figure 13:
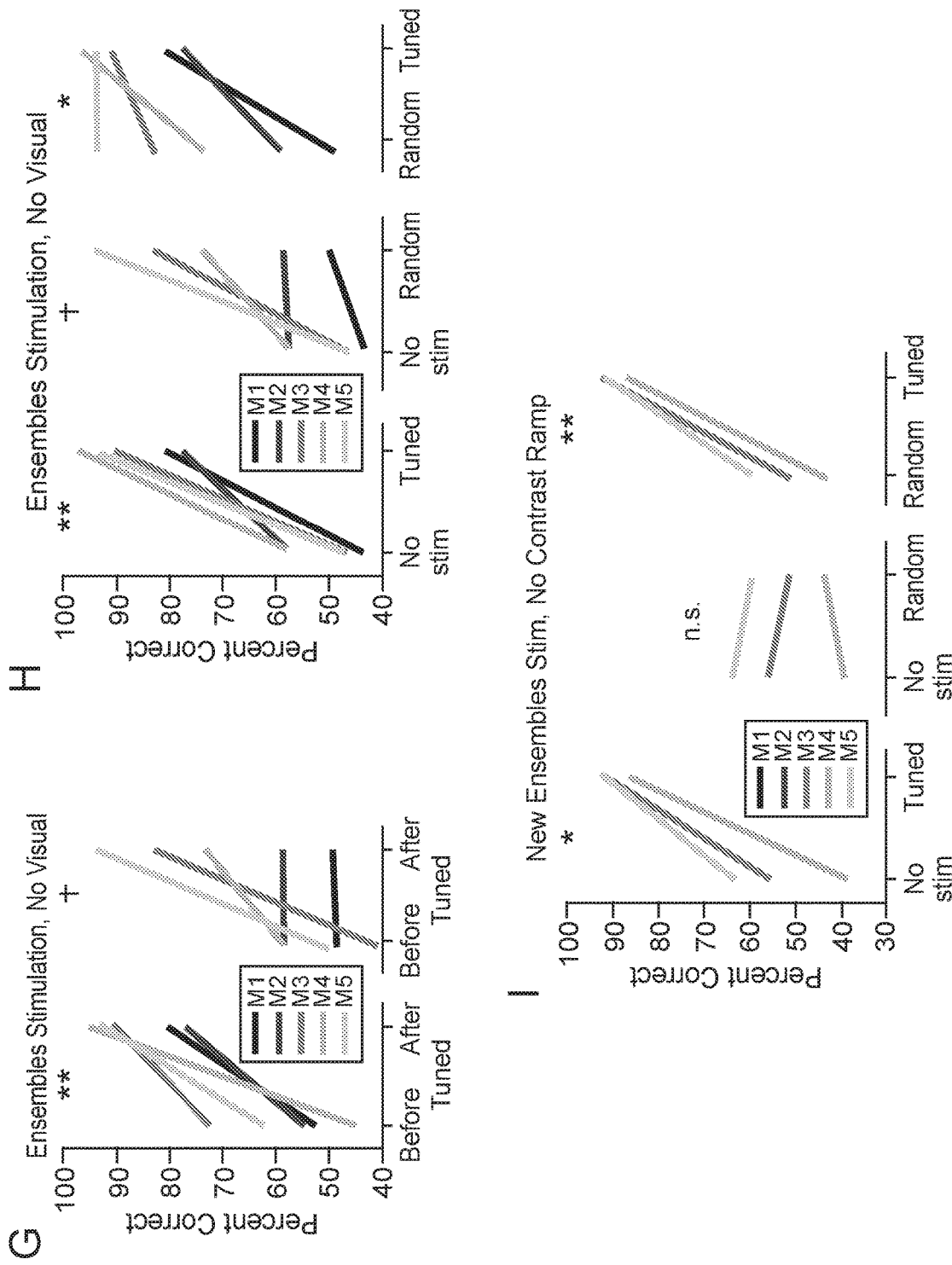
Figure 13:
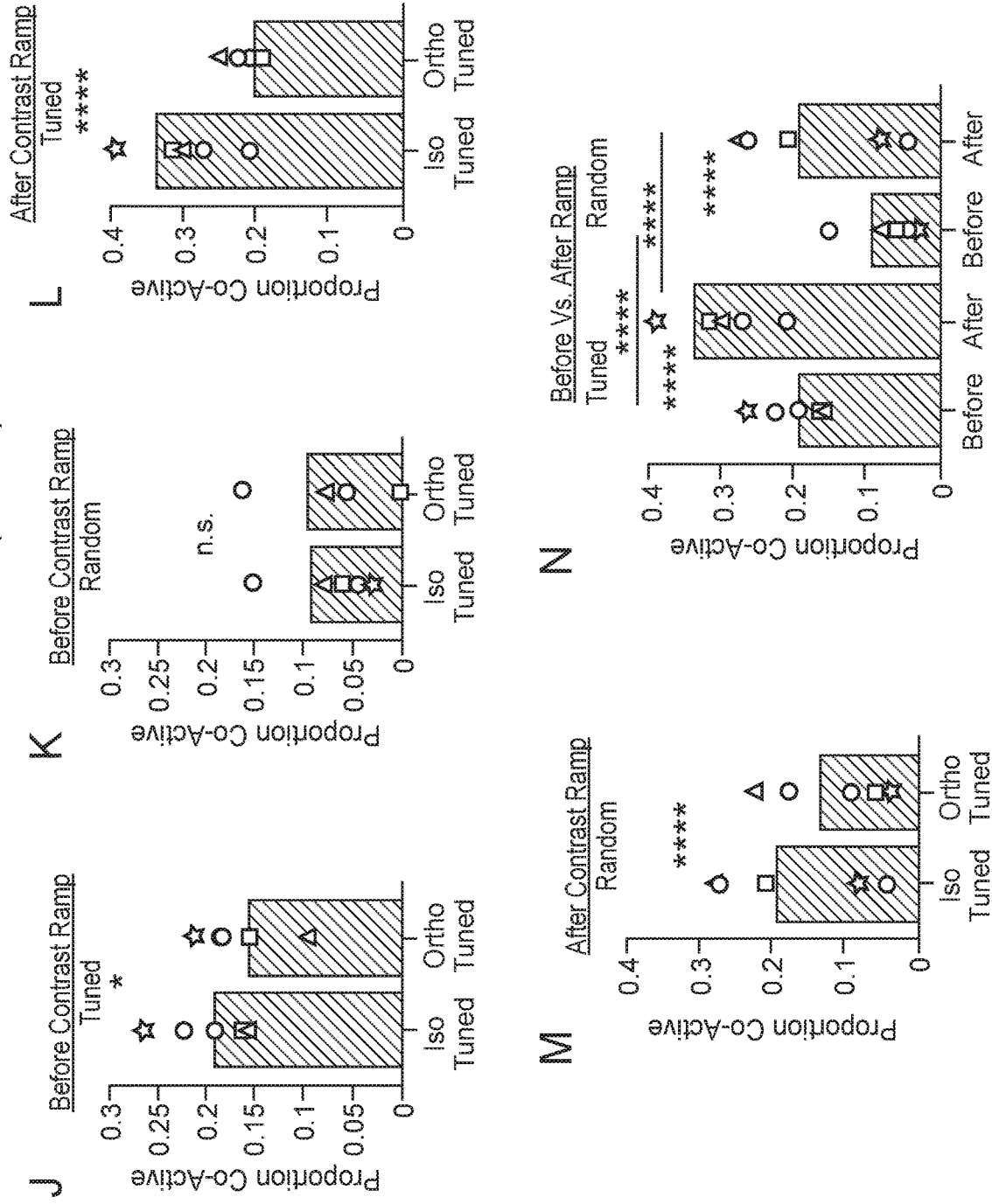

To explore how specific individually-defined cell ensembles in V1 may elicit specific local circuit dynamics, we initiated a series of experiments based on cellular-resolution stimulation of visually-tuned ensembles in V1 while recording from the surrounding neural population across layers 2/3 and 5 of cortex (FIGS. 12-13). Mice were head-fixed in the MultiSLM and free to run on a floating ball (FIGS. 12A and 13A). In the first cohort (n=4 mice), there was no task-specific training before visual stimulus presentation, in vivo imaging and optogenetic stimulation (FIG. 12). In the second cohort (FIG. 13, n=5 mice), mice were first trained to discriminate visual stimuli before moving to imaging and optogenetics during perceptually-driven behavior; these two classes of cohort allow distinguishing whether similar or different patterns result from additional modulation related to training/plasticity or behavioral state (e.g., goal-directed attentional or top-down influences). Trained mice also crucially enabled testing whether specific visual network recruitment patterns could suffice to drive or behaviorally favor specific perceptual experiences or decisions, and to quantify the effect of individual neurons in specific layers on perceptual phenomena.

Mice transduced in V1 with AAV8-CaMKIIa-GCaMP6m-p2a-ChRmine-TS-Kv2.1-HA viewed drifting sine wave gratings while $Ca^{2+}$ signals were recorded across layers 2/3 and 5 with the MultiSLM (FIG. 12A-12C). Gratings were vertical) (0° or horizontal (90°) (FIG. 12B) and were presented in one of several contrasts on each trial (2, 12, 25, 50%). In this first cohort, each trial began with a 5 kHz tone and followed the same basic structure as for visually-trained mice discussed below except there was no training, i.e. no reward/punishment. In each mouse, orientation-tuned ensembles were identified, comprised of dozens of neurons across layers with orientation selectivity index (OSI)>0.5 (FIGS. 12B and 12C; 0°: mean=30.5 cells, range=[26 37]; 90°: mean=29.5 cells, range=[19 40]). Two additional ensembles were defined to match the number of cells in each orientation-tuned ensemble, but with member neurons selected at random from the surrounding population (FIG. 12C). The same neurons could be recorded and stimulated across sessions due to micron-scale precise alignment at each placement of the mouse in the MultiSLM (FIG. 22).

On randomly interleaved trials (FIG. 12D), sine-wave gratings were presented to the animal, or one of the cellular ensembles was stimulated (tuned or random ensembles, with comparable efficacy; FIG. 23C). Ensemble optogenetic stimulation was observed to drive robust time-locked responses in the targeted neurons in the absence of visual stimulation, emulating activity observed in the naturally-occurring (visual stimulus-evoked) ensembles (FIG. 12E); also observed was co-activation of non-stimulated neurons in the surrounding volume that were more likely to be similarly- than orthogonally-tuned to the targeted ensemble (FIGS. 12F and 25A, left, p=0.025; data from n=20 sessions in n=4 mice). This preferential recruitment of iso-tuned neurons in the surrounding population, even in the absence of visual stimulation, provided an initial indication that cortically-initiated activity in V1 cells defined by natural, visually-evoked activity recruits percept-specific downstream ensembles.

To further examine the potential encoding properties and computational significance of this pattern recruited in the surrounding network, we developed a neural decoding approach involving both principal components analysis (PCA) and binary classification (schematized in FIG. 12G). From each experimental animal, we first identified a subset of held-out neurons, termed "unstimulated neurons," that had never been optogenetically stimulated under any experimental circumstances—and also were not within spatial proximity to any stimulated neuron (achieved by defining a cylindrical exclusion area around each optogenetic target neuron with 20 μm lateral radius and infinite axial extent; this exclusion protocol also applied for FIGS. 12F, 25A). This conservative approach excluded most neurons from further population analysis (1885±232 [mean±SD] neurons, or 46±4% of all neurons in each dataset, from n=4 mice; FIG. 23A) but crucially addressed the risk of neurons directly stimulated only by virtue of proximity to optogenetic targets becoming erroneously assigned as part of a downstream secondarily-recruited ensemble. We next examined the single-trial fluorescence responses of all remaining unstimulated neurons in response to each visual stimulus. These visually-evoked population responses were used to identify principal component vectors for projecting population activity—not only for data collected during presentation of visual stimuli, but also for data collected during optogenetic stimulation. We then used these single-trial visual responses, leveraging the fact that each trial occurred during either the 0° or 90° stimulus, to train binary classifiers to predict visual stimulus type from the held-out unstimulated neuron responses (via sparse logistic regression). These classifiers were trained only on visually-evoked responses and were used to predict stimulus type for all experimental conditions (i.e. during visual, optogenetic, or no stimulation).

The PCA results can be seen in FIG. 12H for two representative mice (analyzed independently; top and bottom row). Each single line in this panel represents the average 19-frame (6.92 s) trajectory traversed by the unstimulated neuron population during 0° (blue) and 90° (red) trial conditions on each experimental day. At the first frame following stimulus onset (denoted by bold red or blue dots), trajectories clearly had begun to diverge as a function of visual stimulus type (left column). Interestingly, neural trajectories were similar between visual stimulus and tuned optogenetic ensemble stimulation conditions for both 0° (blue) and 90° (red) trial types (compare the first two columns). In contrast, there was no apparent segregation of neural trajectories arising from random stimulation (of cells that were not selective for either the 0° or 90° visual stimulus; third column), nor in the absence of any sort of stimulation (fourth column). This segregation of trajectories among held-out unstimulated-cell ensembles in different stimulus conditions was reproducible within individual mice and across mice: the top two principal components shown explained the majority of the variance seen in the visually-evoked data (FIG. 23B; top two components explain 76.21±2.09% and top four explain 89.96±0.46%).

The population activity of unstimulated neurons thus encodes the stimulus similarly during tuned optogenetic stimulation and visual stimulation, but not random optogenetic stimulation. This finding was developed in more quantitative detail with the use of binary classifiers. After training on the visual stimulation data alone, the classifiers were able to find a sparse set of weights on the unstimulated neurons that cleanly separated the two visual conditions (grating orientations) (FIGS. 23D-23K). By subtracting the trial-averaged fluorescence responses of these neurons seen during the 0° visual conditions, from responses of these neurons seen during the 90° visual conditions, distinct groups of cells were resolved that exhibited differential recruitment during each visual stimulus (FIG. 12I, left column)—a pattern of neuron recruitment that was also largely reproduced with tuned optogenetic stimulation (FIG. 12I, second column) but seen neither with random stimulation nor unstimulated activity (FIG. 12I, third and fourth columns; for summary data from these and additional mice see FIG. 24). Together, these results underscore that population responses among the unstimulated neurons following tuned optogenetic stimulation are similar to those observed during visual stimulation—but distinct from those seen during random optogenetic stimulation (FIG. 12J). By examining classifier prediction accuracy, these results were confirmed quantitatively: classifier performance was evaluated for each experimental condition (i.e. visual, tuned, random, and no stimulation), and each condition was tested for five days in four different mice. We found no significant difference in prediction accuracy between random ensemble stimulation and the unstimulated condition (p=0.46, n=20 total conditions of each type, pooled across 4 mice and 5 conditions/mouse; Wilcoxon signed-rank test; FIG. 12K), whereas data taken from tuned optogenetic stimulation conditions yielded predictions superior to those seen in random data (p<0.001, n=20 conditions of each type, Wilcoxon signed-rank test; FIG. 12K). Together these data point to the existence of distributed subnetworks encoding specific visual features, that can be specifically recruited by targeted optogenetic selection of multiple individually-specified neurons.

Recruiting Specific Percepts at Cellular Resolution: Behavioral and Physiological Readouts We next tested whether activation of these identified subnetworks could be capable of modulating or even eliciting specific percepts and behaviors, and to what extent potency of these subnetworks could be influenced by task-engagement, experience or plasticity. To enable a well-controlled behavioral readout, a second cohort of mice (n=5) was habituated on the floating ball and trained to discriminate the two drifting-grating orientations at high performance levels in a Go/No Go task (FIGS. 13A-13C). Once mice reliably discriminated orthogonal visual stimuli (at 12%, 25% and 50% contrast; trained animals were unable to discriminate 2% contrast gratings (FIG. 13C), while performing well at 12%), ensembles composed of identified cells responding to either the Target (0°, Go) or Distractor (90°, No Go) stimulus (OSI>0.5) were identified by 2P $Ca^{2+}$ imaging with conservative criteria as before (here animals performed discrimination motivated by reward/punishment during our image-based identification). Interestingly, using the same imaging/analysis criteria as in FIG. 12, we found more orientation-tuned neurons in the trained cohort vs. the naïve cohort (30±6.8 neurons [mean±SD] per naïve mouse ensemble, 40.7±8.7 [mean±SD] per trained mouse ensemble, p<0.05 two-tailed t-test), consistent with an increase in size, tuning sharpness and/or reliability of the population representation as a result of performing the visual discrimination task. We also noted that there was an insignificant difference in the mean size of Target (mean=43.2 cells, range [33 55]) versus Distractor (mean=38.2 cells, range [28 46]) ensembles across trained mice (p=0.29, two-tailed paired t-test comparing ensemble sizes); we ensured direct assessment of behavioral performance and neural dynamics using equally-sized ensembles in each mouse in later experiments (see FIG. 15).

The trial structure then transitioned to one wherein, following a brief auditory cue, a drifting grating was presented alone, or a tuned or random ensemble was optogenetically stimulated without a drifting grating present, or a drifting grating was presented simultaneously with optogenetic stimulation of either a functionally-corresponding orientation-tuned ensemble or a random (but otherwise matched) ensemble (FIGS. 13D, 13E). Used for subsequent sessions were the same two tuned ensembles in each mouse (termed Target for 0° cells, and Distractor for 90° cells), and two distinct neuron count-matched ensembles randomly selected from among the cells responding selectively to neither Target nor Distractor gratings (designated as random ensembles, one for use with each of the Target or Distractor conditions). While 75% of trials were maintained as high-contrast visual stimuli to promote task engagement and prevent extinction of the behavioral task, mice were presented with a subset of trials in which one of the ensembles was stimulated, but no visual stimulus was presented. Just as for the visual discrimination behavior, if the animal correctly licked during the answer window when the tuned or random Target ensembles were stimulated, water reward was delivered. Conversely, if licking occurred during stimulation of the tuned or random Distractor ensembles, an aversive air puff was provided along with a time out at the end of the trial; missed Target trials (false negatives) also led to a time out. In this way, licking behavior during tuned or random ensemble stimulation was consistently rewarded or punished according to each ensemble's associated visual percept.

While most of the mice did not immediately discriminate the optogenetically stimulated ensembles (n=4/5), interestingly, one mouse did correctly discriminate stimulation of the tuned ensembles alone (without any visual stimulation) in the course of the first session, (p<0.05, two-tailed Fisher's exact test, hit rate vs. false alarm rate, n=22 trials, d'=2.21). For all the other animals, we gradually increased the visual contrast of the paired visual/optogenetic condition from 2% to 5% contrast over the course of several sessions (typically one session per contrast; we termed this process the "contrast ramp"). In these mice, concomitant optogenetic stimulation of orientation-specific ensembles succeeded in improving behavioral discrimination across the contrast ramp, including at the perceptual threshold of the animals (FIG. 13F, ~3-4% contrast; p<0.05, two-way ANOVA, main effect of stimulation type, 4/4 mice that proceeded through training). Remarkably, after conclusion of the contrast ramp, under the no-visual-stimulus condition (0% contrast) mice achieved high performance discrimination of tuned ensemble optogenetic stimulation alone (FIGS. 13G, 13H, p<0.01, n=5 mice, two-tailed paired t-test before vs. after contrast ramp, and tuned ensemble vs. no stimulation). Results were much more variable for random (non-orientation-tuned) ensemble stimulation across mice, with some mice significantly improving behavior (the fixed random ensembles had been consistently associated with either the Target grating, rewarded condition or the Distractor grating, no go/penalized condition) and others not (FIGS. 13G, 13H; p=0.097, n=5 two-tailed paired t-test before vs. after contrast ramp; p=0.07 after ramp vs. no stimulation). Indeed, tuned ensemble stimulation drove higher performance across mice than did the random ensemble stimulation (p<0.05, two-tailed paired t-test, n=5). We also observed that a higher fraction of neurons within tuned ensembles were recruited by optogenetic stimulation modulation than with stimulation of random ensembles (FIG. 25D, p<0.001, paired t-test, n=3 mice).

We next asked whether such a contrast ramp would be required to drive behaviorally-potent responses to any stimulated ensemble. To test this idea, we identified a new population of cells within the same receptive field in V1 (changing the origin of our z axis by Δz=30 μm) during the visual-only task in order to identify entirely new tuned ensembles that had never been optogenetically stimulated. All mice that progressed through this new protocol (n=3), including one that had learned previously to correctly associate a random ensemble with the Target grating/reward condition (M3; behavior in FIGS. 13H and 13I), were able to correctly discriminate stimulation of the entirely new orientation-tuned ensembles without any contrast ramp experiments (FIG. 13I, p<0.05, two-tailed paired t-test vs. no stim; each mouse also independently demonstrated significant discrimination performance to tuned ensembles stimulation, p<0.01 two-tailed Fisher's exact test comparing hit rate vs. false alarm rate for each mouse; 1-2 sessions per animal). Conversely, mice could not discriminate the new set of random ensembles (p=0.64, paired t-test, n=3), and tuned-ensemble stimulation performance far exceeded random-ensemble stimulation performance (p<0.01, two-tailed paired t-test, n=3). These results indicate that the optogenetic tuned-ensemble-driven performance is not simply the result of learning an association between cellular activity in an ensemble and reward (otherwise random-ensemble stimulation would work as well as tuned). Discriminating random ensembles may indeed require additional learning/plasticity mechanisms, but tuned functional ensemble stimulation appears to support an immediately-interpretable and discriminable percept that can be used by the animal as it would use the visual percepts with which it had been trained.

The ability of some mice to learn to discriminate random ensembles, and the improvement observed for discrimination of tuned ensembles following the low-contrast pairing experiments, suggests that plasticity may occur in the visual cortical network to enhance specific perceptual pathways supporting behavior. Task learning has been hypothesized to strengthen specific pathways related to decision circuits, and increased magnitude, tuning sharpness, and reliability of sensory responses have been observed in specific populations as a result of learning similar sensory-guided tasks including orientation discrimination, suggesting that local plasticity in V1 may indeed occur. Comparing recruitment of tuned networks in our trained vs. naïve cohorts, we observed that learning the visual task alone modestly enhanced specific network recruitment in response to visual stimuli (FIG. 25A, right, $p<0.05$; $\chi^2$ two tailed test, n=20 sessions in 4 mice); thus plasticity may indeed occur, but goal-directed attention, top-down modulation and general task-related states are likely to play a role as well.

Beyond changes associated with learning and performing the task itself, we asked what effects the pairing of visual stimuli with optogenetic ensemble-stimulation might have on specific visual circuit dynamics (FIGS. 13J-N). Whereas selective recruitment of iso-tuned (significantly more so than orthogonally-tuned) populations was observed for tuned ensemble stimulation before the contrast ramp in trained mice (FIG. 13J, $p<0.05$, $\chi^2$ two tailed test, n=6 session in 5 mice), as observed in naïve mice (FIG. 25A), random ensemble stimulation did not recruit visual-percept specific populations (FIG. 13K, p=0.87, $\chi^2$ two tailed test, n=6 session in 5 mice). Following the contrast ramp experiments, tuned stimulation recruited much more powerfully the iso-tuned population (FIGS. 13L and 13N; $p<0.0001$, $\chi^2$ two-tailed test: iso-tuned vs. orthogonally tuned, n=15 sessions in 5 mice; $p<0.0001$, $\chi^2$ two-tailed test before vs. after the contrast ramp, same sessions as random-ensemble stimulation). Strikingly, random ensemble stimulation also now recruited the iso-tuned local populations (with tuning matching the grating direction with which that specific random ensemble had been paired during the contrast ramp training; FIG. 13M, $p<0.0001$, $\chi^2$ two tailed test vs. orthogonally tuned). The magnitude of iso-tuned population recruitment also increased after vs. before contrast ramp experiments (FIG. 13N, $p<0.0001$, $\chi^2$ two tailed test), consistent with the newly-learned ability of specific mice to perform random-ensemble discrimination (mouse identity legend as in FIGS. 13G-13N). Still, tuned ensembles were much more effective at recruiting iso-tuned populations than random ensembles (FIG. 13N $p<0.0001$, $\chi^2$ two tailed test). Importantly, all of these local network recruitment analyses were conducted in the trial epoch before any reward or punishment was delivered, contingent on licking behavior.

This pattern of results dissociates specific network plasticity from more general, behavior-dependent brain state effects. That all mice immediately performed well in high-contrast visual conditions (range=[88.3% 96.8%] correct across n=5 mice for 12% visual contrast stimuli) at the outset of the contrast ramp experiments indicates that task-related brain states were likely already present. Yet, random-stimulation did not generalize from one ensemble to another and did not exhibit selective recruitment of visually-tuned populations until after the visual contrast ramp and optogenetic stimulation experiments (FIG. 13M). In this way, the random-ensemble stimulation conditions help control for the influence of top-down and brain-state factors which would be present during the random-stimulation conditions as well as during tuned stimulation from the outset of the contrast ramp (though the possible role of selective feedback emerging after learning remains). These results point to connections being formed or strengthened between specific random ensembles and specific local visually-tuned and percept-selective populations, allowing mice to recruit appropriate visual pathways and perform appropriate discrimination associated with specific random-ensemble stimulation. While the mechanism of this linkage formation remains unclear, the functionally-broad inputs received by visual cortical neurons, even if weak, may provide a pre-existing substrate in the network for learning new associations and building or linking pathways. Furthermore, synaptic plasticity mechanisms including sprouting of new synapses have been shown to occur over the time-frame of days—consistent with timescales present here. Local circuit plasticity, forming or strengthening specific connections between stimulated ensembles (both random and tuned) and surrounding populations, may serve to amplify specific cortical network activity originating from a fraction of the broader network.

Specific Naturally- or Artificially-Recruited Ensembles Support Behavior

Figure 14:
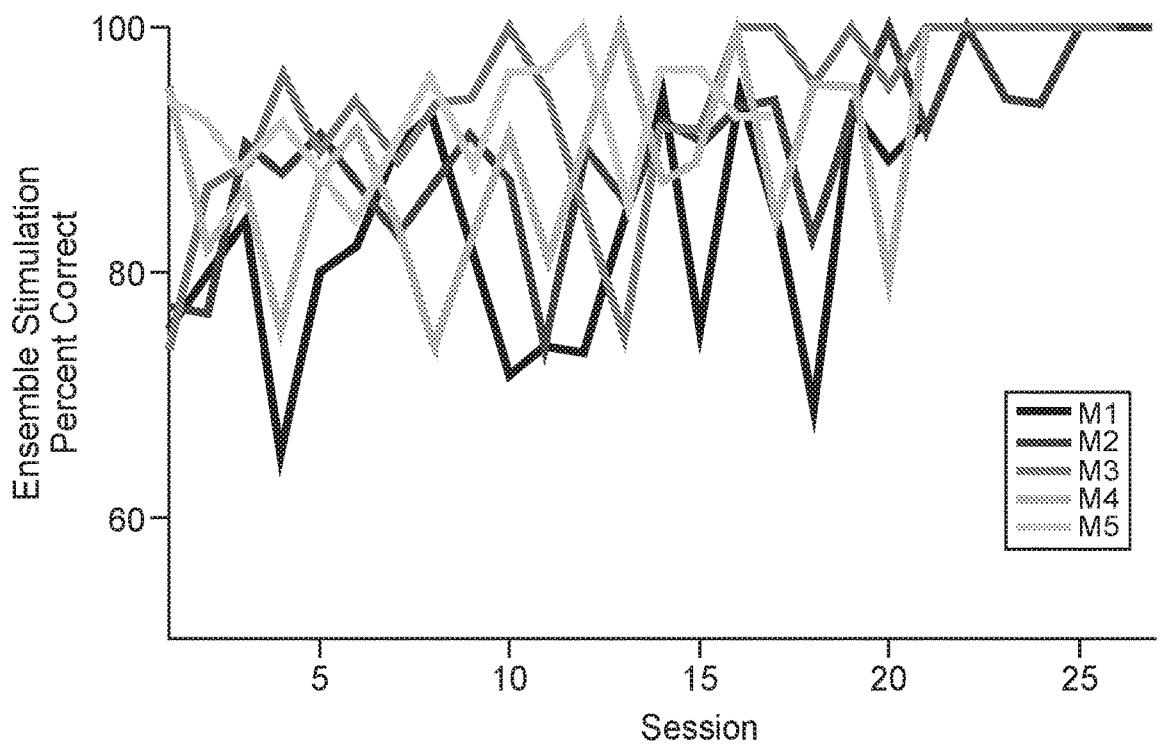
FIG. 14, A-I depicts dynamics of tuned and behaviorally potent visual ensembles.
Figure 14:
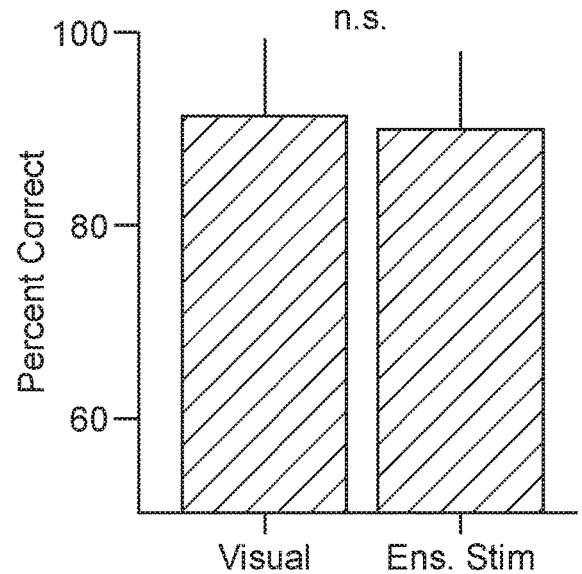
Figure 14:
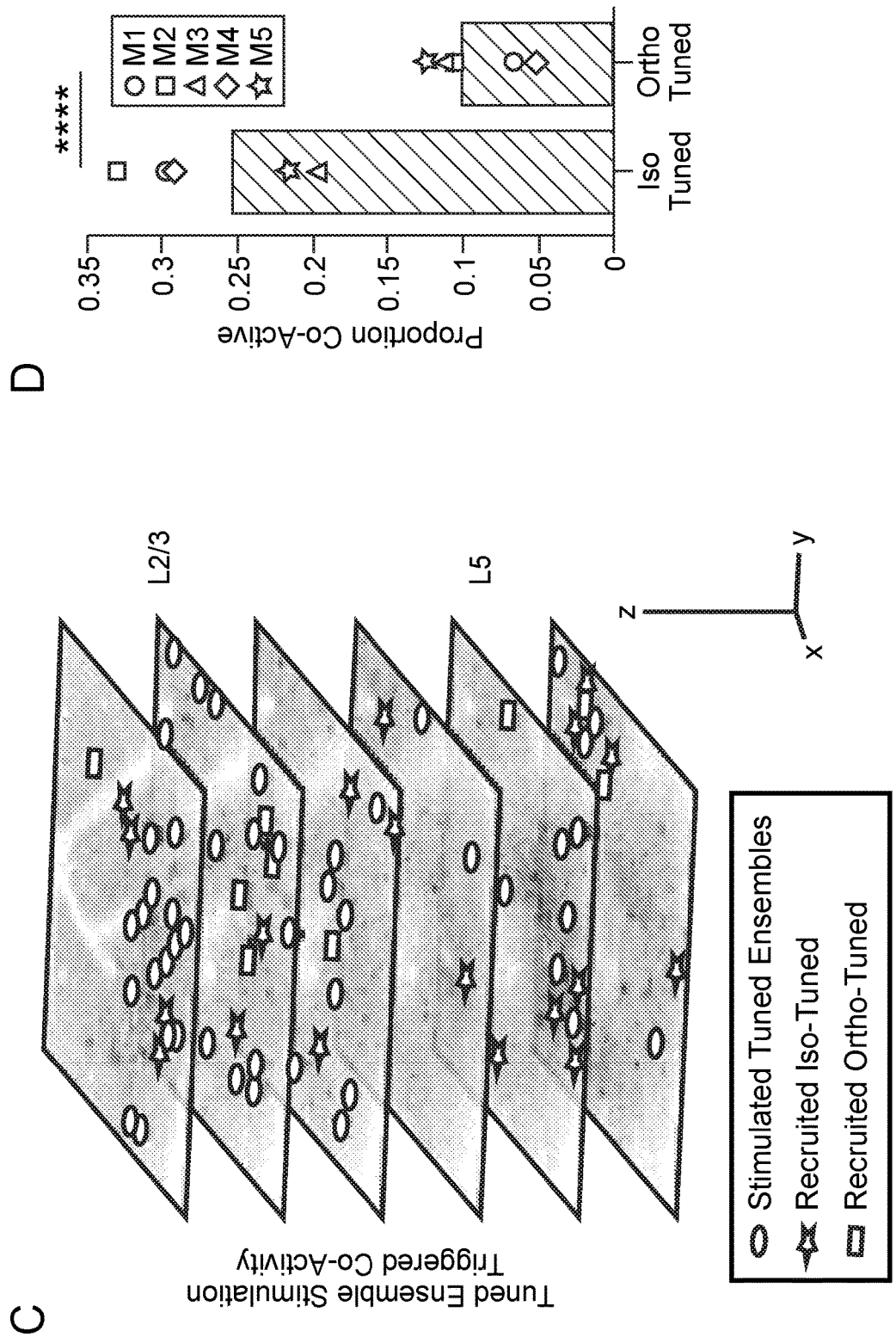
Figure 14:
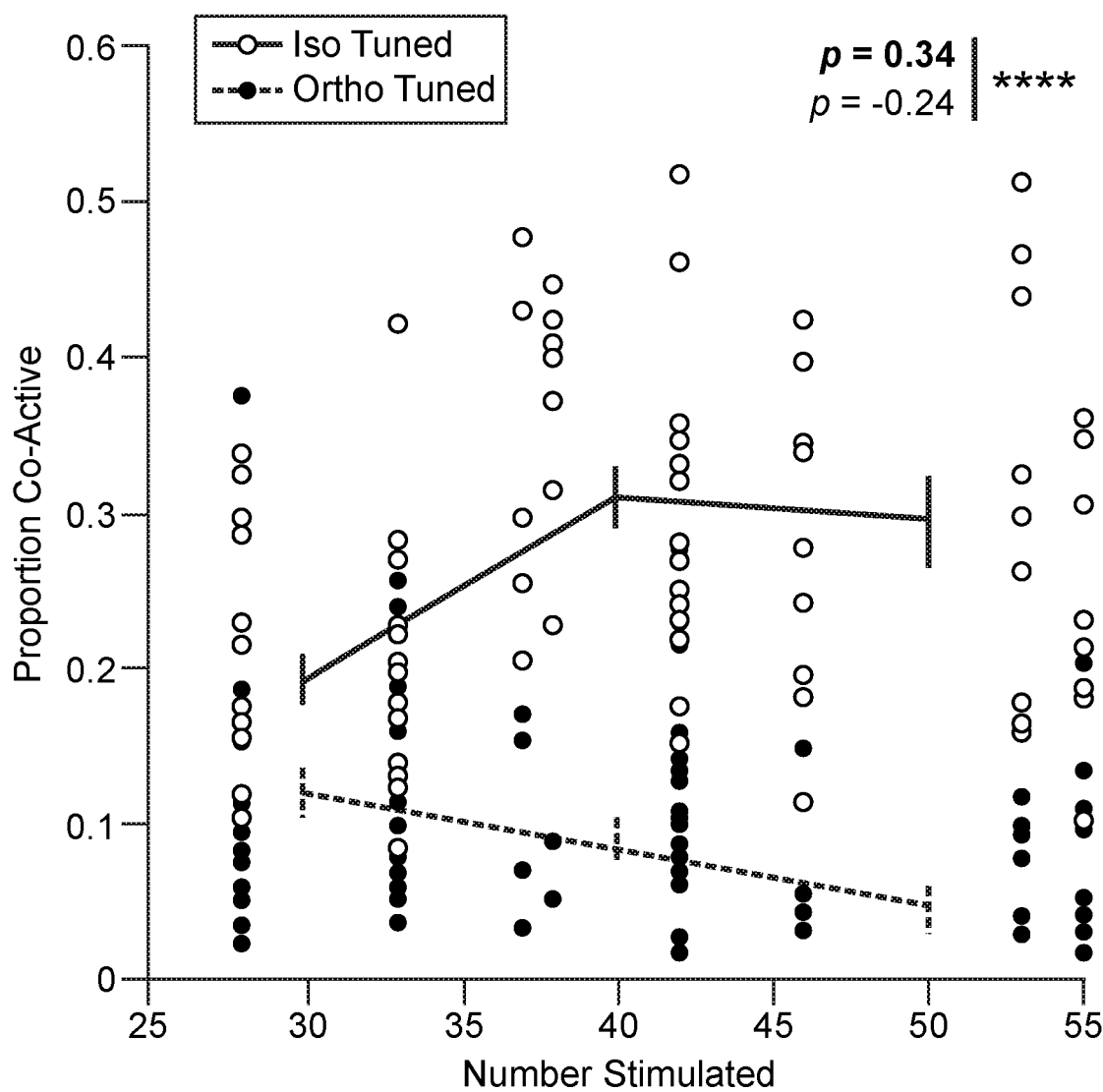
Figure 14:
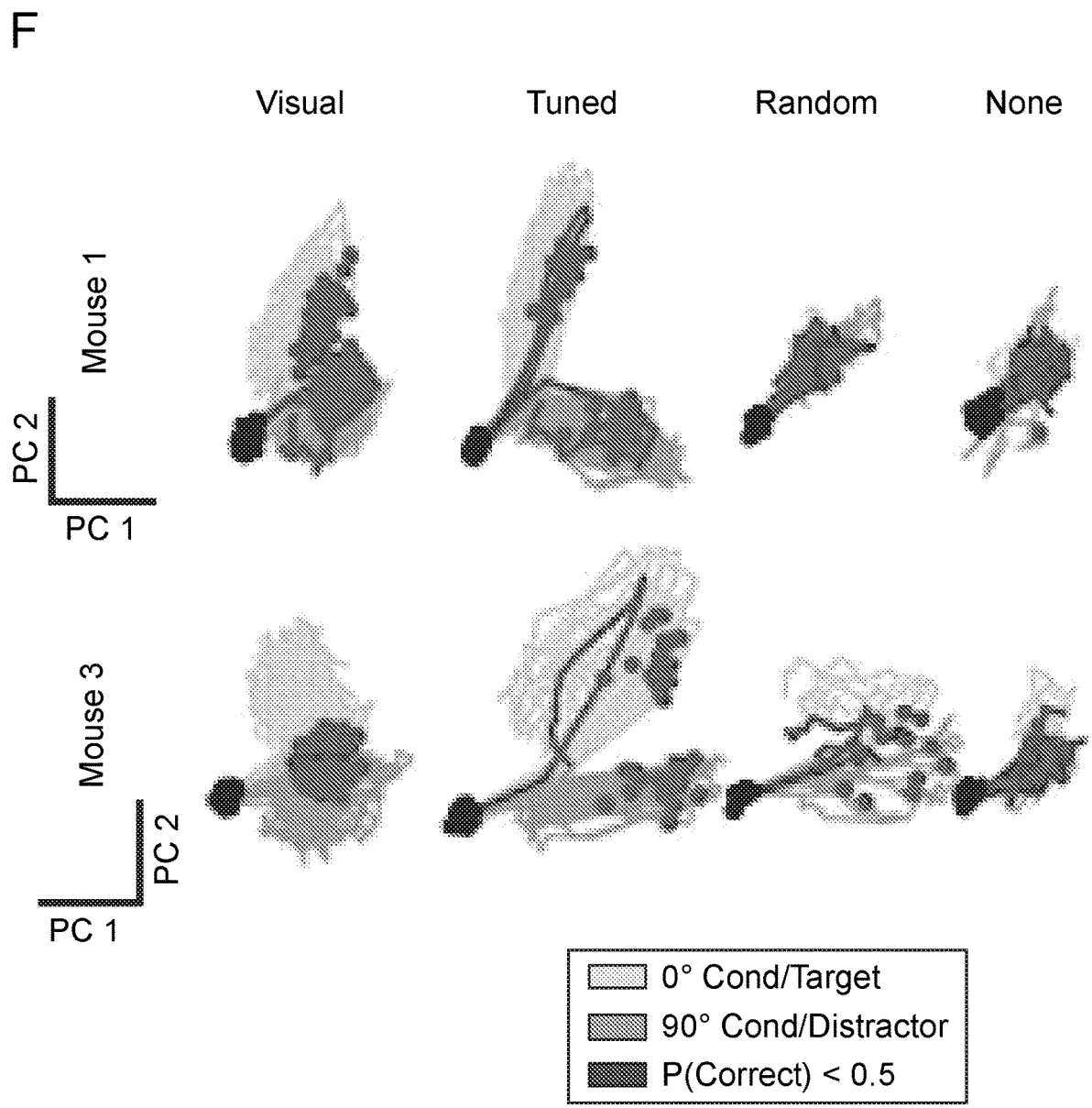
Figure 14:
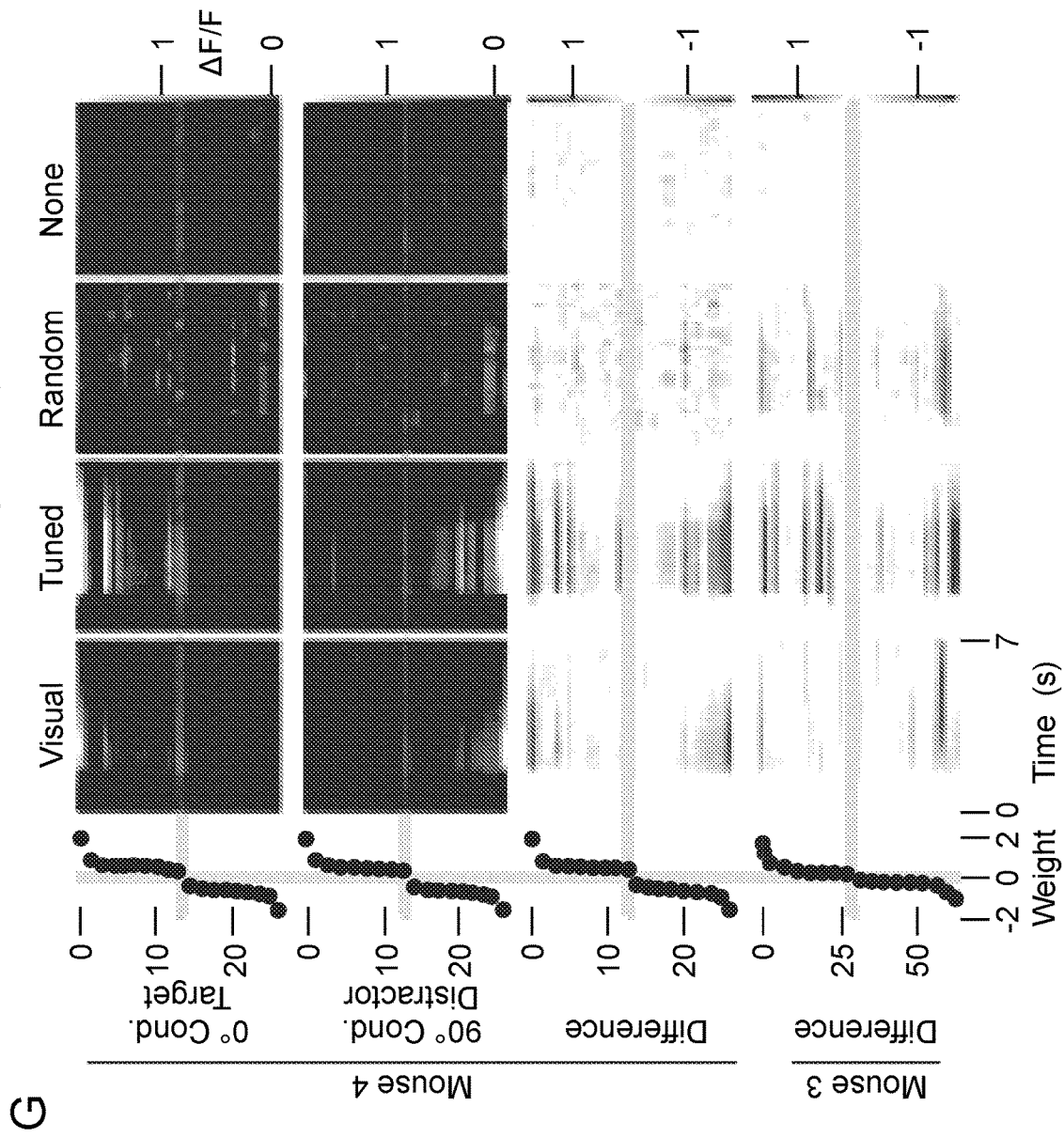
Figure 14:
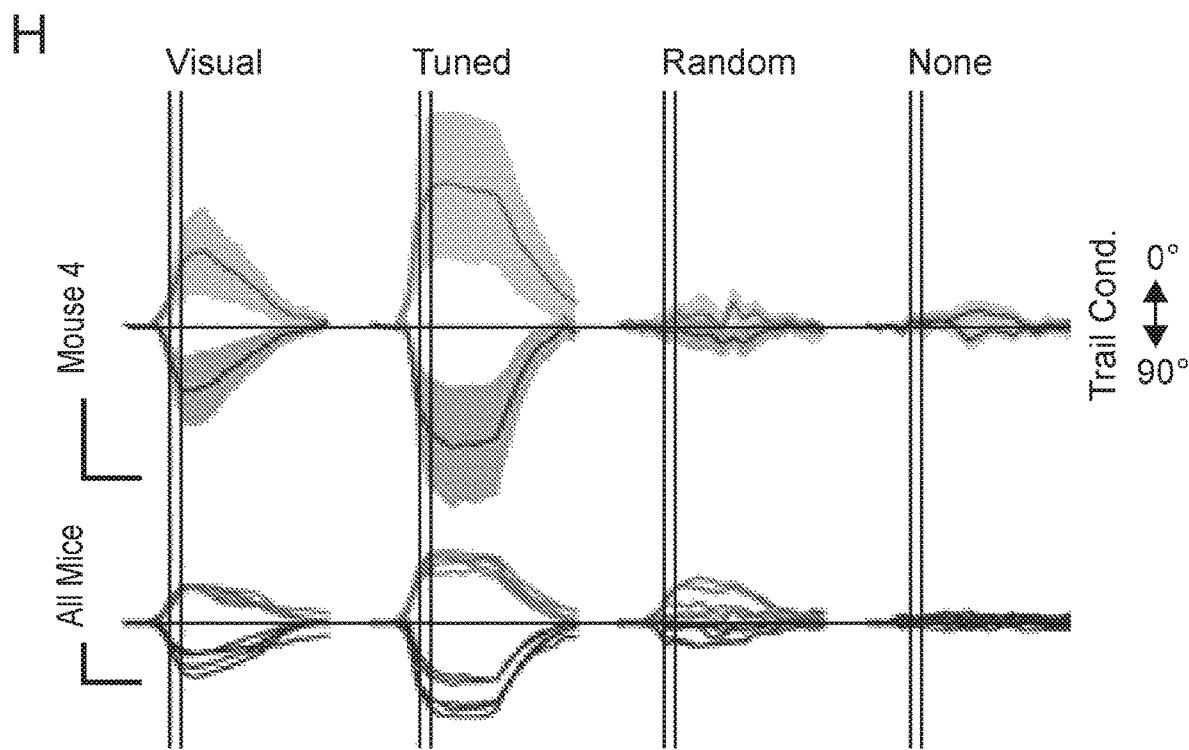
Figure 14:
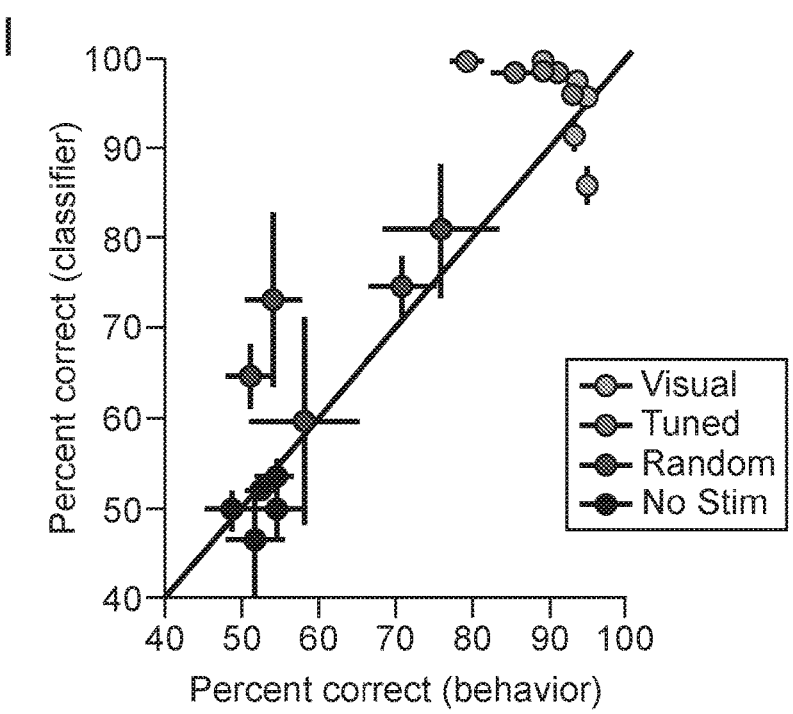

Our ability to return to the same ensembles and surrounding populations with micron-level resolution allowed us to explore stability of visual-percept specific networks and artificial-percept discrimination behavior over several weeks (FIGS. 14 and 22). Mice performed both visual and artificial-percept discrimination behaviors with high performance over the course of many weeks, with statistically significant performance on almost every experimental session (FIG. 14A, 109/112 visual and 107/112 tuned ensemble sessions with $p<0.05$ hit rate vs. false alarm rate, two-tailed Fisher's exact test). Behavioral performance was nearly identical for visual orientation discrimination and optogenetic ensemble discrimination (FIG. 13B, 91.12±0.75% correct for visual discrimination vs. 89.47±0.78% correct [mean±SEM] for tuned ensemble discrimination, p=0.13, two-tailed paired t-test, n=112 sessions across 5 mice).

We measured recruitment of iso-tuned and orthogonally-tuned neurons across all of these sessions; as before (FIGS. 12 and 13), finding co-active neurons among the held-out untargeted population across cortical layers during specific ensemble stimulation in the absence of visual stimulation (FIG. 14C). Iso-tuned neurons were much more likely to be thus recruited than were orthogonally-tuned neurons (FIG. 14D, $p<0.0001$, $\chi^2$ two tailed test, data from n=58 sessions in 5 mice). Iso-tuned population recruitment increased with the number of neurons stimulated (FIG. 14E; Spearman's $\rho=0.34$, $p<0.001$, n=116 data points across 5 mice). Conversely, recruitment of orthogonally tuned neurons decreased in probability as the number of stimulated neurons increased (FIG. 14E; Spearman's $\rho=-0.24$, $p<0.01$, n=116 data points across 5 mice), and thus selective recruitment was generally much more robust than orthogonal recruitment across all neuron-count conditions tested (FIG. 14E; $p<0.0001$, Fisher's z transformation).

We further analyzed the elicited activity of neurons that had not been directly stimulated, as identified in each behavioral mouse in a manner identical to that used for the naïve mice (FIG. 25B; see FIG. 12G for a schematic of the analysis procedure). We first identified principal component (PC) vectors using data taken during the presentation of visual stimuli and used these PC dimensions to project all of the experimental condition types (FIG. 14F). In a pattern like that observed in naïve mice (compare to FIG. 12H), the first two principal components explained the majority of the variance (the top two components explained 67.97±4.56% (mean±SEM) and the top four components accounted for 85.85±1.81%) (FIG. 25C). Neural trajectories during both visual and tuned stimulation closely matched each other, with the Target and Distractor trajectories separating upon stimulation onset (imaging frame following stimulus onset denoted by dark blue or red dot) in both the visual and tuned stimulation conditions, and exhibited far less separation during random stimulation (e.g. no separation detectable in Mouse 1 (FIG. 14F, top row, third column), and only slight separation in Mouse 3 (FIG. 14F; bottom row/third column)—a mouse that notably learned (FIGS. 13H and 13I) to reliably discriminate random ensembles.

Further evidence supported the idea that these dimensions in PC space, whether visually or optogenetically-elicited, correspond to visual/perceptual dimensions rather than dimensions related to behavior/action. This is of critical importance to address, since behavioral task engagement can modulate activity in V1. The neural trajectories (reproduced in all mice and using multiple methods in FIG. 27) from conditions where the mouse performed the incorrect licking behavior more than 50% of the time were indistinguishable from trajectories in conditions with high performance (see FIG. 14F, dark blue and red lines correspond to these low performance conditions). This result revealed independence of the V1 trajectories from strictly motor- or action decision-related effects, since trajectory type tracked with available percept rather than action taken.

Upon application of our binary classifiers trained only on data taken from the unstimulated neurons during presentation of visual gratings (FIGS. 25E-N), the learned classifier weights were found to correspond to neurons with selective responses for the 0° or 90° visual stimuli as expected—but crucially also to neurons selectively recruited by their corresponding optogenetic ensembles (FIG. 14G; three additional mice shown in FIG. 26). This result would be consistent with a model in which similar neural representations across conditions reveal the formation of a percept during optogenetic stimulation similar to that of the corresponding visual stimulus. Interestingly, the magnitude of this recruited population-response appeared even larger during tuned optogenetic ensemble stimulation than during visual stimulation (FIGS. 14G and 14H), in contrast to the results seen in naïve animals. This pattern is consistent with training resulting in enhanced network recruitment of iso-tuned neurons, and may explain how random stimulation could in some cases yield population responses that weakly discriminate condition type (FIGS. 14F-14H, bottom row, third column in each of those three panels). In contrast to this apparent effect of learning and task-related enhancement, random stimulation never evoked a large population response in naïve animals (FIGS. 12H-12K and 24).

We identified high correlation between mouse behavior and ensemble classifier performance, across mice and condition type (FIG. 14I; $r^2=0.66$, $p<1e-70$). Both the classifier and behavioral data operated near saturation on real visual data, and on tuned stimulation conditions. In contrast, random stimulation resulted in lower, but still better-than-chance neural and behavioral discrimination (consistent with the local plasticity mechanisms described above). Together these results indicate that the selective stimulation of a small number of appropriate neurons is sufficient to ignite widespread network recruitment in V1 similar to that recruited by a visual stimulus, and that this specific ignition suffices to support corresponding specific behavior.

Quantitative Circuit Architecture Underlying Layer-Specific Perceptual Thresholds The ability to record across cortical layers and return to the same populations each day (FIG. 22) next allowed systematic quantification of the influences of distinct numbers of stimulated neurons in each cortical layer on intra- and inter-laminar communication and behavior. In a subset of trials, we stimulated subsets of neurons selected (at random) from the original tuned ensembles, with particular attention to layer and total number of neurons stimulated. We found that stimulating only layer 2/3 tuned ensembles led to selective recruitment of iso-tuned neurons in both layer 2/3 and layer 5, with stronger recruitment occurring within layer 2/3 (FIG. 15A, $p<0.0001$ for all comparisons: recruited iso-tuned vs. ortho-tuned, and within layer 2/3 vs. layer 5, $\chi^2$ two tailed tests). Increasing the number of neurons stimulated in layer 2/3 led to an increase in the fraction of co-active iso-tuned cells within both layer 2/3 and layer 5 (FIG. 15B, Spearman's $\rho=0.46$, $p<0.01$, $n=46$ data points, within layer 2/3, $\rho=0.51$, $p<0.01$, $n=36$ data points, within layer 5, $p=0.78$ two-tailed Fisher's z transformation comparing $\rho$ values).

Stimulating only layer 5 tuned ensembles led to selective recruitment within layer 5, but interestingly did not lead to robust recruitment in layer 2/3, and layer 5 to layer 2/3 recruitment was not visual-percept selective (FIG. 15C, $p<0.0001$, iso vs. ortho tuned in layer 5, and layer 5 vs. layer 2/3 iso tuned, $\chi^2$ two tailed tests; recruitment in layer 2/3 was not significantly different between iso and ortho tuned populations, $p=0.58$, $\chi^2$ two tailed test). As the number of neurons stimulated increased in layer 5, a greater fraction of iso-tuned neurons in the surrounding population was recruited in layer 5 but not layer 2/3 (FIG. 15D, Spearman's $\rho=0.62$, $p<0.01$, $n=24$ data points for layer 5 recruitment; $\rho=0.19$, $p=0.38$, $n=24$ data points for layer 2/3 recruitment), and the correlation was stronger for layer 5 than even the weak positive trend for layer 2/3 (FIG. 15D, $p<0.05$, Fisher's z transformation). Enhanced recruitment of layer 5 was a consistent theme; stimulating full selective ensembles across layers led to selective recruitment within both layer 2/3 and layer 5, with the strongest iso-tuned recruitment in layer 5 (FIG. 28A, $p<0.0001$ all comparisons shown between iso vs. ortho-tuned and layer 2/3 vs. layer 5, $\chi^2$ two tailed tests). Furthermore, as we increased the number of neurons stimulated in each respective layer, the proportion of iso-tuned neurons in the surrounding population increased more rapidly within layer 5 (when layer 5 was stimulated) than within layer 2/3 (when layer 2/3 was stimulated) (FIG. 28B, $p<0.01$, ANCOVA, controlling for the covariate of number stimulated; corresponding data replotted from panels FIGS. 15B and 15D on the same axes).

These layer-specific results indicate selective functional connectivity within layer 2/3, to a greater extent within layer 5, and from layer 2/3 to layer 5. Strong functional connectivity is markedly lacking from layer 5 to layer 2/3, and functional effects of that projection appear non-specific in terms of the visual-percept information investigated here. This arrangement suggests V1 may implement a circuit capable of modular amplification of concordant information within layer 2/3 and within layer 5 independently, and provides a functionally selective link from layer 2/3 to 5 likely supporting influence of feedforward pathways converging on cortex from thalamus in vision. Both superficial and deep layers support cortico-cortical connectivity between areas, but layer 5 is uniquely involved in certain long-range projections including to subcortical structures, and may be specially positioned in the circuit to convey information more broadly across the brain to influence ongoing dynamics supporting cognition and diverse behaviors.

To test this prediction that layer 5 activity would be more potent in driving perceptual behavior than layer 2/3—and more generally, to quantify the sensitivity of network ignition and its relationship to behavior with single-cell resolution—we examined the link between the number of iso-tuned neurons that were simultaneously optogenetically stimulated, and consequences on both network activation and behavior. We used the binary classifiers described earlier to reveal that, across subjects, there was a critical number of stimulated neurons required for driving a robust population response that could drive high discrimination performance (FIGS. 15E-F; for psychometric curve fitting, see FIGS. 28C-28G for results for individual mice). Classifier performance saturated at nearly 100% beyond a relatively small number of stimulated neurons (approximately 20), indicating that sufficient information is available in a small population for robust discrimination. This result from neural data agreed well with the same analysis applied to the aggregate behavioral performance (FIGS. 15G-15H). However, behavioral performance was somewhat inferior to that of the classifier applied to neural data—evidenced by a lack of behavioral experiments with near perfect performance. This suggests that countervailing influences on behavior, such as attention, motivation, impulsivity or satiation, may prevent successful report of the percept on all trials, and may also indicate that V1 network recruitment does not always recruit the necessary brain-wide network for driving behavior. Importantly, in the great majority of cases, and adhering to a very similar threshold, percept-specific network ignition coincided with behavioral report of the specific percept.

The psychometric curves in FIGS. 15E and 15G further indicated that layer 5 neurons may be more potent at driving neural and behavioral discrimination than those in layer 2/3. To test this hypothesis in more detail, we restricted our analysis to only experiments where comparable numbers of neurons were stimulated between layers 2/3 and 5 (FIGS. 15F and 15H). This subset of data was used in a two-way ANOVA to compare the effect of laminar position on ensemble ability to influence classifier performance (FIG. 15F) or animal behavior (FIG. 15H). In each case, equivalent numbers of layer 5 neurons were more successful at driving high performance ($F_{1,49}=8.11$, $p<0.01$ for the classifier data; $F_{1,49}=5.47$, $p=0.023$ for behavioral data, main effect of layer).

To assess the minimum threshold for ensemble discrimination here, we carried out experiments to determine the fewest possible neurons needed to drive significant discrimination behavior in the most sensitive mouse. This mouse could discriminate two neurons per ensemble in layer 5 with high performance (d'=2.11, $p=0.037$, two-tailed Fisher's exact test, n=24 trials; a second mouse also demonstrated significant discrimination of two-neuron ensembles in layer 5, $p=0.036$), but could not discriminate single neurons ($p>0.21$ for 4 sets of single neurons tested). Relevant to perceptual thresholds for cortical neuron activity detection, these results provide thresholds for specific ensemble discrimination related to natural percepts, with specific linkage to network recruitment and cortical layer.

Theory and Modeling of Low-Thresholds for Cortical Ignition

A striking finding of our experimental data is that stimulation of an exceedingly small number of selectively-tuned neurons can ignite the activity of a large fraction of the iso-tuned ensemble (FIGS. 15B, 15D and 15F). Despite such high sensitivity (low cell-count threshold for V1 ignition), spontaneous activity in V1 remains quite low, with a mean firing rate of about 0.2-2 Hz, depending on layer (84, 85). What then are the theoretical principles that enable such high sensitivity to small amounts of external stimulation, while still maintaining stable, low levels of spontaneous activity? We developed an analytic theory of ignition based on a model of N neurons firing at a Poisson rate in the spontaneous state, representing a selective neural ensemble. Because fluctuations of the total number of active neurons in this ensemble are proportional only to the square-root of the ensemble size, we find that it is possible to prove one can set very low thresholds for ignition, requiring stimulation of only order $\sqrt{N}$ neurons, without destabilizing the spontaneous activity. Our calculations reveal that stimulating as few as 20-30 neurons may reliably ignite large V1 ensembles for biologically plausible assumptions about the total tuned ensemble size, spontaneous firing rates, and single neuron integration times.

Finally, we demonstrated a proof-of-principle instantiation of the phenomenon of low-threshold ignition in a model neural circuit (see FIGS. 15I-15K), of order 1000 excitatory and inhibitory neurons. The key principles for generating low threshold ignition were found to be: (1) a fast recurrent excitatory subnetwork (which by itself would be highly unstable), (2) a slow inhibitory network that provides strong inhibition to the excitatory subnetwork, (3) recurrent excitatory connectivity not strong enough to destabilize a low spontaneous activity state in the combined excitatory-inhibitory network, and (4) this same recurrent excitation is strong enough that further excitation of a small number of excitatory cells can trigger ignition (FIG. 15I). The slower inhibition then brings the excitation back down so the ignition is transient (FIG. 15J). Thus overall, our combined technology development, experiment and theory suggest that, at least in the context of the percept discrimination behavior explored here, V1 operates in a striking and specific dynamic regime very close to a boundary of instability (FIG. 15K), enabling stimulation of a very small number of neurons to reliably trigger neural ignition, and consequently, percept-guided behavior. Thus remarkably, V1 may be exquisitely organized to amplify activity input, without allowing spontaneous activity to trigger false percepts.

Discussion

In this example, we have identified visual stimulus-specific tuned ensembles within mouse V1 and discovered that when small subsets of these ensembles were sufficiently activated, widespread specific ignition of the full ensemble and concomitant behavioral performance resulted. These specific ensemble recruitment dynamics were seen even in untrained mice, became more robust with learning of a visual task involving discrimination of the corresponding percepts, and were further strengthened by optogenetic drive of percept-selective tuned subsets during discrimination behavior. Fewer cells were required in layer 5 than in layer 2/3 to elicit the local ensemble ignition phenomenon as well as the correct behavior, and propagation of ignition occurred more robustly from superficial to deep layers than in the reverse direction. We further demonstrated that with repeated optogenetic targeting of randomly-selected cells during the training of behavioral responses to visual stimuli, these non-tuned cells could become linked into the visual percept-specific ensembles; indeed, activity driven in these random cells could subsequently drive the percept-specific ensemble and corresponding behavior, consistent with candidate Hebbian mechanisms for circuit plasticity underlying learning.

The volumetric all-optical approach developed and employed here revealed numerous cortical functional-architecture insights relating to visual perception in the behaving mammal. Since activity originating (by optogenetic stimulation) in multiple individually-defined, functionally-related V1 cells with overlapping "salt-and-pepper" organization in the same retinotopic cortical location led to ignition of distributed functionally-specific ensembles, and to correct and specific behavior, circuit mechanisms must therefore be capable of discriminating activity in spatially overlapping ensembles of neurons so that different behaviors can be selected. Thus, behaviorally-relevant connectivity within densely-innervated local cortical regions (i.e., within a cortical column) cannot be explained solely by location, and must be non-random, instead reflecting patterns important for specific functional representations and actions. Consistent with this interpretation, monosynaptic/reciprocally-connected subnetworks of similarly-tuned neurons in layer 2/3 of mouse V1 have been recently reported, using ex vivo paired recording and electron-microscopy connectomic studies of nearby cells. The specific recruitment that we observe within layer 2/3 in vivo, especially when only layer 2/3 neurons are stimulated, may depend upon this wiring architecture. Our results are also consistent with a recent study of the relationship between orientation tuning and monosynaptic input to layer 2/3 V1 neurons, using single-cell initiated monosynaptic rabies tracing in vivo; this study also found that layer 2/3 inputs to a layer 2/3 pyramidal cell tend to be similarly tuned with the post-synaptic cell. Conversely, it was reported that inputs from layer 5 to the layer 2/3 cell were more likely, on average, to prefer a different orientation than the post-synaptic neuron—consistent with our findings that layer 5 to layer 2/3 recruitment was not tuning-specific. Regarding our findings that tuned-ensemble recruitment within layer 5 was more robust than within layer 2/3—and that activity in fewer layer 5 neurons was required to drive both network-level discrimination (quantified by performance of a binary classifier) and behavioral performance—it may be relevant that layer 5 includes key corticocortical and corticostriatal output neurons and that striatum-projecting layer 5 neurons have especially high reciprocal connectivity in somatosensory cortex. Indeed, preferential recruitment and increased potency of layer 5 activity on behavior may also reveal properties of particular projections carried most strongly by layer 5 that are important for driving perception and behavior.

Since our targeting of tuned V1 cells was based on natural activity of those cells during behaviorally-verified visual perception—and since the resulting optogenetically-initiated dynamics not only triggered correct behaviors but also matched visually-evoked ensemble dynamics in cortex at a detailed level, percepts arising from even sparse optogenetic stimulation may resemble those evoked by specific visual stimuli. This possibility is supported by our finding that mice could immediately discriminate newly-provided, never-previously targeted, percept-selective ensembles, and behave correctly. Yet, it is important to underscore that full perceptual and behavioral responses are expected to involve activation of diverse cortical and subcortical brain areas, and generally larger neural populations spanning greater retinotopic and functional dimensions (particularly when considering naturalistic scenes in contrast to the low-dimensional visual stimuli used here). For example, a multitude of cortical and subcortical areas have been linked to perceptual decision-making, and visual perception has been hypothesized to involve reverberating activation of parietal and prefrontal cortical areas, driven by early visual pathways. In mice, several higher visual and posterior parietal cortical areas receive direct input from V1 (including specific connections related to feature encoding), which may play roles in behavior. New methods for functional imaging over much of the cortical surface may further illuminate the significance of these projections, and allow tests of whether the V1 ignition phenomenon is associated with propagation of signals beyond V1 required to perceive and act upon visual percepts.

Figure 9:
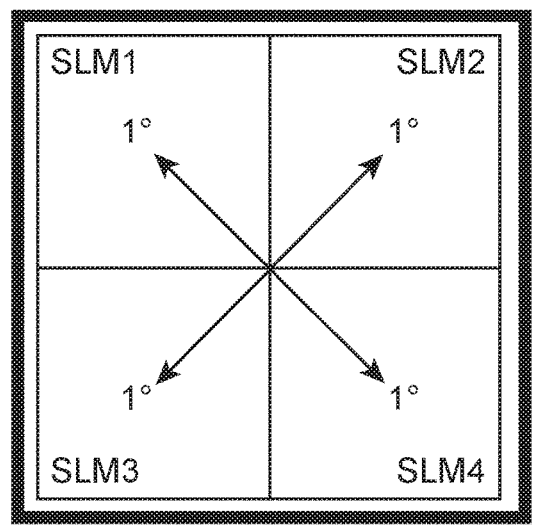
FIG. 9, A-E depict a 4× multiplexed spatial light modulator light projection system for expanded addressable field of view (FOV) according to certain embodiments.
Figure 9:
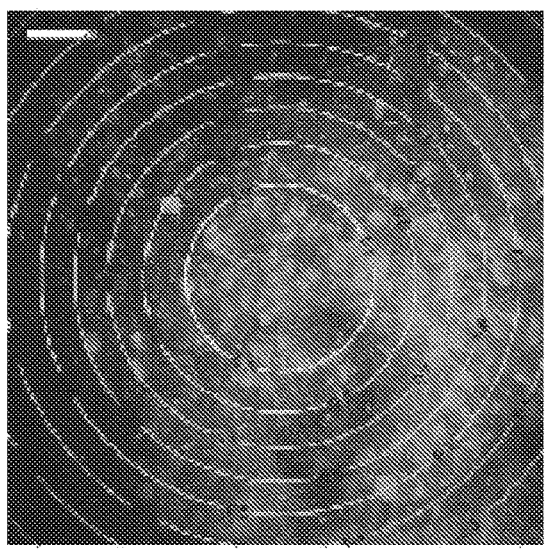
Figure 9:
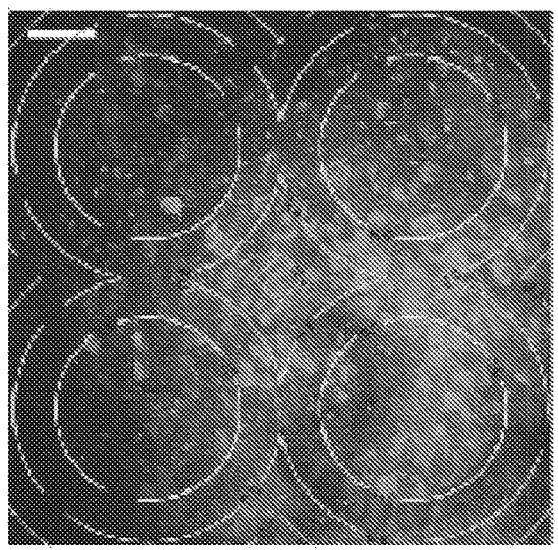
Figure 9:
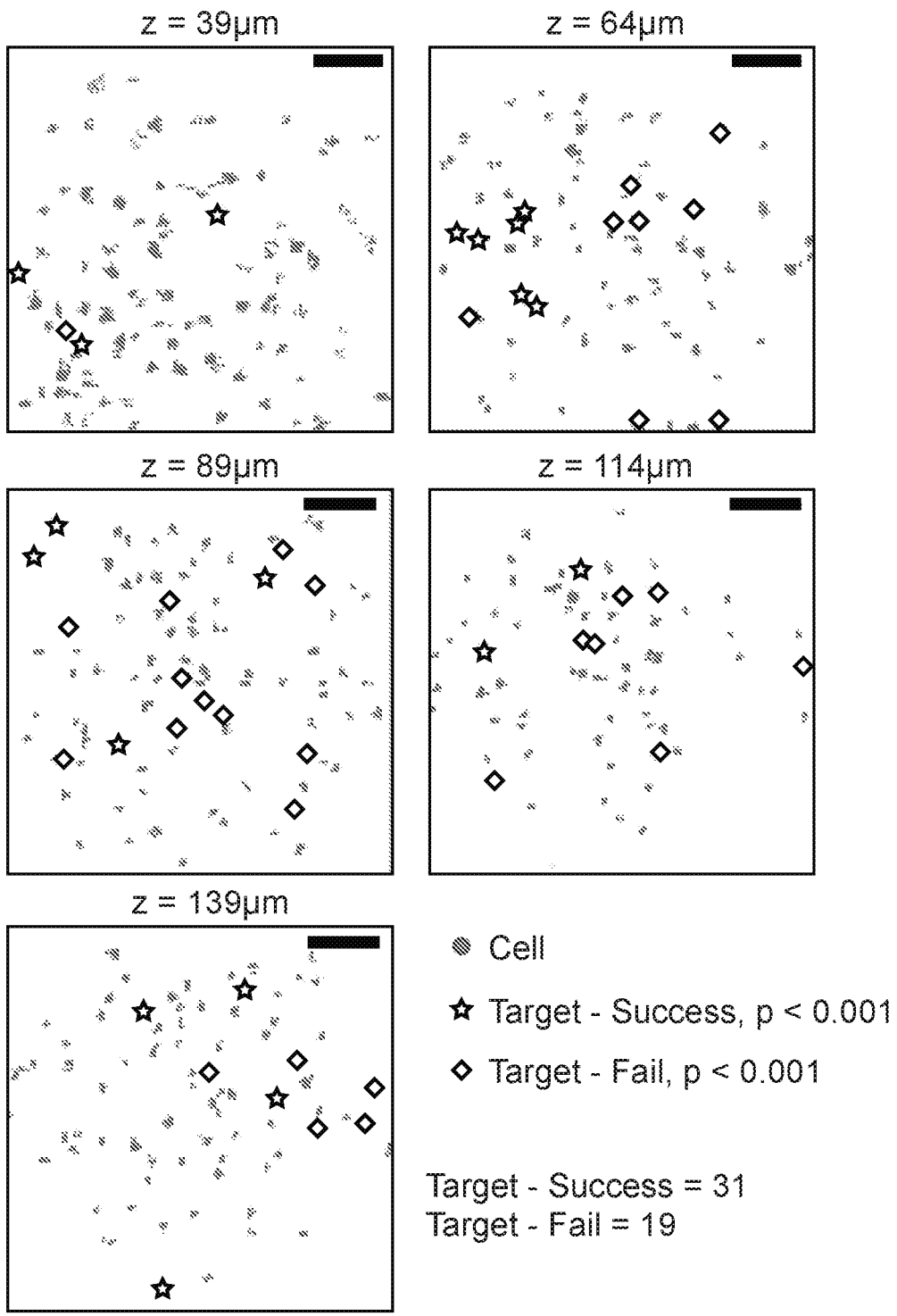
Figure 9:
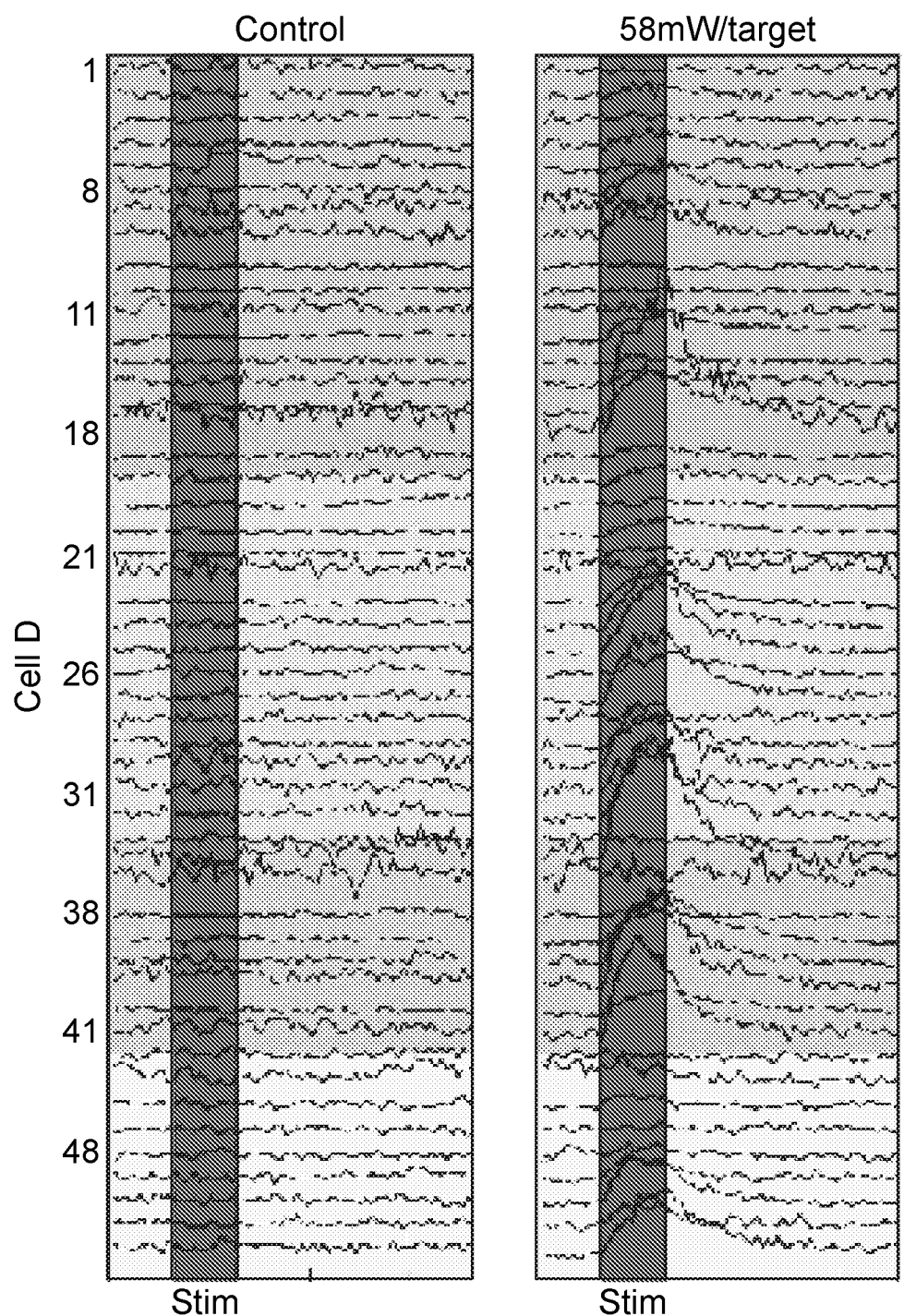

The MultiSLM approach readily allows expanding the addressable field of view in tandem with wide-field mesoscopic imaging methods (e.g. via spatial tiling; see FIGS. 8 and 9). Such investigation of broader networks over multiple areas will be further enabled by the unprecedented sensitivity and potency of ChRmine in allowing safe and effective optical recruitment of large ensembles of individually-defined cells. Improvements in temporal resolution and signal-to-noise of next-generation optical sensors may help further advance precise emulation of observed large-scale network activity, leveraging the high temporal resolution of the MultiSLM/ChRmine combination. Integration with advanced, deep cellular-resolution readouts such as GRIN lenses and Neuropixels electrodes may in the future also enable assessment of relevant subcortical circuits; for example, distinct types of V1 layer 5 pyramids (and to a lesser extent layer 2/3 pyramids) project to dorsomedial striatum, known to be important for associative sensorimotor and neuroprosthetic learning relevant to these behaviors. Finally, studying the ignition of specific sensory experiences with ensemble stimulation under different conditions (e.g. in brain states modulated by behavioral, electromagnetic, or pharmacological intervention, or even via genetic background) may help advance development of therapeutic strategies, for neuroprosthetics as well as for neuropsychiatric symptoms such as those involving hallucinations or delusions. More broadly, the ability to track and control large cellular-resolution ensembles over time during learning, and to selectively link new cells and ensembles together into behaviorally relevant circuitry, may have important implications for studying and leveraging plasticity underlying learning and memory in health and disease.

Neural Ignition in a Poisson Model

Consider a population of N neurons that, in a spontaneous network state, all fire in a Poisson manner at a low spontaneous rate r. In the context of our work, this population of neurons corresponds to a selectively tuned neural ensemble of excitatory cells that are similarly tuned to the same oriented grating. Let n denote the total number of neurons that fire in the entire population within a time window T. In the spontaneous state, n is then a Poisson random variable with mean $\mu=NrT$ and standard deviation $\sigma=\sqrt{NrT}$. For large values of NrT we can approximate n as a Gaussian random variable with the same mean and standard deviation. Now further suppose the neurons are recurrently connected in a way such that if the total number of neurons n that fire within a time window T, either due to spontaneous fluctuations or due to external excitation, exceeds a threshold $\theta$, then the network undergoes an ignition event in which a large fraction of the network fires. This implies that if we optogenetically stimulate a number of $N_s$ neurons within a time window T, while the network is in the spontaneous state, we will be able to trigger an ignition event with some probability $P(N_s)$. This probability should become close to 1 as $N_s$ becomes large. An interesting network property is the minimum number of neurons we need to stimulate so that we obtain an ignition event with a high probability, for example a probability of 0.95. We will denote this number of neurons required to obtain an ignition event with such high probability by $N_h$. Our data suggests the intriguing observation that this minimal number $N_h$ required for ignition is much less than the total number of neurons N in the selectively tuned ensemble.

However, we also wish to ensure that the rate of spontaneous ignition events $r_s$ due to spontaneous activity remains low. This spontaneous ignition rate is given by $r_s=P(0)/T$ where $P(0)$ is the probability of ignition if $N_s=0$ cells are optogenetically stimulated. The key issue is then whether it is possible to choose biologically plausible parameters so that one can stimulate population ignition events with high probability with a very small $N_h \ll N$, while still ensuring the rate of spontaneous ignition events $r_s \ll 1$ Hz remains very small. To address this issue, we compute both $r_s$ and $N_h$ as a function of $NrT$ and the ignition threshold $\theta$. First, we note that $P(N_s)$ is simply the probability that $n+N_s$ is greater than $\theta$, where n is the random number of neurons already spontaneously active during the stimulation window. Here we are assuming that the $N_s$ neurons we are stimulating are not already spontaneously active, which is a good assumption when both n and $N_s$ are much smaller than N. This is the regime in which the data lies and the regime in which we will eventually apply our theory. Thus $P(N_s)$ is simply the probability that a Gaussian random variable with mean $NrT+N_s$ and standard deviation $\sqrt{NrT}$ exceeds the threshold $\theta$. We denote by $H(x)$ the probability that a standard Gaussian variable with zero mean and standard deviation exceeds x; i.e.

$$H(x) = \int_x^\infty \frac{dz}{\sqrt{2\pi}} e^{-z^2/2}.$$

Then $P(N_s)$ is given by $$P(N_s) = H\left(z_\theta - \frac{N_s}{\sqrt{NrT}}\right),$$

where $$z_\theta = \frac{\theta - NrT}{\sqrt{NrT}}$$

is a z-scored version of the threshold for ignition that reflects how many neurons one needs to stimulate to go from the spontaneous mean $\mu=NrT$ to the threshold $\theta$, measured as a fraction of the spontaneous standard deviation $\sigma=\sqrt{NrT}$. The function $P(N_s)$ is a monotonically increasing function of $N_s$. From this function, we can obtain $$r_s=H(z_\theta)/T.$$

And we obtain $N_h$ as the solution to $P(N_h)=0.95$. If we denote $x_h$ as the solution to $H(x_h)=0.95$, then we obtain $$N_h=\sqrt{NrT}(z_\theta+|x_h|),$$

where the numerical value of $x_h$ is given by $x_h=-1.65$.

These results quantitatively capture the tradeoff induced by varying the threshold $\theta$. Increasing $\theta$ also increases the z-scored threshold $z_\theta$, and thereby decreases the spontaneous rate $r_s$ of ignition events, but also increases the minimum number of neurons $N_h$ needed to reliably trigger ignition with high probability. Conversely, decreasing $\theta$ makes the network more sensitive by reducing $N_h$, but also increases the rate $r_s$ of false positive spontaneous ignition events. However, varying $\theta$ yields dramatically different effects on $r_s$ and $N_h$. In particular, increasing $\theta$ (and therefore increasing the z-scored threshold $z_\theta$) exponentially suppresses $r_s$ but only leads to a modest, linear increase in $N_h$. Therefore, by setting a relatively low threshold for ignition so that the z-scored threshold $z_\theta$ is a fixed constant, independent of the network size N (i.e. say 5 or 10), then we can make the spontaneous rate exponentially small in $z_\theta$, while still ensuring that the minimum number of neurons $N_h$ needed to reliably trigger ignition remains proportional to the standard deviation of the spontaneous fluctuations, which grows only as the square-root of the tuned-ensemble size N. In essence, this corresponds to a situation in which the network ensemble has a low ignition threshold that lies just above what spontaneous fluctuations could reliably reach. However, the threshold is not so high that a small number of additional stimulated neurons of size proportional to the size of these same fluctuations, can push the network over the ignition threshold.

We can now employ biologically plausible numbers to test this simple framework. Assuming that an estimate for the tuned-ensemble size is given by N of order of magnitude in the thousands, we take N=5000 for simplicity. Previous studies of spontaneous activity in mouse primary visual cortex suggest a low spontaneous rate of r=0.2 Hz in layer 2/3 (with higher rates of ~2 Hz in layer 5). We consider a time window of T=20 ms, proportional to the typical membrane time constant over which neurons can integrate spikes. This yields a total population mean spike count of $\mu=NrT=20$ and spontaneous fluctuations of standard deviation $\sigma=\sqrt{NrT}=4.47$. Now suppose we set a threshold $\theta$ corresponding to a z-scored threshold $z_\theta=5$. Then $r_s=H(z_\theta)/T=1.43*10^{-5}$ Hz. With this small rate of spontaneous events, we would observe on average 1 spontaneous ignition event every 19 hours. However, we could still reliably trigger an ignition event by optogenetically stimulating only $N_h=\sqrt{NrT}(z_\theta+|x_h|)=4.47*(5+1.65)=30$ neurons, which is much less than the ensemble size of N=5000, and similar to what we observe in our data. Thus overall, this analysis provides a simple and quantitative framework for thinking about how low thresholds for ignition can be. Furthermore, when combined with our experiments, this framework suggests that V1 may have organized its internal connectivity and thresholds so as to be highly sensitive to events that simultaneously excite exceedingly small numbers selectively tuned neurons, without suffering from unreasonable rates of false positive spontaneous ignition events.

Nonlinear Neural Network Model of Neural Ignition

While the above simple analytic theory reveals that low thresholds for ignition in large neural populations can be feasible, it does not demonstrate a proof of principle for low ignition thresholds in an actual network model, and moreover leaves unspecified any network mechanism for ignition. Here we provide one possible network model that can instantiate low thresholds for ignition. The model consists of N=2000 rate neurons, characterized by their activity vector, x, which evolves in continuous time through the differential equation $\tau_k \dot{x}_k = -x_k + \Sigma_{l=1}^N J_{kl} \theta(x_l)$ where $\theta(x)$ is a heaviside function that is zero if its argument is negative, and 1 if its argument is positive. We split the population into two equal blocks of excitatory (e) and inhibitory (i) cells or size $$\frac{N}{2}$$

each. We let A,B be variables denoting the population identities, so that A, B$\in\{e, i\}$.

We choose the connectivity from any neuron in population B to any neuron in population A to be random Gaussian, with a common variance $\sigma^2$, but a mean $\mu_{AB}$ that depends on both the source and target population. In particular, we choose the inhibitory to inhibitory connections to have zero mean ($\mu_{ii}=0$), and we choose the mean inhibitory to excitatory connectivity ($\mu_{ei}=\sim 10$) to reflect strong inhibition of the excitatory subpopulation. We varied the mean excitatory strength $\mu_{ee}$ and $\mu_{ie}$, finding a boundary in this two dimensional plane separating two regimes in which the fraction of spontaneously active excitatory neurons $f_e$ (where $f_A = \langle \theta(x_k) \rangle_k \forall k \in A$) is either high or low, depending on whether the mean recurrent $\mu_{ee}$ excitation is above or below a value set by $\mu_{ie}$. Intuitively, in parameter space there is an instability to all the excitatory neurons becoming strongly active if recurrent excitation is too high. We chose the parameters so as to lie sufficiently below the boundary of instability such that the spontaneous ignition rate due to network fluctuations remained small, but close enough to this boundary such that a small excitatory stimulus can still transiently perturb the excitatory neurons to a high firing rate. This led to the choice of parameters $\mu_{ee}=15$ and $\mu_{ie}=11$, although there is a manifold of parameter choices that would yield similar results. Moreover, we ensure that the excitatory population is fast, so that $\tau_k=1$ for all all excitatory neurons, and we ensure that the inhibitory neurons are slow, with $\tau_k=20$ for all inhibitory neurons. Finally, for computational purposes, we approximate the heaviside function as $$\theta(x) = \frac{1}{2} \tanh(cx) + \frac{1}{2} \text{ where } c \gg 1.$$

Overall, this network modeling reveals several principles required for low threshold ignition: (1) a fast excitatory subnetwork that by itself is highly unstable, (2) a slow inhibitory network that provides strong inhibition to the excitatory subnetwork, (3) recurrent excitatory connectivity that should not be so strong as to destabilize a low spontaneous-activity state in the combined excitatory-inhibitory network, and (4) this same recurrent connectivity should nevertheless be strong enough so that further excitation of a small number of excitatory cells can trigger ignition. After ignition is triggered in the fast excitatory population, this population will excite the inhibitory subpopulation, which will rise more slowly, and then this inhibitory population will later inhibit the excitatory population, bringing all the firing rates back down again, ensuring that ignition is a transient event. As demonstrated in the main figures, stimulation of order ~10-30 excitatory neurons in a network of 1000 excitatory neurons is sufficient to reliably trigger such transient ignition.

High Conductance of ChRmine

Although ChRmine was discovered through our functional metagenomic screening targeting for joint exhibition of properties required for the experiments shown here, the mechanisms underlying its unique functionality remain unclear. However, recent advances in structural understanding of channelrhodopsins (ChRs) have provided a foundation for understanding of the basis of ion selectivity and spectral sensitivity. Although ChRmine shows low similarity to previously studied ChRs, mechanistically important features, such as transmembrane domains 3,6 and 7 comprising the retinal-binding pocket and ion-conducting pathway, exhibit high sequence homology (FIG. 16), suggest structural explanations for the properties of ChRmine based on structural and biochemical studies of other ChRs.

In ChRmine, Asp115 (Glu162 in C1C2 and Glu129 in CrChR2), which may form a counter-ion network along with Asp253 (Asp292 in C1C2 and Asp253 in CrChR2) to the protonated retinal Schiff base, is thus one carbon shorter than its glutamate counterparts in C1C2 or CrChR2 (FIG. 16). This difference may slightly destabilize the hydrogen-bonding network between the protonated Schiff base and its counter-ion, which would lead to elevation of the energy of the ground state of the protein and result in less energetic, more red-shifted photons sufficing for driving the transition to the light-activated state. Moreover, the homology model (FIG. 17F, built on C1C2 crystal structure as a template) reveals that overall electrostatic surface potential of ChRmine is even more negatively charged than that of the lower-photocurrent cation-conducting channelrhodopsin C1C2, suggesting a more suitable ion-conducting pore/vestibule structure for deterring anion flux and thus allowing greater cation flux. This model would be consistent with prior findings showing how surface electrostatics determine ChR ion selectivity, and together may explain how ChRmine can give rise to higher photocurrent magnitude than other cation ChRs. Further structural and spectroscopic studies are clearly needed to completely understand the molecular mechanisms of ChRmine.

Temporal and Spatial Multiplexing of Spatial Light Modulators (MultiSLM)

A general description of the theory and possible embodiments of this brain interface, MultiSLM, are provided here. For more details on the instantiations used in the manuscript, see FIGS. 8, 11, 18-20 Additional instantiations are described in FIGS. 8-9.

MultiSLM was designed as an optical hardware solution for spatially specific >kHz targeting of any of the thousands of neurons located throughout a three-dimensional (3D) volume of tissue. While imaging neural activity (e.g., fluorescent activity reporter), simultaneous photostimulation (e.g., with optogenetics) of user-specified targets is possible—both at high spatial resolution (<1 µm lateral). One to hundreds of diffraction limited spots can be generated in precise locations, simultaneously (within <1 ms), using holograms generated by combining high peak power lasers with an array of several customized, high-resolution spatial light modulators (SLMs) which are controlled by custom computational hardware and software.

In addition to enhancing the individual performance of an SLM, the MultiSLM approach presented here utilizes multiplexing of multiple optical beams (e.g. using polarization-states or chromatic-dependent optics) to gain additional utility beyond a single SLM device. Generally, laser light can originate from 1 or more lasers and be de-multiplexed into at least 2 distinct channels. The channels can be de-multiplexed using an array of strategies for beam separation across multiple channels simultaneously, or directed to different channels (SLMs) in rapid sequence, with temporal precision on the order of microseconds. A number of strategies are available to add additional SLM modules—yielding 4 or more SLMs in one system (FIGS. 8 and 9). These channels are then multiplexed after the SLMs into a common optical axis by using dichroic mirrors, polarization beam splitters, high speed polarization switches (or electro-optic modulators) and/or 50/50 beamsplitters, which are carefully aligned with angle and polarization tuning.

When multiplexing across SLMs, two operation modes—sequential and simultaneous—can be realized and the choice of multiplexing mechanism will influence the performance of these two mode options, as discussed in more detail below. In Sequential Mode, the refresh times are staggered across individual SLMs (each with ~500 Hz refresh rate); thus, the effective temporal resolution of distinct ensemble addressing can exceed 1 kHz. In Simultaneous Mode, multiple SLMs are simultaneously projecting to the sample, allowing more neurons to be targeted at precisely the same time (for example, over a larger volume if the SLMs are spatially tiled; FIG. 9). In all designs, no optical interference is expected to occur between distinct MultiSLM system optical paths since different polarizations, wavelengths and/or optical path lengths are used (and in all presented instantiations, the femto-second, pulsed stimulation laser(s) are synchronized at the source and pulsed with low duty cycle on the nanosecond scale).

Temporal precision and excitation duration (<640 µs) are tightly controlled with custom software and electro-optic modulators (Pockels cells and/or polarization switches), for example, to drive a single spike in each targeted neuron using optogenetics. The SLM modulated light reflects off a set of high-speed galvanometer mirrors which move the SLM generated hologram rapidly in the volume, for example, to create a spiral motion spanning the size of a typical neuron. This pattern could be divided into multiple "mini-spirals" to span most of the neuron cell body more rapidly, with greater efficiency. This motion moves the spot around the cell body of the neuron using empirically-derived parameters for velocity and spatial resolution to reliably yield a spike in the neuron (reaching saturating photocurrent in the best case, or at least enough photocurrent to reliably elicit a spike). It should be noted that, alternatively, a disc of light or virtually any image pattern can be created using SLM-based holography to stimulate an entire neuron cell body, or other part of a neuron, such as a dendritic spine, without the need to move the galvanometer mirrors, but with a lower light power density and thus far lower multiphoton efficiency (in standard two-photon excitation, light power density—modeled as numerical aperture of the system producing the excitation spot—is thought to influence the multiphoton effect exponentially to the fourth power, and is the single largest determinant of multiphoton excitation probability). Additionally, a grid of dots or other arbitrary pattern of light can be created to match the features (i.e., neuron cell body locations) in the volume for imaging or stimulation. In the instantiation presented in the current manuscript, the galvanometer mirrors are part of a modified two-photon microscope which has two additional sets of galvanometer mirrors, including a resonant scanner dedicated to imaging at high rates.

The wavelengths for SLM optogenetic stimulation are chosen to excite optogenetic actuators (e.g., ChRmine) at or near their peak excitation wavelengths, while minimally exciting neural activity sensors (e.g., GCaMP). This allows simultaneous opsin stimulation and neural activity imaging from the same population of neurons. Thus, the effects of stimulated patterns of activity on local dynamics can be read out in real time with neural activity imaging at single cell resolution. In low stimulation-duty cycle experiments, it may be advantageous to simply omit stimulation epochs from imaging data (as in the current manuscript), since the stimulation laser will elicit some unwanted activity sensor fluorescence. More generally, synchronizing imaging and photostimulation lasers (typically kHz-MHz repetition rates of tens to hundreds of femtosecond pulses) could permit photostimulation to occur out of phase with imaging at the level of laser pulse times (by varying optical path lengths), such that light and fluorescence artifacts caused by optogenetic photostimulation could be completely removed with a lock-in amplifier, chopper circuit operating on the MHz or GHz scale (depending on the laser source repetition rates; fluorescence decay time constants of activity reporters, such as those based on green fluorescent protein (GFP), are likely to be on the order of a few nanoseconds and thus within a fraction of the period of high repetition rate lasers, e.g., 12.5 ns for 80 MHz). Even if lasers are not synchronized with each other, high-speed electronic acquisition circuits could at least partially remove photostimulation artifacts by precisely gating acquisition on laser pulse times. Similar high-speed, laser-synchronized electronic acquisition circuits have been demonstrated previously for spatiotemporal multiplexed two-photon imaging. These approaches may thus have utility not only for artifact subtraction, but also for multiplexed imaging applications using MultiSLM holography for excitation of multiple points of interest at once in combination with non-scanning acquisition and computational methods that measure and estimate location information of recorded signals in 3D.

As demonstrated in this manuscript, essentially any neurons in the three-dimensional field of view accessible with a single two-photon objective are addressable to stimulate with high precision. Thus, natural patterns of activity can be precisely replayed into the population, for example, to create artificial perceptions, or to artificially reinforce learning. Furthermore, the generated pattern of activity can be altered in precise ways, or combined with other experimental manipulations, to help understand the necessity and sufficiency of quantifiable features of the pattern on neural coding robustness, perception and behavior. In these ways, this novel device and experimental strategy may open fundamental new insights into the complexities of the brain.

MultiSLM Sequential Mode: The MultiSLM design allows for the overall hologram generation rate of the system to surpass the hologram generation rate of any single SLM in the system, by staggering the triggering of individual SLMs in the system, each running at maximum hologram generation rate (plus dwell time on a given hologram). The following equations describe the design and limits on the Sequential Mode of operation.

$$P_{SLM} = L + r_{SLM} + (2*\sigma_L) + (2*\sigma_r)$$

where $P_{SLM}$ is the period in time that the SLM takes to reach complete formation of a hologram (including time to load phase mask onto the SLM and time for the liquid crystal to respond and reach desired phase level to successfully generate the hologram, see FIG. 19B), $r_{SLM}$ is the mean hologram generation time of the SLM from start to completion, L is the mean latency from input trigger to beginning of hologram generation by the SLM, $\sigma_L$ is the standard deviation of latency from trigger input to the time the SLM begins transitioning to the next hologram, and $\sigma_r$ is the standard deviation of $r_{SLM}$. Assuming a normal distribution of L and $r_{SLM}$, this achieves an estimate of $P_{SLM}$ that is true 95% of the time.

Following from this, the hologram refresh rate of a given SLM in the system is:

$$R_{SLM} = \frac{1}{P_{SLM}}$$

The hologram refresh rate of the MultiSLM system in Sequential Mode, $R_{seq}$, that is the rate at which new holograms can be created, is:

$$R_{seq} = \frac{N_{SLM}}{P_{SLM} + d}$$

Where d is the duration that a formed hologram is displayed (e.g., to illuminate the sample for a desired period of time typically on the order of hundreds of microseconds), and $N_{SLM}$ is the number of SLMs in the MultiSLM system.

So far, this assumes that $P_{SLM}$ and d are each the same for all SLMs in the system. More generally, periods, durations, latencies and jitters can be determined for each SLM in the system and summed to determine $R_{seq}$:

$$R_{seq} = \sum_{i=1}^{N_{SLM}s} \frac{N_{SLM}}{P_{SLMi} + d_i}$$

The period of the MultiSLM system, $P_{seq}$, is:

$$P_{seq} = \frac{1}{R_{seq}}$$

The duty cycle of stimulation, D, is defined as:

$$D = \frac{d * N_{SLM}}{P_{seq}}$$

assuming equal interval in time between illumination of each SLM in the MultiSLM system. 100% duty cycle is achieved for all:

$$P_{seq} \leq d * N_{SLM}$$

The maximum hologram refresh rate of the MultiSLM system, $MAX(R_{seq})$, occurs with 100% duty cycle when $$P_{seq} = d * N_{SLM}$$

and laser exposure duration times for each SLM in the MultiSLM system, $LaserExposure_{Time}$, are spaced sequentially in time such that:

$$LaserExposure_{Time_i+1} = LaserPulse_{Time_i} + \left(\frac{P_{seq}}{N_{SLM}}\right)$$

and the laser pulse duration, $LaserExposure_{Duration}$, equals d:

$$LaserExposure_{Duration} = d$$

and triggers to a given SLM, $T_i$, repeat with period $P_{trig}$, such that:

$$P_{trig} = P_{seq}$$

assuming that all SLMs in the system have equal $P_{SLM}$ (otherwise, timings should account for the different periods of each SLM to achieve the same effect). $MAX(R_{seq})$ increases as d approaches zero.

Furthermore, the improvement in hologram refresh rate of the MultiSLM compared to the hologram refresh rate of a single SLM in the system, $R_{SLM}$, is:

$$MAX(R_{seq}) = (R_{SLM} + d) * N_{SLM}$$

Increased temporal precision [beyond that afforded by the $MAX(R_{seq})$ at 100% duty cycle] can by generated for all:

$$P_{seq} > d * N_{SLM}$$

leading to lower than 100% duty cycle. This also has the effect of lowering the average power delivered to the sample proportional to the reduction in duty cycle (see below). Higher temporal precision could be applied in a burst mode (that is the array of SLMs are illuminated in rapid sequence at or near 100% duty at the higher rate and overall in less time than $P_{seq}$, followed by a time period to allow the completion of $P_{seq}$) or the higher temporal precision can be achieved while maintaining equal, sequential spacing between SLMs as described above for the 100% duty cycle implementation.

The maximum temporal precision, MAX(p), that is the precision in stimulation time that can be guaranteed by the system, is ultimately limited by the Pockels cell response time (or more generally whatever device is used to modulate the laser beam such as electo-optic modulator, acousto-optic modulator, polarization switch, shutter, etc), $r_{PC}$:

$$MAX(p) = r_{PC}$$

assuming modulator driver electronics with equal or better temporal precision as $r_{PC}$ (if this assumption is not met, then the limiting factor is driver signal sample rate). Furthermore, it is assumed that:

$$r_{PC} << d$$

A exposure of laser power to illuminate the hologram is calibrated in intensity depending on the hologram generated (e.g., calibrated to achieve equal hologram spot intensity regardless of imaging depth in scattering tissue), is created by a calibrated signal sent by the modulator electronics, which in conjunction with a polarizing beam splitter and beam dump, achieves the desired power level for the hologram after the light has passes through all optics and biological tissue. Additional software corrections in the hologram generation code can normalize the intensity of spots across the field of view (FOV) to account for diffraction efficiency fall off from the center of the FOV. The timing of the laser exposure for a given SLM should have duration d and be synchronized to start with the completion time of the hologram generation by an SLM, such that:

$$LaserExposure_{Time_i} = T_i + P_{SLM_i}$$

In Sequential Mode, the overall laser power stimulated at one time corresponds to the laser power of the laser exposure generated, $LaserExposure_{Power}$, at that time to illuminate a single hologram generated by a single SLM in the system, without overlap with illumination of other SLMs. Thus, the maximum exposure power, $MAX(LaserExposure_{Power})$, is limited to the maximum power allowable for any one SLM ($SLM_{damagethresh}$) or hologram ($Hologram_{thresh}$). The power may be further limited based on the peak power allowable into the biological tissue, $PeakPower_{biothresh}$, which may depend on the duration of d.

Thus:

$$LaserExposure_{Power} < SLM_{damagethresh}(d)$$

and $$LaserExposure_{Power} < Hologram_{thresh}$$

and $$LaserExposure_{Power} < PeakPower_{biothresh}(d)$$

Furthermore, an allowable average power limit may further constrain the allowable LaserExposure$_{Power}$, for example, in the case when accumulated heating over a longer period of time must be avoided, such as over the full period of the system, P$_{seq}$ (but other time durations can be used depending on the application). Depending on empirically determined limits of power into biological tissue, a limit may be set taking the form of:

$$\sum_{i=1}^{N_{SLM}} \frac{LaserExposure_{Power_i}}{P_{seq}} * D < AveragePower_{biothresh}$$

where lower duty cycle (D) can increase the allowable LaserExposure$_{Power}$, up to peak power limitations.

MultiSLM Simultaneous Mode: In some configurations, the MultiSLM system can be run in synchronized mode, such that independent holograms generated across all of the SLMs are illuminated by laser exposures at the same time, $$LaserExposure_{Time_i} =$$
$$LaserExposure_{Time_{i+1}} = ... = LaserExposure_{Time_{N_{SLM}}}$$

In this configuration, the damage threshold of a single SLM can be overcome by distributing more power onto more than one SLM.

$$MAX(Power_{simul}) \le SLM_{damagethresh}(d) * N_{SLM}$$

As in the case of Sequential Mode, power limits will still remain in place regarding peak and average power into the biological tissue, and would be summed across laser power used for each SLM in the system:

$$\sum_{i=1}^{N_{SLM}} LaserExposure_{Power_i} < PeakPower_{biothresh}(d)$$

$$\sum_{i=1}^{N_{SLM}} \frac{LaserExposure_{Power_i}}{P_{seq}} < AveragePower_{biothresh}$$

Some sources of noise depending on the stimulation pattern (hologram) could benefit from distributing the pattern generation across multiple SLMs, instead of a single SLM. For example, complex holograms involving generation of many spots, or complex shapes may be achieved with fewer artifacts (e.g., higher intensity spots or pattern with lower background and/or lower speckle). Since each laser source(s) can produce synchronized pulses across multiple optical paths (corresponding to each optical path in the MultiSLM system), with temporal delay lines for each path (as will occur easily given the extremely low duty cycle of the pulsed laser source and the typical length differences between optical paths on an optical table), the holograms are not generated simultaneously at the femtosecond timescale, but would be synchronized at the microsecond timescale. This design removes any chance of optical interference between the holograms generated on each SLM in the MultiSLM system.

In Simultaneous Mode, duty cycle would be lower than Sequential Mode; and depends on d and the period of the slowest SLM in the system:

$$D_{simul} = \frac{d}{MAX(P_{SLM})}$$

Since all SLMs are illuminated at the same time, the maximum period is limited by the period by the period of the slowest SLM in the system:

$$P_{simul} = MAX(P_{SLM}) + d$$

The refresh rate in Simultaneous Mode is comparable to the refresh rate of a single SLM:

$$R_{simul} \approx MAX(R_{SLM})$$

and is equal to the inverse of P$_{simul}$:

$$R_{simul} = \frac{1}{P_{simul}}$$

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for selectively stimulating a plurality of light-responsive neurons in a sample, the method comprising:
    irradiating a sample comprising a plurality of light-responsive neurons with a plurality of holographic images that are each configured to stimulate one or more light-responsive neurons in the sample, wherein the holographic images are created by light projection system that includes:
    a plurality of light sources;
    a plurality of optical adjustment components;
    a plurality of spatial light modulators;
    a controller;
    a processor; and a computer-readable medium comprising instructions that, when executed by the processor, cause the controller to:
operate the light sources, optical adjustment components and spatial light modulators to generate and display a plurality of holographic images, wherein light beams from the light sources are combined by orthogonal polarization;
direct each of the holographic images to a projection location; and
project the holographic images onto the sample at a rate greater than or equal to 1 kHz.

2. The method according to claim 1, wherein each light source is a fixed wavelength light source.

3. The method according to claim 1, wherein each light source is a laser.

4. The method according to claim 3, wherein each laser is configured to pulse out of phase with each other.

5. The method according to claim 3, wherein the lasers are synchronized.

6. The method according to claim 5, wherein the lasers are configured with a temporal delay.

7. The method according to claim 1, wherein the optical adjustment component comprises a beam splitter, a beam polarizer, or a light modulator.

8. The method according to claim 7, wherein the beam splitter is used to create an orthogonal beam path.

9. The method according to claim 8, wherein the plurality of optical adjustment components further comprises a half waveplate, wherein
the half waveplate is positioned before at least one spatial light modulator, wherein the half waveplate is used to rotate a light beam such that the light beam is directed to the spatial light modulator, or
the half waveplate is positioned after at least one spatial light modulator, wherein the half waveplate is used to rotate a first light beam such that the first light beam is directed to the beam splitter, wherein the beam splitter combines said first light beam with a second light beam onto a common optical path.

10. The method according to claim 1, wherein the plurality of holographic images is sequentially projected onto the sample.

11. The method according to claim 1, wherein the holographic image is in the shape of a spiral or the holographic image is scanned in a spiral motion.

12. The method according to claim 1, wherein the holographic image is in the shape of a neuron.

13. The method according to claim 1, wherein the holographic image is the size of neuron.

14. The method according to claim 1, wherein the plurality of holographic images is scanned across the sample with a galvanometer mirror.

15. The method according to claim 1, wherein the sample comprises one or more functionally-defined collections of a plurality of neurons.

16. The method according to claim 15, wherein the neurons comprise a neural activity-dependent fluorescent moiety.

17. The method according to claim 16, wherein the neural activity-dependent fluorescent moiety is a light-activated polypeptide.

18. The method according to claim 17, wherein irradiating the sample with the plurality of holographic images is sufficient to approximate neural activity-dependent fluorescence generated by a natural stimulus.

19. The method according to claim 17, wherein the light-activated polypeptide is a depolarizing or hyperpolarizing light-activated polypeptide.

20. The method according to claim 17, wherein the light-activated polypeptide is an ion channel or an ion pump.

21. The method according to claim 17, wherein the light-activated polypeptide is selected from: ChR2, ChRime, iC1C2, C1C2, GtACR2, NpHR, eNpHR3.0, C1V1, VChR1, VChR2, SwiChR, Arch, ArchT, KR2, ReaChR, ChiEF, Chronos, ChRGR, CsChrimson, bReaCh-ES, and variants thereof.

22. The method according to claim 16, wherein the sample comprises genetically modified neurons expressing the one or more activity-dependent fluorescent moieties.

23. The method according to claim 1, wherein the plurality of light sources has orthogonal beam paths for illuminating each of the spatial light modulators.

24. The method according to claim 1, wherein the plurality of optical adjustment components comprises a prism, wherein
the prism is positioned before at least one spatial light modulator, wherein the prism directs a light beam to the spatial light modulator, or
the prism is positioned after at least one spatial light modulator, wherein the prism applies a tilt angle to a light beam.

25. The method according to claim 1, wherein the plurality of optical adjustment components comprises a dichroic mirror, wherein light beams having different wavelengths are combined with the dichroic mirror.

26. The method according to claim 1, wherein each light beam is phase shifted relative to other light beams, wherein each light beam has an optical path of a different length.

27. The method according to claim 1, wherein the light projection system comprises a plurality of electro-optic light modulators, Pockels cells, acousto-optic modulators, or polarization switches, wherein polarization of the light beams is dependent on an amount of voltage applied to each electro-optic light modulator, Pockels cell, acousto-optic modulator, or polarization switch, wherein each electro-optic light modulator, Pockels cell, acousto-optic modulator, or polarization switch is followed by a polarization beam splitter that switches an optical path of a light beam based on the polarization of the light beam to allow selection of a specific spatial light modulator for illumination depending on the amount of voltage applied.

28. The method according to claim 27, wherein power level, timing, and duration of illumination of each spatial light modulator can be controlled by the plurality of electro-optic light modulators, Pockels cells, acousto-optic modulators, or polarization switches, wherein selected spatial light modulators can be illuminated simultaneously or sequentially.

29. The method according to claim 1, wherein the light projection system comprises a plurality of electro-optic light modulators, Pockels cells, acousto-optic modulators, or polarization switches, wherein polarization of the light beams is dependent on an amount of voltage applied to each electro-optic light modulator, Pockels cell, acousto-optic modulator, or polarization switch, wherein each electro-optic light modulator, Pockels cell, acousto-optic modulator, or polarization switch is followed by a polarization beam splitter to allow orthogonal polarizations of light occurring on the same optical path at different times to be combined based on the polarization of the light beams depending on the amount of voltage applied.

30. The method according to claim 1, wherein the plurality of optical adjustment components comprises a plurality of prisms, wherein each prism is positioned after a different spatial light modulator, wherein each prism applies a tilt angle to a light beam such that the field of view of each spatial light modulator is directed to a different location, wherein the holographic images are projected onto different regions of the sample.

* * * * *